United States Patent
Perrow et al.

(10) Patent No.: US 11,696,786 B2
(45) Date of Patent: *Jul. 11, 2023

(54) INSTRUMENT FOR INSERTING A SPINAL DEVICE

(71) Applicant: Pioneer Surgical Technology, Inc., Marquette, MI (US)

(72) Inventors: Scott J. Perrow, Ishpeming, MI (US); Joseph Mohar, Marquette, MI (US); Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 295 days.

This patent is subject to a terminal disclaimer.

(21) Appl. No.: 17/193,763

(22) Filed: Mar. 5, 2021

(65) Prior Publication Data
US 2021/0290277 A1   Sep. 23, 2021

Related U.S. Application Data

(63) Continuation of application No. 16/229,873, filed on Dec. 21, 2018, now Pat. No. 10,980,575, which is a
(Continued)

(51) Int. Cl.
*A61B 17/80* (2006.01)
*A61B 17/70* (2006.01)
(Continued)

(52) U.S. Cl.
CPC ........ *A61B 17/7059* (2013.01); *A61B 17/808* (2013.01); *A61B 17/8014* (2013.01);
(Continued)

(58) Field of Classification Search
CPC ................. A61B 17/808; A61B 17/861; A61F 2/4603; A61F 2/4605; A61F 2/4606;
(Continued)

(56) References Cited

U.S. PATENT DOCUMENTS 3,413,741 A   12/1968   Fagan et al.
3,695,259 A   10/1972   Yost
(Continued)

FOREIGN PATENT DOCUMENTS

CA   2395609   8/2001
CA   2482403   9/2003
(Continued)

OTHER PUBLICATIONS

Bao, Qi-Bin and Yuan, Hansen A., "Artificial Disc Technology", Neurosurg. Focus, vol. 9, No. 4, Oct. 2000, 7 pp.
(Continued)

*Primary Examiner* — Samuel S Hanna
(74) *Attorney, Agent, or Firm* — Fitch, Even, Tabin & Flannery LLP

(57) ABSTRACT

In one aspect, a bone anchor assembly is provided having a bone anchor with a head, a resilient locking cap extending about a portion of the bone anchor head, and a cap drive member having a depending annular wall. In another form, a bone plate system is provided including a bone plate having an elongated throughbore and a resilient support member received therein. In another aspect, an insertion device is provided for manipulating and inserting a spinal device at or within a spinal joint. The insertion device is configured to actively pivot the implant about the implant gripping end of the device and to allow manipulation and release of the implant in any pivoted orientation from approximately 0 to 90 degrees.

15 Claims, 92 Drawing Sheets

Related U.S. Application Data continuation of application No. 14/954,179, filed on Nov. 30, 2015, now Pat. No. 10,159,514, which is a continuation of application No. 13/725,420, filed on Dec. 21, 2012, now Pat. No. 9,198,769.

(60) Provisional application No. 61/580,055, filed on Dec. 23, 2011.

(51) Int. Cl.
  *A61B 17/86* (2006.01)
  *A61B 17/88* (2006.01)
  *A61F 2/44* (2006.01)

(52) U.S. Cl.
  CPC ...... *A61B 17/8038* (2013.01); *A61B 17/8042* (2013.01); *A61B 17/8047* (2013.01); *A61B 17/861* (2013.01); *A61B 17/8888* (2013.01); *A61F 2/442* (2013.01)

(58) Field of Classification Search
  CPC ...... A61F 2/4607; A61F 2/4609; A61F 2/461; A61F 2/4611; A61F 2/4612; A61F 2/4614; A61F 2002/4615; A61F 2002/4616; A61F 2/4618; A61F 2002/4619; A61F 2002/462; A61F 2002/4622
  See application file for complete search history.

(56) References Cited

U.S. PATENT DOCUMENTS

| | | |
|---|---|---|
| 3,800,433 A | 4/1974 | Kubodera |
| 3,844,291 A | 10/1974 | Moen |
| 3,867,728 A | 2/1975 | Stubstad et al. |
| 3,875,595 A | 4/1975 | Froning et al. |
| 3,975,778 A | 8/1976 | Newton, III |
| 4,021,382 A | 5/1977 | Stoy |
| 4,081,402 A | 3/1978 | Levy |
| 4,147,764 A | 4/1979 | Levy |
| 4,309,777 A | 1/1982 | Patil |
| 4,349,921 A | 9/1982 | Kuntz |
| 4,388,921 A | 6/1983 | Sutter |
| 4,454,612 A | 6/1984 | McDaniel |
| 4,484,570 A | 11/1984 | Sutter |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz |
| 4,759,769 A | 7/1988 | Hedman |
| 4,863,476 A | 9/1989 | Shepperd |
| 4,863,477 A | 9/1989 | Monson |
| 4,917,704 A | 4/1990 | Frey |
| 4,932,969 A | 6/1990 | Frey |
| 4,936,848 A | 6/1990 | Bagby |
| 4,946,378 A | 8/1990 | Hirayama |
| 4,997,432 A | 3/1991 | Keller |
| 5,002,576 A | 3/1991 | Fuhrmann |
| 5,020,519 A | 6/1991 | Hayes |
| 5,035,716 A | 7/1991 | Downey |
| 5,047,055 A | 9/1991 | Bao |
| 5,053,036 A | 10/1991 | Perren |
| 5,057,111 A | 10/1991 | Park |
| 5,071,437 A | 12/1991 | Steffee |
| 5,092,866 A | 3/1992 | Breard |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack |
| 5,147,404 A | 9/1992 | Downey |
| 5,171,279 A | 12/1992 | Mathews |
| 5,171,281 A | 12/1992 | Parsons |
| 5,176,710 A | 1/1993 | Hahn |
| 5,192,326 A | 3/1993 | Bao |
| 5,242,443 A | 9/1993 | Kambin |
| 5,258,005 A | 11/1993 | Christian |
| 5,258,031 A | 11/1993 | Salib |
| 5,258,043 A | 11/1993 | Stone |
| 5,273,742 A | 12/1993 | Gould |
| 5,306,308 A | 4/1994 | Gross |
| 5,306,309 A | 4/1994 | Wagner |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buttner-Janz |
| 5,423,826 A | 6/1995 | Coates |
| 5,425,773 A | 6/1995 | Boyd |
| 5,443,512 A | 8/1995 | Parr |
| 5,458,642 A | 10/1995 | Beer et al. |
| 5,458,643 A | 10/1995 | Oka |
| 5,462,362 A | 10/1995 | Yuhta |
| 5,480,440 A | 1/1996 | Kambin |
| 5,480,449 A | 1/1996 | Hamilton |
| 5,507,772 A | 4/1996 | Shutt |
| 5,507,816 A | 4/1996 | Bullivant |
| 5,514,180 A | 5/1996 | Heggeness |
| 5,520,690 A | 5/1996 | Errico |
| 5,522,899 A | 6/1996 | Michelson |
| 5,531,746 A | 7/1996 | Errico |
| 5,534,028 A | 7/1996 | Bao |
| 5,549,612 A | 8/1996 | Yapp |
| 5,549,679 A | 8/1996 | Kuslich |
| 5,556,431 A | 9/1996 | Buttner-Janz |
| 5,556,433 A | 9/1996 | Gabriel |
| 5,562,736 A | 10/1996 | Ray |
| 5,562,738 A | 10/1996 | Boyd |
| 5,571,189 A | 11/1996 | Kuslich |
| 5,578,034 A | 11/1996 | Estes |
| 5,584,887 A | 12/1996 | Kambin |
| 5,595,563 A | 1/1997 | Moisdon |
| 5,601,553 A | 2/1997 | Trebing |
| 5,607,426 A | 3/1997 | Ralph |
| 5,609,643 A | 3/1997 | Colleran |
| 5,645,596 A | 7/1997 | Kim |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray |
| 5,674,296 A | 10/1997 | Bryan |
| 5,676,701 A | 10/1997 | Yuan |
| 5,676,702 A | 10/1997 | Ratron |
| 5,681,311 A | 10/1997 | Foley |
| 5,683,392 A | 11/1997 | Richelsoph |
| 5,683,465 A | 11/1997 | Shinn |
| 5,693,100 A | 12/1997 | Pisharodi |
| 5,702,450 A | 12/1997 | Bisserie |
| 5,713,900 A | 2/1998 | Benzel et al. |
| 5,716,416 A | 2/1998 | Lin |
| 5,720,751 A | 2/1998 | Jackson |
| 5,728,762 A | 3/1998 | Reich |
| 5,733,287 A | 3/1998 | Tepic |
| 5,735,853 A | 4/1998 | Olerud |
| 5,755,797 A | 5/1998 | Baumgartner |
| 5,755,798 A | 5/1998 | Papavero |
| 5,782,832 A | 7/1998 | Larsen |
| 5,782,833 A | 7/1998 | Haider |
| 5,797,912 A | 8/1998 | Runciman |
| 5,800,433 A | 9/1998 | Benzel |
| 5,824,093 A | 10/1998 | Ray |
| 5,824,094 A | 10/1998 | Serhan |
| 5,843,082 A | 12/1998 | Yuan |
| 5,860,980 A | 1/1999 | Axelson, Jr. |
| 5,863,293 A | 1/1999 | Richelsoph |
| 5,865,845 A | 2/1999 | Thalgott |
| 5,865,846 A | 2/1999 | Bryan |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,904,683 A | 5/1999 | Pohndorf |
| 5,919,235 A | 7/1999 | Husson |
| 5,941,885 A | 8/1999 | Jackson |

(56) References Cited

U.S. PATENT DOCUMENTS

| | | |
|---|---|---|
| 5,954,635 A | 9/1999 | Foley et al. |
| 5,954,722 A | 9/1999 | Bono |
| 5,964,760 A | 10/1999 | Richelsoph |
| 5,964,761 A | 10/1999 | Kambin |
| 5,964,807 A | 10/1999 | Gan |
| 5,969,020 A | 10/1999 | Shalaby |
| 5,976,186 A | 11/1999 | Bao |
| 5,980,572 A | 11/1999 | Kim |
| 6,001,130 A | 12/1999 | Bryan |
| 6,010,503 A | 1/2000 | Richelsoph |
| 6,019,793 A | 2/2000 | Perren |
| 6,022,350 A | 2/2000 | Ganem |
| 6,022,376 A | 2/2000 | Assell |
| 6,030,389 A | 2/2000 | Wagner |
| 6,036,693 A | 3/2000 | Yuan |
| 6,039,763 A | 3/2000 | Shelokov |
| RE36,758 E | 6/2000 | Fitz |
| 6,074,390 A | 6/2000 | Zucherman |
| 6,090,111 A | 7/2000 | Nichols |
| 6,093,205 A | 7/2000 | McLeod |
| 6,093,207 A | 7/2000 | Pisharodi |
| 6,096,044 A | 8/2000 | Boyd |
| 6,110,210 A | 8/2000 | Norton |
| 6,113,639 A | 9/2000 | Ray |
| 6,117,173 A | 9/2000 | Taddia |
| 6,127,597 A | 10/2000 | Beyar |
| 6,132,432 A | 10/2000 | Richelsoph |
| 6,132,465 A | 10/2000 | Ray |
| 6,136,031 A | 10/2000 | Middleton |
| 6,139,550 A | 10/2000 | Michelson |
| 6,139,579 A | 10/2000 | Steffee |
| 6,139,721 A | 10/2000 | Baldiraghi |
| 6,143,031 A | 11/2000 | Knothe |
| 6,146,422 A | 11/2000 | Lawson |
| 6,152,927 A | 11/2000 | Farris |
| 6,156,067 A | 12/2000 | Bryan |
| 6,162,252 A | 12/2000 | Kuras |
| 6,174,311 B1 | 1/2001 | Branch |
| 6,179,874 B1 | 1/2001 | Cauthen |
| 6,183,518 B1 | 2/2001 | Ross |
| 6,187,048 B1 | 2/2001 | Milner |
| 6,190,387 B1 | 2/2001 | Zucherman |
| 6,193,720 B1 | 2/2001 | Yuan |
| 6,193,721 B1 | 2/2001 | Michelson |
| 6,206,924 B1 | 3/2001 | Timm |
| 6,214,005 B1 | 4/2001 | Benzel |
| 6,224,630 B1 | 5/2001 | Bao |
| 6,226,548 B1 | 5/2001 | Foley |
| 6,228,085 B1 | 5/2001 | Theken |
| 6,235,033 B1 | 5/2001 | Brace |
| 6,240,926 B1 | 6/2001 | Chingan |
| 6,241,731 B1 | 6/2001 | Fiz |
| 6,251,140 B1 | 6/2001 | Marino |
| 6,258,089 B1 | 7/2001 | Campbell |
| 6,261,291 B1 | 7/2001 | Talaber |
| 6,264,695 B1 | 7/2001 | Stoy |
| 6,280,475 B1 | 8/2001 | Bao |
| 6,283,968 B1 | 9/2001 | Mehdizadeh |
| 6,283,998 B1 | 9/2001 | Eaton |
| 6,287,309 B1 | 9/2001 | Baccelli |
| 6,287,313 B1 | 9/2001 | Sasso |
| 6,290,703 B1 | 9/2001 | Ganem |
| 6,306,136 B1 | 10/2001 | Baccelli |
| 6,309,393 B1 | 10/2001 | Tepic |
| 6,315,795 B1 | 11/2001 | Scarborough |
| 6,315,797 B1 | 11/2001 | Middleton |
| 6,331,179 B1 | 12/2001 | Freid |
| 6,342,055 B1 | 1/2002 | Eisermann et al. |
| 6,348,071 B1 | 2/2002 | Steffee |
| 6,352,557 B1 | 3/2002 | Ferree |
| 6,355,040 B1 | 3/2002 | Richelsoph |
| 6,368,350 B1 | 4/2002 | Erickson |
| 6,371,990 B1 | 4/2002 | Ferree |
| 6,375,682 B1 | 4/2002 | Fleischmann |
| 6,383,186 B1 | 5/2002 | Michelson |
| 6,395,032 B1 | 5/2002 | Gauchet |
| 6,398,783 B1 | 6/2002 | Michelson |
| 6,402,784 B1 | 6/2002 | Wardlaw |
| 6,402,785 B1 | 6/2002 | Zdeblick |
| 6,413,259 B1 | 7/2002 | Lyons |
| 6,416,528 B1 | 7/2002 | Michelson |
| 6,419,704 B1 | 7/2002 | Ferree |
| 6,428,542 B1 | 8/2002 | Michelson |
| 6,428,544 B1 | 8/2002 | Ralph |
| 6,428,575 B2 | 8/2002 | Koo |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph |
| 6,436,140 B1 | 8/2002 | Liu |
| 6,436,141 B2 | 8/2002 | Castro |
| 6,436,142 B1 | 8/2002 | Paes |
| 6,436,146 B1 | 8/2002 | Hassler |
| 6,440,133 B1 | 8/2002 | Beale |
| 6,440,168 B1 | 8/2002 | Cauthen |
| 6,440,170 B1 | 8/2002 | Jackson |
| 6,454,769 B2 | 9/2002 | Wagner |
| 6,454,771 B1 | 9/2002 | Michelson |
| 6,458,133 B1 | 10/2002 | Lin |
| 6,478,822 B1 | 11/2002 | Leroux |
| 6,485,491 B1 | 11/2002 | Farris |
| 6,485,591 B1 | 11/2002 | Nakao |
| 6,488,716 B1 | 12/2002 | Huang |
| 6,503,250 B2 | 1/2003 | Paul |
| 6,508,839 B1 | 1/2003 | Lambrecht |
| 6,517,580 B1 | 2/2003 | Ramadan |
| 6,527,776 B1 | 3/2003 | Michelson |
| 6,527,804 B1 | 3/2003 | Gauchet |
| 6,530,929 B1 | 3/2003 | Justis |
| 6,533,786 B1 | 3/2003 | Needham |
| 6,540,785 B1 | 4/2003 | Gill |
| 6,547,823 B2 | 4/2003 | Scarborough |
| 6,562,047 B2 | 5/2003 | Ralph |
| 6,565,565 B1 | 5/2003 | Yuan |
| 6,575,975 B2 | 6/2003 | Brace |
| 6,579,290 B1 | 6/2003 | Hardcastle |
| 6,579,320 B1 | 6/2003 | Gauchet |
| 6,579,321 B1 | 6/2003 | Gordon |
| 6,582,466 B1 | 6/2003 | Gauchet |
| 6,592,586 B1 | 7/2003 | Michelson |
| 6,592,624 B1 | 7/2003 | Fraser |
| 6,595,993 B2 | 7/2003 | Donno |
| 6,599,290 B2 | 7/2003 | Bailey |
| 6,602,255 B1 | 8/2003 | Campbell |
| 6,602,291 B1 | 8/2003 | Ray |
| 6,610,091 B1 | 8/2003 | Reiley |
| 6,613,053 B1 | 9/2003 | Collins |
| 6,616,666 B1 | 9/2003 | Michelson |
| 6,620,163 B1 | 9/2003 | Michelson |
| 6,626,907 B2 | 9/2003 | Campbell |
| 6,648,888 B1 | 11/2003 | Shluzas |
| 6,660,006 B2 | 12/2003 | Markworth |
| 6,663,635 B2 | 12/2003 | Frigg |
| 6,666,866 B2 | 12/2003 | Martz |
| 6,669,697 B1 | 12/2003 | Pisharodi |
| 6,669,700 B1 | 12/2003 | Farris |
| 6,679,883 B2 | 1/2004 | Hawkes |
| 6,679,915 B1 | 1/2004 | Cauthen |
| 6,682,562 B2 | 1/2004 | Viart |
| 6,695,846 B2 | 2/2004 | Richelsoph et al. |
| 6,740,088 B1 | 5/2004 | Kozak |
| 6,743,257 B2 | 6/2004 | Castro |
| 6,749,614 B2 | 6/2004 | Teitelbaum |
| 6,755,829 B1 | 6/2004 | Bono |
| 6,755,833 B1 | 6/2004 | Paul |
| 6,770,095 B2 | 8/2004 | Grinberg |
| 6,783,550 B2 | 8/2004 | MacArthur |
| 6,793,656 B1 | 9/2004 | Mathews |
| 6,793,658 B2 | 9/2004 | Lehuec |
| 6,793,678 B2 | 9/2004 | Hawkins |
| 6,875,212 B2 | 4/2005 | Shaolian |

(56) References Cited

U.S. PATENT DOCUMENTS

| | | |
|---|---|---|
| 6,884,242 B2 | 4/2005 | Lehuec |
| 6,890,334 B2 | 5/2005 | Brace |
| 6,890,335 B2 | 5/2005 | Grabowski |
| 6,899,716 B2 | 5/2005 | Cragg |
| 6,916,320 B2 | 7/2005 | Michelson |
| 6,936,050 B2 | 8/2005 | Michelson |
| 6,936,051 B2 | 8/2005 | Michelson |
| 6,936,071 B1 | 8/2005 | Marnay |
| 6,951,538 B2 | 10/2005 | Ritland |
| 6,964,664 B2 | 11/2005 | Freid |
| 6,964,667 B2 | 11/2005 | Shaolian |
| 6,969,390 B2 | 11/2005 | Michelson |
| 7,001,387 B2 | 2/2006 | Farris |
| 7,001,389 B1 | 2/2006 | Navarro |
| 7,001,433 B2 | 2/2006 | Songer |
| 7,011,660 B2 | 3/2006 | Sherman |
| 7,048,739 B2 | 5/2006 | Konieczynski |
| 7,052,499 B2 | 5/2006 | Steger |
| 7,060,069 B2 | 6/2006 | Kozak |
| 7,063,701 B2 | 6/2006 | Michelson |
| 7,063,702 B2 | 6/2006 | Michelson |
| 7,074,221 B2 | 7/2006 | Michelson |
| 7,077,844 B2 | 7/2006 | Michelson |
| 7,081,117 B2 | 7/2006 | Bono |
| 7,083,621 B2 | 8/2006 | Shaolian |
| 7,090,674 B2 | 8/2006 | Doubler |
| 7,090,676 B2 | 8/2006 | Huebner |
| 7,125,426 B2 | 10/2006 | Moumene |
| 7,137,984 B2 | 11/2006 | Michelson |
| 7,141,051 B2 | 11/2006 | Janowski |
| 7,156,876 B2 | 1/2007 | Moumene |
| 7,175,624 B2 | 2/2007 | Konieczynski |
| 7,204,837 B2 | 4/2007 | Paul |
| 7,229,443 B2 | 6/2007 | Eberlein |
| 7,264,621 B2 | 9/2007 | Coates |
| 7,273,481 B2 | 9/2007 | Lombardo |
| 7,309,340 B2 | 12/2007 | Fallin |
| 7,476,239 B2 | 1/2009 | Jackson |
| 7,476,240 B2 | 1/2009 | Raymond |
| 7,618,418 B2 | 11/2009 | Malandain |
| 7,625,381 B2 | 12/2009 | Michelson |
| 7,641,676 B2 | 1/2010 | Mathieu |
| 7,648,520 B2 | 1/2010 | Markworth |
| 7,651,517 B2 | 1/2010 | Konieczynski |
| 7,699,880 B2 | 4/2010 | Orbay |
| 7,758,616 B2 | 7/2010 | Lehuec |
| 7,766,947 B2 | 8/2010 | Hawkes |
| 7,789,899 B2 | 9/2010 | Markworth |
| 7,794,482 B2 | 9/2010 | Mathieu |
| 7,846,190 B2 | 12/2010 | Ball |
| 7,857,839 B2 | 12/2010 | Duong |
| 7,909,859 B2 | 3/2011 | Mosca |
| 7,914,561 B2 | 3/2011 | Konieczynski et al. |
| 7,918,878 B2 | 4/2011 | Songer |
| 7,922,727 B2 | 4/2011 | Songer |
| 7,931,678 B2 | 4/2011 | Konieczynski |
| 7,931,681 B2 | 4/2011 | Carls |
| 7,935,137 B2 | 5/2011 | Gorhan |
| 7,976,550 B2 | 7/2011 | Trudeau |
| 7,981,142 B2 | 7/2011 | Konieczynski |
| 8,007,523 B2 | 8/2011 | Wagner |
| 8,012,156 B2 | 9/2011 | Marquez Alvarez |
| 8,034,089 B2 | 10/2011 | Matthis |
| 8,075,602 B2 | 12/2011 | Lombardo |
| 8,100,955 B2 | 1/2012 | Blain |
| 8,114,160 B2 | 2/2012 | Janowski |
| 8,118,872 B2 | 2/2012 | Trudeau |
| 8,142,485 B2 | 3/2012 | Buhren |
| 8,152,838 B2 | 4/2012 | Ensign |
| 8,163,019 B2 | 4/2012 | Bao |
| 8,172,885 B2 | 5/2012 | Songer |
| 8,192,439 B2 | 6/2012 | Songer |
| 8,231,676 B2 | 7/2012 | Trudeau |
| 8,241,360 B2 | 8/2012 | Bao |
| 8,246,655 B2 | 8/2012 | Jackson |
| 8,257,396 B2 | 9/2012 | Jackson |
| 8,262,570 B2 | 9/2012 | White |
| 8,262,731 B2 | 9/2012 | Songer |
| 8,287,575 B2 | 10/2012 | Murner |
| 8,308,774 B2 | 11/2012 | Hoffman |
| 8,313,515 B2 | 11/2012 | Brennan |
| 8,343,165 B2 | 1/2013 | Berrevoets |
| 8,372,084 B2 | 2/2013 | Pernsteiner |
| 8,388,684 B2 | 3/2013 | Bao |
| 8,409,213 B2 | 4/2013 | Trudeau |
| 8,414,616 B2 | 4/2013 | Berrevoets |
| 8,425,529 B2 | 4/2013 | Milz et al. |
| 8,470,040 B2 | 6/2013 | Kovarik |
| 8,480,716 B2 | 7/2013 | Perrow |
| 8,512,344 B2 | 8/2013 | Hoffman |
| 8,551,141 B2 | 10/2013 | Gephart |
| 8,597,357 B2 | 12/2013 | Trudeau |
| 8,603,141 B2 | 12/2013 | Hochschuler |
| 8,623,019 B2 | 1/2014 | Perrow et al. |
| 8,641,719 B2 | 2/2014 | Gephart |
| 8,702,600 B2 | 4/2014 | Perrow |
| 8,715,350 B2 | 5/2014 | Janowski |
| 8,808,382 B2 | 8/2014 | Bao |
| 9,033,988 B2 | 5/2015 | Gephart et al. |
| 9,072,609 B2 | 7/2015 | Kovarik |
| 9,089,437 B2 | 7/2015 | Ahn |
| 9,101,493 B2 | 8/2015 | Trudeau |
| 9,113,852 B2 | 8/2015 | Perrow |
| 9,113,972 B2 | 8/2015 | Trudeau |
| 9,132,021 B2 | 9/2015 | Mermuys |
| 9,198,764 B2 | 12/2015 | Greenberg |
| 9,198,769 B2 | 12/2015 | Perrow et al. |
| 9,216,098 B2 | 12/2015 | Trudeau |
| 9,220,606 B2 | 12/2015 | Janowski |
| 9,233,011 B2 | 1/2016 | Trudeau |
| 9,241,807 B2 | 1/2016 | Mohar |
| 9,492,211 B2 | 11/2016 | Perrow |
| 10,159,514 B2 | 12/2018 | Perrow et al. |
| 10,980,575 B2 | 4/2021 | Perrow |
| 2001/0010021 A1 | 7/2001 | Boyd |
| 2001/0012938 A1 | 8/2001 | Zucherman |
| 2001/0016772 A1 | 8/2001 | Lee |
| 2001/0016773 A1 | 8/2001 | Serhan |
| 2001/0016776 A1 | 8/2001 | Zuckerman |
| 2001/0020476 A1 | 9/2001 | Gan |
| 2001/0021851 A1 | 9/2001 | Eberlein |
| 2001/0027343 A1 | 10/2001 | Keller |
| 2001/0032019 A1 | 10/2001 | Vandyke |
| 2001/0032020 A1 | 10/2001 | Besselink |
| 2001/0037112 A1 | 11/2001 | Brace |
| 2001/0047208 A1 | 11/2001 | Michelson |
| 2001/0051829 A1 | 12/2001 | Middleton |
| 2002/0013600 A1 | 1/2002 | Scribner |
| 2002/0016595 A1 | 2/2002 | Michelson |
| 2002/0022843 A1 | 2/2002 | Michelson |
| 2002/0022883 A1 | 2/2002 | Burg |
| 2002/0022888 A1 | 2/2002 | Serhan |
| 2002/0026197 A1 | 2/2002 | Foley |
| 2002/0026244 A1 | 2/2002 | Trieu |
| 2002/0029082 A1 | 3/2002 | Muhanna |
| 2002/0029083 A1 | 3/2002 | Zucherman |
| 2002/0035400 A1 | 3/2002 | Bryan |
| 2002/0045942 A1 | 4/2002 | Ham |
| 2002/0045944 A1 | 4/2002 | Muhanna |
| 2002/0049498 A1 | 4/2002 | Yuksel |
| 2002/0058939 A1 | 5/2002 | Wagner |
| 2002/0072766 A1 | 6/2002 | Hunt |
| 2002/0082608 A1 | 6/2002 | Reiley |
| 2002/0082701 A1 | 6/2002 | Zdeblick |
| 2002/0087480 A1 | 7/2002 | Sauriol |
| 2002/0099444 A1 | 7/2002 | Boyd |
| 2002/0106393 A1 | 8/2002 | Bianchi |
| 2002/0107571 A1 | 8/2002 | Foley |
| 2002/0107572 A1 | 8/2002 | Foley |
| 2002/0107573 A1 | 8/2002 | Steinberg |
| 2002/0120269 A1 | 8/2002 | Lange |
| 2002/0120270 A1 | 8/2002 | Trieu |
| 2002/0120272 A1 | 8/2002 | Yuan |
| 2002/0120273 A1 | 8/2002 | Needham |

(56) References Cited

U.S. PATENT DOCUMENTS

| | | |
|---|---|---|
| 2002/0120334 A1 | 8/2002 | Crozet |
| 2002/0120336 A1 | 8/2002 | Santilli |
| 2002/0128655 A1 | 9/2002 | Michelson |
| 2002/0156474 A1 | 10/2002 | Wack |
| 2002/0156528 A1 | 10/2002 | Gau |
| 2002/0161368 A1 | 10/2002 | Foley |
| 2002/0165612 A1 | 11/2002 | Gerber |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0004519 A1 | 1/2003 | Torode |
| 2003/0009226 A1 | 1/2003 | Graf |
| 2003/0023311 A1 | 1/2003 | Trieu |
| 2003/0028197 A1 | 2/2003 | Hanson |
| 2003/0028251 A1 | 2/2003 | Mathews |
| 2003/0040799 A1 | 2/2003 | Boyd |
| 2003/0045939 A1 | 3/2003 | Casutt |
| 2003/0055427 A1 | 3/2003 | Graf |
| 2003/0060826 A1 | 3/2003 | Foley |
| 2003/0060828 A1 | 3/2003 | Michelson |
| 2003/0073998 A1 | 4/2003 | Pagliuca |
| 2003/0074076 A1 | 4/2003 | Ferree |
| 2003/0078583 A1 | 4/2003 | Biedermann |
| 2003/0100951 A1 | 5/2003 | Serhan |
| 2003/0125742 A1 | 7/2003 | Yuan |
| 2003/0135276 A1 | 7/2003 | Eckman |
| 2003/0135277 A1 | 7/2003 | Bryan |
| 2003/0135278 A1 | 7/2003 | Eckman |
| 2003/0149434 A1 | 8/2003 | Paul |
| 2003/0176921 A1 | 9/2003 | Lawson |
| 2003/0187440 A1 | 10/2003 | Richelsoph |
| 2003/0199876 A1 | 10/2003 | Brace |
| 2003/0204260 A1 | 10/2003 | Ferree |
| 2003/0204261 A1 | 10/2003 | Eisermann |
| 2003/0208203 A1* | 11/2003 | Lim .................. A61B 17/7083 606/279 |
| 2003/0208204 A1 | 11/2003 | Bailey |
| 2003/0220691 A1 | 11/2003 | Songer |
| 2003/0225408 A1 | 12/2003 | Nichols |
| 2003/0225409 A1 | 12/2003 | Freid |
| 2003/0229347 A1 | 12/2003 | Sherman |
| 2003/0236447 A1 | 12/2003 | Ritland |
| 2004/0019356 A1 | 1/2004 | Fraser |
| 2004/0024462 A1 | 2/2004 | Ferree |
| 2004/0030391 A1 | 2/2004 | Ferree |
| 2004/0039384 A1 | 2/2004 | Boehm |
| 2004/0044410 A1 | 3/2004 | Ferree |
| 2004/0059333 A1 | 3/2004 | Carl |
| 2004/0073315 A1 | 4/2004 | Justin et al. |
| 2004/0082960 A1 | 4/2004 | Davison |
| 2004/0082999 A1 | 4/2004 | Mathys |
| 2004/0087951 A1 | 5/2004 | Khalili |
| 2004/0092952 A1 | 5/2004 | Newton |
| 2004/0093082 A1 | 5/2004 | Ferree |
| 2004/0097935 A1 | 5/2004 | Richelsoph |
| 2004/0102846 A1 | 5/2004 | Keller |
| 2004/0117019 A1 | 6/2004 | Trieu |
| 2004/0117022 A1 | 6/2004 | Marnay |
| 2004/0127897 A1 | 7/2004 | Freid |
| 2004/0127899 A1 | 7/2004 | Konieczynski |
| 2004/0127900 A1 | 7/2004 | Konieczynski |
| 2004/0127904 A1 | 7/2004 | Konieczynski |
| 2004/0133201 A1 | 7/2004 | Shluzas et al. |
| 2004/0133278 A1 | 7/2004 | Marino |
| 2004/0138662 A1 | 7/2004 | Landry |
| 2004/0143265 A1 | 7/2004 | Landry |
| 2004/0143266 A1 | 7/2004 | Kozak |
| 2004/0147928 A1 | 7/2004 | Landry et al. |
| 2004/0147937 A1 | 7/2004 | Dunbar |
| 2004/0153065 A1 | 8/2004 | Lim |
| 2004/0153069 A1 | 8/2004 | Paul |
| 2004/0153157 A1 | 8/2004 | Keller |
| 2004/0172022 A1 | 9/2004 | Landry |
| 2004/0204712 A1 | 10/2004 | Kolb |
| 2004/0204760 A1 | 10/2004 | Fitz |
| 2004/0210221 A1 | 10/2004 | Kozak |
| 2004/0215190 A1 | 10/2004 | Nguyen |
| 2004/0230100 A1 | 11/2004 | Shluzas |
| 2004/0230191 A1 | 11/2004 | Frey |
| 2004/0236334 A1 | 11/2004 | Michelson |
| 2005/0004519 A1 | 1/2005 | Vanjaarsveldt |
| 2005/0004593 A1 | 1/2005 | Simonson |
| 2005/0021030 A1 | 1/2005 | Pagliuca |
| 2005/0021031 A1 | 1/2005 | Foley |
| 2005/0021042 A1 | 1/2005 | Marnay |
| 2005/0021143 A1 | 1/2005 | Keller |
| 2005/0021149 A1 | 1/2005 | Borruto |
| 2005/0027293 A1 | 2/2005 | Lehuec |
| 2005/0033297 A1 | 2/2005 | Davison |
| 2005/0033298 A1 | 2/2005 | Hawkes |
| 2005/0033299 A1 | 2/2005 | Shluzas |
| 2005/0033437 A1 | 2/2005 | Bao |
| 2005/0060034 A1 | 3/2005 | Berry |
| 2005/0065516 A1 | 3/2005 | Jahng |
| 2005/0065517 A1 | 3/2005 | Chin |
| 2005/0071011 A1 | 3/2005 | Ralph |
| 2005/0075540 A1 | 4/2005 | Shluzas |
| 2005/0075644 A1 | 4/2005 | DiPoto |
| 2005/0080418 A1 | 4/2005 | Simonson |
| 2005/0085813 A1 | 4/2005 | Spitler |
| 2005/0085911 A1 | 4/2005 | Link |
| 2005/0085917 A1 | 4/2005 | Marnay |
| 2005/0090822 A1 | 4/2005 | DiPoto |
| 2005/0090824 A1 | 4/2005 | Shluzas |
| 2005/0090833 A1 | 4/2005 | DiPoto |
| 2005/0090899 A1 | 4/2005 | DiPoto |
| 2005/0107789 A1 | 5/2005 | Sweeney |
| 2005/0131408 A1 | 6/2005 | Sicvol |
| 2005/0131419 A1 | 6/2005 | McCord |
| 2005/0131420 A1 | 6/2005 | Techiera |
| 2005/0131421 A1 | 6/2005 | Anderson |
| 2005/0131422 A1 | 6/2005 | Anderson |
| 2005/0137593 A1 | 6/2005 | Gray |
| 2005/0149022 A1 | 7/2005 | Shaolian |
| 2005/0149036 A1 | 7/2005 | Varieur |
| 2005/0149053 A1 | 7/2005 | Varieur |
| 2005/0154389 A1 | 7/2005 | Selover |
| 2005/0159651 A1 | 7/2005 | Raymond et al. |
| 2005/0165485 A1 | 7/2005 | Trieu |
| 2005/0171540 A1 | 8/2005 | Lim |
| 2005/0171551 A1 | 8/2005 | Sukovich |
| 2005/0177156 A1 | 8/2005 | Timm |
| 2005/0177164 A1 | 8/2005 | Walters |
| 2005/0182409 A1 | 8/2005 | Callahan |
| 2005/0192570 A1 | 9/2005 | Jackson |
| 2005/0192579 A1 | 9/2005 | Jackson |
| 2005/0192580 A1 | 9/2005 | Dalton |
| 2005/0192589 A1 | 9/2005 | Raymond |
| 2005/0192671 A1 | 9/2005 | Bao |
| 2005/0215999 A1 | 9/2005 | Birkmeyer |
| 2005/0216002 A1 | 9/2005 | Simonson |
| 2005/0228380 A1 | 10/2005 | Moore |
| 2005/0228400 A1 | 10/2005 | Chao |
| 2005/0234456 A1 | 10/2005 | Malandain |
| 2005/0245942 A1 | 11/2005 | DiPoto |
| 2005/0251137 A1 | 11/2005 | Ball |
| 2005/0251192 A1 | 11/2005 | Shluzas |
| 2005/0266581 A1 | 12/2005 | Droit |
| 2005/0267474 A1 | 12/2005 | Dalton |
| 2005/0273105 A1 | 12/2005 | Konieczynski |
| 2005/0273131 A1 | 12/2005 | Shluzas |
| 2005/0273132 A1 | 12/2005 | Shluzas |
| 2005/0273133 A1 | 12/2005 | Shluzas |
| 2005/0283245 A1 | 12/2005 | Gordon et al. |
| 2005/0288671 A1 | 12/2005 | Yuan |
| 2006/0004453 A1 | 1/2006 | Bartish |
| 2006/0004455 A1 | 1/2006 | Leonard |
| 2006/0020342 A1 | 1/2006 | Ferree |
| 2006/0036244 A1 | 2/2006 | Spitler |
| 2006/0041260 A1 | 2/2006 | Orbay |
| 2006/0041614 A1 | 2/2006 | Oe |
| 2006/0074432 A1 | 4/2006 | Stad |
| 2006/0074445 A1 | 4/2006 | Gerber et al. |

(56) References Cited

U.S. PATENT DOCUMENTS

| | | |
|---|---|---|
| 2006/0079900 A1 | 4/2006 | Mathieu |
| 2006/0089651 A1 | 4/2006 | Trudeau |
| 2006/0106387 A1 | 5/2006 | Fanger |
| 2006/0111714 A1 | 5/2006 | Foley |
| 2006/0116689 A1 | 6/2006 | Albans |
| 2006/0122602 A1 | 6/2006 | Konieczynski |
| 2006/0122604 A1 | 6/2006 | Gorhan |
| 2006/0149256 A1 | 7/2006 | Wagner |
| 2006/0155278 A1 | 7/2006 | Warnick |
| 2006/0161157 A1 | 7/2006 | Mosca |
| 2006/0173456 A1 | 8/2006 | Hawkes |
| 2006/0200135 A1 | 9/2006 | Sherman |
| 2006/0200147 A1 | 9/2006 | Ensign |
| 2006/0212122 A1 | 9/2006 | Perera |
| 2006/0229614 A1 | 10/2006 | Foley |
| 2006/0235393 A1 | 10/2006 | Bono |
| 2006/0235399 A1 | 10/2006 | Carls |
| 2006/0235411 A1 | 10/2006 | Blain |
| 2006/0235426 A1 | 10/2006 | Lim et al. |
| 2006/0235527 A1 | 10/2006 | Buettner-Janz |
| 2006/0235528 A1 | 10/2006 | Buettner-Janz |
| 2006/0235531 A1 | 10/2006 | Buettner-Janz |
| 2006/0241600 A1 | 10/2006 | Ensign |
| 2006/0241616 A1 | 10/2006 | Konieczynski |
| 2006/0241618 A1 | 10/2006 | Gasser |
| 2006/0247630 A1 | 11/2006 | Iott |
| 2006/0247636 A1 | 11/2006 | Yuan |
| 2006/0264962 A1 | 11/2006 | Chin |
| 2006/0271087 A1 | 11/2006 | Vondyck |
| 2006/0276791 A1 | 12/2006 | Shluzas |
| 2006/0276792 A1 | 12/2006 | Ensign |
| 2007/0010817 A1 | 1/2007 | De Coninck |
| 2007/0027547 A1 | 2/2007 | Rydell |
| 2007/0055235 A1 | 3/2007 | Janowski |
| 2007/0078460 A1 | 4/2007 | Frigg |
| 2007/0093817 A1 | 4/2007 | Barrus |
| 2007/0093826 A1 | 4/2007 | Hawkes |
| 2007/0093827 A1 | 4/2007 | Warnick |
| 2007/0093838 A1 | 4/2007 | Khodadadyan-Klostermann |
| 2007/0093850 A1 | 4/2007 | Harris et al. |
| 2007/0100454 A1 | 5/2007 | Burgess |
| 2007/0123879 A1 | 5/2007 | Songer |
| 2007/0142843 A1 | 6/2007 | Dye |
| 2007/0185491 A1 | 8/2007 | Foley |
| 2007/0198015 A1 | 8/2007 | Foley |
| 2007/0213714 A1 | 9/2007 | Justis |
| 2007/0225711 A1 | 9/2007 | Ensign |
| 2007/0225717 A1 | 9/2007 | Hawkes |
| 2007/0288004 A1 | 12/2007 | Alvarez |
| 2008/0009870 A1 | 1/2008 | Lombardo |
| 2008/0009880 A1 | 1/2008 | Warnick |
| 2008/0015597 A1 | 1/2008 | Whipple |
| 2008/0039839 A1 | 2/2008 | Songer |
| 2008/0039840 A1 | 2/2008 | Songer |
| 2008/0045956 A1 | 2/2008 | Songer |
| 2008/0077153 A1 | 3/2008 | Pernsteiner |
| 2008/0077241 A1 | 3/2008 | Nguyen |
| 2008/0109081 A1 | 5/2008 | Bao |
| 2008/0114359 A1 | 5/2008 | Murner |
| 2008/0140129 A1 | 6/2008 | Dalton |
| 2008/0154277 A1 | 6/2008 | Machalk |
| 2008/0172054 A1 | 7/2008 | Claypool |
| 2008/0172094 A1 | 7/2008 | Mathieu |
| 2008/0177330 A1 | 7/2008 | Ralph |
| 2008/0195155 A1 | 8/2008 | Hoffman |
| 2008/0208262 A1 | 8/2008 | Butler |
| 2008/0208263 A1 | 8/2008 | Butler |
| 2008/0228233 A1 | 9/2008 | Hoffman |
| 2008/0234750 A1 | 9/2008 | Woods |
| 2008/0243192 A1 | 10/2008 | Jacene |
| 2008/0269809 A1 | 10/2008 | Garamszegi |
| 2008/0288081 A1 | 11/2008 | Scrafton |
| 2008/0306488 A1 | 12/2008 | Altarac |
| 2008/0306489 A1 | 12/2008 | Altarac |
| 2008/0319488 A1 | 12/2008 | Helgerson |
| 2009/0036933 A1 | 2/2009 | Dube |
| 2009/0043390 A1 | 2/2009 | Meisel |
| 2009/0054901 A1 | 2/2009 | Oh |
| 2009/0164023 A1 | 6/2009 | Devine |
| 2009/0185904 A1 | 7/2009 | Landberg |
| 2009/0228054 A1 | 9/2009 | Hoffman |
| 2009/0270927 A1 | 10/2009 | Perrow |
| 2009/0326580 A1 | 12/2009 | Anderson |
| 2010/0160977 A1 | 6/2010 | Gephart |
| 2010/0179595 A1 | 7/2010 | Jackson |
| 2010/0249797 A1 | 9/2010 | Trudeau |
| 2010/0312279 A1 | 12/2010 | Gephart |
| 2011/0054621 A1 | 3/2011 | Lim |
| 2012/0185045 A1 | 7/2012 | Morris |
| 2012/0203344 A1 | 8/2012 | Trudeau |
| 2012/0310287 A1 | 12/2012 | Bao |
| 2013/0190825 A1 | 7/2013 | Perrow |
| 2013/0296941 A1 | 11/2013 | Perrow |
| 2014/0277473 A1 | 9/2014 | Perrow |
| 2014/0324104 A1 | 10/2014 | Kilpela |
| 2015/0100130 A1 | 4/2015 | Perrow |
| 2015/0265414 A1 | 9/2015 | Mermuys |
| 2016/0081723 A1 | 3/2016 | Perrow |

FOREIGN PATENT DOCUMENTS

| | | |
|---|---|---|
| CA | 2548780 A1 | 7/2005 |
| CN | 1697633 | 11/2005 |
| DE | 9000094 U1 | 1/1991 |
| DE | 29911422 U1 | 8/1999 |
| DE | 10226496 | 6/2001 |
| DE | 10130825 | 3/2002 |
| EP | 0179695 | 4/1986 |
| EP | 0346129 A1 | 12/1989 |
| EP | 0773008 A1 | 5/1997 |
| EP | 0919209 A1 | 6/1999 |
| EP | 0988833 | 3/2000 |
| EP | 1104665 A1 | 6/2001 |
| EP | 1205160 | 5/2002 |
| EP | 1336383 | 8/2003 |
| EP | 1340468 | 9/2003 |
| EP | 1346697 | 9/2003 |
| EP | 1858422 | 11/2007 |
| FR | 2372622 | 6/1978 |
| FR | 2723841 | 3/1996 |
| FR | 2787014 | 6/2000 |
| FR | 2797179 | 2/2001 |
| FR | 2799116 | 4/2001 |
| FR | 2805985 | 9/2001 |
| FR | 2824261 A1 | 11/2002 |
| JP | 63300758 A2 | 12/1988 |
| JP | 1308557 A2 | 12/1989 |
| JP | 02111358 | 4/1990 |
| JP | 2215461 A2 | 8/1990 |
| JP | 2224659 A2 | 9/1990 |
| JP | 2224660 A2 | 9/1990 |
| JP | 04303444 A | 10/1992 |
| JP | 05277141 A | 10/1993 |
| JP | 06285099 | 10/1994 |
| JP | 08098850 A | 4/1996 |
| JP | 08098851 A2 | 4/1996 |
| JP | 11009618 A | 1/1999 |
| JP | 11137585 A | 5/1999 |
| JP | 2008284348 A | 11/2008 |
| WO | 198803781 | 6/1988 |
| WO | 9011740 | 10/1990 |
| WO | 9105521 | 5/1991 |
| WO | 9116867 | 11/1991 |
| WO | 9316664 | 9/1993 |
| WO | 9500082 | 1/1995 |
| WO | 9601598 | 1/1996 |
| WO | 199608206 | 3/1996 |
| WO | 9611642 | 4/1996 |
| WO | 9627339 | 9/1996 |
| WO | 199639975 | 12/1996 |
| WO | 199722306 | 6/1997 |
| WO | 9805274 | 2/1998 |
| WO | 9819617 | 5/1998 |
| WO | 199834553 | 8/1998 |

(56) References Cited

FOREIGN PATENT DOCUMENTS

| WO | 199834556 | 8/1998 |
|---|---|---|
| WO | 199851226 | 11/1998 |
| WO | 9855053 | 12/1998 |
| WO | 9904718 | 2/1999 |
| WO | 9911203 | 3/1999 |
| WO | 9922675 | 5/1999 |
| WO | 9930651 | 6/1999 |
| WO | 200003653 | 1/2000 |
| WO | 0013619 A1 | 3/2000 |
| WO | 0042953 | 7/2000 |
| WO | 0059412 | 10/2000 |
| WO | 200066011 | 11/2000 |
| WO | 200078238 | 12/2000 |
| WO | 200126566 | 4/2001 |
| WO | 0132100 | 5/2001 |
| WO | 200149191 | 7/2001 |
| WO | 0115638 A1 | 8/2001 |
| WO | 0168003 | 9/2001 |
| WO | 02058574 | 8/2002 |
| WO | 02087480 | 11/2002 |
| WO | 03035129 | 5/2003 |
| WO | 2003063714 | 8/2003 |
| WO | 03099172 | 12/2003 |
| WO | 2004017847 A2 | 3/2004 |
| WO | 2004047650 | 6/2004 |
| WO | 2004071339 | 8/2004 |
| WO | 2005009298 | 2/2005 |
| WO | 2005041818 | 5/2005 |
| WO | 2005051240 | 6/2005 |
| WO | 2005053550 | 6/2005 |
| WO | 2006016384 A1 | 2/2006 |
| WO | 2006061114 | 6/2006 |
| WO | 2006091863 | 8/2006 |
| WO | 2008024937 | 2/2008 |
| WO | 2008051707 | 5/2008 |
| WO | 2008055648 | 5/2008 |

OTHER PUBLICATIONS

Depuy Spine, Inc., Charite Artificial Disc Centreline TDR Instrumentation, Surgical Technique, Dec. 2004, 21 pp.
Depuy Spine, Inc.; Charite Artificial Disc Product Catalog, Dec. 2004, 16 pp.
European Patent Office, Supplemental EPO Search Report for Application No. 03738960.8, dated Feb. 20, 2008, 6 pp.
European Patent Office, Supplemental EPO Search Report for Application No. EP 07842616, dated Mar. 20, 2012, 7 pp.
European Patent Office, Supplemental EPO Search Search Report for Application No. EP04796064, dated Mar. 22, 2012, 8 pp.
Feder, Barnaby J., "When F.D.A. Says Yes, but Insurers Say No", The New York Times, Jul. 6, 2005, 2 pp.
Foley, M.D., Kevin T., Schwender, MD., James D., and Rouben, MD., David P., PyrametriX.RTM. Advance: Instrument Set Technique, surgical brochure provided by manufacturer Medtronic Sofamor Danek, Inc., 2005, (25 pages).
State Intellectual Property Office, First Notification of Office Action for Application No. 200780040650.7, dated Dec. 15, 2010, 9 pp.
Zdeblick, T. et al, Cervical Interbody Fusion Cages, An Animal Model With and Without Bone Morphogenetic Protein, Spine, 1998, vol. 23, No. 7, 9 pp.

* cited by examiner

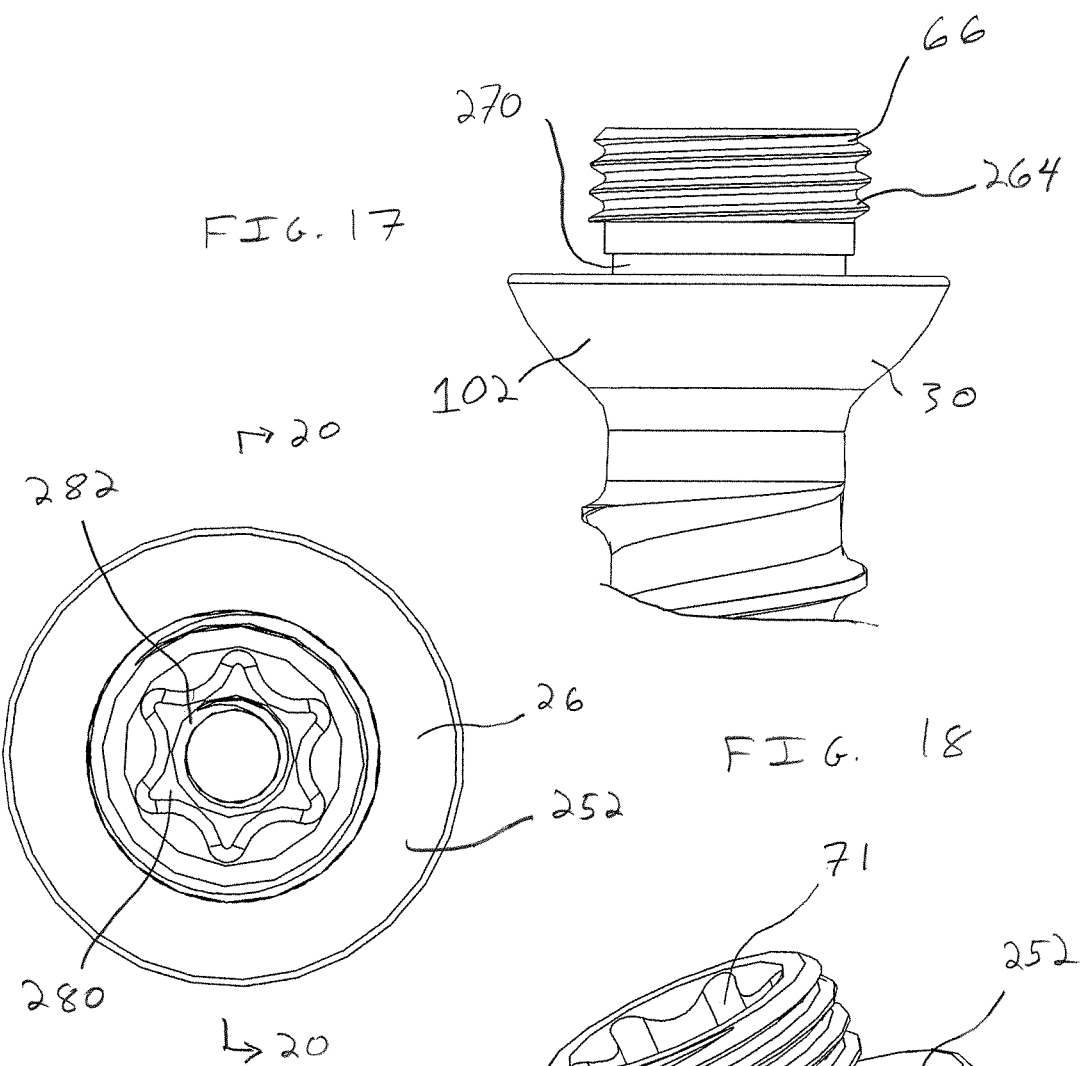
FIG. 17
FIG. 18
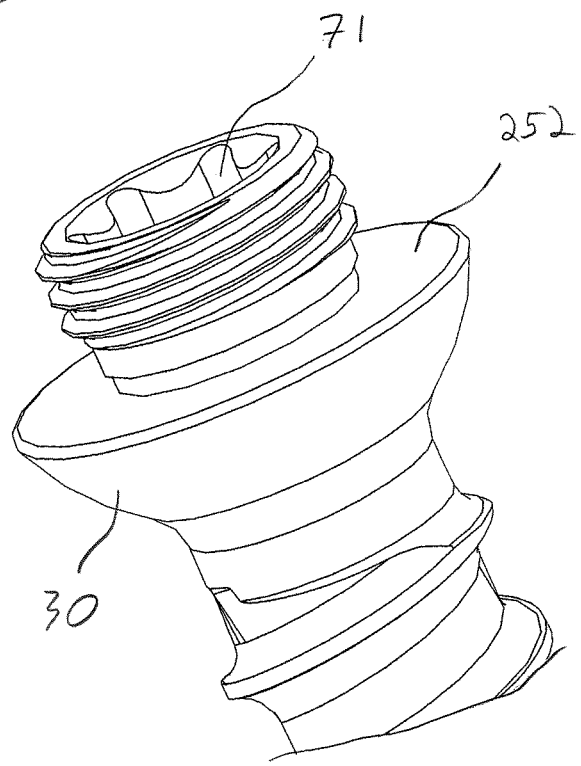
FIG. 19

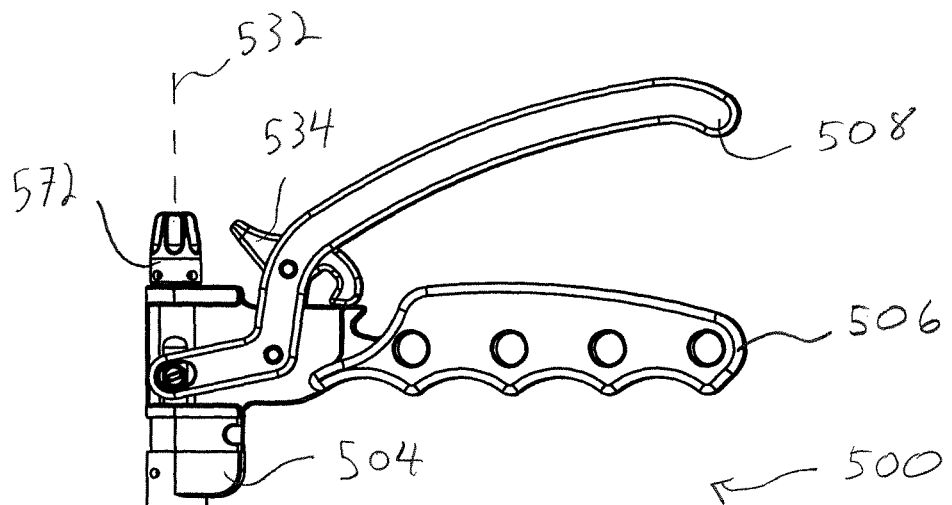
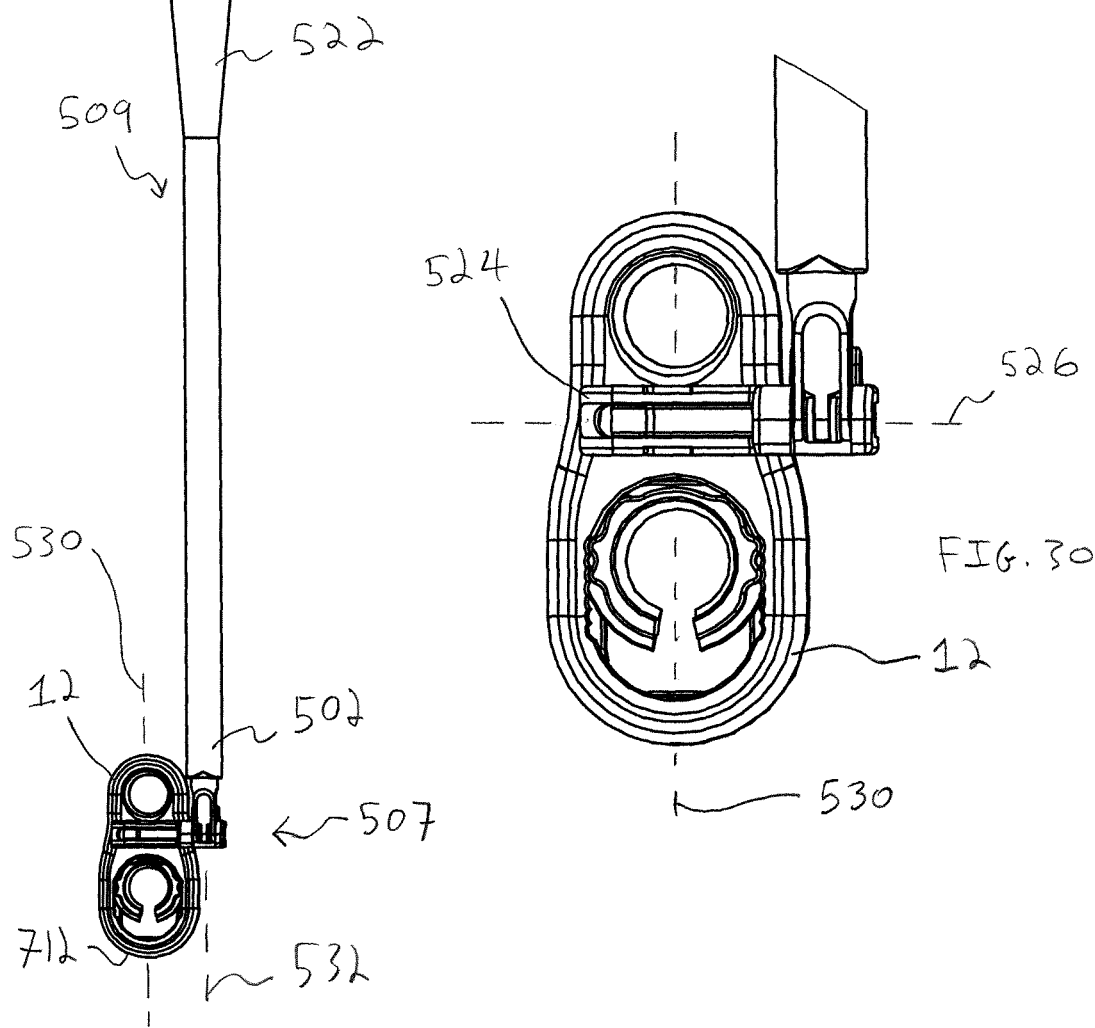
FIG. 29
FIG. 30

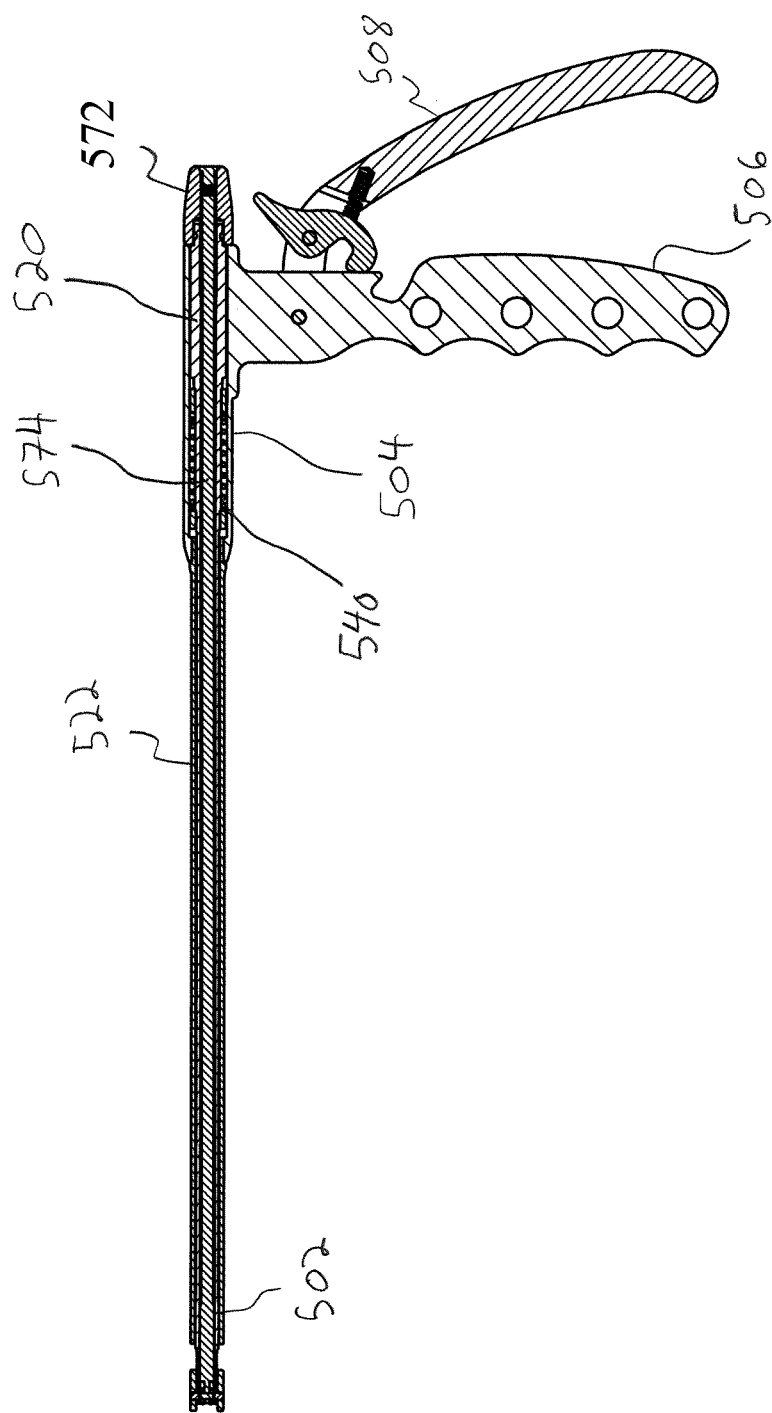

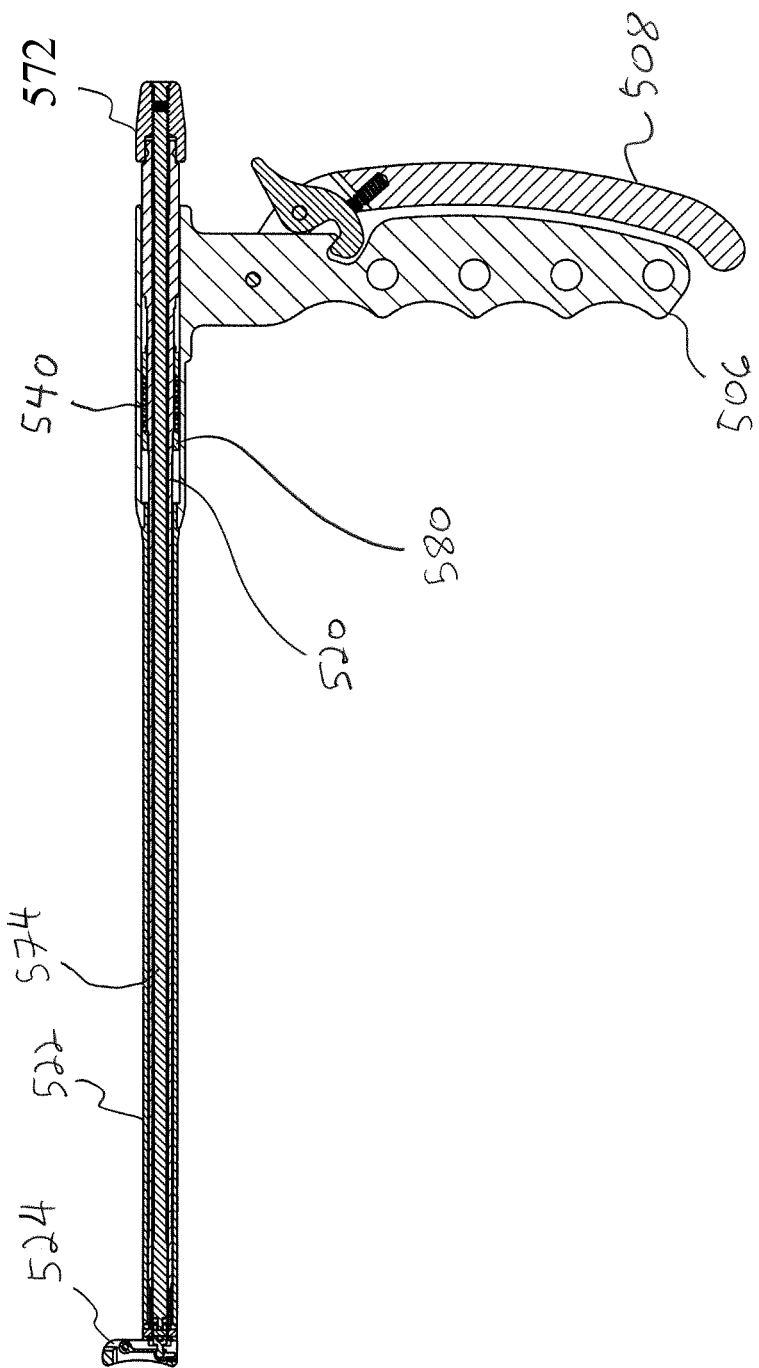

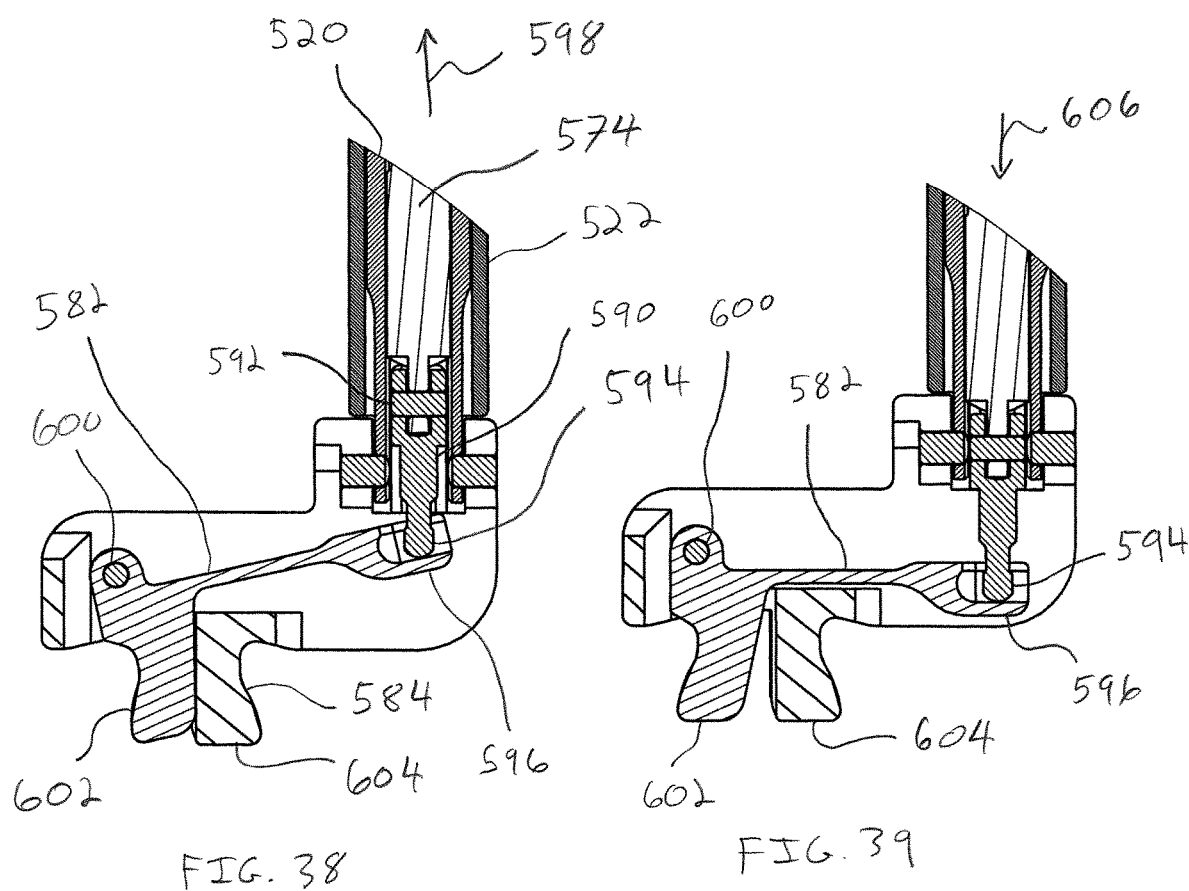

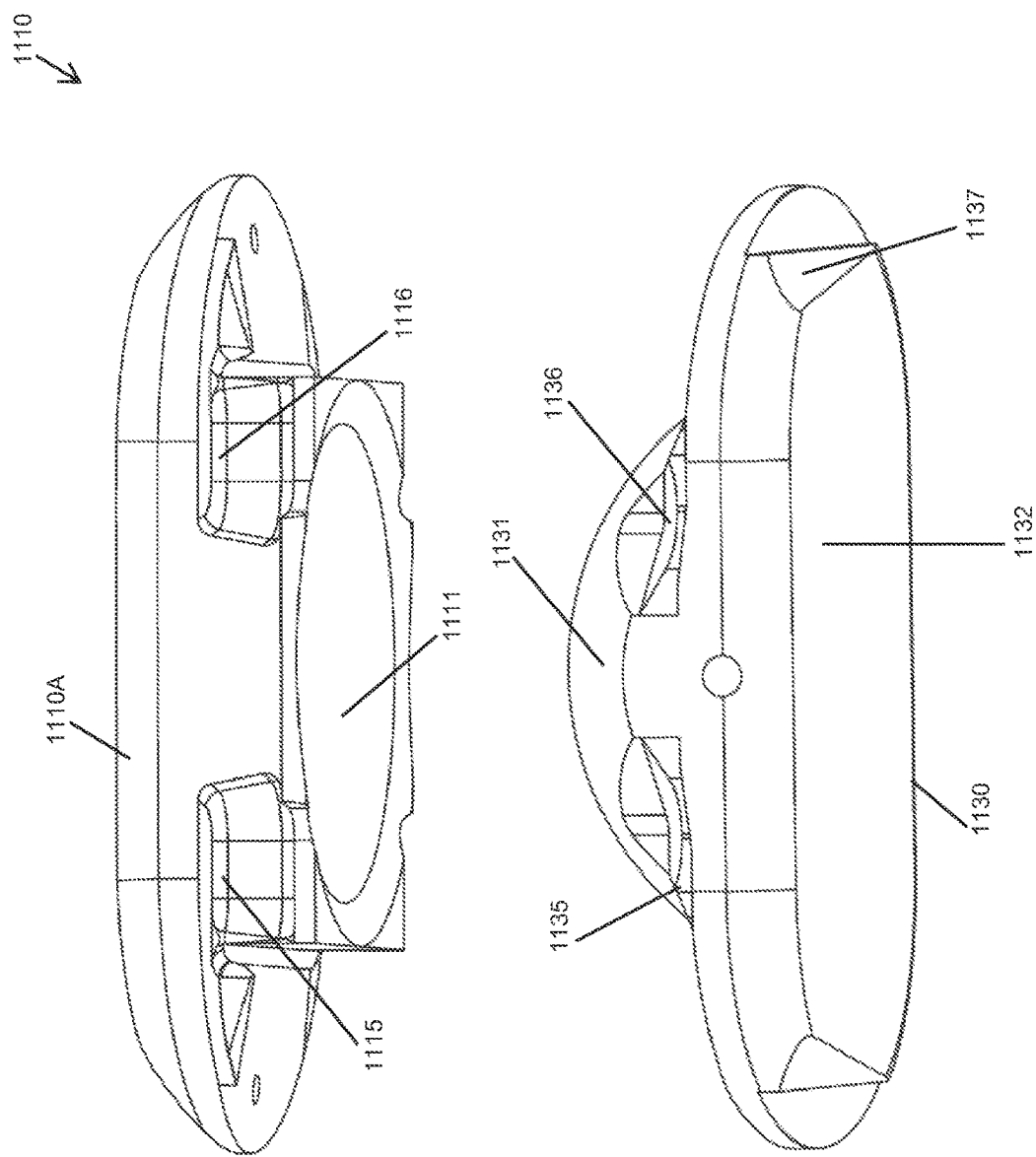

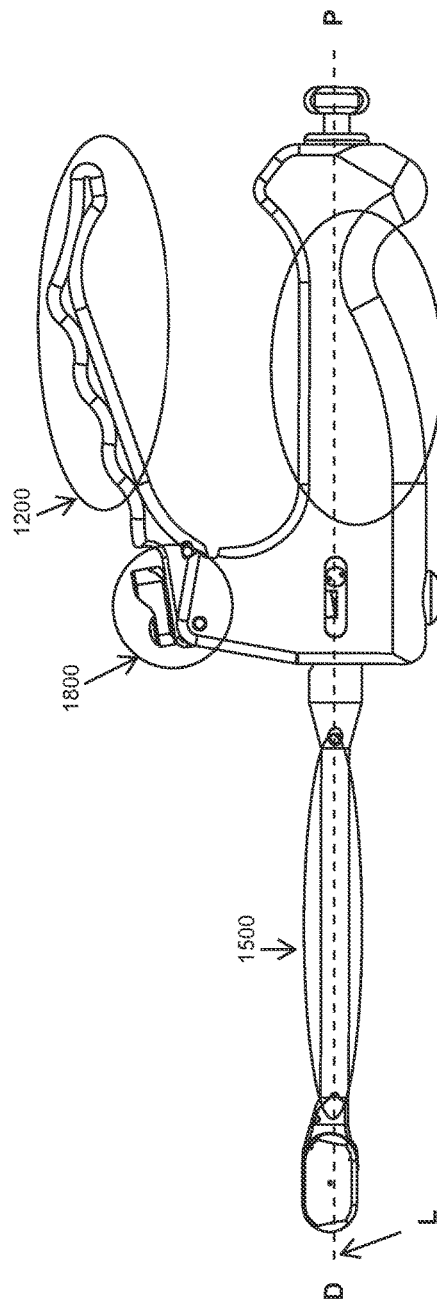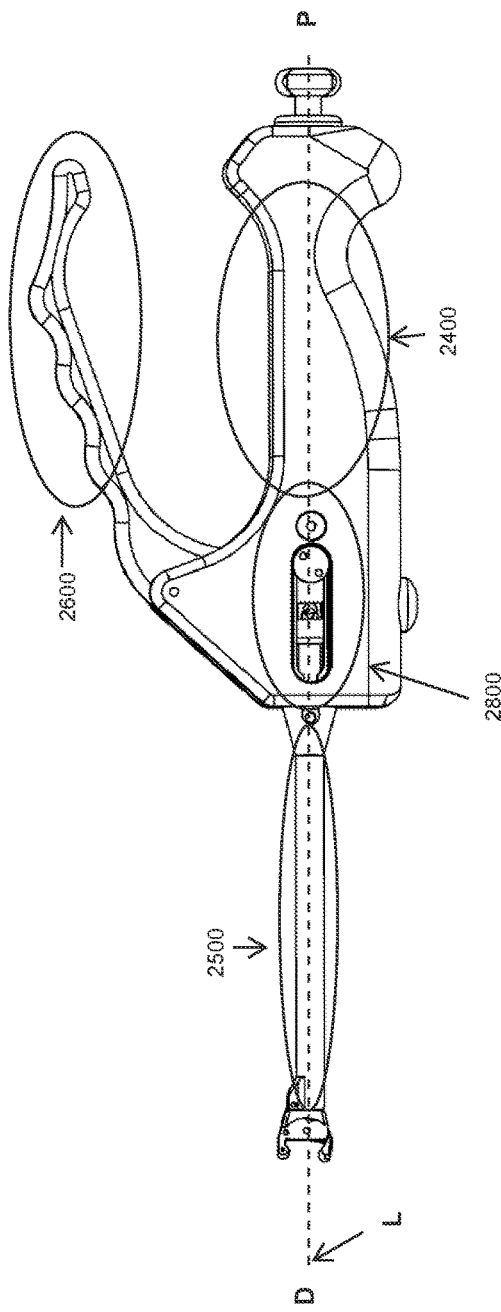

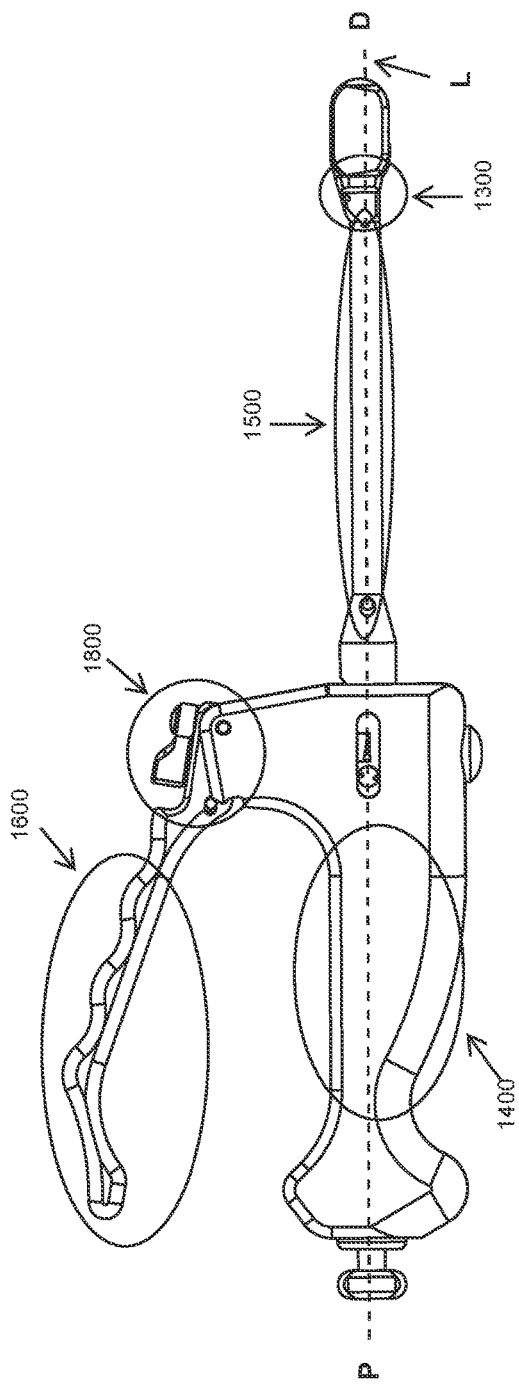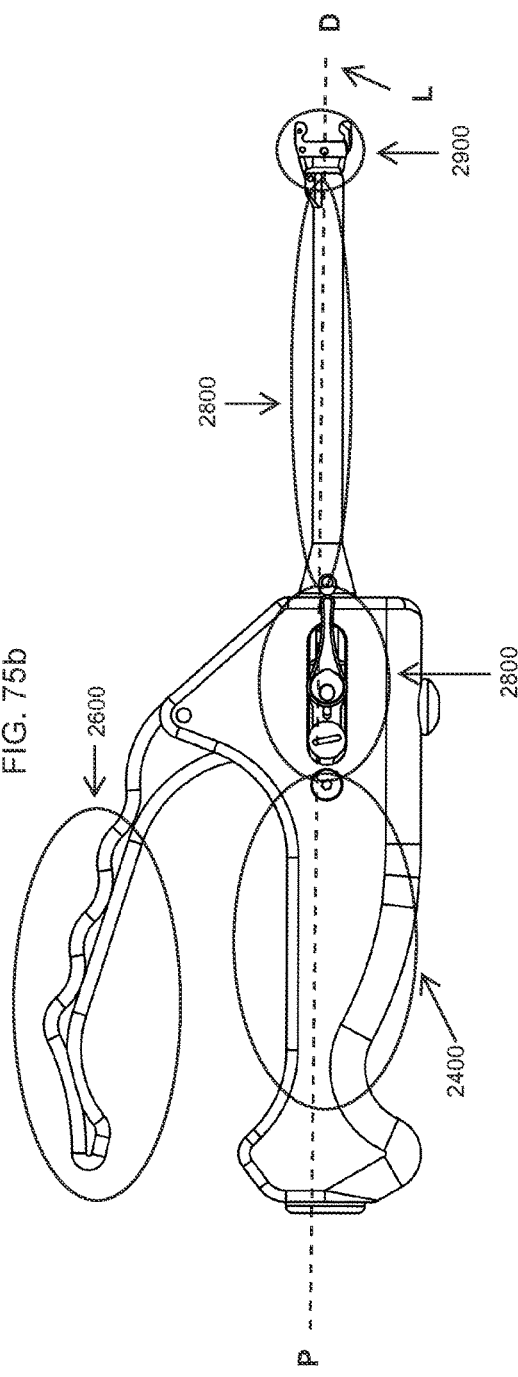

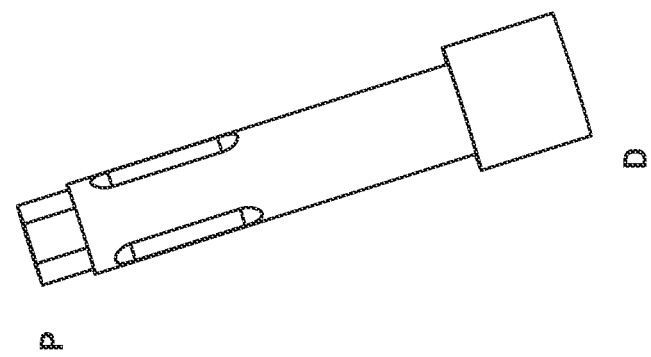
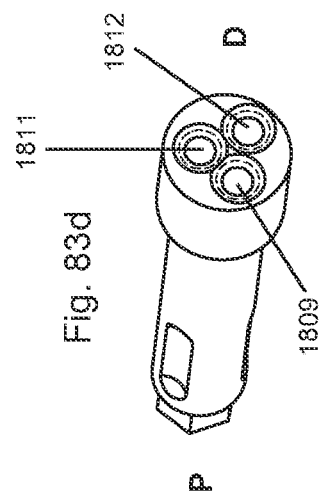
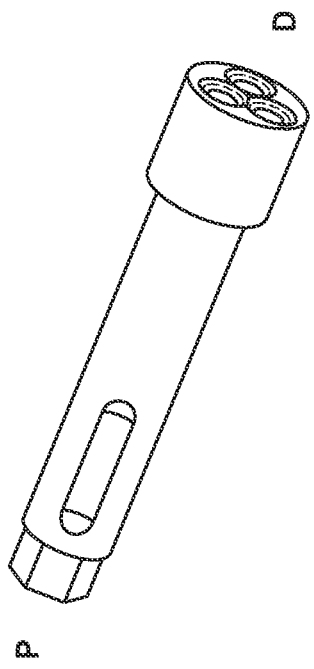
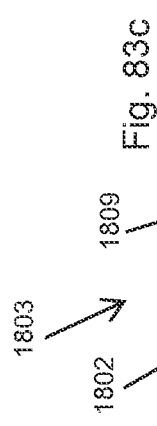

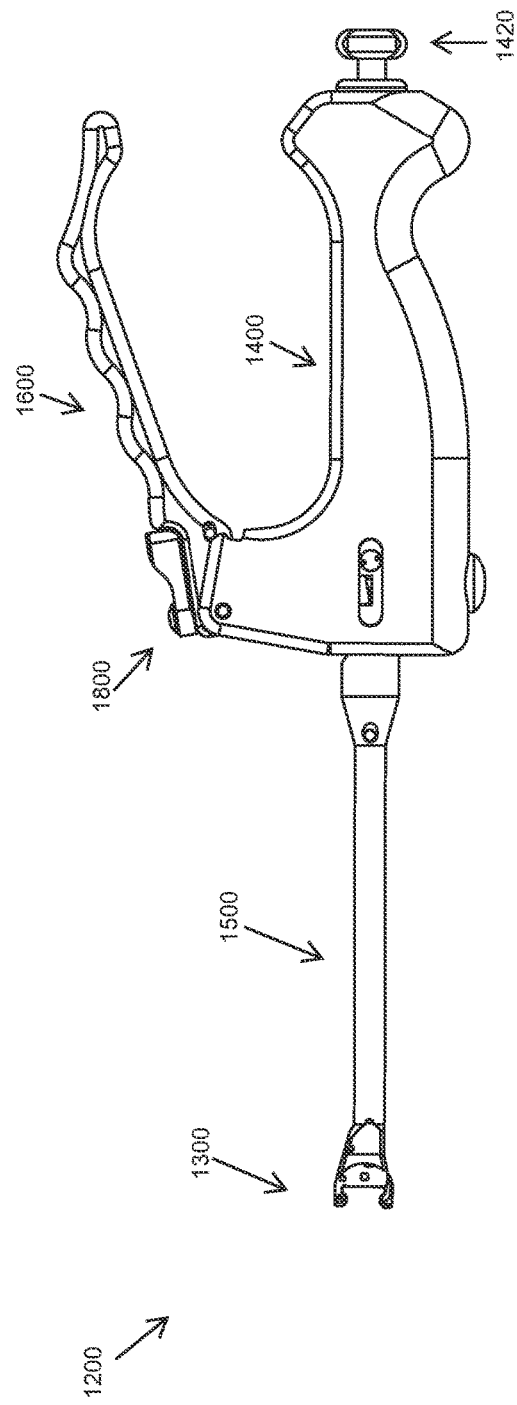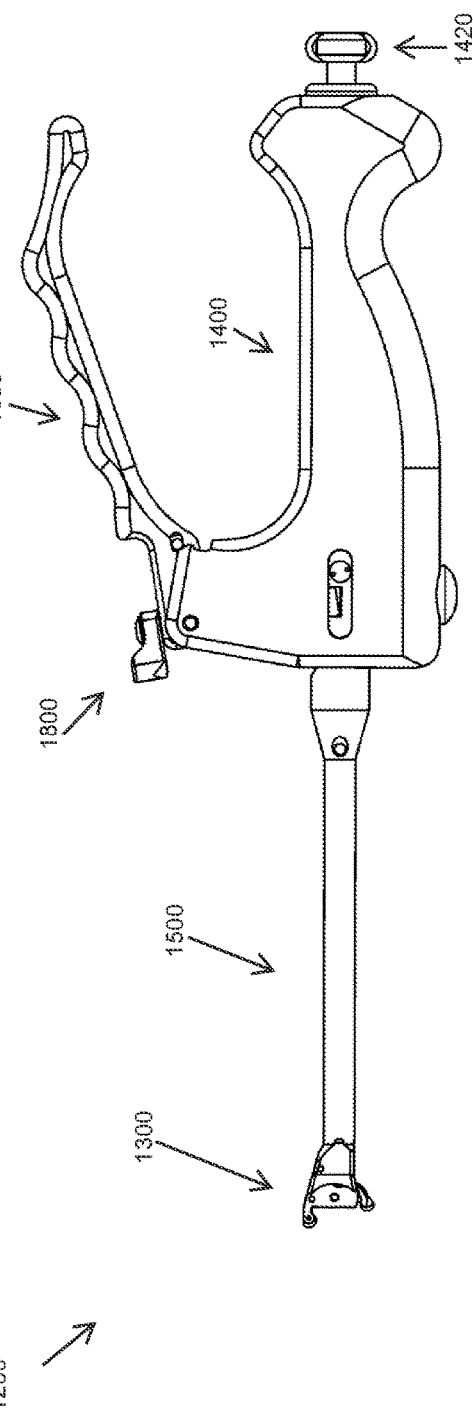

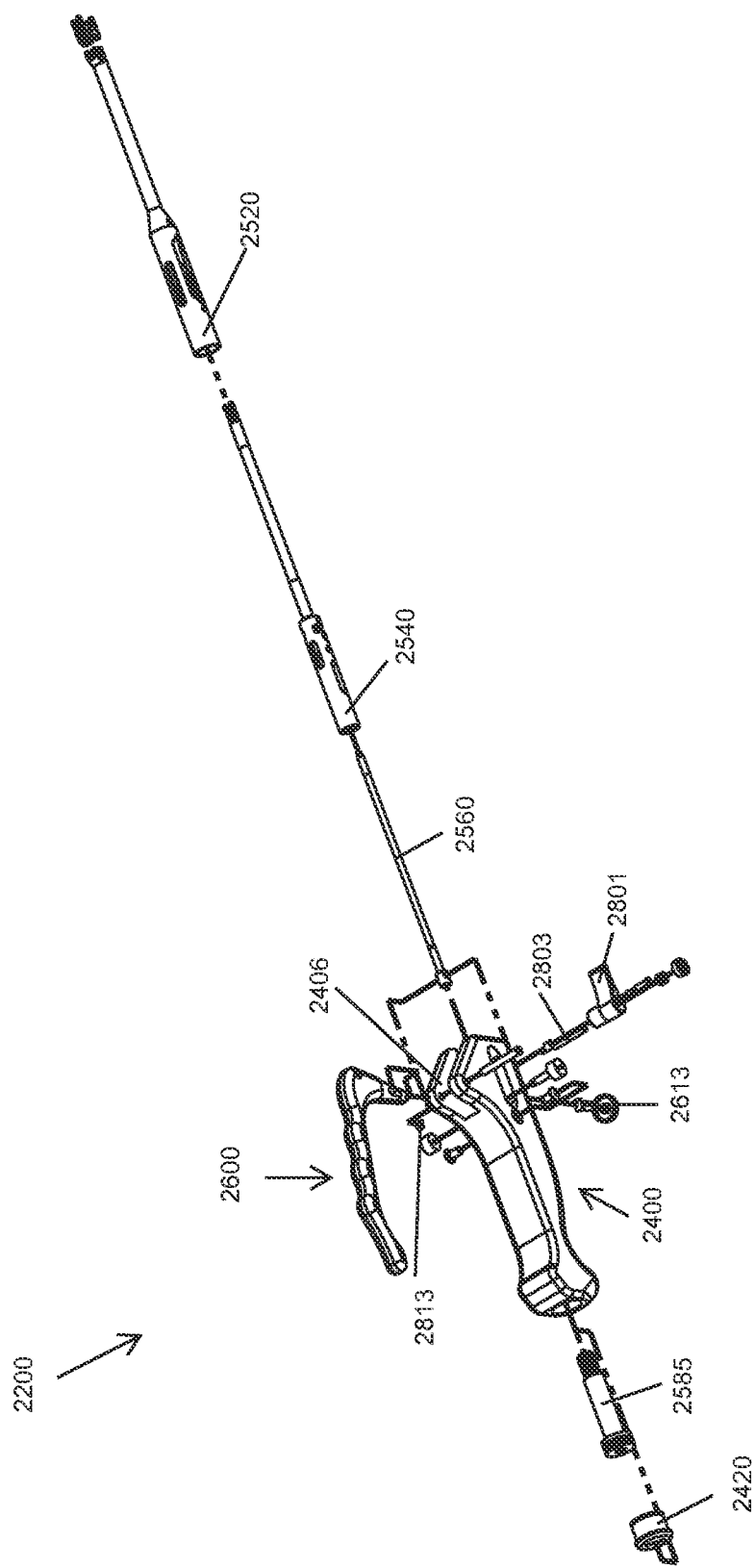

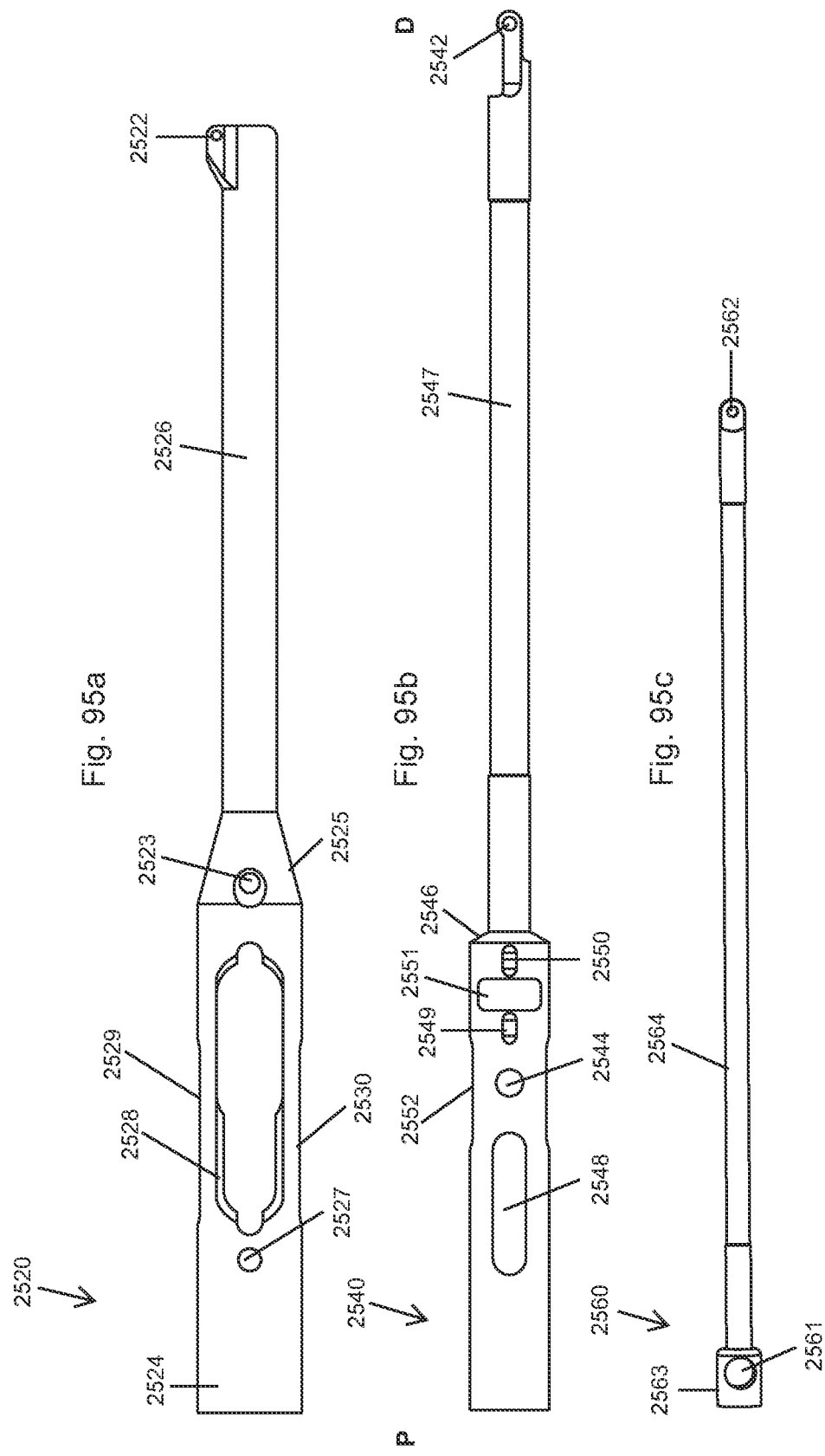

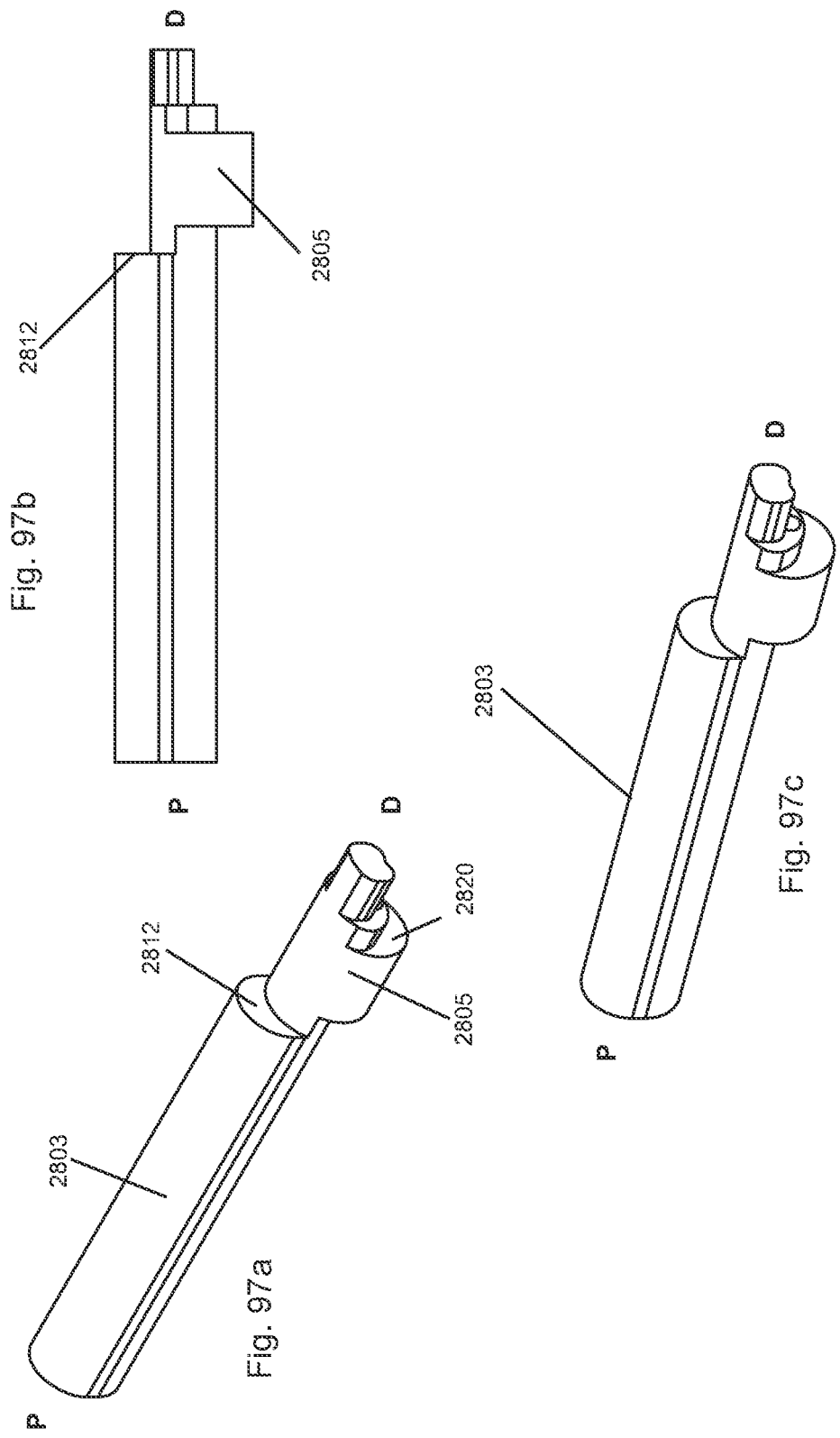

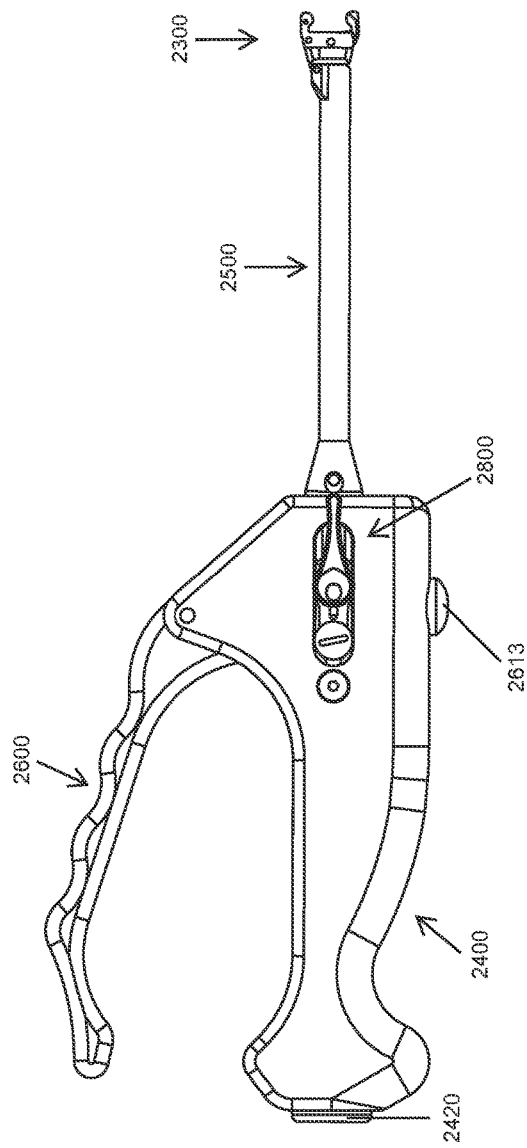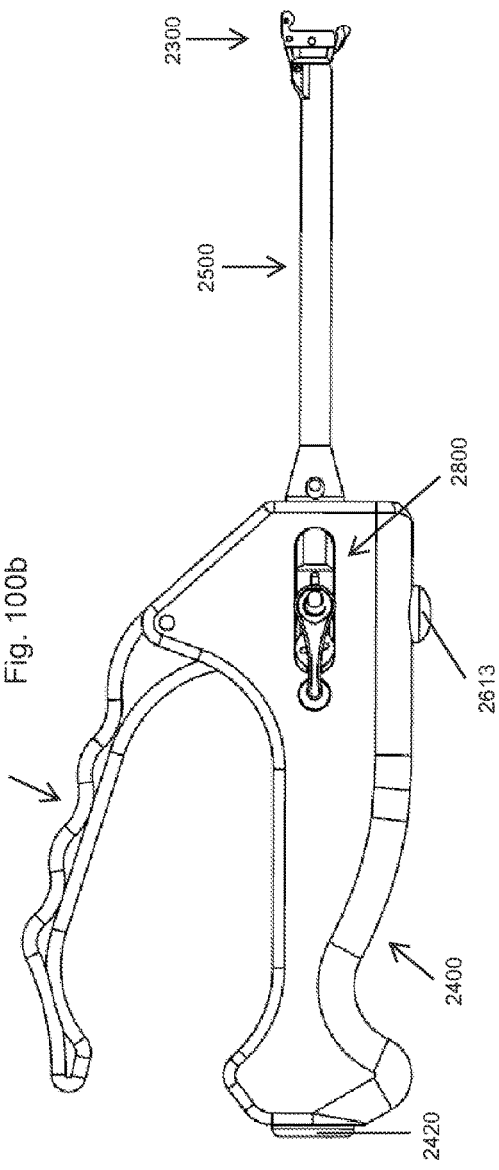

INSTRUMENT FOR INSERTING A SPINAL DEVICE

CROSS-REFERENCE TO RELATED APPLICATION

This application is a continuation of U.S. patent application Ser. No. 16/229,873, filed Dec. 21, 2018, which is a continuation of U.S. patent application Ser. No. 14/954,179, filed Nov. 30, 2015, now issued as U.S. Pat. No. 10,159,514 on Dec. 25, 2018, which is a continuation of U.S. patent application Ser. No. 13/725,420, filed Dec. 21, 2012, now issued as U.S. Pat. No. 9,198,769 on Dec. 1, 2015, which claims the benefit of U.S. Provisional Patent Application No. 61/580,055, filed Dec. 23, 2011, all of which are hereby incorporated by reference in their entireties.

BACKGROUND

In the field of orthopedic surgery, in particular minimally invasive orthopedic surgery, the physician often works through a very small incision, a small cannulated tube or a retractor. Since the working space for the surgeon is a small confined channel, specialized instruments are necessary to safely navigate the distance from outside the skin of the patient to adjacent the surgical site within the body of the patient. These specialized instruments, depending on the type of surgery, may include custom rongeurs, rasps, curettes and spinal device insertion instruments.

When performing an orthopedic joint replacement surgery, in particular intervertebral disc or nucleus replacement surgery, it is often difficult to properly and confidently position an implant in the position desired by the surgeon. It is desirable to utilize an implant insertion instrument that firmly holds the implant, while allowing the surgeon to release the instrument to safely perform fluoroscopy. It is yet even more desirable, after fluoroscopy, to be able to redirect, manipulate and release the implant percutaneously once the desired position of the implant has been achieved.

When performing an intervertebral disc or a nucleus replacement surgery, the surgeon may have a preference, or patient anatomy may dictate, the origin and direction of entry into the body of the patient including; anterior, lateral or posterior. Each method of entry presents the surgeon with specific challenges that are typically met with instruments corresponding to the decided method of entry. It would be desirable to have a spinal implant insertion instrument that would meet the specific surgeon challenges of anterior, lateral and posterior methods of entry.

SUMMARY OF THE INVENTION

Implanting a spinal device, such as a spinal implant posteriorly, as will be discussed, presents the surgeon with additional challenges and concerns as this method requires the implant to be negotiated from either side of the spinal canal to within the disc space. In one aspect in order to perform this task, the implant can be an articulating, multi-component artificial disc device that may be held firmly while permitting the implant to form a wedge shape for ease of insertion into the disc space, and be manipulated percutaneously within the disc space from a first posterior-anterior orientation to a second orientation substantially transverse to the first in order to avoid interruption of the spinal canal.

Embodiments of a spinal implant insertion instrument, more specifically an insertion instrument for manipulating and inserting an articulating spinal nucleus device will be described herein. These embodiments are particularly adapted to meet the challenges of minimally invasive anterior, lateral and specifically posterior approaches to the spine.

In another embodiment, the spinal device may be a spinal plate. A spinal plate insertion instrument adapted to grasp, hold, manipulate, pivot, and release a spinal plate is described. In particular, the instrument allows for inserting the plate in an insertion configuration, wherein a longitudinal axis of the plate is generally aligned with an insertion direction or parallel to and offset from a longitudinal axis of the tool to minimize the required size of the incision. The instrument is configured to rotate or pivot the plate into a bone engaging configuration, wherein the longitudinal axis of the plate is generally transverse to the longitudinal axis of the tool.

BRIEF DESCRIPTION OF THE DRAWINGS

FIG. 17 is an elevational view of the bone screw of the bone anchor assembly of FIG. 16 showing the head of the bone screw having a rounded lower surface;

FIG. 18 is a top plan view of the bone screw of FIG. 17 showing a recess for receiving a driving tool;

FIG. 19 is a perspective view of the bone screw of FIG. 17 showing a radially extending bearing surface of the bone screw configured to support the resilient locking cap and a threaded wall upstanding from the bearing surface;

FIG. 29 is an elevational view of an inserter tool configured to be used to insert the bone plate of FIG. 1 during surgery;

FIG. 30 is an enlarged partial view of a distal end of the inserter tool of FIG. 29 showing the distal end connected to the bone plate;

FIG. 35A is a cross-sectional view of the inserter tool taken across line 35A-35A in FIG. 29A showing the lever in the open position and a pivot shaft of the inerter tool shifted distally;

FIG. 35B is a cross-sectional view of the inserter tool taken across line 35B-35B in FIG. 32B showing the lever in the closed position and the pivot shaft shifted proximally with the bone plate removed for clarity;

FIGS. 38 and 39 are enlarged cross-sectional views generally taken across line 35B-35B in FIG. 32A showing the gripping portion arms in the release and engagement configurations;

FIG. 73 is a side perspective view of a spinal nucleus replacement device including the top shell of FIG. 69 and the bottom shell of FIG. 62;

FIG. 74a is a left side view of one embodiment of an implant insertion instrument according to the present invention holding a spinal nucleus replacement device;

FIG. 74b is a left side of an alternative embodiment of an implant insertion instrument according to the present invention;

FIG. 75a is a right side view of the implant insertion instrument of FIG. 74a;

FIG. 75b is a right side view of the implant insertion instrument of FIG. 74b;

FIG. 79 is an exploded schematic view of the implant insertion instrument of FIG. 74a;

FIGS. 80a-80d are side, end, perspective, and plan views, respectively, of a handle portion of the implant insertion instrument of FIG. 74a;

FIG. 81a is a side view of an external shaft of the implant insertion instrument of FIG. 74a;

FIG. 81b is a side view of a rotation shaft of the implant insertion instrument of FIG. 74a;

FIG. 81c is a side view of an inner elongate release shaft of the implant insertion instrument of FIG. 74a;

FIG. 82 is an exploded perspective view of the rotation and release mechanisms of the implant insertion instrument of FIG. 74a;

FIG. 83a-d are various views of the elongate release lever shaft of the release mechanism shown in FIG. 82;

FIGS. 84-92 are various views of the instrument of FIG. 74a demonstrating the operation of the instrument;

FIG. 93 is an exploded view of an alternate embodiment of an insertion instrument according to the present invention;

FIGS. 95a-c are elevation views of shaft members of the insertion instrument of FIG. 93;

FIGS. 97a-c are various views of a release lever shaft of the insertion instrument of FIG. 93;

FIGS. 98-107 are various views of the instrument of FIG. 93 demonstrating the operation of the instrument;

DETAILED DESCRIPTION OF THE PREFERRED EMBODIMENTS

Figure 1:
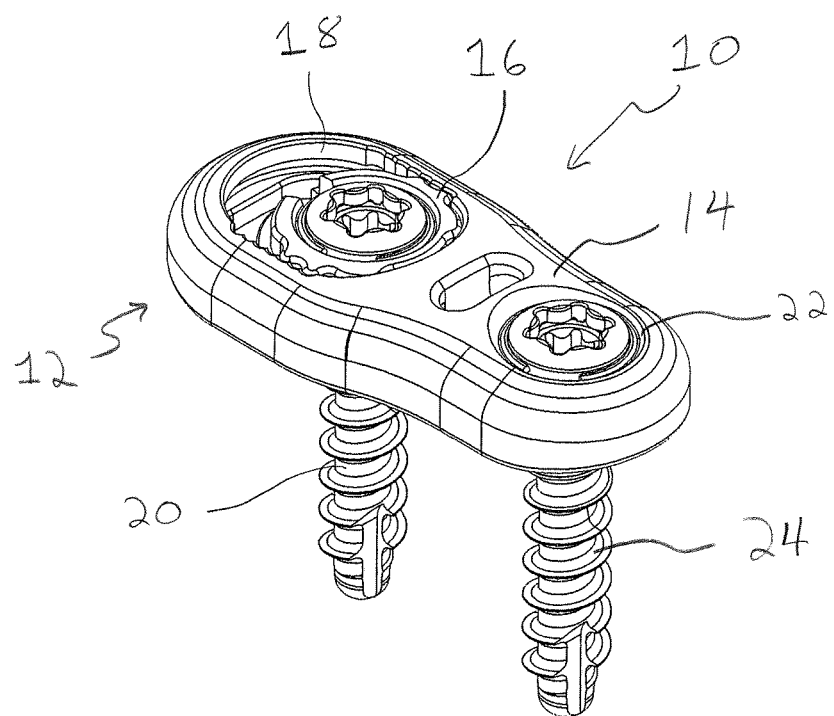
FIG. 1 is a perspective view of a bone plate system in accordance with the present invention showing a bone plate and a pair of bone anchor assemblies connected thereto.
Figure 11:
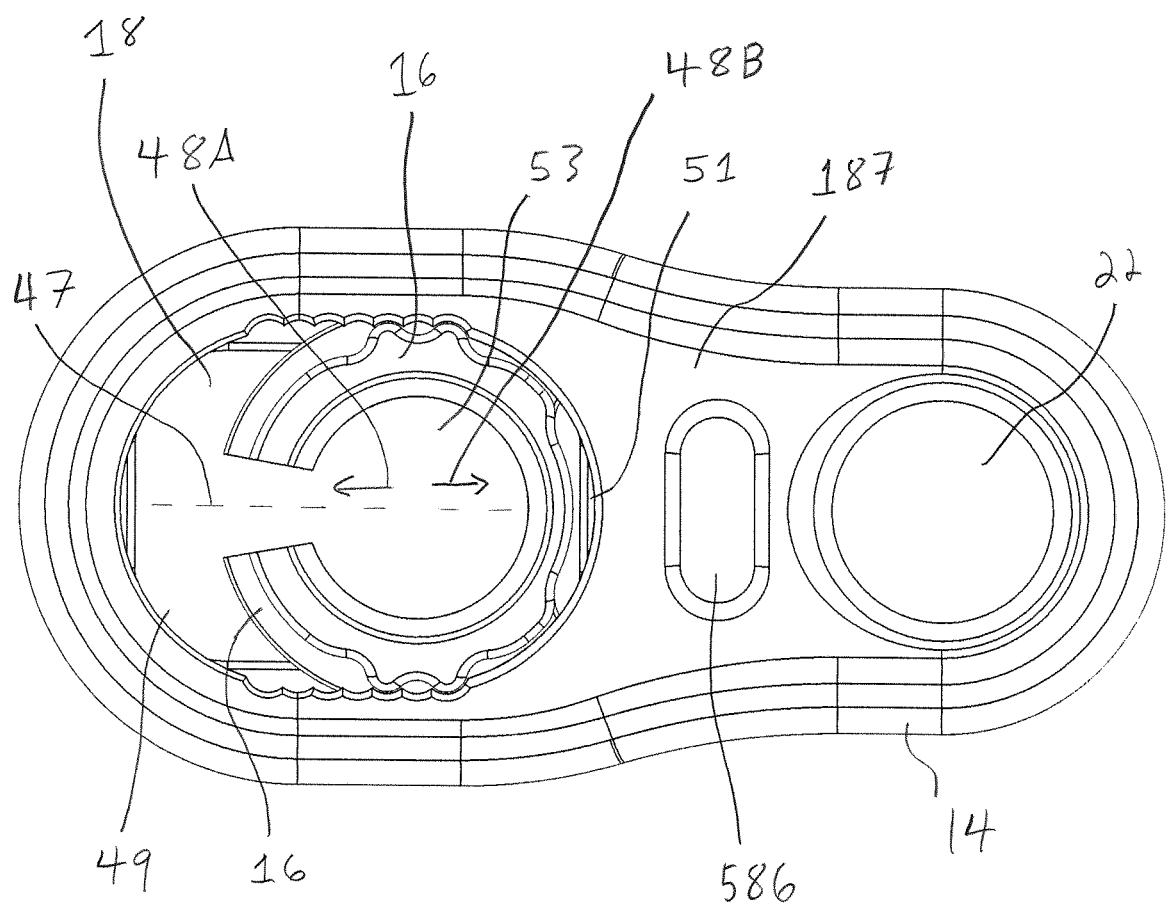
FIG. 11 is a top plan view of the bone plate system of FIG. 1 with the bone anchor assemblies removed to show an opening of the resilient support member in which one of the bone anchor assemblies is received.

With reference to FIGS. 1 and 11, a bone plate system 10 is provided having a bone plate 12 with a bone plate member 14 and a movable resilient support member 16. The support member 16 may be moved along an elongated throughbore 18 of the bone plate member 14 to provide flexibility during installation of the bone plate system 10. More specifically, the bone plate system 10 includes a pair of bone anchor assemblies 20, 24 for securing the bone plate 12 to a pair of bones, with the bone anchor assembly 20 being driven into an opening 53 of the support member 16 and a bone anchor assembly 24 being driven into a non-elongated throughbore 22 of the bone plate member 14 (see FIG. 11). The bone anchor assemblies 20, 24 are preferably preassembled for ease of handling during surgery and can be readily driven into the support member opening 53 and bone plate throughbore 22 to secure the bone plate 12 to bones. Before the bone anchor assembly 20 is driven into the support member opening 53, the resilient support member 16 may be moved within the elongated throughbore 18 to increase or decrease the distance between the support member opening 53 and the non-elongated throughbore 22, and the resulting positions of the bone anchor assemblies 20, 24, in order to permit the bone anchor assemblies 20, 24 to be driven into desired areas of the underlying bones. Once the bone anchor assembly 20 has been driven into the support member opening 53 and received therein, the support member 16 and the bone anchor assembly 20 may be secured at a desired location along the throughbore 18 to restrict translational movement of the bone anchor assemblies 20, 24 relative to each other, as discussed in greater detail below. Thus, the bone plate system 10 provides enhanced flexibility during installation by allowing the position of the support member 16 within the elongated throughbore 18 to be adjusted in situ to conform to the anatomy of the patient before securing the bone plate 12 to the bones using the bone anchor assemblies 20, 24.

Figure 2:
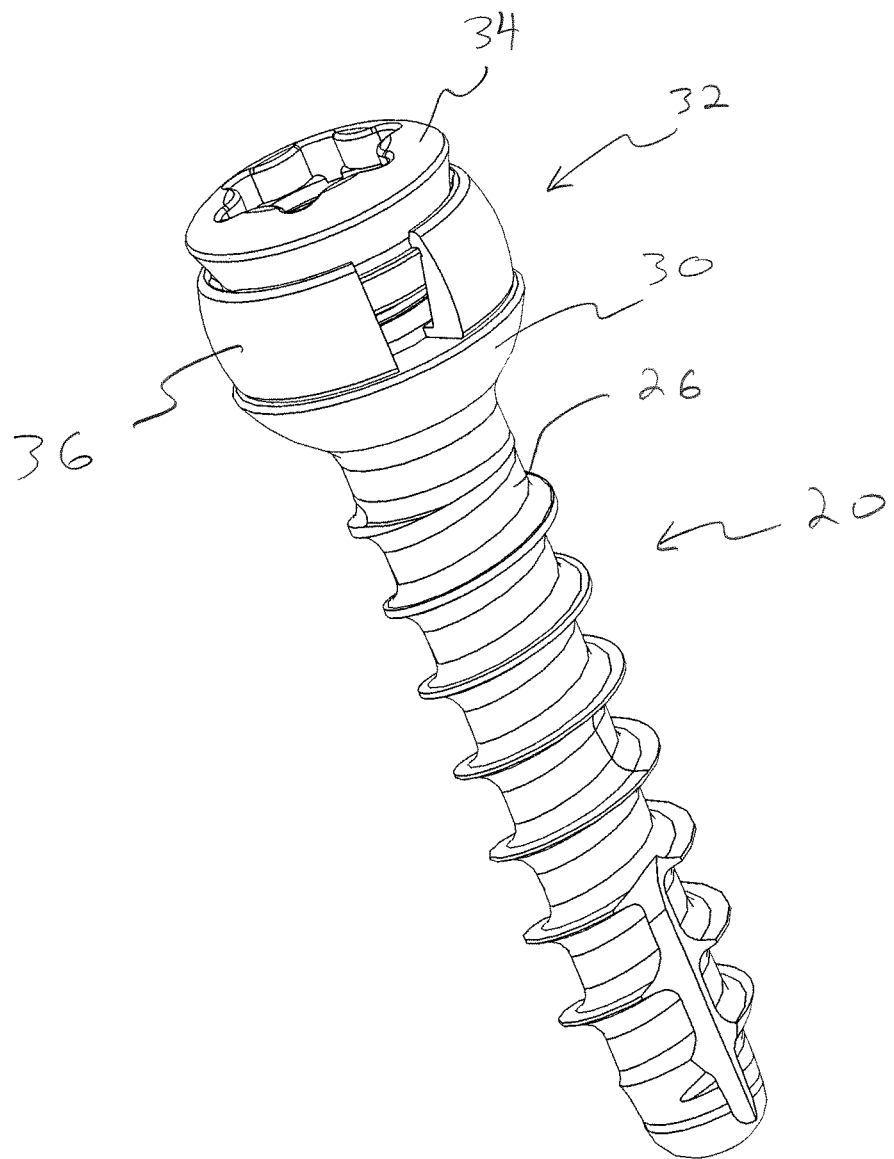
FIG. 2 is a perspective view of one of the bone anchor assemblies of FIG. 1 showing a bone screw, cap drive member, and a resilient locking cap of the bone anchor assembly.

With reference to FIG. 2, the bone anchor assemblies 20, 24 are similar and each have a bone anchor, such as a bone screw 26, for engaging a bone. The bone screw 26 has a bone screw head 30 and an actuator device 32 carried thereon, as shown in FIG. 2. The actuator device 32 is configured to be driven to a locked position after the bone screw 26 has been seated within the support member opening 53. Driving the actuator device 32 of the bone anchor assembly 20 to the locked position tightly engages the bone anchor assembly 20 with the support member 16. Driving the actuator device 32 of the bone anchor assembly 20 also locks the support member 16 to the bone plate member 14 at a selected position along the elongated throughbore 18, as discussed in greater detail below. Similarly, driving the actuator device 32 of the bone anchor assembly 24 to its locked position tightly engages the bone anchor assembly 24 to the plate member 14 within the non-elongated throughbore 22.

Figures 3, 4:
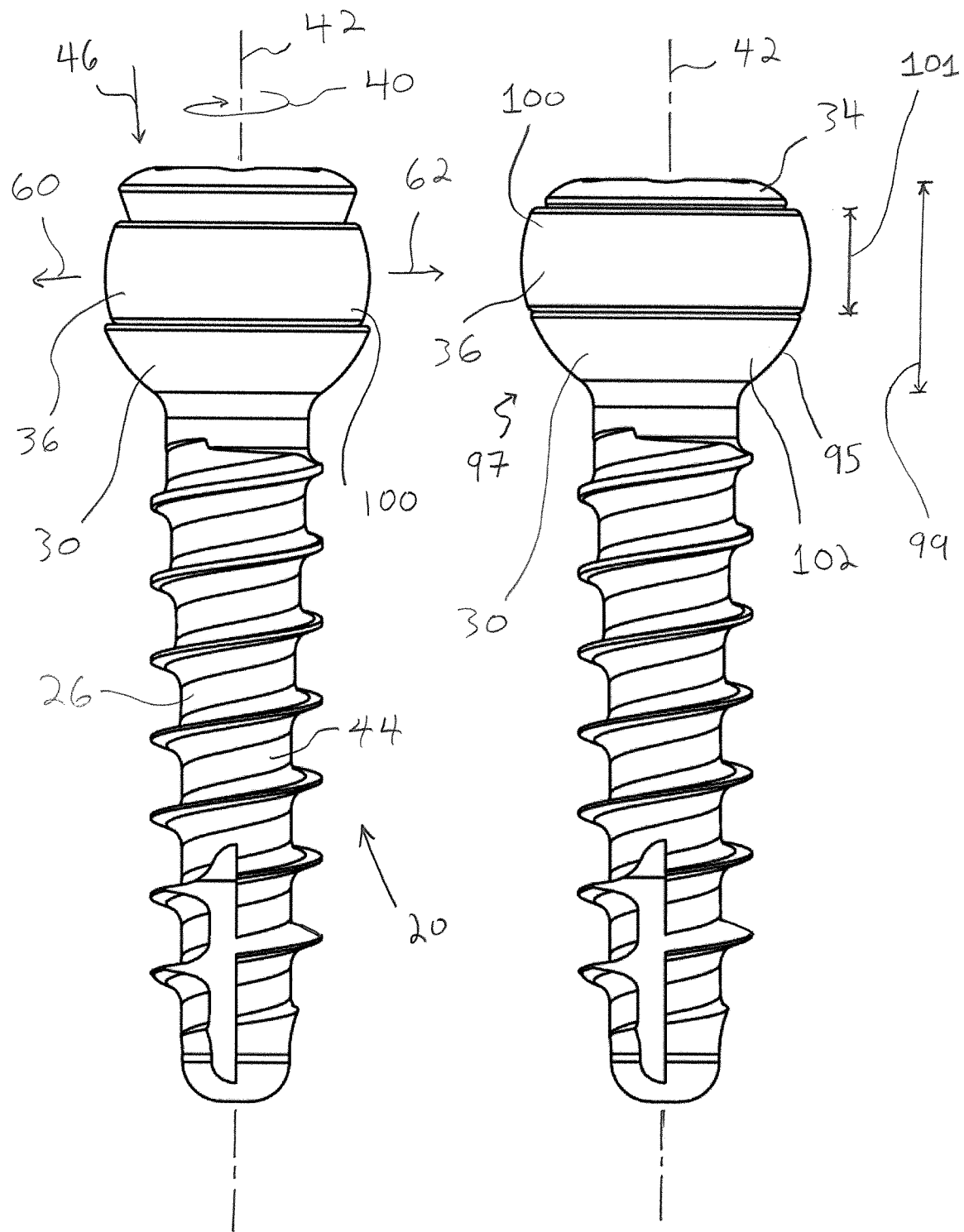
FIG. 3 is an elevational view of one of the bone anchor assemblies of FIG. 1 showing the cap drive member of the bone anchor assembly in an unlocked position.
FIG. 4 is an elevational view similar to FIG. 3 showing the cap drive member shifted to a locked position which radially expands the resilient locking cap of the bone anchor assembly.

In one form, the actuator device 32 includes a cap drive member 34 connected to the bone screw head 30 and a resilient locking cap 36 disposed on the bone screw head 30, as shown in FIG. 2. The connection between the cap drive member 34 and the bone screw head 30 may be a threaded engagement so that clockwise rotation of the cap drive member 34 in direction 40 about a longitudinal axis 42 of the bone anchor assembly 20 advances the cap drive member 34 in direction 46 toward the bone screw head 30, as shown in FIGS. 3 and 4. Movement of the cap drive member 34 in direction 46 toward the bone screw head 30 causes outward expansion of the locking cap 36 in directions 60, 62, which expands the support member 16 and secures the support member 16 and bone anchor assembly 20 at a desired position along the elongated throughbore 18.

Figure 6:
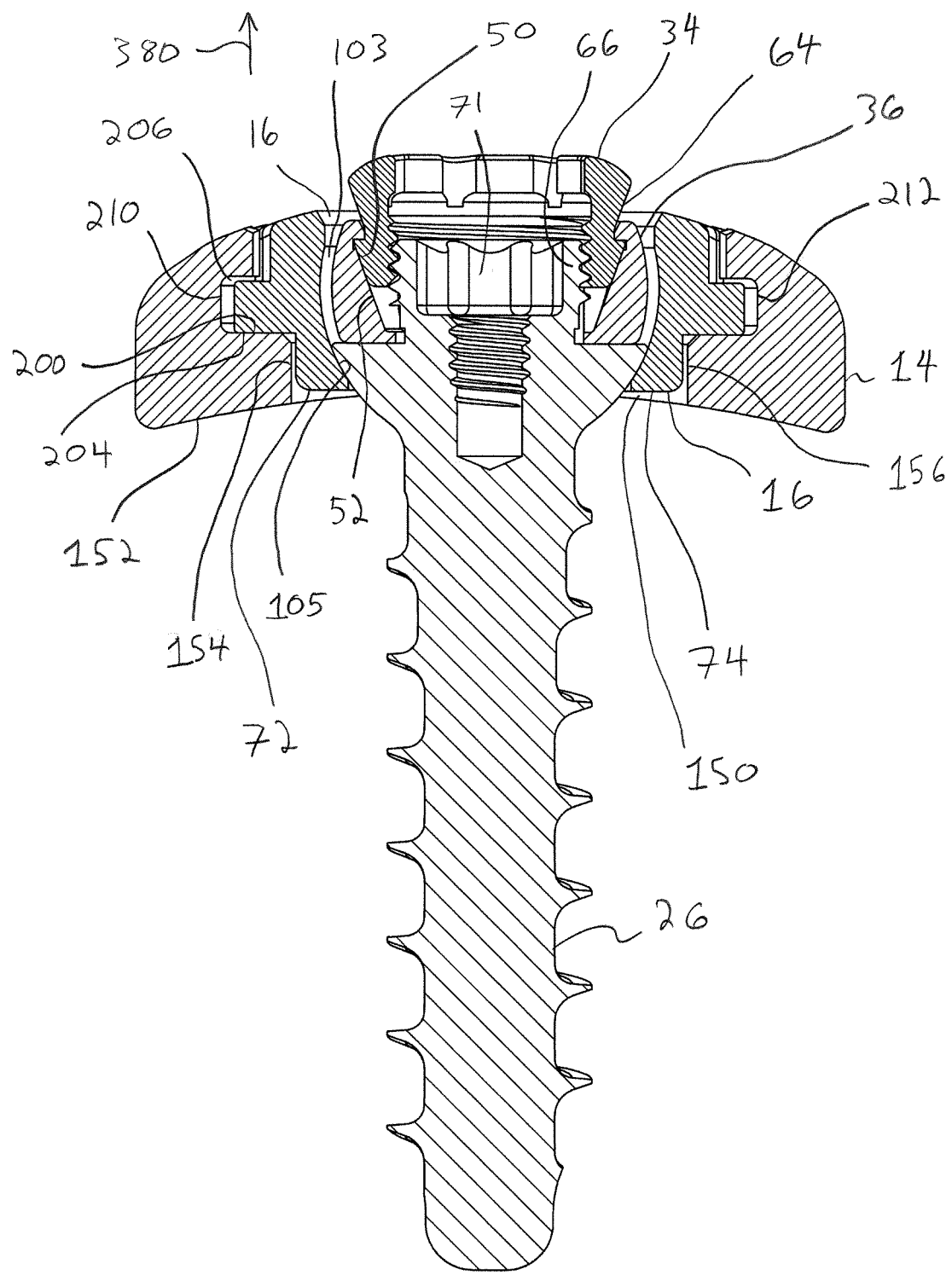
FIG. 6 is a cross-sectional view taken across line 6-6 in FIG. 5 showing a head portion of the bone anchor assembly received in the resilient support member with the cap drive member of the bone anchor assembly in the unlocked position.
Figure 7:
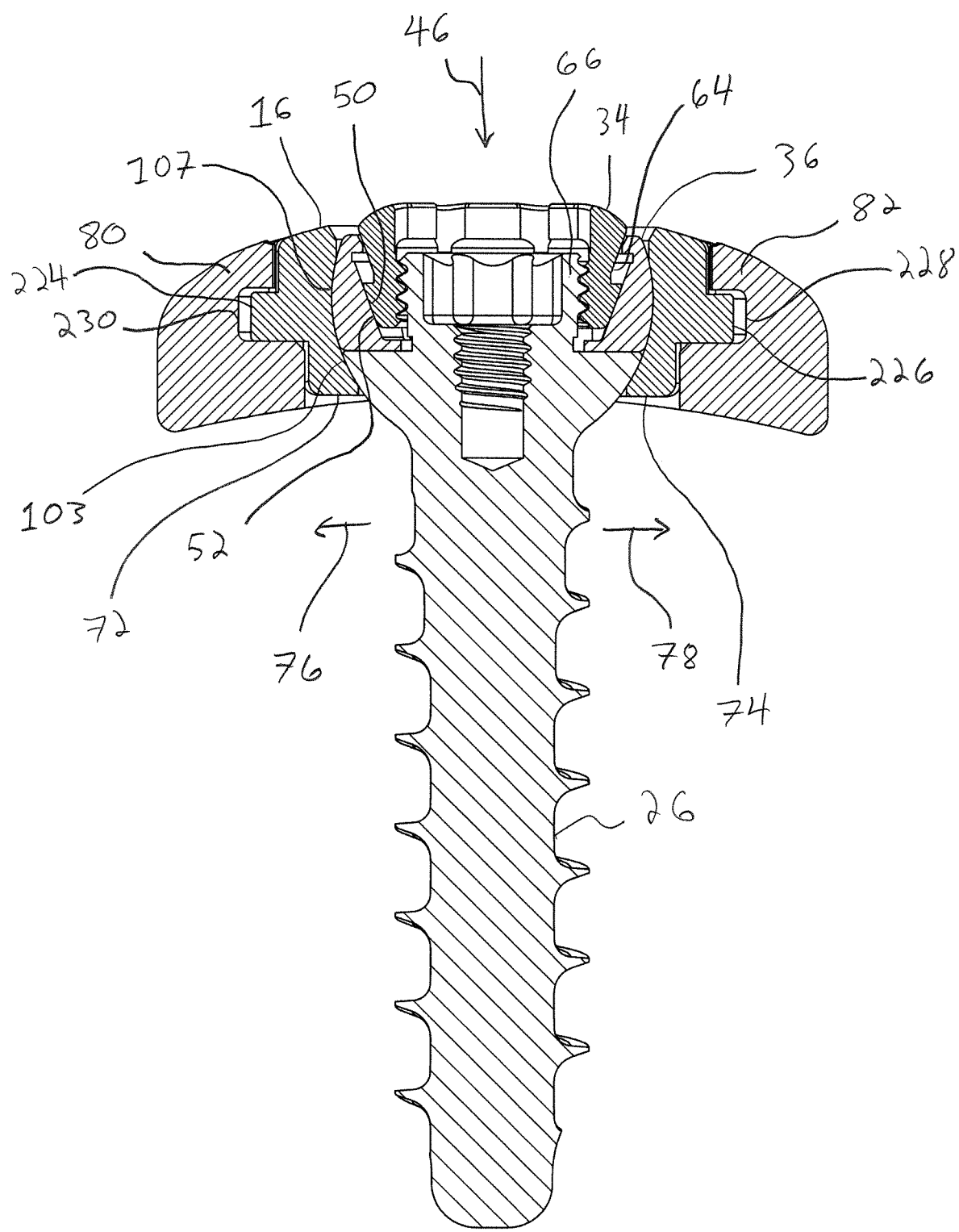
FIG. 7 is a cross-sectional view similar to FIG. 6 showing the cap drive member shifted to the locked position which expands the locking cap and the resilient support member of the bone plate.
Figure 16:
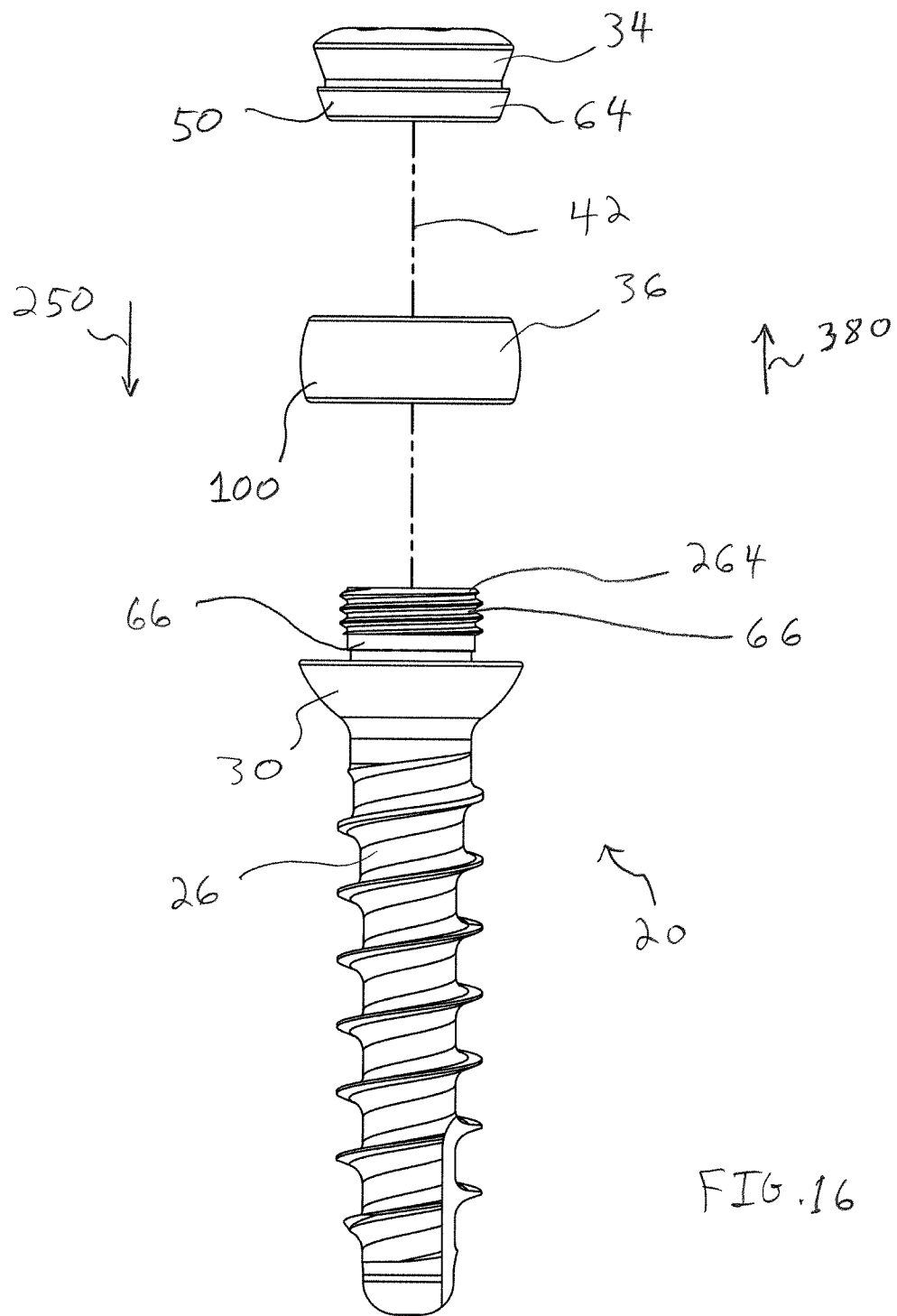
FIG. 16 is an exploded elevational view of one of the bone anchor assemblies of FIG. 1.
Figure 20:
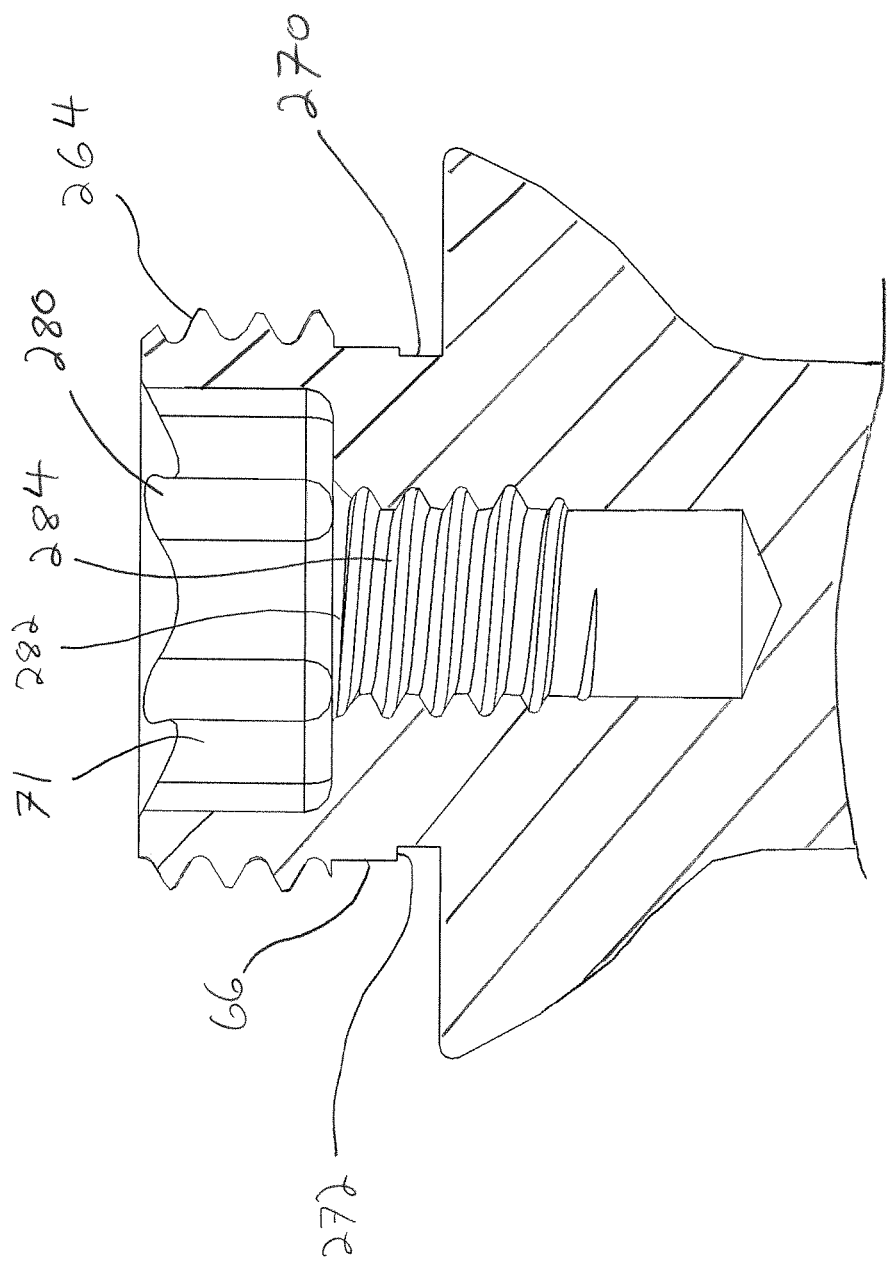
FIG. 20 is a cross-sectional view taken across line 20-20 in FIG. 18 showing a central axial bore for receiving a screw retention portion of the driving tool.
Figure 21:
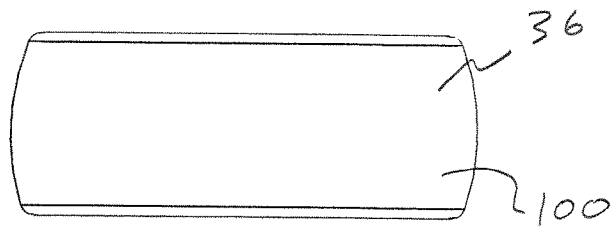
FIG. 21 is an elevational view of the resilient locking cap of the bone anchor assembly of FIG. 16 showing a rounded outer surface of the resilient locking cap.

With reference to FIGS. 6, 7, and 16, the cap drive member 34 has a depending wall 64 extending about a portion of the bone screw head 30, such as screw head upstanding wall 66. The depending wall 64 of the cap drive member 34 is disposed radially between the bone screw wall 66 and the locking cap 36. The depending wall 64 and the bone screw wall 66 each have a generally tubular shape and are concentrically aligned when the cap drive member 34 is connected to the bone anchor head 30. Further, the locking cap 36 has a generally annular shape extending around the cap drive member 34 when the cap drive member 34 and the locking cap 36 are connected to the bone screw head 30. The concentric engagement of the bone screw wall 66, cap drive member depending wall 64, and locking cap 36 allows the cap drive member depending wall 64 to directly transfer loading exerted on the locking cap 36, such as loads from post-operative shifting of the vertebra, against the bone screw wall 66 without the use of thin, radially extending members as in some prior bone anchor assemblies. Further, the cap drive member depending wall 64 can directly transfer loading from the locking cap 36 to the bone screw wall 66 with substantially no deflection or other flexing of the cap drive member depending wall 64, which increases the strength of the engagement between the bone anchor assemblies 20, 24 and the bone plate 14.

The cap drive member 34 and locking cap 36 have engagement surfaces, such as cam surfaces 50, 52, configured to engage and expand the locking cap 36 with movement of the cap drive member 34 from an unlocked to a locked position, as shown in FIGS. 6 and 7. The cam surface 50 is disposed on a radially outer portion 55 (see FIG. 28) of the cap drive member depending wall 64 and the cam surface 52 is disposed on a radially inner portion 57 (see FIG. 24) of the locking cap 36 so that the cam surfaces 50, 52 engage about and radially outward from the bone screw wall 66. The bone screw head 30 may be substantially rigid, and positioning the cam surfaces 50, 52 about and radially outward from the bone screw head portion 66 permits the cap drive member 34 to expand the locking cap 36 without utilizing a weakened screw head as in some prior approaches.

Another advantage of the cam surfaces 50, 52 of the cap drive member 34 and locking cap 36 being disposed about and radially outward from the bone screw wall 66 is that the cam surfaces 50, 52 are positioned outside of a drive recess 71 of the bone screw head 30, as shown in FIGS. 6 and 7. The drive recess 71 is generally unobstructed by the cap drive member 34 and locking cap 36 so that the size of the drive recess 71 can be relatively large without reducing the strength of the cap drive member depending wall 64. Similarly, the bone screw upstanding wall 66 extending about the drive recess 71 can be relatively thick to further enhance the strength of the bone screw head 30 without compromising the strength of the locking cap depending wall 64. This approach stands in contrast to some prior bone screw assemblies, which utilize a c-ring having radially extending portions configured to contact a locking member. In these prior screw assemblies, increasing the size of a drive recess of the bone screw assembly required that the radially extending portions be lengthened or that the portions of the bone screw head surrounding the drive recesses be thinned, both of which reduce the strength of those prior bone screw assemblies.

With reference to FIG. 11, the resilient support member 16 may be moved in directions 48A, 48B along an axis 47 of the elongated throughbore 18 before the bone anchor assembly 20 is driven into the opening 53 and the cap drive member 34 shifted to the locked position. This adjustability allows a surgeon to position the support member 16 so that the opening 53 is adjacent a desired portion of an underlying bone. For example, the bone plate system 10 may be used to stabilize a pair of vertebrae 720, 722 with an implant 724 having a width 804 (see FIG. 46). If the implant width 804 is relatively large, the support member 16 may be moved in direction 48A in order to increase the distance between the support member opening 53 and non-elongated throughbore 22 and the resulting positioning of the bone anchors 20, 24. The support member 16 can be moved in direction 48A until the support member opening 53 is located adjacent the vertebra 722, for example, so that the bone anchor assembly 20 may be driven through the opening 53 and into an end plate of the vertebra. Conversely, if the implant 724 has a smaller width 804, the support member 16 may be moved in direction 48B to decrease the distance between the support member opening 53 and the non-elongated throughbore 22 and the resulting distance between the bone anchor assemblies 20, 24.

Figure 5:
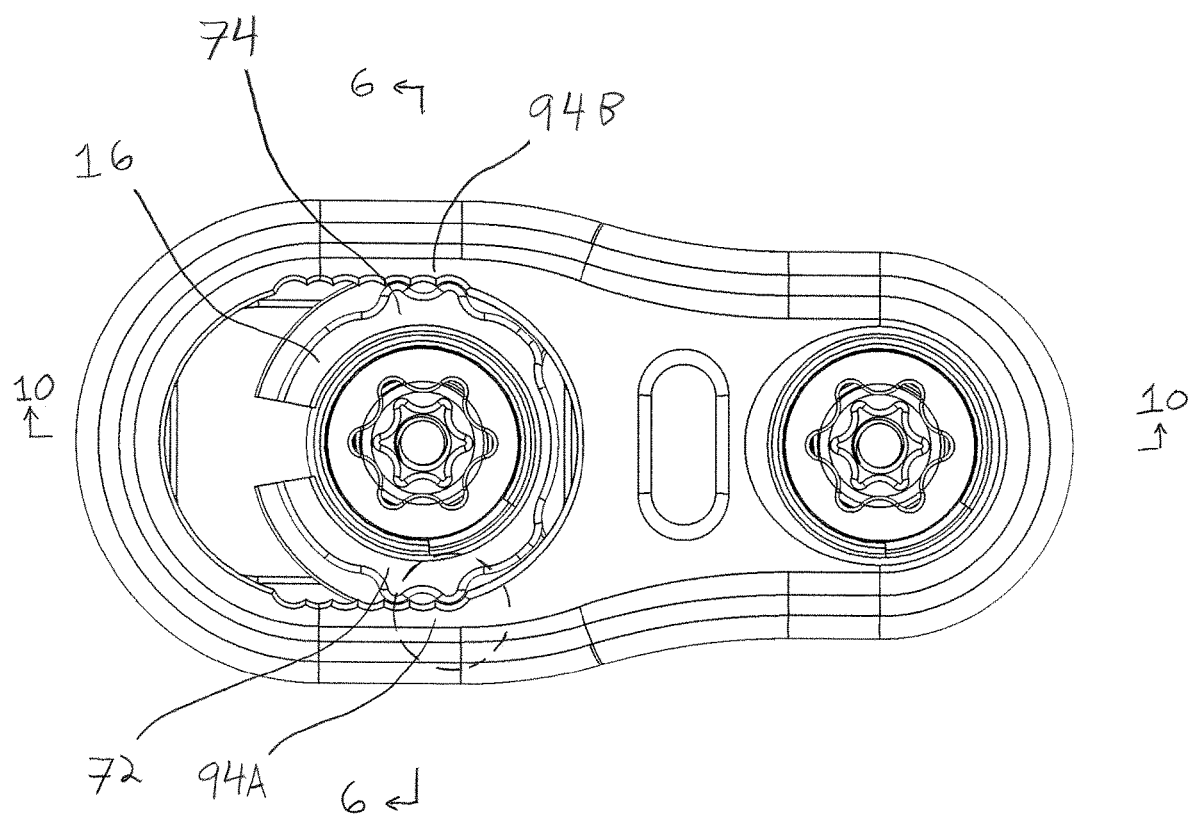
FIG. 5 is a top plan view of the bone plate system of FIG. 1 showing one of the bone anchor assemblies received in a resilient support member in an elongated throughbore of the bone plate and the other bone anchor assembly received in a non-elongated throughbore of the bone plate.
Figure 8:
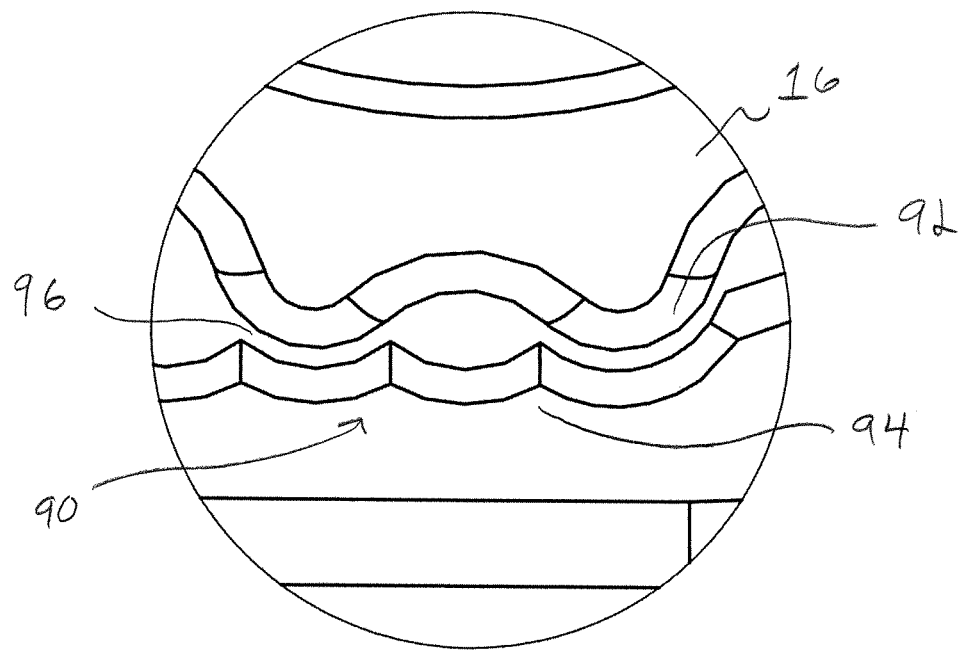
FIG. 8 is a partial, enlarged view of the area shown in the dashed circle of FIG. 5 showing projections of the resilient support member spaced from teeth of the bone plate before the cap drive member has been driven to the locked position.
Figure 9:
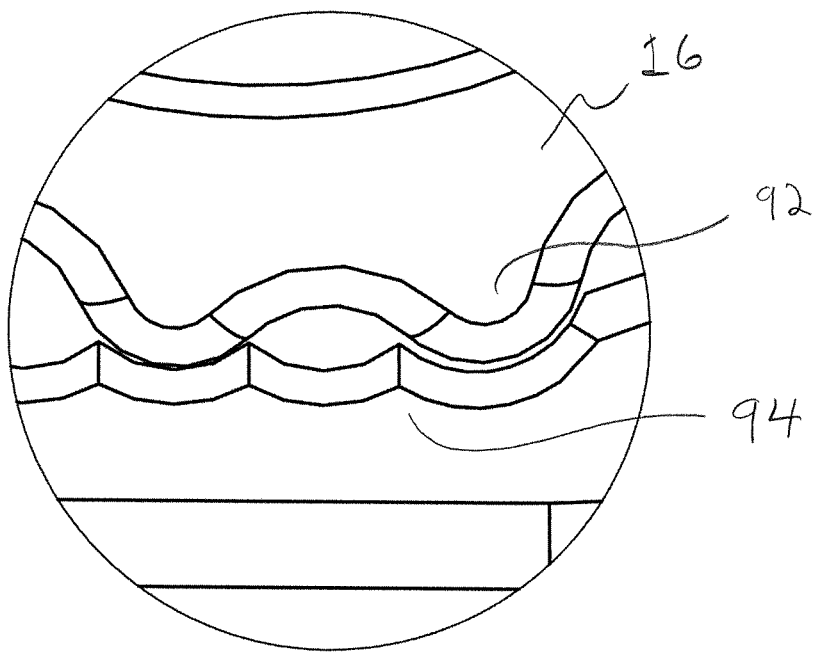
FIG. 9 is a partial, enlarged view similar to FIG. 8 showing the projections of the support member engaged with the teeth of the bone plate after the cap drive member of the bone anchor assembly has been driven to the locked position.

With the support member 16 in the desired location along the elongated throughbore 18, the bone anchor assembly 20 may be driven into the support member opening 53 and the position of the support member 16 and bone anchor assembly 20 may then be locked along the throughbore 18, as shown in FIGS. 5-7. More specifically, the resilient support member 16 has a pair of side portions 72, 74 on opposite sides of the opening 53 configured to be engaged by the resilient locking cap 36. The plate member 14 and support member 16 also have interfering portions 90, such as support member projections 92 and plate member teeth 94, configured to engage and limit movement of the support member 16 relative to the bone plate member 14, as shown in FIGS. 8 and 9. Shifting the cap drive member 34 of the bone anchor assembly 20 in direction 46 (see FIGS. 3 and 4) to the locked position expands the locking cap 36, presses a partially spherical outer surface 100 of the locking cap 36 against a pocket surface 103 of the support member 16, and shifts support member portions 72, 74 apart in directions 76, 78 toward throughbore walls 80, 82, as shown in FIGS. 6 and 7.

Expansion of the resilient support member 16 shifts the support member projections 92 and plate member teeth 94 from an adjustment orientation, where there is a gap spacing 96 between the projections 92 and teeth 94, into a locked orientation where the projections 92 and teeth 94 are engaged, as shown in FIGS. 8 and 9. The engaged projections 92 and teeth 94 restrict translational movement of the support member 16 and bone anchor assembly 20 received therein along the elongated throughbore 18. Thus, the support member projections 92 and bone plate teeth 94 can be quickly shifted from the adjustment orientation to the locked orientation to lock the position of the support member 16 and bone anchor assembly 20 simply by shifting the cap drive member 34 to the locked position after the bone screw head 30 has been seated in the opening 53. This easy-to-use location locking mechanism advantageously provides the bone anchor stability of a bone plate having static bone anchor locations as well as the installation flexibility of a bone plate having elongated throughbores. Further, the engaged projections 92 and teeth 94 may also restrict rotation of the support member 16 about the bone anchor longitudinal axis 46 within the throughbore 18 to increase the stability of the bone anchor 20 within the elongated throughbore 18.

In one form, the tolerances between the support member projections 92 and bone plate teeth 94 produce a slight ratcheting action when the projections 92 and teeth 94 are in the adjustment orientation and the support member 16 is moved along the elongated throughbore 18. The slight ratcheting action may be desirable in some applications to restrict the support member 16 from moving out of a desired position along the throughbore 18 before the bone anchor assembly 20 is driven into the support member opening 53 (see FIG. 48). In another form, the support member projections 92 and the bone plate teeth 94 may be in clearance with one another when they are in the adjustment orientation. The interfering portions of the support member 16 and the bone plate member 14 may have a variety of possible configurations. For example, the interfering portions may include one or more pins located on the support member 16 and one or more corresponding recesses on the bone plate member 14. In another approach, the interfering portions may include one or more tabs of the support member 16 and one or more corresponding slots on the bone plate member 14.

Figure 10:
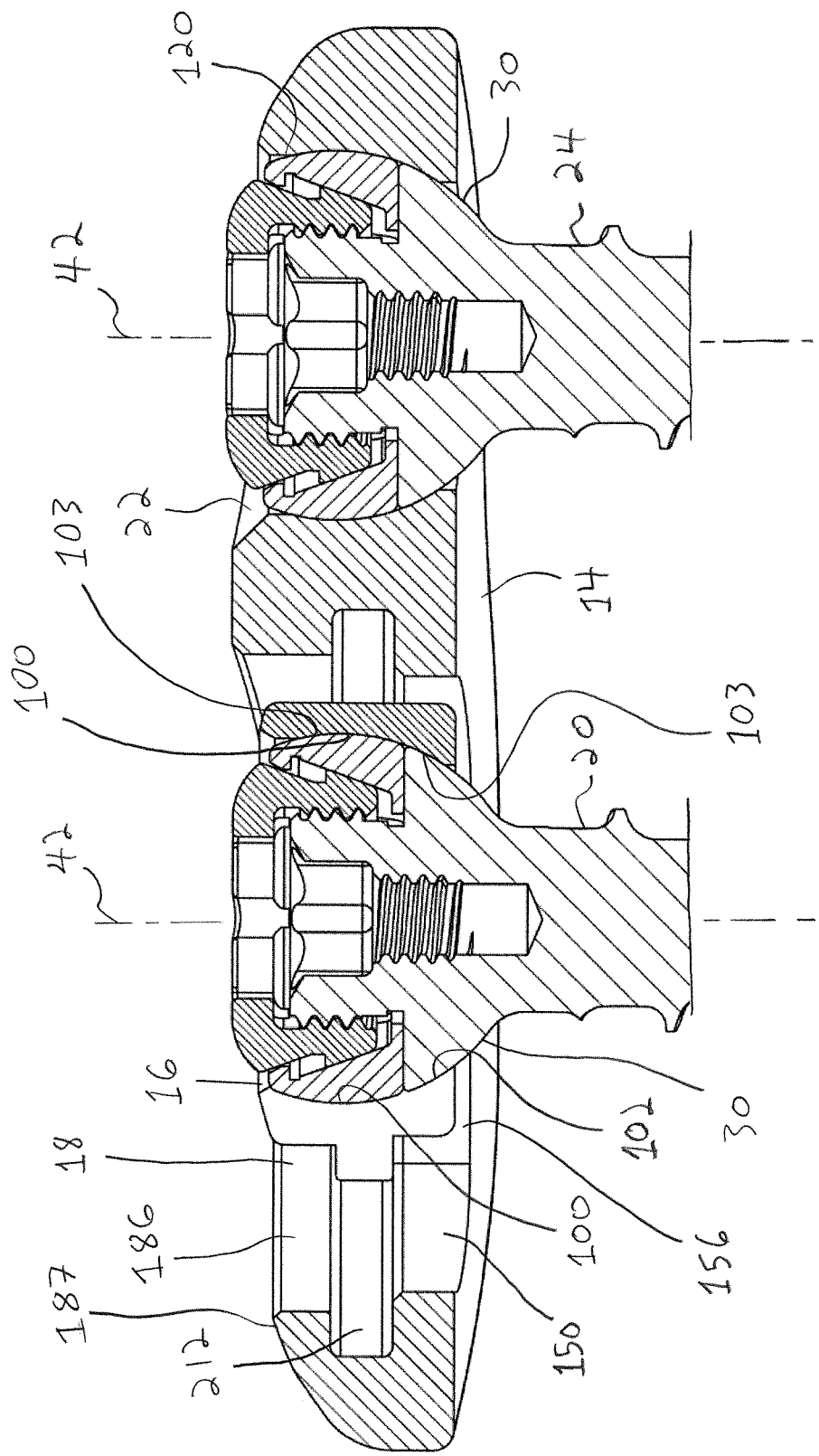
FIG. 10 is a cross-sectional view taken across line 10-10 in FIG. 5 showing generally spherical head portions of the bone anchor assemblies received in partially spherical pockets of the resilient support member and the non-elongated throughbore.

With reference to FIGS. 3 and 4, shifting the cap drive member 34 to the locked position shifts the partially spherical outer surface 100 of the locking cap 36 radially outward until the outer surface 100 is generally flush with a partially spherical lower surface 102 of the screw head 30. With the locking cap 36 in its expanded configuration, the surfaces 100, 102 form a larger, partially spherical outer surface 95 of a head portion of the bone anchor assembly 20. Further, the support member 16 has the partially spherical pocket surface 103 and the non-elongated throughbore 22 has a partially spherical pocket surface 120 each with a respective radius of curvature that is complimentary to the curvatures of the outer surfaces 100, 102 with the locking caps 36 in their expanded configurations, as shown in FIG. 10. The head portions 97 of the bone anchor assemblies 20, 24 thereby form a ball-and-socket connection between the bone anchor assemblies 20, 24 and the bone plate 12. The ball-and-socket connections permit a controlled pivoting of the bone anchor assemblies 20, 24 to accommodate post-operative movement of the bones.

With reference to FIGS. 6 and 7, driving the bone anchor 26 into the support member opening 53 also seats the screw head lower surface 102 against a seating portion 105 of the pocket surface 103 which can be used to lag the bone plate member 14 against a bone. Further, the engagement between the bone screw head lower surface 102 and the seating portion 105 of the pocket surface 103 provides a direction connection between the bone screw 26 and the bone plate 12. This direct connection increases the strength of the engagement between the bone screw 26 and the bone plate 12 and permits the bone screw 26 to directly transfer loading to the bone plate 12.

The cap drive member 34 is then shifted to the locked position which expands the locking cap 36 and brings the cap outer surface 100 into engagement with an engagement portion 107 of the pocket surface 103. Driving the cap drive member 34 into the locked position firmly engages the partially spherical outer surface 100 of the locking cap 36 with the engagement portion 107 of the pocket surface 103. Thus, with the screw head 30 seated in the support member opening 53 and the cap drive member 34 shifted to the locked position, both the cap outer surface 100 and the head lower surface 102 are frictionally engaged with the support member seating surface 103. This frictional engagement provides controlled resistance to pivoting movement of the bone anchor assembly 20 relative to the support member 16.

With reference to FIGS. 3 and 4, the bone anchor assembly head portion 97 has a height 99 along the bone anchor assembly longitudinal axis 42 and the locking cap partially spherical outer surface 100 has a height 101 that is approximately half the height 99 of the bone anchor assembly head portion 97. In some forms, the height 101 could be approximately a quarter of the height 99, approximately three-quarters of the height 99, or another proportion although the locking cap height 101 is preferably greater than a quarter of the head portion height 99 in order to preserve a sufficiently large partially spherical lower surface 102 of the bone screw head 30. The relatively large axial extent or height 101 of the locking cap outer surface 100 provides a large amount of surface area of the locking cap outer surface 100 which can engage the support member pocket surface 103. This increases the frictional engagement of the locking cap 36 with the support member 16 and limits pivoting of the bone anchor assembly 20 once the cap drive member 34 has been shifted to the locked position.

With reference to FIG. 10, the partially spherical seating surfaces 103 extends along the locking cap outer surfaces 100 substantially the entire length of the outer surface 100 along the longitudinal axis 42 of the bone anchor assembly 20. By extending substantially the entire axial extent of the locking cap outer surface 100, the frictional engagement between the locking cap outer surface 100 and the support member seating surface 103 can be maximized. For example, when the bone screw 20 undergoes pivoting (such as due to post-operative movement of bones) or when the bone anchor assembly 20 is driven obliquely into the opening 53 of the support member 16, there is still a majority of the locking cap outer surface 100 engaged with the support member pocket surface 103 despite the transverse orientation of the locking cap 36 relative to the support member 16. The partially spherical seating surface 120 of the non-elongated throughbore 22 is similar to the support member seating surface 103 and provides similar advantages in terms of engagement and controlled pivoting between the bone anchor assembly 24 and the plate member 14.

The materials of the bone screw 26, locking cap 36, and bone plate member 14 may be selected, in part, to provide a desired amount of frictional engagement between the bone anchor assembly 20 and the support member 16 which controls pivoting of the bone anchor 20. The surface texture of the surfaces 100, 102, 103, and 120 may also be configured to provide a desired amount of frictional engagement therebetween and resulting resistance to pivoting of the bone anchor assemblies 20, 24 relative to the bone plate 12. For example, the roughness of one or more of the surfaces 100, 102, 103, and 120 can be increased, such as by blasting, in order to increase the frictional engagement between the support member 16 and the bone anchor assembly 20 and increase resistance to pivoting of the bone anchor assembly 20.

Figure 12:
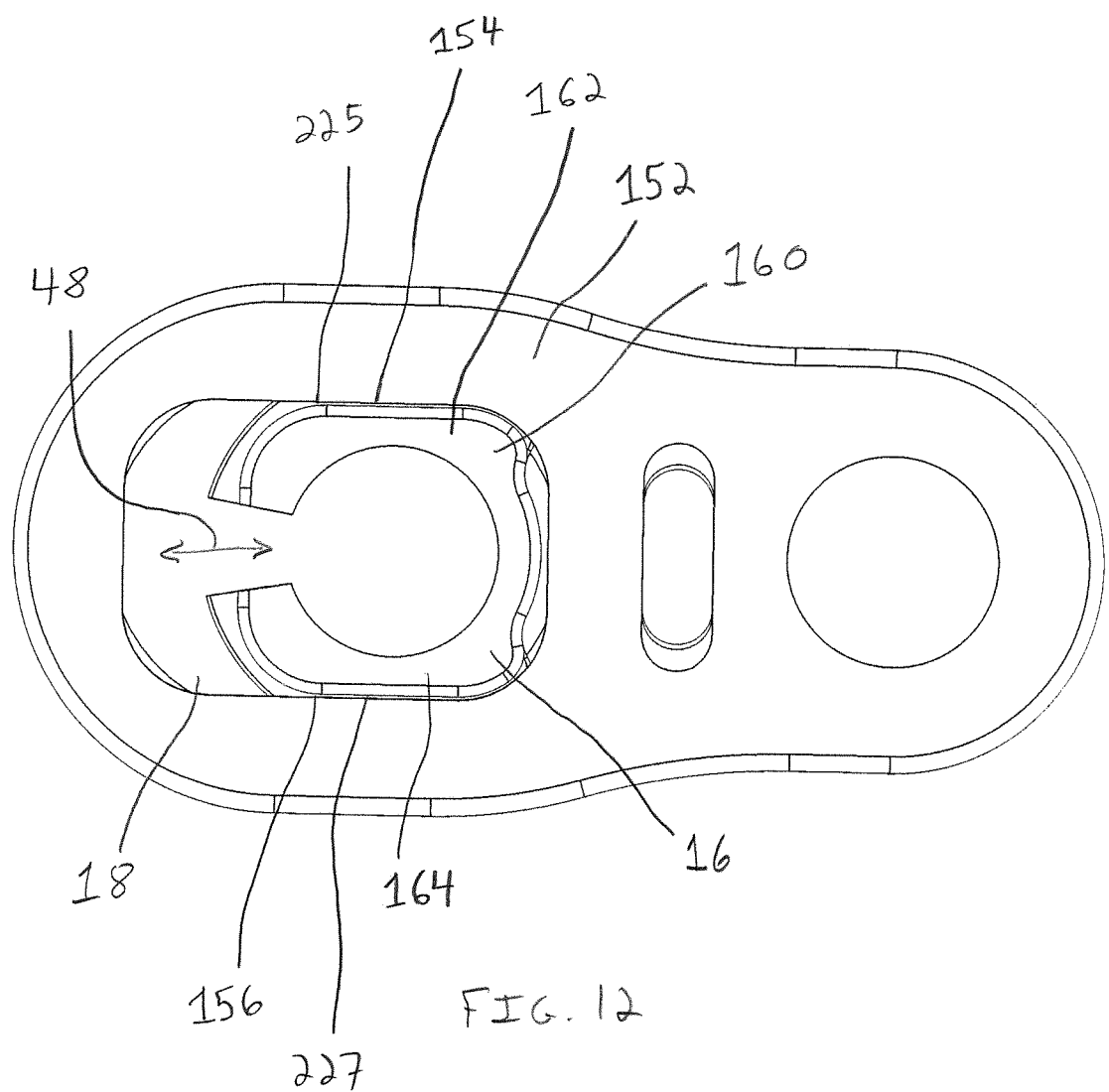
FIG. 12 is a bottom plan view of the bone plate of FIG. 1 showing a generally rectangular lower opening of the elongated throughbore and a generally rectangular lower portion of the support member fit within the lower opening of the elongated throughbore.
Figure 15:
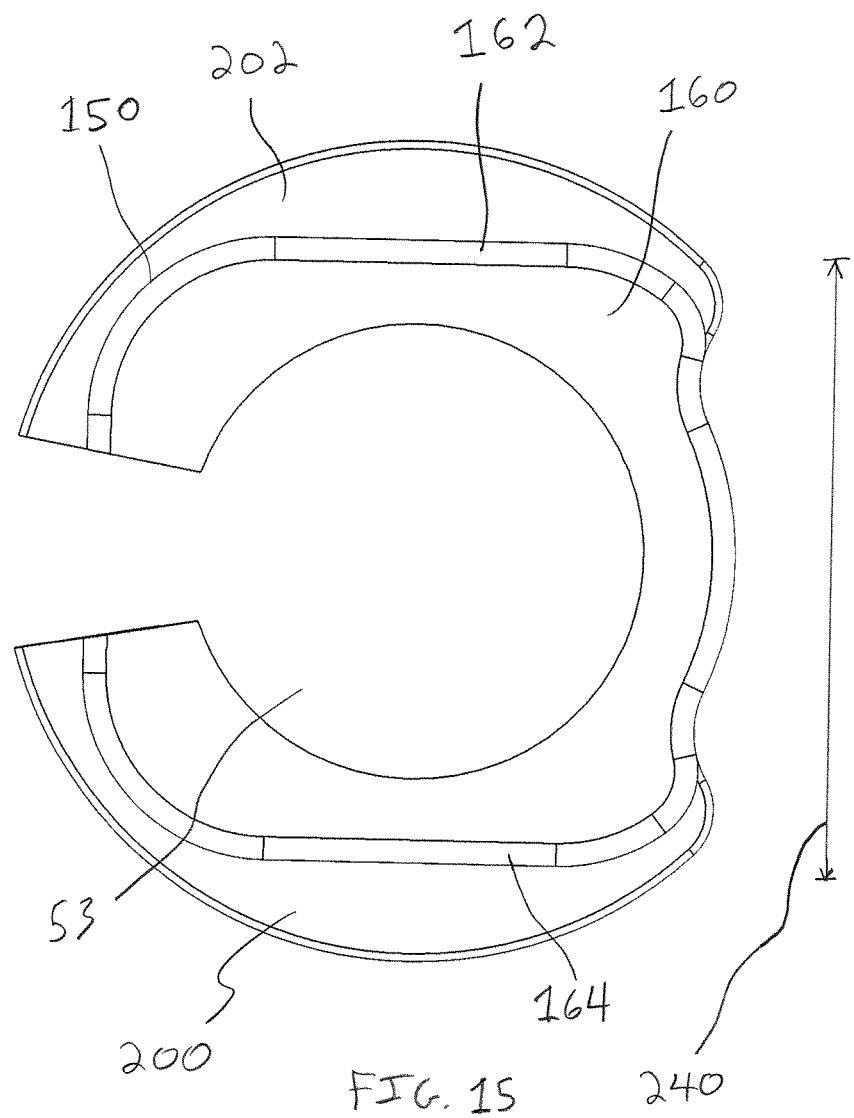
FIG. 15 is a bottom plan view of the support member of FIG. 13 showing the flange of the support member extending radially beyond the generally rectangular lower portion of the support member.

With reference to FIGS. 6, 12, and 15, the support member 16 and throughbore 18 have cooperating features configured to limit rotation of the support member 16 and generally restrict the support member 16 to movement along the axis 47 of the elongated throughbore 18. In one form, the throughbore 18 has a narrow section 150 near a bottom surface 152 of the bone plate member 14. The narrow section 150 includes flat guide surfaces 154, 156 on opposite sides have the throughbore 18 extending along the axis 46 of the throughbore 18. The support member 16 has a narrow lower portion 160 configured to fit within the throughbore narrow section 150 between the guide surfaces 154, 156. The support member lower portion 160 has a pair of lower walls 162, 164 configured to abut the guide surfaces 154, 156, as shown in FIGS. 12 and 15. The plate member lower walls 162, 164 engage the support member guide surfaces 154, 156 and resist rotary movement of the support member 16 within the throughbore 18. This further increases the stability of the construct of the bone plate member 14, support member 16, and bone anchor assembly 20.

Figure 13:
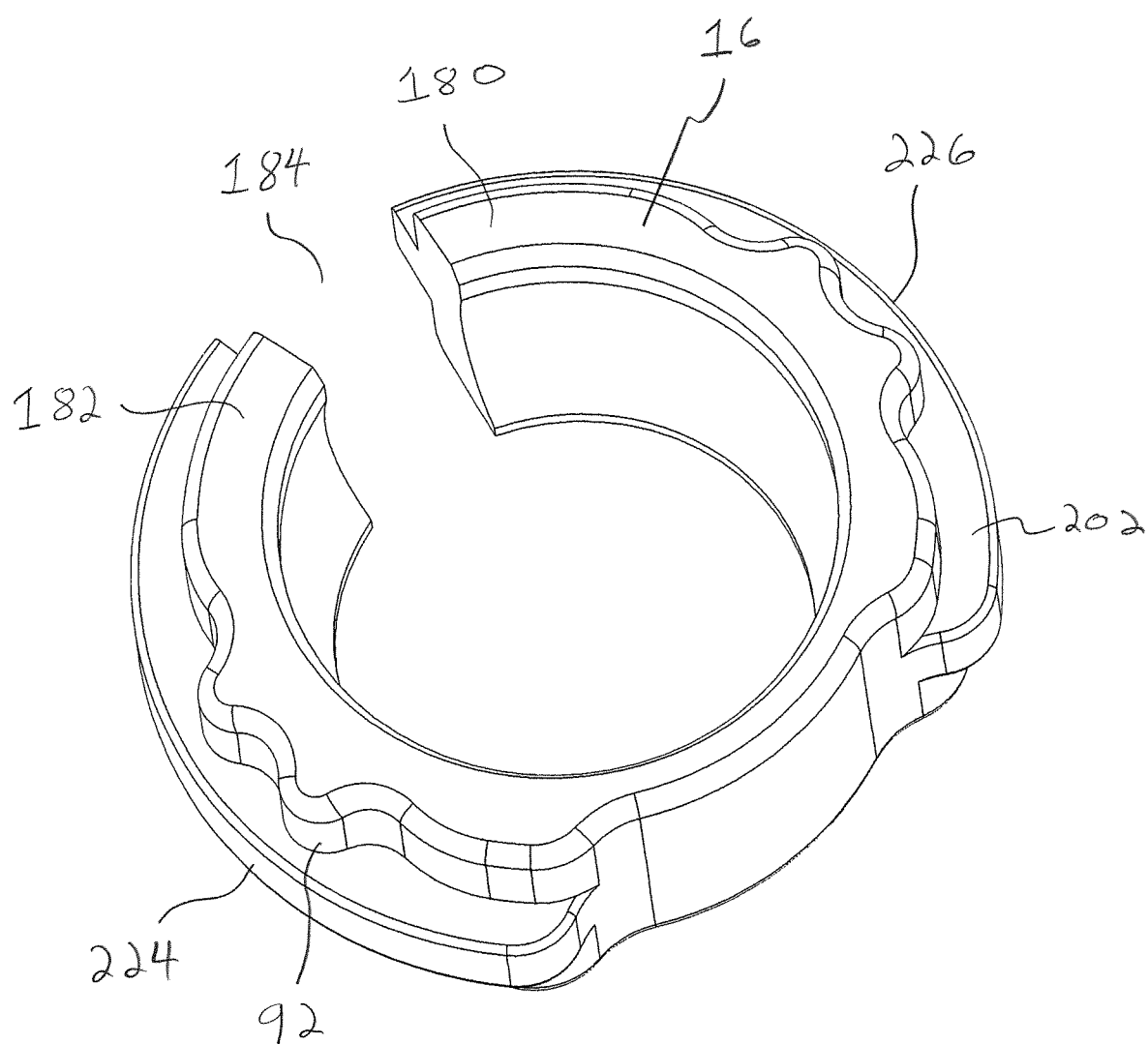
FIG. 13 is a perspective view of the resilient support member of the bone plate system of FIG. 1 showing a split-ring configuration of the support member.
Figure 14:
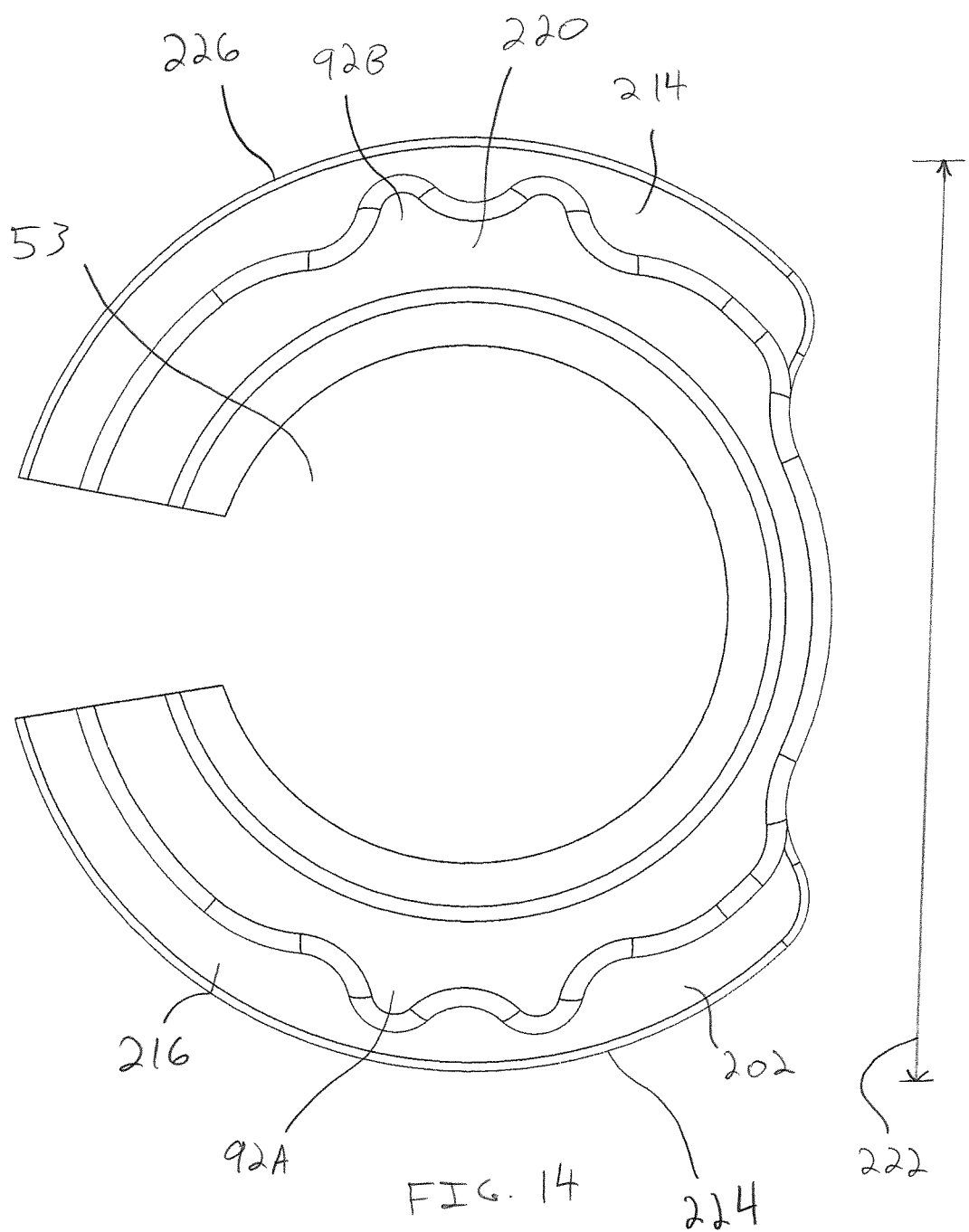
FIG. 14 is a top plan view of the support member of FIG. 13 showing the projections of the support member extending radially outward for engaging the teeth of the bone plate.

With reference to FIGS. 13-15, the support member 16 has a c-ring shape including a pair of opposed ends 180, 182 separated by a gap 184. The gap 184 permits the ends 180, 182 to move apart with radial expansion of the locking cap 36 due to shifting of the cap drive member 34 to the locked position (see FIGS. 6 and 7). The gap 184 also permits the support member 16 to be compressed, with ends 180, 182 shifting toward each other, during insertion of the support member 16 through an enlarged upper section 186 of the throughbore 18 adjacent an upper surface 187 of the plate member 14 (see FIGS. 10 and 11). The compressed support member 16 may be advanced into the throughbore 18 until a lower surface 200 of a flange 202 of the support member 16 contacts a lower support surface 204 of a channel 206 of the plate member 14, as shown in FIG. 6. The compressed support member 16 may then be released to permit the ends 180, 182 to expand apart and the flange 202 to shift outward into the channel 206. At this point, the resilient support member 16 is retained in the elongated throughbore 18 and may be shifted therealong as discussed above. The engagement between the support member flange 202 and the plate member channel 206 permits the bone anchor 20 to lag the bone plate 12 against a bone by seating the bone anchor 30 within the support member opening 53. Further, the engagement between the support member flange 202 and the plate member channel 206 transfers axial loading between the bone anchor 20 and bone plate 12 and restricts pull-through of the bone anchor assembly 20 out of the elongated throughbore 18.

The channel 206 includes sections 210, 212 on opposite sides of the throughbore 18 (see FIGS. 6 and 7) sized to receive corresponding portions 214, 216 of the support member flange 202 (see FIG. 14). The support member flange 202 has outer surfaces 224, 226 and the channel sections 210, 212 have guide surfaces 228, 230 which guide the support member 16 along the throughbore 18, as shown in FIG. 6. With reference to FIG. 14, the support member 16 has a body 220 with a width of 222 selected to permit the projections 92a, 92b to be in the adjustment orientation relative to the bone plate teeth 94a, 94b when the support member 16 is in the unexpanded configuration. The width 222 also provides a small amount of clearance between the flange outer surfaces 224, 226 and the channel guide surfaces 228, 230 which permits the support member 16 to be moved longitudinally within the elongated throughbore 18. With reference to FIGS. 12 and 15, the narrow section 150 of the support member 16 may have a width 240 between the support member lower walls 162, 164 which provides slight gaps 225, 227 between the walls 162, 164 and the plate member guide surfaces 154, 156. These gaps limit interference between the walls 162, 164 when the support member 16 is in the unexpanded and expanded configurations, although the gaps 162, 164 are smaller when the support member has been expanded. Limiting interference between the support member lower walls 162, 164 and the plate member guide surfaces 154, 156 may be desirable to ensure that the support member projections 92A, 92B fully engage the plate member teeth 94A, 94B despite variation in tolerances of the plate member 14, support member 16, and bone anchor assembly 20 during manufacturing.

Figure 48:
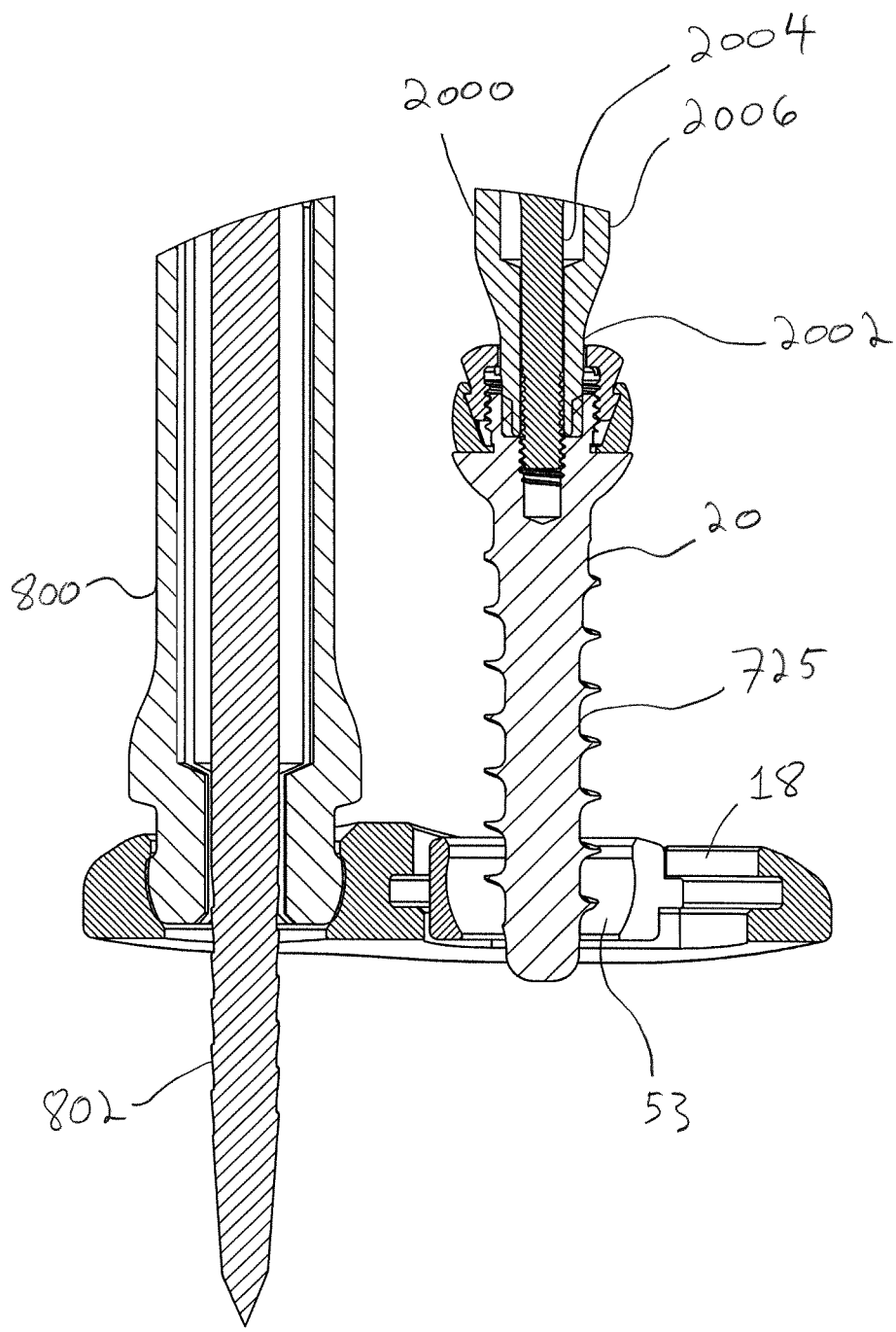

With reference to FIGS. 16-28, the bone anchor assembly 20 is described in greater detail. The bone screw head 30 has a partially spherical lower surface 102, a shoulder bearing surface 252 extending inward from the lower surface 102, and the wall 66 upstanding from the shoulder bearing surface 252. The upstanding wall 66 has a connection structure, such as threads 264, for connecting to the cap drive member 34. The upstanding wall 66 also includes the drive structure 71 for receiving a driving tool 2000, as shown in FIG. 48. In one form, the drive structure 71 includes a drive recess 280 for receiving a distal end of the driving tool, such as a socket, a hex socket, or a Phillips recess. For example, the drive recess 280 may be a T20 Torx drive to provide a firm engagement between the driving tool 2000 and the bone screw 26 during insertion and driving of the bone anchor assemblies 20, 24. The bone screw head 30 may also have a retention structure 282 configured to engage a retention portion of the driver tool 2000 and maintain the bone anchor assembly 20 on the driving tool 2000 until the bone anchor assembly 20 has been driven into bone. In one form, the retention structure 282 has threads 284 configured to engage threads of an internal retention shaft 2004 (see FIG. 48) of the driving tool 2000.

With reference to FIGS. 21-24, the locking cap 36 has an outer wall 310 with a split-ring configuration and engagement members 312 extending inwardly from the outer wall 310. The engagement members 312 have retention tips 314 sized to fit within a groove 270 extending around a base of the annular wall 66 (see FIGS. 17 and 20). The retention tips 314 have upper stop surfaces 316 that are positioned below a stop surface 272 of the bone screw groove 270 when the locking cap 36 has been assembled onto the screw head 30. The surfaces 272, 316 are in axial overlapping relation such that the surfaces 272, 316 contact and restrict removal of the locking cap 36 in direction 380 (see FIG. 16) once the locking cap 36 has been assembled onto the bone screw head 30.

Figure 22:
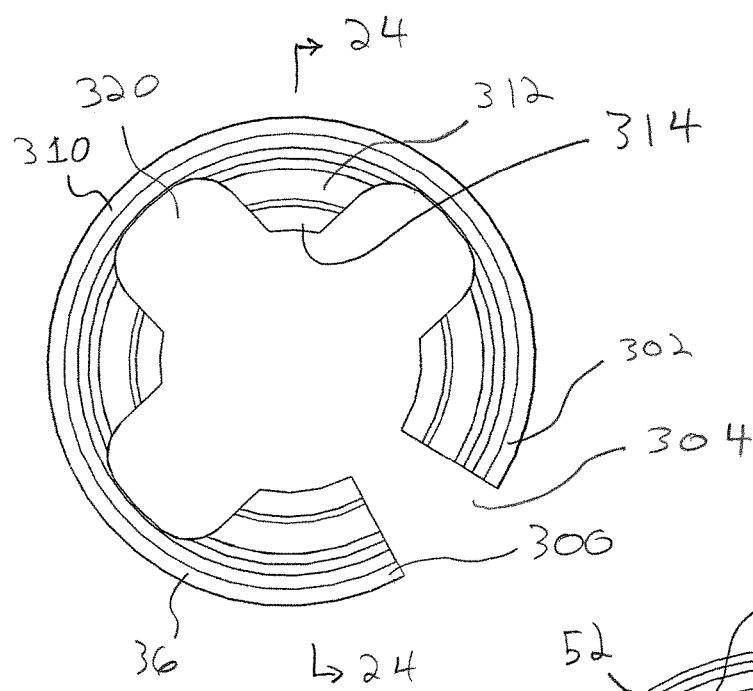
FIG. 22 is a top plan view of the locking cap of FIG. 21 showing an outer annular wall and radially extending portions of the locking cap.
Figure 24:
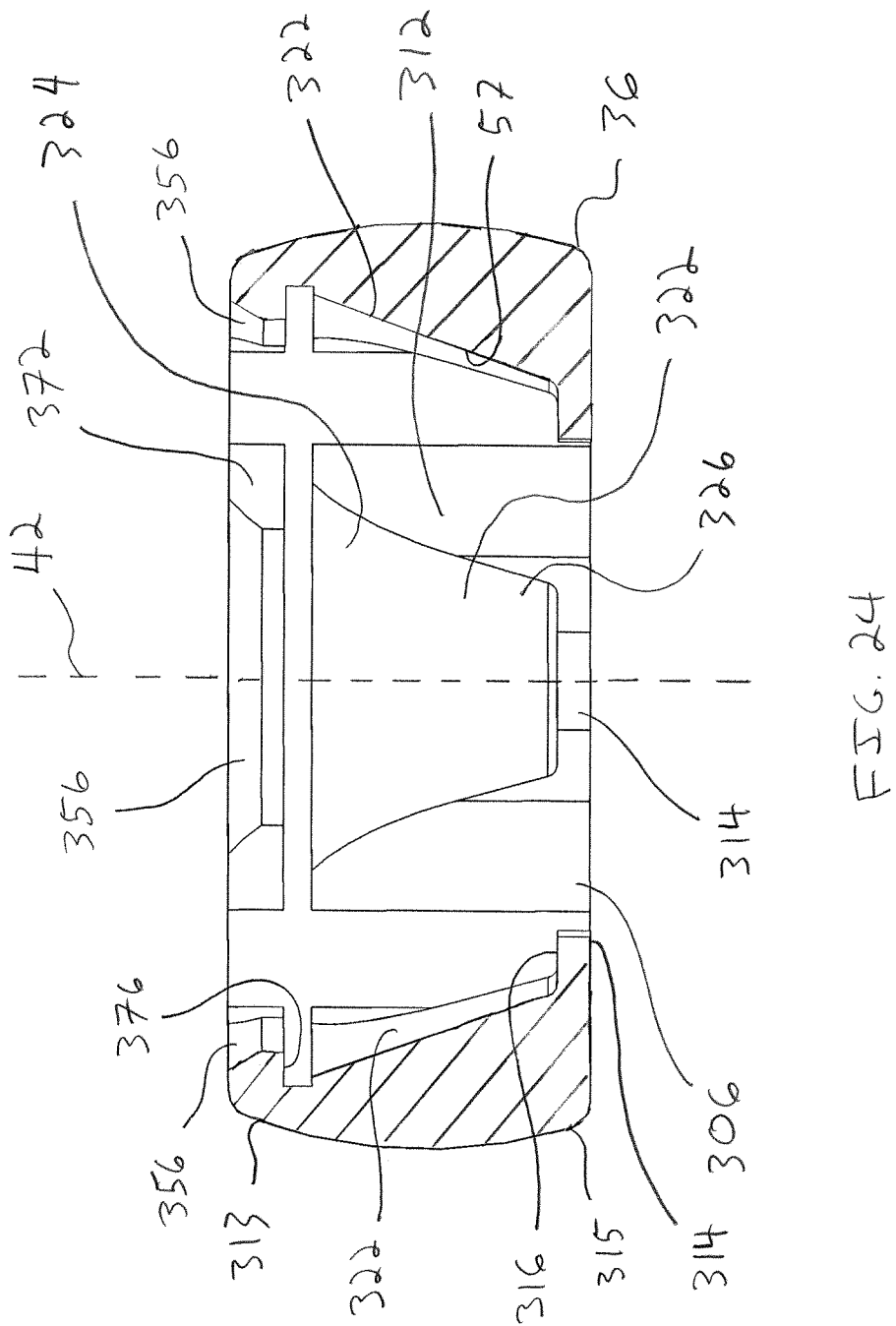
FIG. 24 is a cross-sectional view taken across line 24-24 in FIG. 22 showing radially inner inclined surfaces against which the cap drive member cams.
Figure 25:
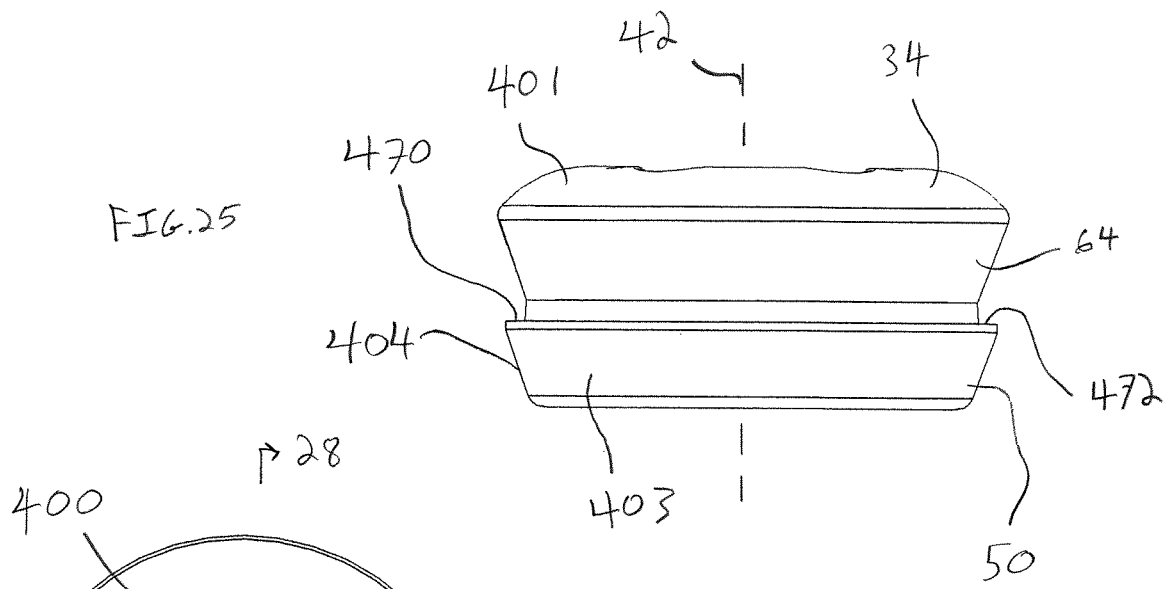
FIG. 25 is an elevational view of the cap drive member of the bone screw of FIG. 16 showing a radially outer, inclined surface of the cap drive member configured to engage the radially inner inclined surfaces of the locking cap.
Figure 26:
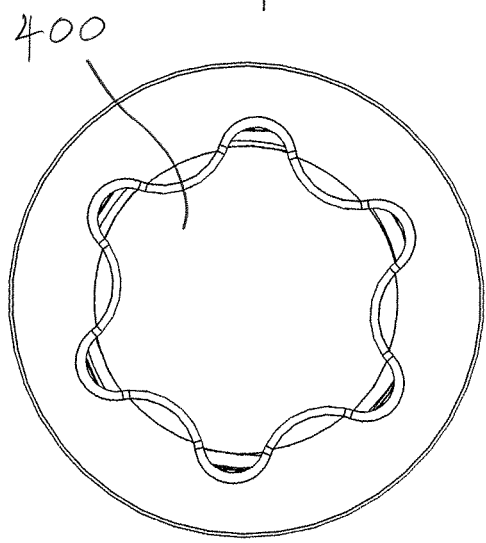
FIG. 26 is a top plan view of the cap drive member of FIG. 17 showing a central opening of the cap drive member.
Figure 27:
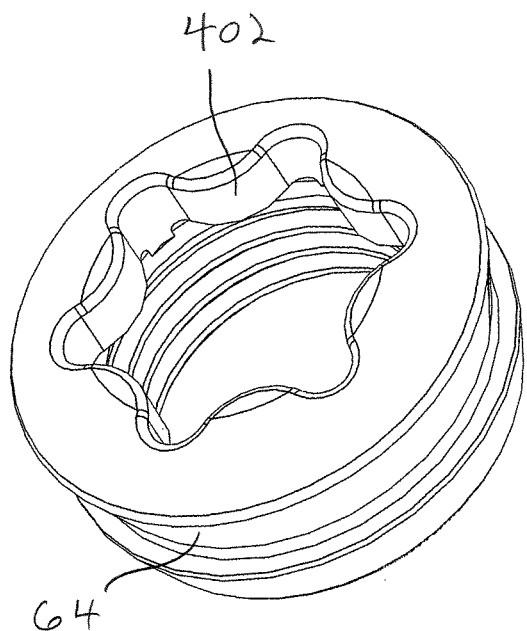
FIG. 27 is a perspective view of the cap drive member of FIG. 17 showing structures of the cap drive member disposed about the central opening configured to engage a locking tool.

The locking cap engagement members 312 are generally wedge shaped and taper radially inward from an upper portion 313 adjacent the cap drive member 34 toward a lower portion 315 adjacent the shoulder bearing surface 252 of the bone screw head 30, as shown in FIG. 24. The locking cap 36 has cutouts 320 between each of the cam members 312 that define the general wedge shape of each engagement member 312 and increase the flexibility of the locking cap 36, as shown in FIG. 22.

Figure 23:
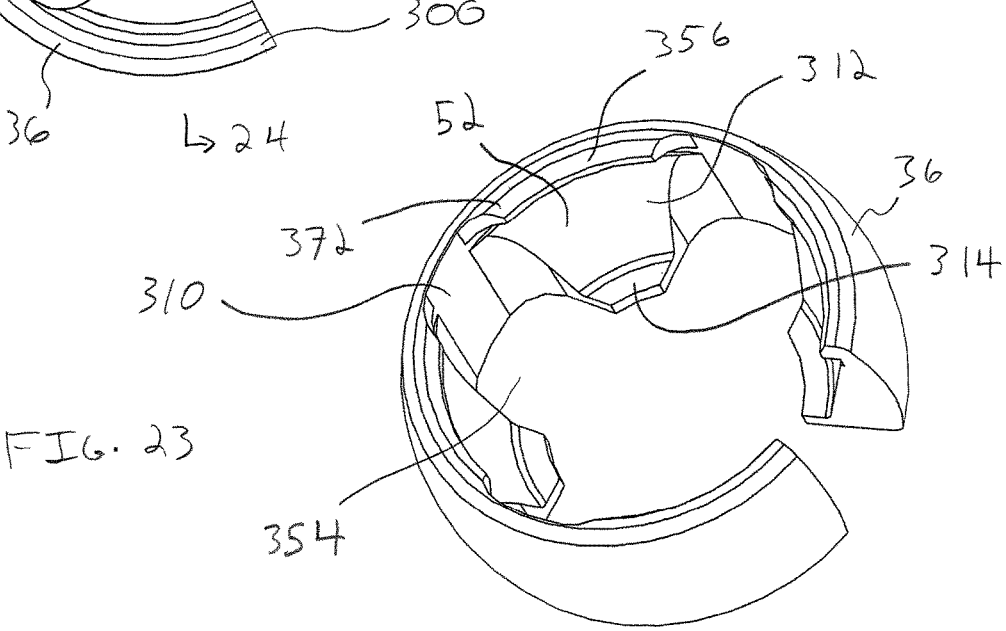
FIG. 23 is a perspective view of the locking cap of FIG. 1 showing a gap spacing between ends of the locking cap.

With reference to FIGS. 23 and 24, the locking cap engagement surface 52 includes a cam surface 322 on each of the engagement members 312 that extends obliquely relative to the bone anchor longitudinal axis 46. The cam surface 322 may extend a majority of the height of the locking cap 36 along the anchor axis 46 and taper from a wider upper portion 324 to a narrow lower portion 326 to produce a relatively large amount of area for the cam surface 322 of each engagement member 312. This increases the overall cam surface area of the locking cap 36 and improves the ease with which the locking cap 32 may expand the locking cap 36. Further, the tapered shape of the cam surface 322 provides a surface for contacting the cap drive member engagement surface 50 while preserving the general wedge-shape of the engagement members 312 which improves the flexibility of the locking cap 36. The cam surface 322 also extends radially inward toward the bone screw upstanding wall 66 which permits the cap drive member engagement surface 50 to engage the cam surfaces 322 even as the locking cap 36 expands away from the upstanding wall 66 as the cap drive member 34 reaches its locked position.

Figure 51:
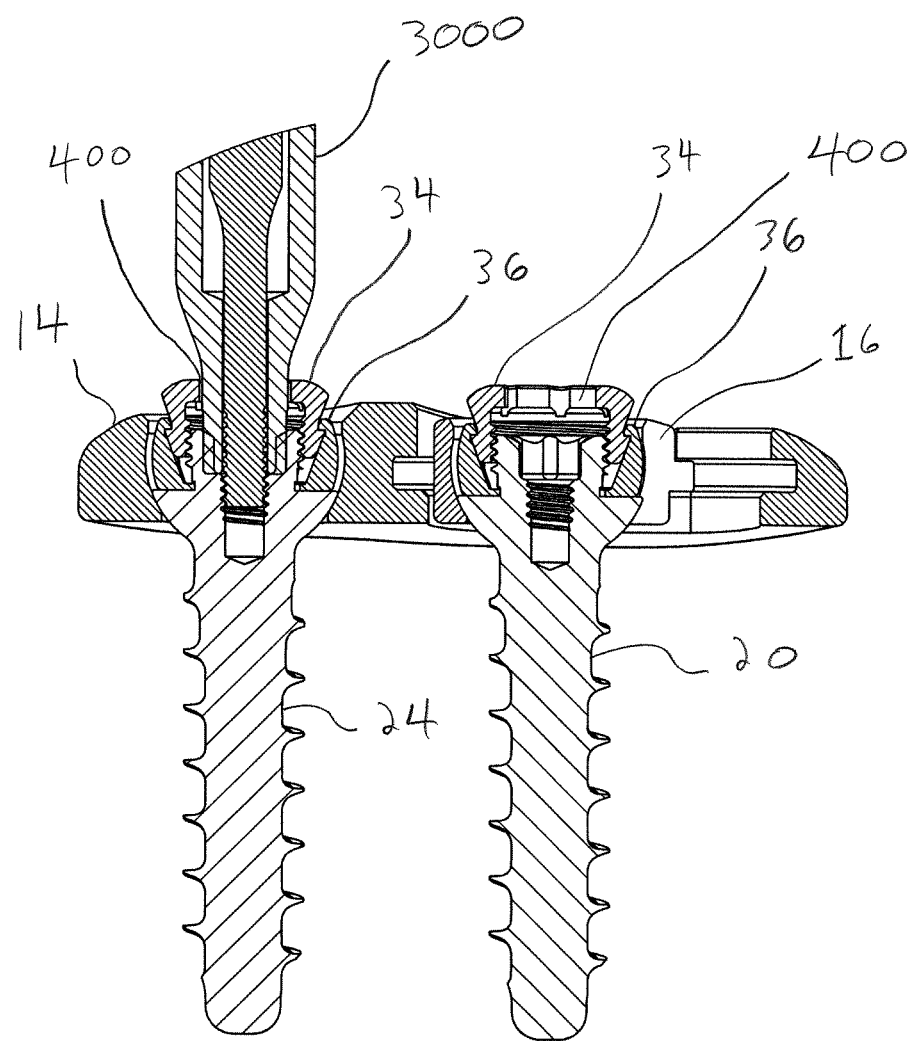
Figure 52:
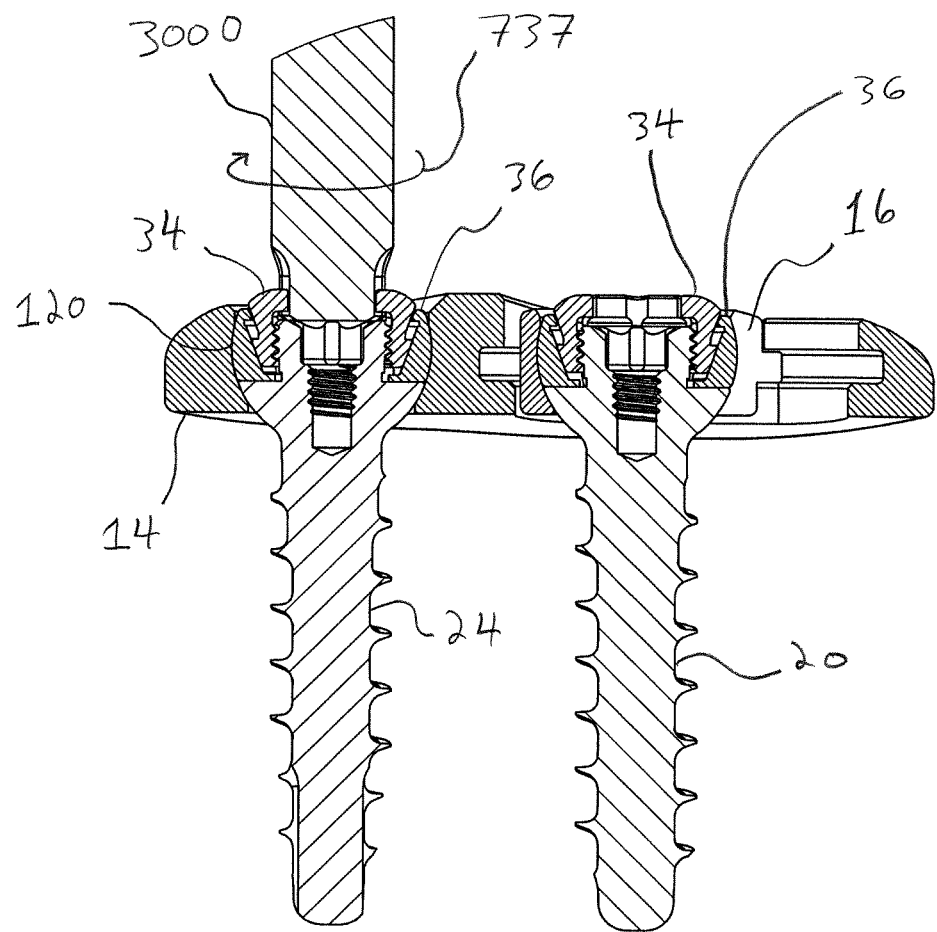
Figure 53:
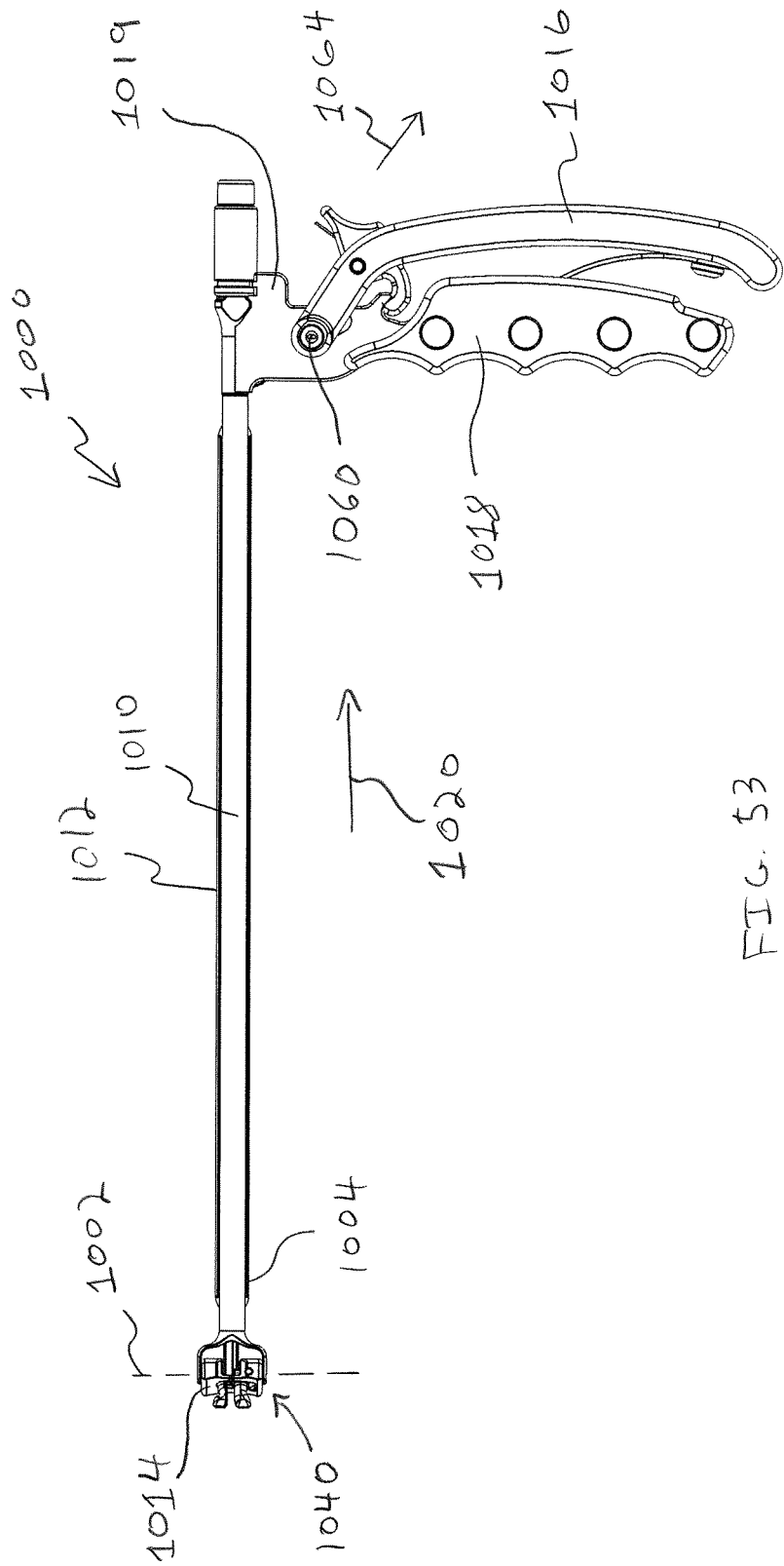
FIG. 53 is a left side elevational view of another inserter tool configured to be used to insert the bone plate of FIG. 1 during surgery.

With reference to FIGS. 25-28, the cap drive member 34 has an upper drive portion 401 with a through opening, such as an upper locking recess 400, sized to receive both the driving tool 2000 (see FIG. 49) and a distal end 3000 of a final tightener 3002 (see FIG. 51). However, the cap drive member 34 has a locking structure 402 configured to engage the final tightener 3002. In one form, the locking structure 402 is a T30 Torx socket, which is larger than a T20 Torx socket of the bone screw drive structure 71. The cap drive member 34 thereby permits a first tool to be used to drive the bone anchor assemblies 20, 24 into bones, and a different, second tool to be used to perform final locking of the bone anchor assemblies 20, 24 to the bone plate 12.

In one form, the cap drive member 34 has a lower end portion 403 and the engagement surface 50 includes a cam surface 404 that extends about the lower end portion 403 inwardly and obliquely relative to the bone anchor longitudinal axis 46. The lower end portion 403 of the cap drive member 34 thereby acts as a wedge to expand the locking cap 36 as the cap drive member 34 is driven to the locked position. The cam surface 404 is disposed radially outward on the cap drive member 34 and has a large surface area due to the diameter of the cap drive member 34. The large surface areas of the cap drive member cam surface 404 and locking cap cam surfaces 322 improve force transfer between the cap drive member 34 and the locking cap 36. Further, the large surface areas of the cap drive member cam surface 404 and locking cap cam surfaces 322 increase the frictional engagement between the cap drive member 34 and locking cap 36 which restricts movement of the cap drive member 34 away from the locked position.

In one form, the cam surface 404 is annular and continuous about the cap drive member 34 which permits the cam surface 404 to remain engaged with the cam surfaces 322 of the locking cap 36 as the drive member 34 is rotatably driven to the locked position.

The cap drive member 34 and locking cap 36 are generally assembled in a direction 250 onto the screw head 30 along the longitudinal axis 42 of the bone anchor assembly 20, as shown in FIG. 16. The locking cap 36 is positioned on the shoulder bearing surface 252 (see FIG. 19) of the screw head 30. Positioning the locking cap 36 onto the bearing surface 252 of the bone screw head 30 may include expanding the locking cap 36 by moving ends 300, 302 thereof apart to enlarge a gap spacing 304 therebetween (see FIG. 22). The locking cap 36 may then be moved axially downwardly onto the bone screw head 30 with the upstanding wall 66 passing into a lower opening 306 of the locking cap 36 (see FIG. 24).

Next, the lower end portion 403 of the cap drive member 34 is advanced into a central opening 354 (see FIG. 23) of the locking cap 36. The locking cap 36 has retention ribs 372 disposed above the engagement members 312 with guide surfaces 356 thereon. Advancing the cap drive member lower portion 403 into the locking cap central opening 354 brings the cap drive member cam surface 404 into contact with tapered guide surfaces 356 of the locking cap retention ribs 372. Continued axial movement of the cap drive member 34 toward the bone screw head 30 causes the cap drive member cam surface 404 to bear against the locking cap guide surfaces 356. This partially expands the locking cap 36 and permits a shoulder 470 of the cap drive member 34 (see FIG. 28) to travel axially beyond the retention ribs 372 of the locking cap 36.

Figure 28:
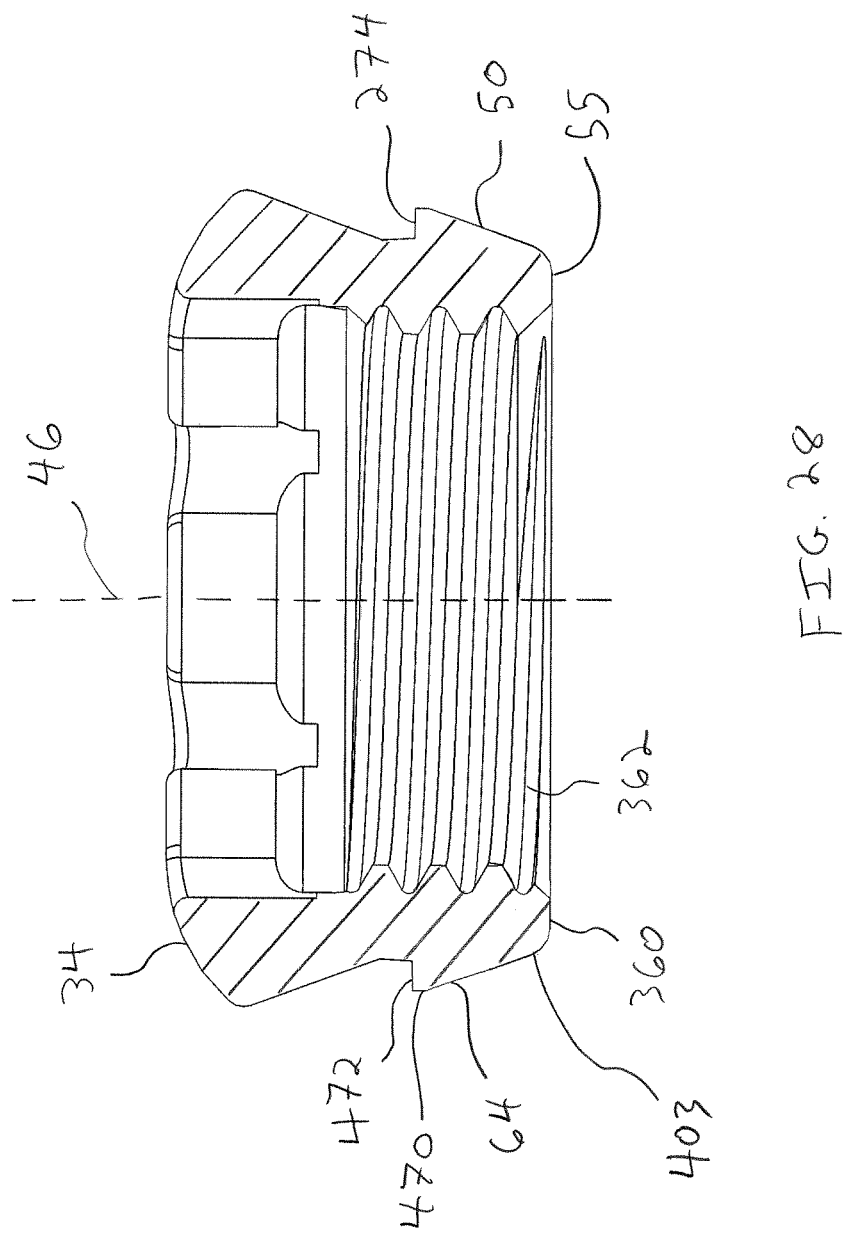
FIG. 28 is a cross-sectional view taken along line 28-28 in FIG. 26 showing an outer profile of the cap drive member.

Once the cap drive member shoulder 470 has passed beyond the locking cap retention ribs 372, the shoulder 470 has a flat annular stop surface 472 that is positioned below stop surfaces 376 on the undersides of the retention ribs 372 of the locking cap 36, as shown in FIGS. 24 and 28. At this point, the stop surfaces 376, 472 are in an axially overlapping and confronting orientation which restricts removal of the cap drive member 34 from within the locking cap 36 in direction 380 (see FIG. 6). Thus, the stop surfaces 272, 316 and 376, 472 of the bone anchor 26, cap drive member 34, and locking cap 36 maintain the cap drive member 34 and locking cap 36 on the bone screw head 30 and keep the bone anchors 20, 24 in the preassembled configuration.

The components of the bone plate system 10 may be made of biocompatible materials, such as stainless steels, titanium or titanium alloys, or other metals or alloys. The components of the bone plate 10 may also be made of one or more polymers, such as polyether ether ketone (PEEK).

Figure 29A:
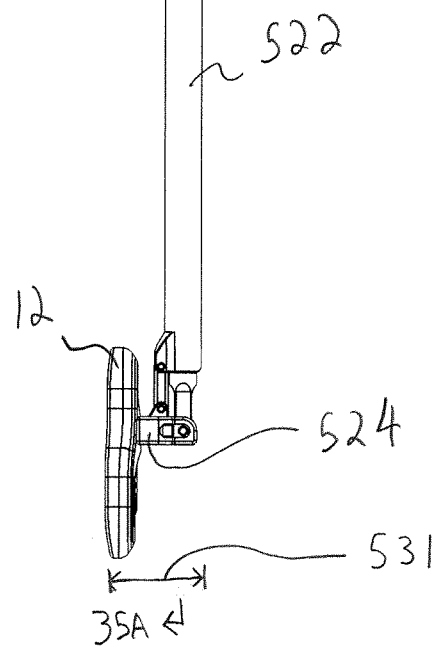
FIG. 29A is a top plan view of the inserter tool of FIG. 29 showing the bone plate in a generally parallel orientation relative to a shaft of the inserter tool.
Figure 31:
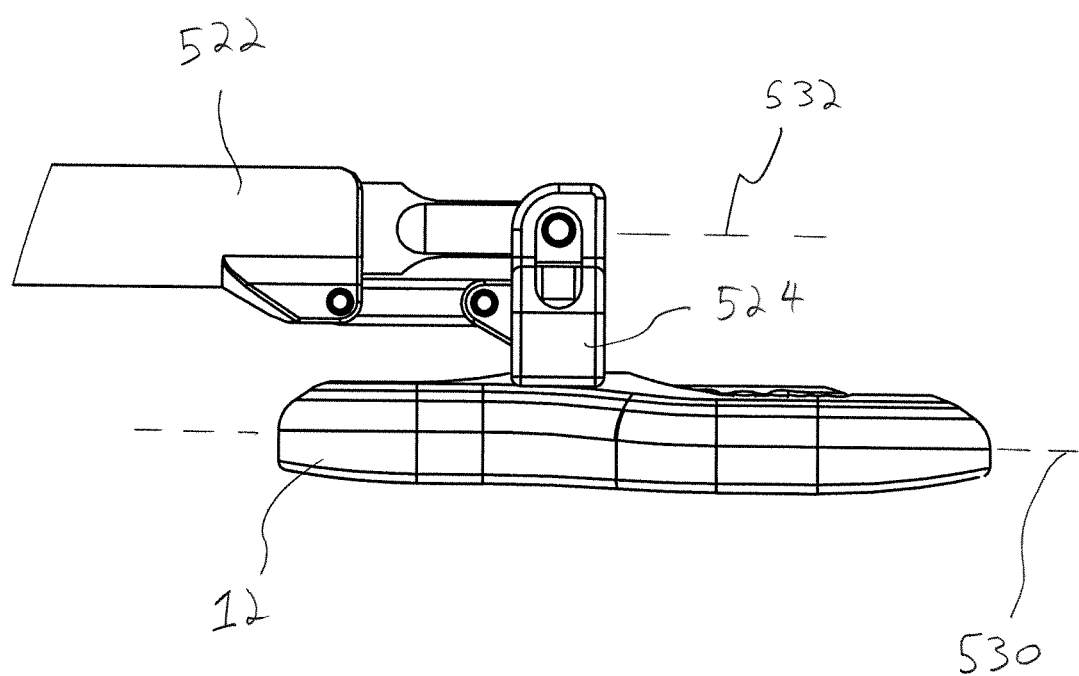
FIG. 31 is an enlarged elevational view of the distal end of the inserter tool of FIG. 29 showing a linkage between the shaft and a pivot body of the inserter tool which is connected to the bone plate.

With reference to FIGS. 29-43, an inserter tool 500 is provided for inserting the bone plate 12 into a confined surgical environment and positioning the bone plate 12 near one or more bones. The inserter tool 500 has a distal end portion 502 configured to releasably connect to the bone plate 12 and a proximal end portion 504 with a grippable handle 506. The inserter tool 500 has a pivot mechanism 507 configured to selectively pivot the bone plate 12, the pivot mechanism 507 having an insertion configuration where a longitudinal axis 530 the bone plate 12 is oriented generally parallel to a longitudinal axis 532 of a shaft 509 of the inserter tool 500 (see FIGS. 29 and 29A) and a positioning configuration where the axis 530 of the bone plate 12 is generally perpendicular to the shaft axis 532 (see FIGS. 32 and 32A). With the pivot mechanism 507 in the insertion configuration, the inserter tool distal end portion 502 and the plate member 12 connected thereto are relatively compact, particularly in a lateral direction transverse to the shaft axis 532, and can be advanced through a surgical channel having a smaller cross-section than if the bone plate 12 was extending perpendicular to the shaft axis 532. The relatively compact configuration of the tool distal end portion 502 and plate member 12 can be seen, for example, by comparing a leading end width 531 of the distal end portion 502 and plate member 12 when the pivot mechanism 507 is in the insertion configuration (see FIG. 29A) to a leading end width 533 when the pivot mechanism 507 is in the positioning configuration (see FIG. 32A). Because the leading end width 531 is smaller than the width 533, the inserter tool distal end portion 502 and plate member 12 may be advanced through a smaller working channel when the pivot mechanism 507 is in the insertion configuration than if the pivot mechanism 507 were in the placement configuration. Thus, the pivot mechanism 507 enables the inserter tool 500 to be used in more tightly confined environments and provides a significant improvement over inserter tools that can grasp an implant in only a perpendicular orientation.

Figures 32, 33:
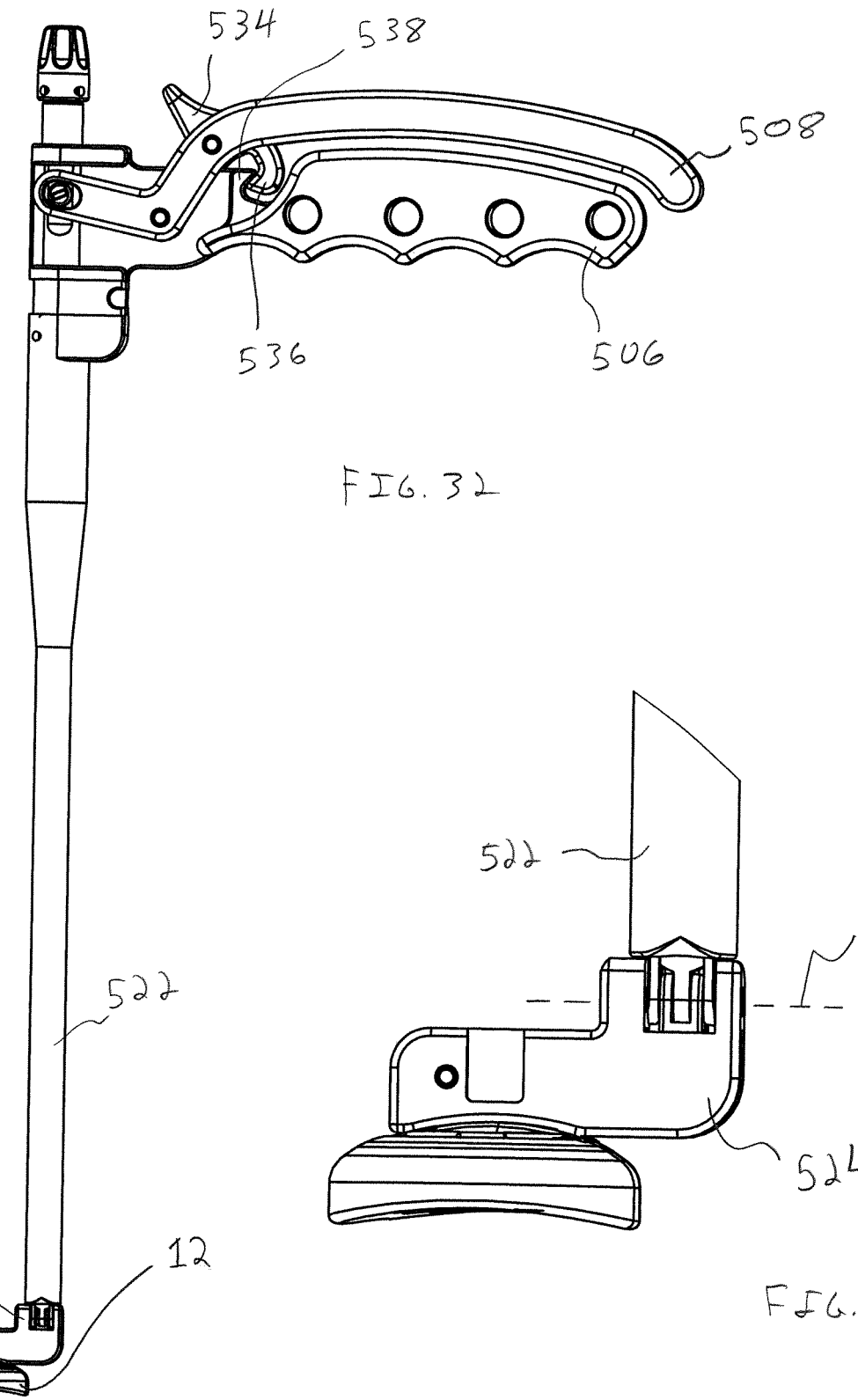
FIG. 32 is an elevational view similar to FIG. 29 showing a lever of the tool moved toward a handle of the tool which causes the inserter tool to pivot the bone plate.
FIG. 33 is an enlarged partial view of the distal end of the inserter tool of FIG. 32 showing the distal end connected to the bone plate.
Figure 32A:
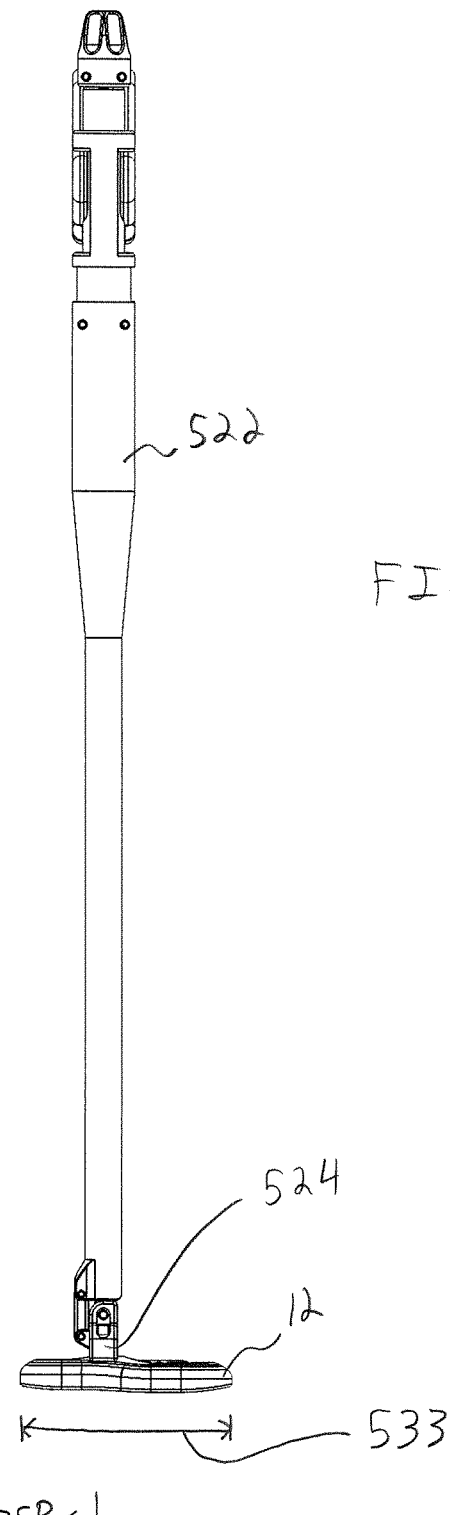
FIG. 32A is a top plan view of the inserter tool of FIG. 32 showing the bone plate pivoted to a generally perpendicular orientation relative to the inserter tool shaft.

Once the inserter tool distal end portion 502 and bone plate 12 reach the surgical site, the pivot mechanism 507 can be shifted and reconfigured to the positioning configuration where the bone plate 12 is generally perpendicular to the shaft 509, as shown in FIGS. 32 and 32A. With the bone plate 12 generally perpendicular to the shaft 509, the handle 506 can be manipulated to move the bone plate 12 within the surgical site and position the bone plate 12 at a desired location on one or more bones (see FIGS. 45 and 46). In this manner, the inserter tool 500 provides improved ability to advance elongate implants, such as the bone plate 12, through a small working channel and then pivot the implant relative to the inserter tool 500 and permit placement of the implant on one or more bones.

Figure 34:
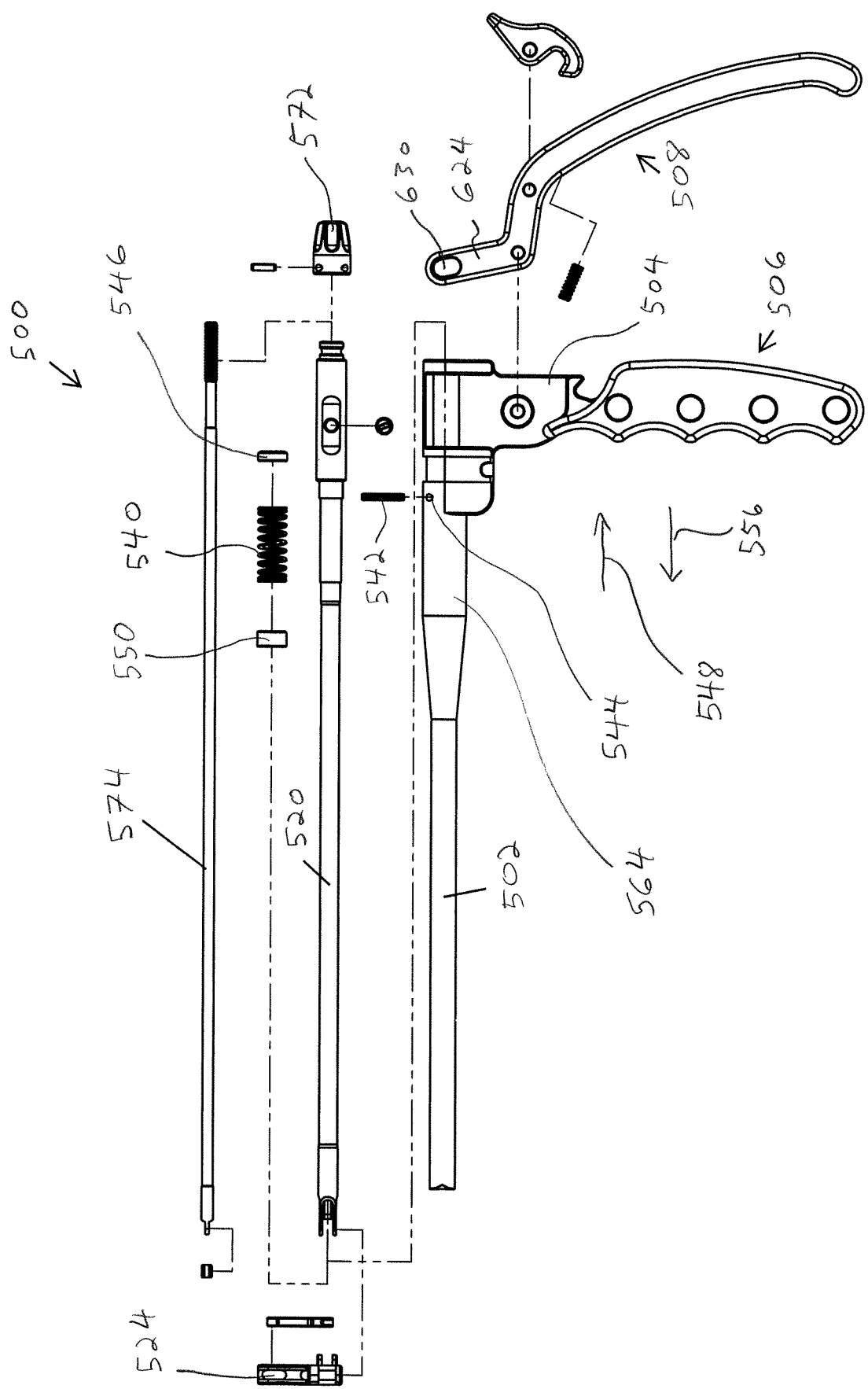
FIG. 34 is an exploded schematic view of the inserter tool of FIG. 29 showing a body shaft, a pivot shaft, and a grip control shaft of the inserter tool.

With reference to FIGS. 29 and 34, the inserter tool shaft 509 includes an outer body shaft 522, an intermediate pivot sleeve 520, and an inner grip control shaft 574. The pivot mechanism 507 includes the handle 508, the pivot sleeve 520, and a pivot body 524 connected to a distal end of the body shaft 522. Moving or compressing the lever 508 toward the handle to a closed position causes the pivot sleeve 520 to slide proximally within the body shaft 522 and pivot the pivot body 524 approximately 90 degrees about a pivot axis 526, as shown in FIGS. 29, 32, 35A, and 35B. The bone plate 12 is connected to the pivot body 524, such that pivoting of the pivot body 524 due to compressing the lever 508 causes the bone plate 12 to pivot relative to the inserter tool shaft 509. More specifically, compressing the lever 508 causes the bone plate 12 to move from an insertion orientation where a longitudinal axis 530 of the bone plate 12 is generally parallel with a longitudinal axis 532 of the shaft 509 to a positioning orientation where the bone plate longitudinal axis 530 is generally perpendicular to the shaft axis 532. The inserter tool 500 has a latch 534 with a hook 536 which may be pivoted to an engaged position where the hook 536 engages a tooth 538 of the handle 506. This allows the surgeon to easily maintain the bone plate 12 in the positioning orientation while performing other steps of the surgery, as will be discussed in greater detail below. Further, the latch 534 may be biased to the engagement position by a spring to restrict the latch 534 from being inadvertently disengaged.

With reference to FIGS. 34, 35A, and 35B, the inserter tool 500 includes a spring 540 arranged to bias the pivot sleeve 520 toward the distal end portion 502 of the inserter tool 500. Moving the lever 508 toward the handle 506 overcomes the bias force from the spring 540 and shifts the sleeve 520 back toward the proximal end portion 504. The outer body 522 includes a pair of pins 542 inserted in holes 544 of the body 522 (see FIG. 34) to support a spring support 546 within the body 522 and prevent the support 544 from traveling in direction 548. Opposite the spring support 546, there is a second spring support 550 fixed to the pivot sleeve 520 and housed within the body shaft 522 when the inserter tool 500 is assembled. Compressing the handle 508 causes the pivot sleeve 520 to move in direction 548 toward the proximal end portion 504, which moves the spring support 550 mounted on the pivot sleeve 520 in direction 548 and compresses the spring 540 between the supports 546, 550. Releasing the handle 508 permits the spring 540 to expand and shift the pivot sleeve 520 in direction 556 back toward the distal end portion 502.

Figures 36, 37:
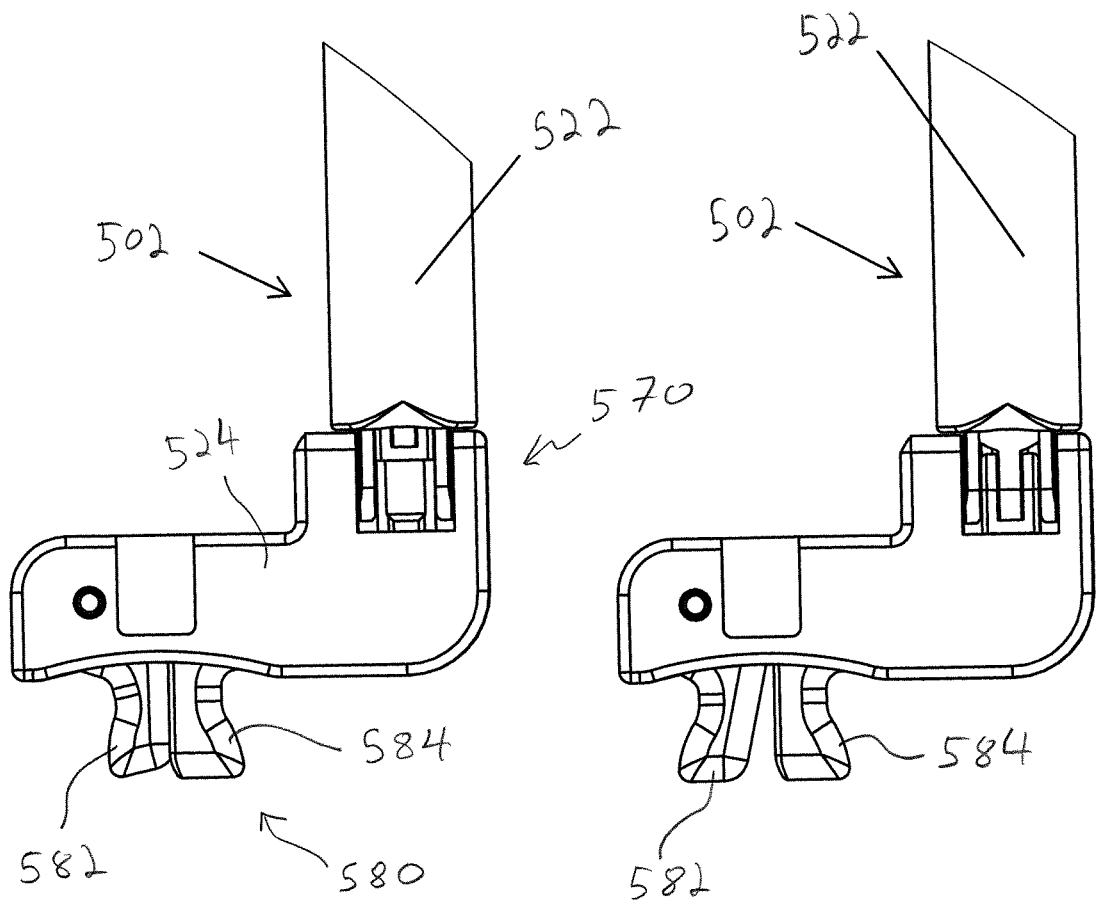
FIG. 36 is an elevational view of the distal end of the inserter tool of FIG. 29 with the bone plate removed therefrom showing a gripping portion of the inserter tool and arms of the gripping portion in a release configuration.
FIG. 37 is an elevational view similar to FIG. 36 showing the gripping portion arms in an engagement configuration.

With reference to FIGS. 35A, 36, and 37, The inserter tool 500 has a gripping device 570 that allows the inserter tool 500 to releasingly engage the bone plate 12. The gripping device 570 includes a grip control member, such as knob 572, and a gripping portion 580 that is configured to engage the bone plate 12. In one form, the gripping device 570 includes the grip control shaft 574 disposed within the pivot sleeve 520 and the knob 572 is threadingly engaged with the grip control shaft 574. Rotation of the knob 572 produces longitudinal movement of the grip control shaft 574 within the pivot shaft 520 and manipulates the configuration of the gripping portion 580.

Figure 40:
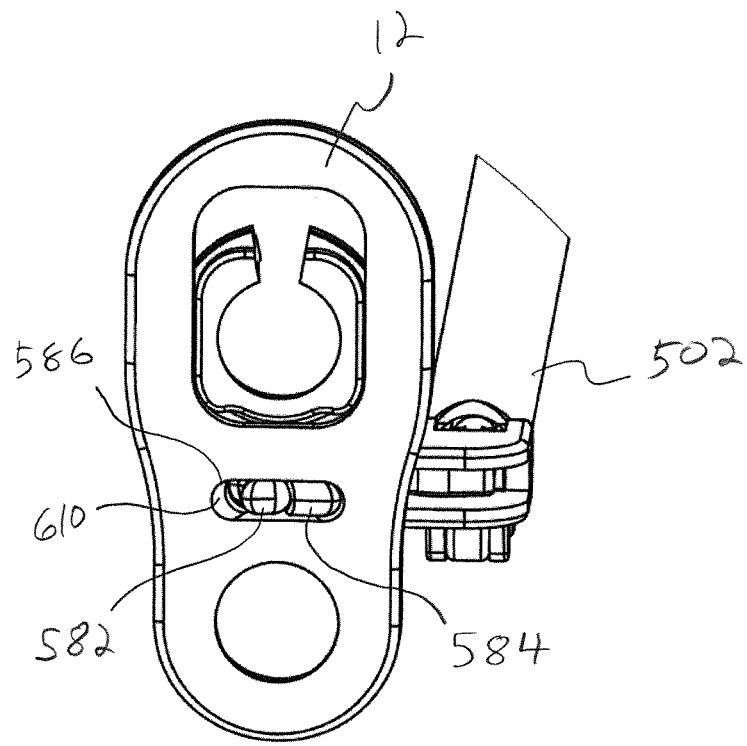
FIGS. 40 and 41 are bottom plan views of the bone plate connected to the distal end of the inserter tool showing the gripping portion arms in the release and engagement configurations.
Figure 41:
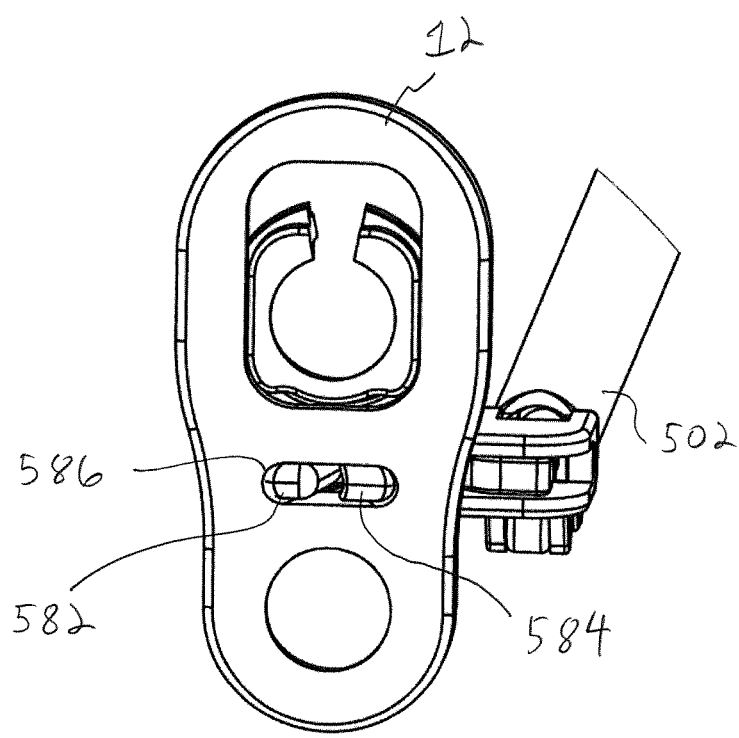

For example, the gripping portion 580 may have a plate engagement arm 582 and a fixed arm 584 sized to fit into a slot 586 of the plate member 14 (see FIGS. 11, 40, and 41). The arm 582 is operably coupled to the grip control shaft 574 by an arm linkage 590. The arm linkage 590 has one end connected to the grip control shaft 574 by a pin 592 and an opposite end connected to the arm 582 by a ball 594 and socket 596 connection, as shown in FIGS. 38 and 39.

With references to FIGS. 38 and 39, shifting the grip control shaft 574 in direction 598 toward the inserter tool proximal end portion 504 pivots the plate engagement arm 582 about a pin 600 of the pivot body 524 and brings a tip 602 of the plate engagement arm 582 toward a tip 604 of the fixed arm 584. Due to the threaded engagement between the knob 572 and the grip control shaft 574, turning the knob 572 in a clockwise direction (as viewed from behind the tool 500) would produce the movement of the grip control shaft 574 in direction 598. Conversely, turning the knob 572 counterclockwise and moving the grip control shaft 574 in direction 606 toward the inserter tool distal end portion 502 pivots the plate engagement arm 582 in an opposite direction about the pin 600 and moves the tip 602 of the plate engagement arm 582 away from the tip 604 of the plate engagement arm 584. By moving the tip 602 of the plate engagement arm 582 away from the tip 604, the arms 582, 584 can exert a compressive force against a wall 610 of the bone plate slot 586 and engage the inserter tool distal end portion 502 to the bone plate 12, shown in FIGS. 40 and 41.

Figures 42, 43:
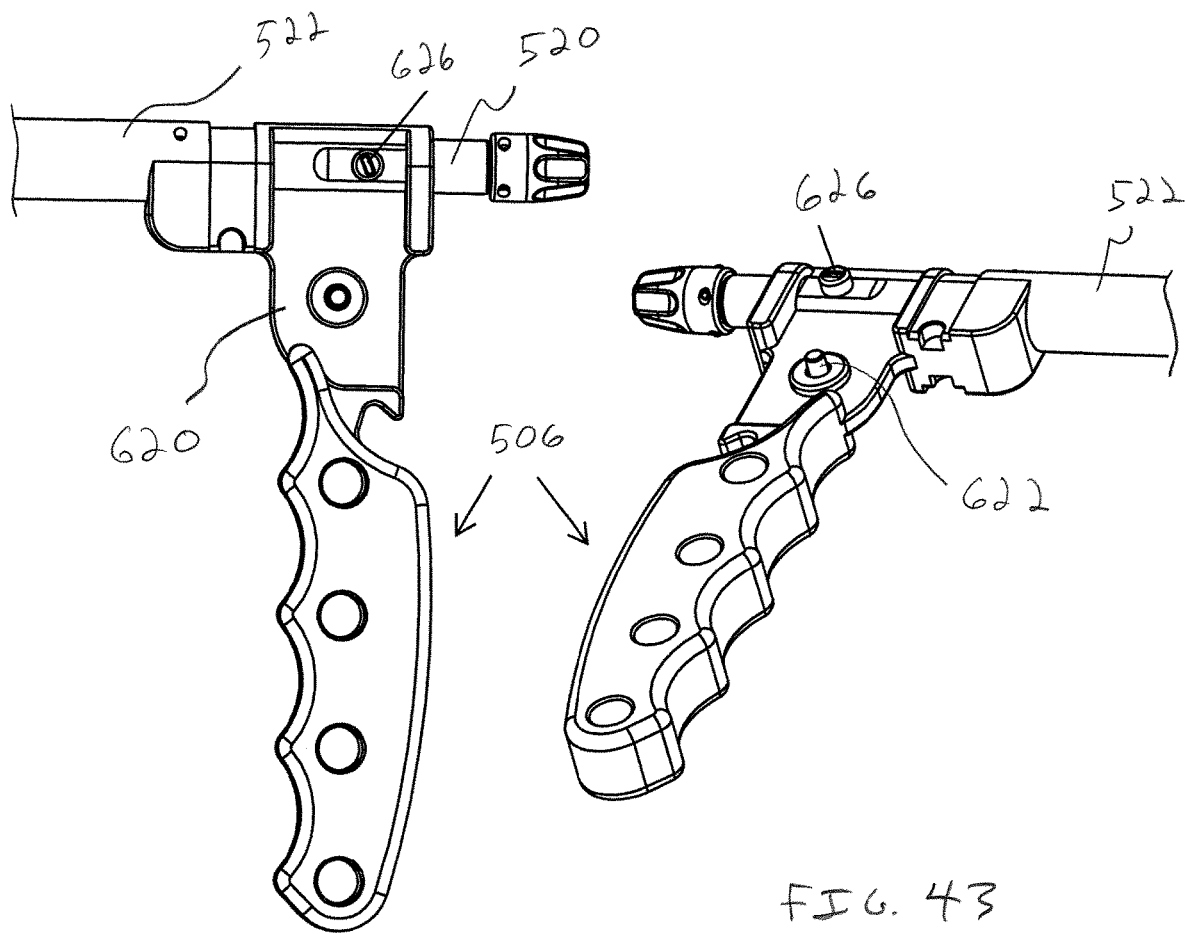
FIGS. 42 and 43 are views of the handle of the inserter tool showing an outer profile of the handle.

With reference to FIGS. 42 and 43, the handle 506 may have a recessed area 620 sized to provide clearance for the lever 508 and a lever pivot pin 622 for connecting the lever 508 to the handle 506. With the lever 508 connected to the lever pivot pin 622, a transmission end 624 of the lever 508 may be connected to a lever bolt 626 mounted on the intermediate pivot shaft 620, as shown in FIGS. 29 and 34. The transmission end 624 of the lever 508 has a slightly elongated opening 630 that is sized to permit the lever bolt 626 to travel along the opening 630. The slight elongation of the opening 630 may be desirable to accommodate the linear movement of the lever bolt 626 and the rotational, pivoting movement of the transmission end 624 of the lever 508.

The components of the inserter tool 500 may be made of various materials that preferably can be sterilized to permit cleaning of the inserter tool 500. In one form, the components are made of various metals and alloys, such as stainless steel.

Figure 44:
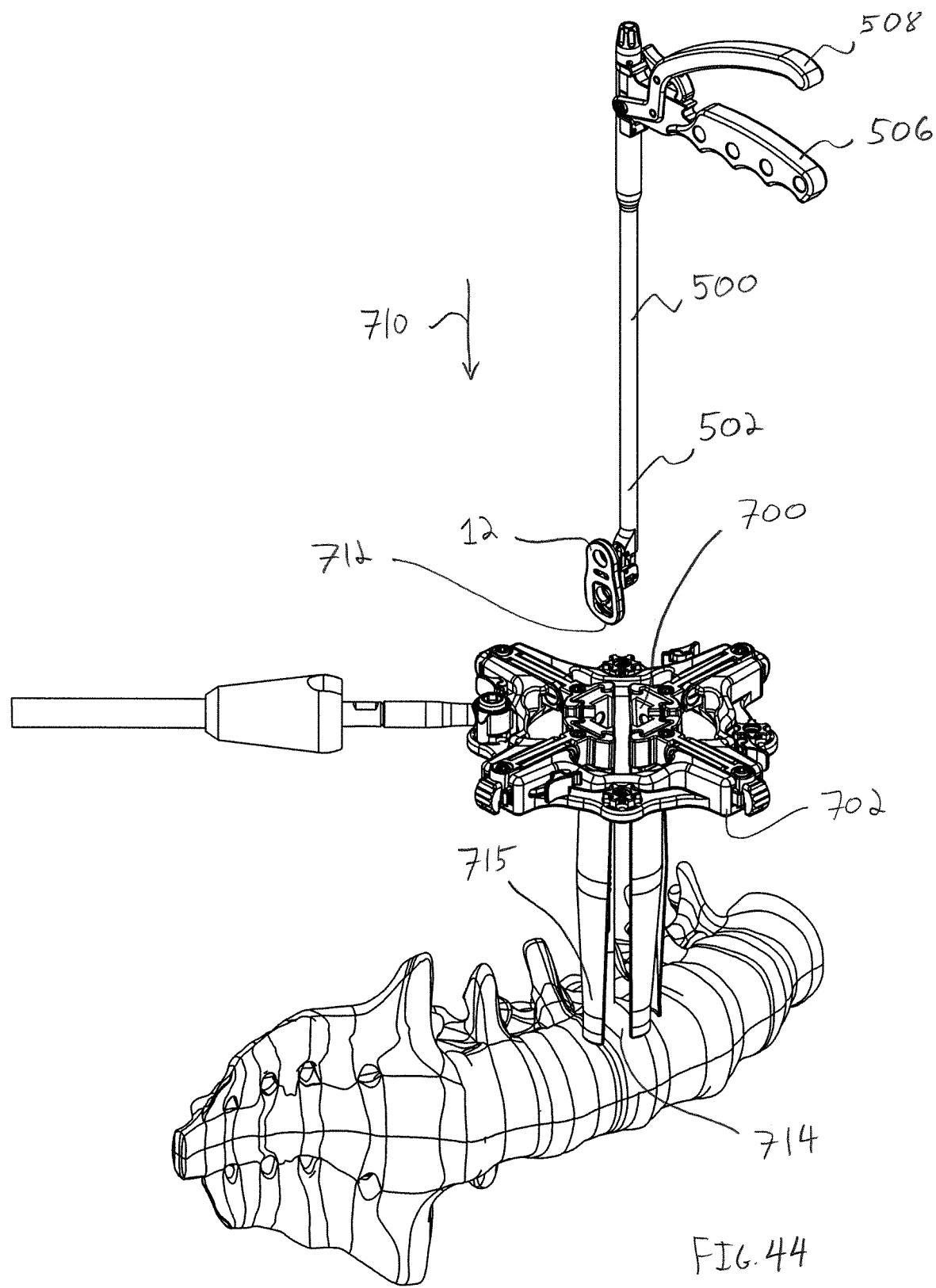
FIGS. 44-52 illustrate a method of implanting the bone plate system of FIG. 1.

With reference to FIGS. 44-52, a method of installing the bone plate system 12 including using the inserter tool 500 is shown. Initially, the distal end portion 502 of the inserter tool 500 is connected to the bone plate 12 and the implant pivot lever 508 of the inserter tool 500 is moved to the open position away from the handle 506 to orient the bone plate 12 in the insertion orientation, as shown in FIG. 44. The inserter tool 500 and connected bone plate 12 are positioned in a generally vertical orientation above a working channel 700 formed by a retractor 702. The inserter tool 500 is then moved downward in direction 710 to advance the distal end portion 502 and the bone plate 12 connected thereto into the working channel 700 until an end 712 of the bone plate 12 is adjacent a surgical site 714. In the illustrated approach, the surgical site 714 is adjacent a pair of vertebrae 720, 722 and an implant 724 therebetween (see FIG. 46).

Figure 45:
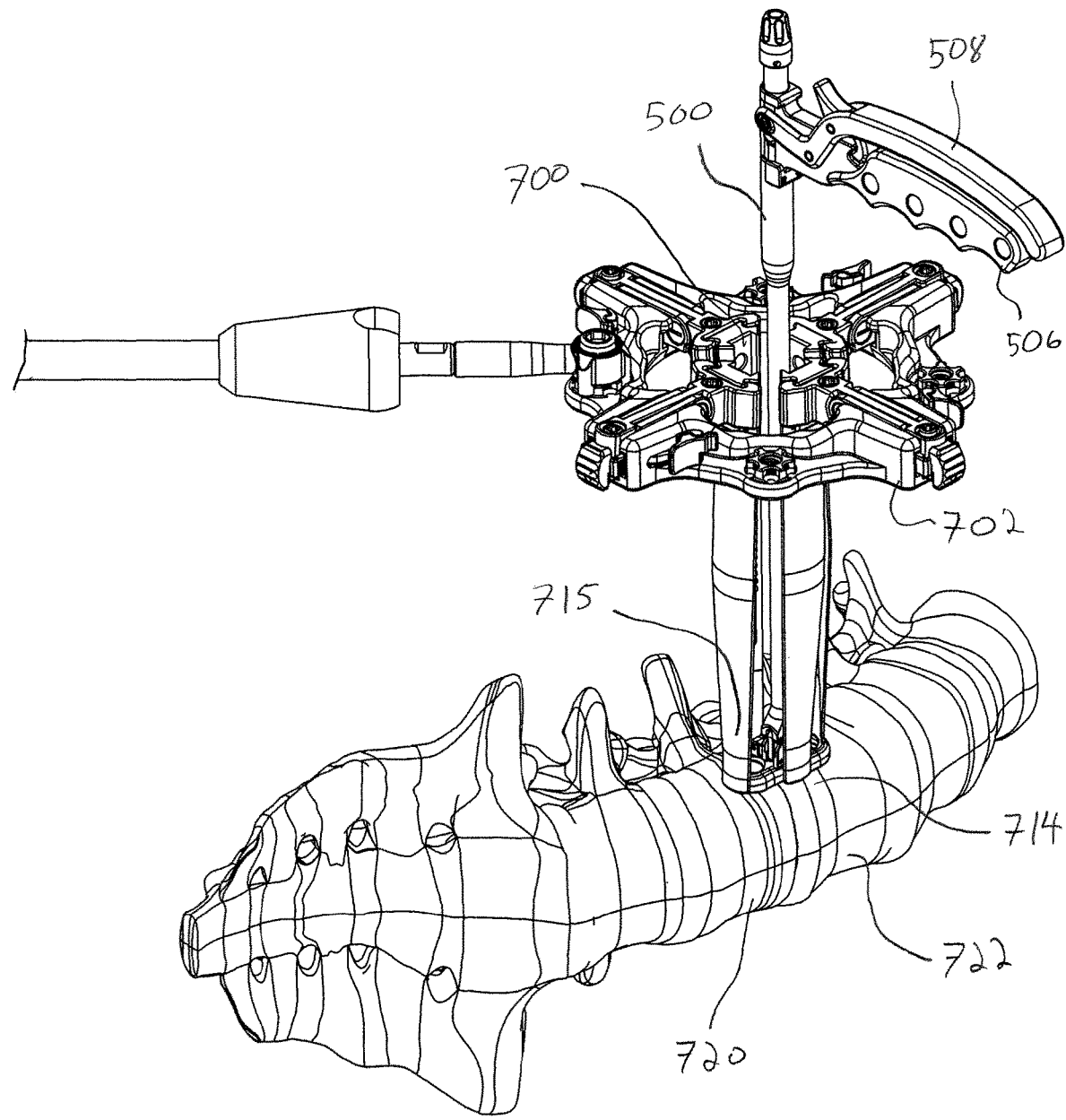
Figure 46:
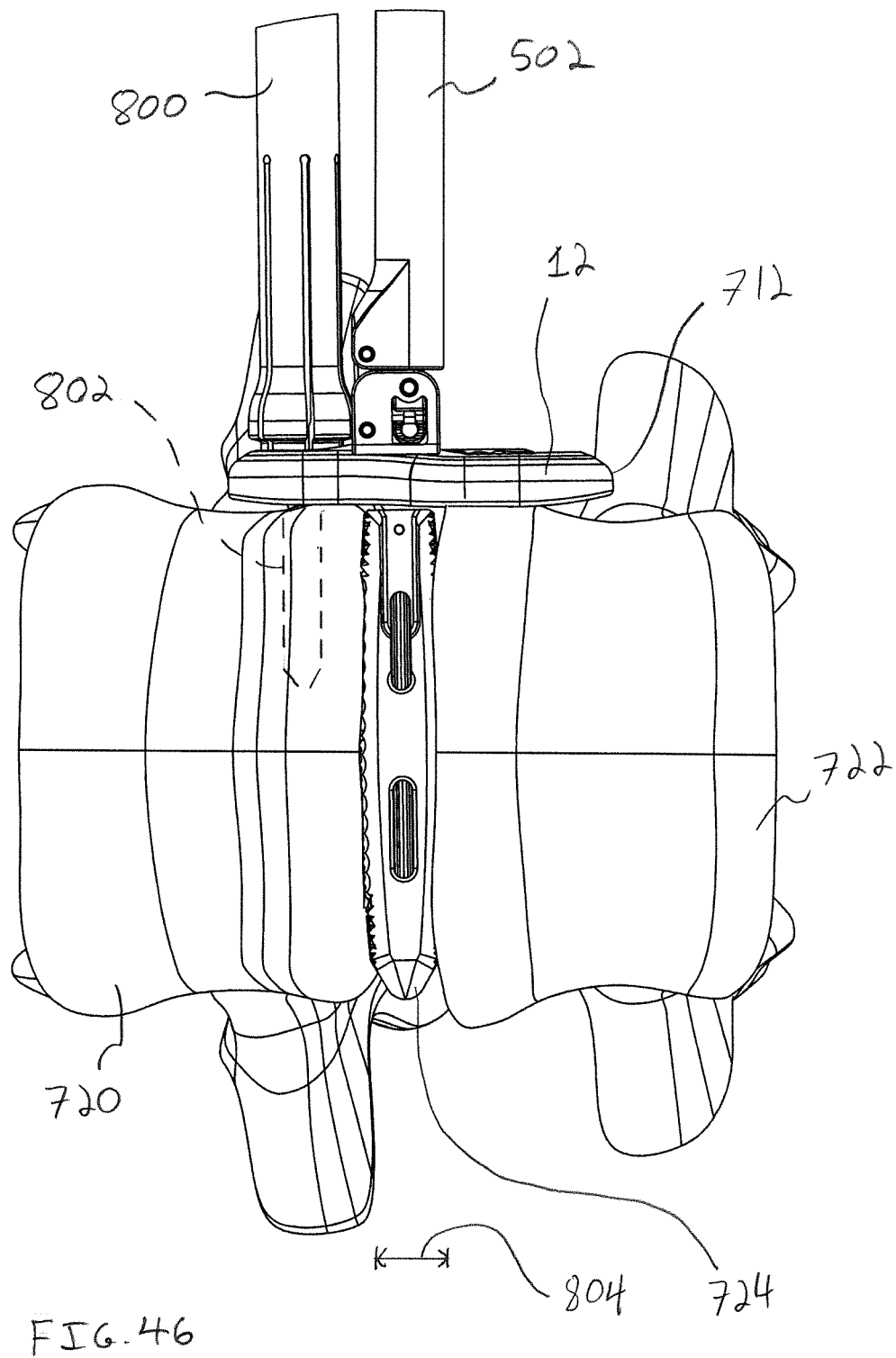

Once the end 712 of the bone plate 12 has reached the surgical site 714, the implant lever 508 is moved toward the handle 506 to pivot the bone plate 12 and move the bone plate 12 from a generally parallel orientation relative to the vertebrae 720, 722 into a generally perpendicular orientation, as shown in FIGS. 45 and 46. Further, the retractor 702 has blades with distal ends 715 that can be angled to extend generally obliquely relative to the working channel 700. This retracts the tissues adjacent the surgical site and provides room for pivoting of the bone plate 12 while maintaining a generally narrow working channel 700.

Figure 47:
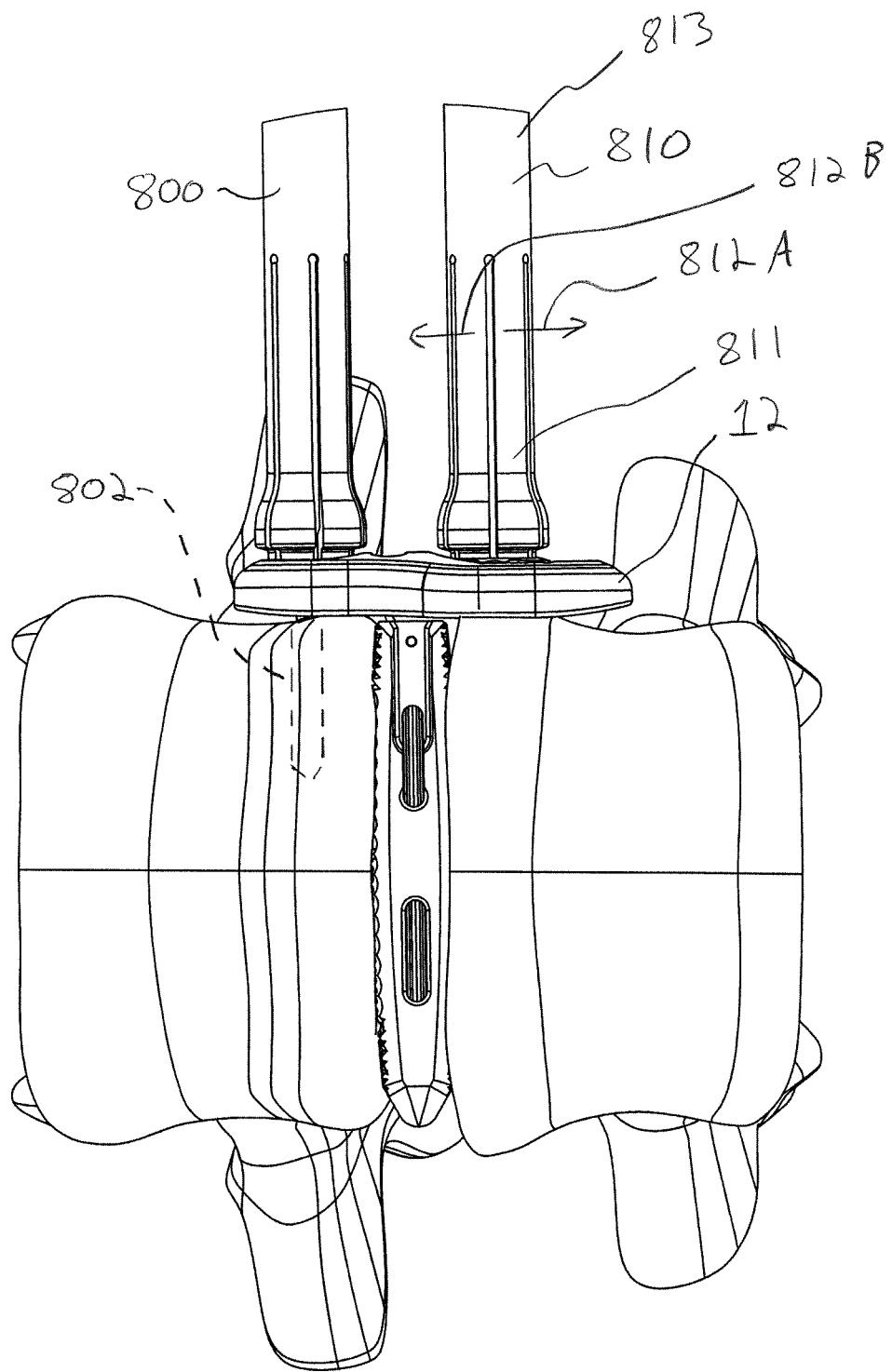

A centering sleeve 800 is then advanced through the working channel 700 and connected to the static throughbore 22 before a temporary fixation pin 802 is advanced down a cannula of the centering sleeve 800 and used to temporarily fix the bone plate 12 to the vertebrae 720. The inserter tool 500 may then be disconnected from the bone plate 12 and removed from the working channel 700. A second centering sleeve 810 is subsequently advanced through the working channel 700 to connect a distal end portion 811 of the centering sleeve 810 to the support member 16, as shown in FIG. 47. The centering sleeve 810 has a proximal portion 813 that may be manipulated by the surgeon to cause movement of the distal end portion 811 and support member 16 connected thereto. More specifically, the distal end portion 811 of the second centering sleeve 810 may be moved in direction 812A or 812B to move the support member 16 in direction 48A or 48B along axis 47 of the elongate throughbore 18 (see FIG. 11). The centering sleeve 810 preferably has a length that positions the proximal end portion 813 outside of the working channel 700 while the distal end portion 811 is connected to the support member 16 to improve the ease of manipulation of the position of the support member 16. Thus, the second centering sleeve 810 may be used to adjust the position of the support member 16 along the elongated throughbore 18 from outside of the working channel 700 and adapt the bone plate 12 to the anatomy of the patient.

For example, if the implant 724 has a relatively large thickness 804, the opening 53 of the support member 16 may not be aligned with of the vertebrae 722 when the bone plate 12 is initially pivoted to the positioning orientation shown in FIG. 46. The centering sleeve 810 can then be moved in direction 812A to move the support member 16 in direction 48A and position the support member opening 53 above the vertebrae 722.

Once the support member 16 is positioned at a desired location along the elongated throughbore 18, the second centering sleeve 810 may be removed from the working channel 700 and the drive tool 2000 connected to the bone anchor assembly 20. Connecting the driving tool 2000 to the bone anchor assembly 20 includes advancing a drive tip 2002 of the driving tool 2000 through the opening 400 of the cap drive member 34 and into engagement with the drive recess 280 (see FIGS. 18 and 26). Connecting the driving tool 2000 to the bone anchor assembly 20 may also include connecting the retention shaft 2004 of the tool 2000 with retention threads 284 of the bone screw 46, as shown in FIG. 48. The driving tool 2000, with the bone anchor assembly 20 connected thereto, can then be advanced through the working channel 700 and to advance a shank 725 of the bone screw 26 into the support member opening 53. (It is noted that vertebrae 720, 722 and implant 724 are removed from FIGS. 48-52 for clarity purposes.) The driving tool 2000 is then used to drive the bone anchor 26 into the underlying vertebrae 722, as shown in FIG. 49.

Figure 49:
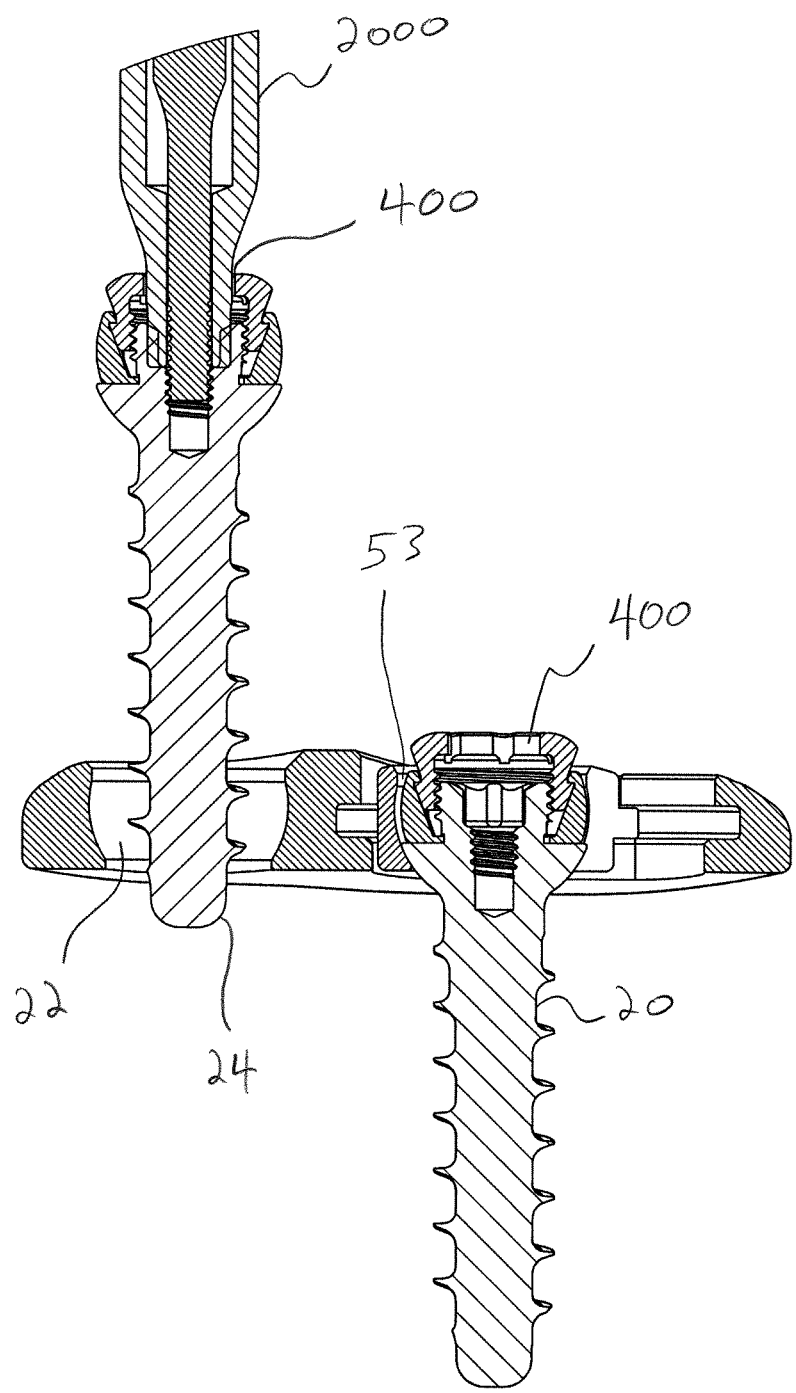
Figure 50:
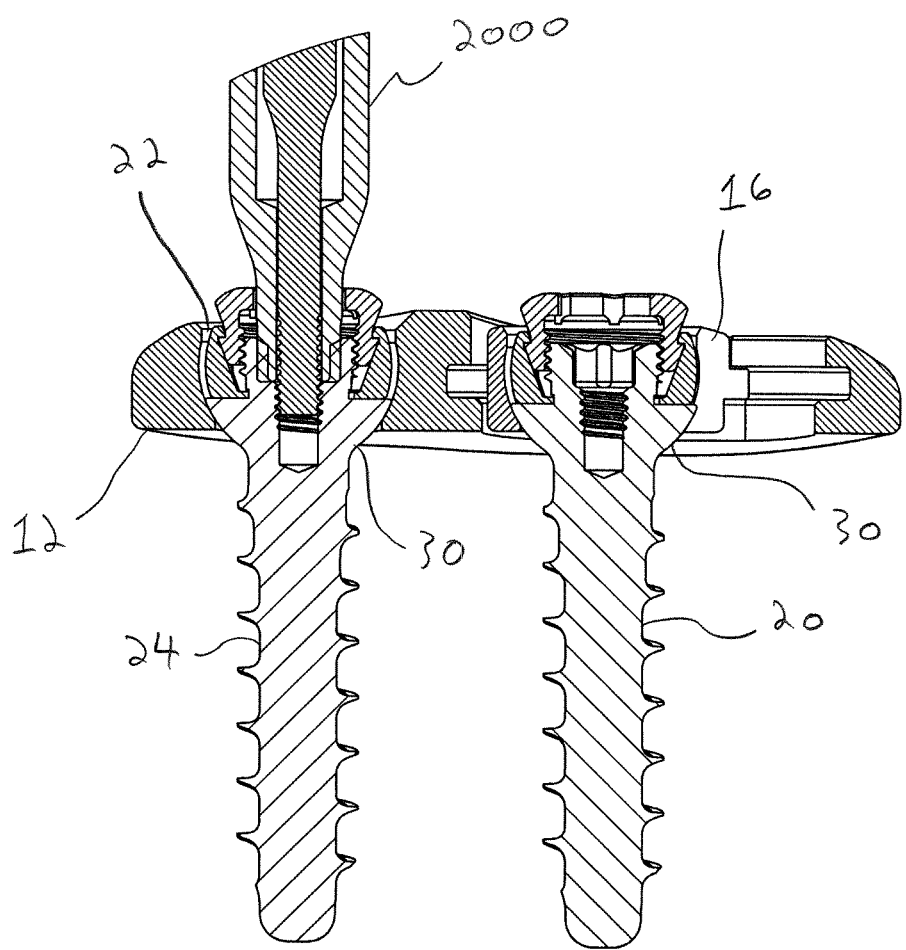

Next, the drive tool 2000 is used to drive the bone anchor assembly 24 into the fixed throughbore 22 using a similar approach taken with respect to bone anchor 20, as shown in FIGS. 49 and 50. With the bone screws 26 of the bone anchor assemblies 20, 24 holding the bone plate 12 against the vertebrae 720, 722, a final tightener 3002 is advanced into the opening 400 of the cap drive member 34 of the bone anchor assembly 24 (see FIG. 26) and turned in direction 737 to shift the cap drive member 34 to the locked position. Turning of the final tightener 3002 and the resulting movement of the cap drive member 34 toward its locked position causes the cap drive member 34 to expand the locking cap 36. This tightly engages the locking cap 36 with the seating surface 120 of the throughbore 22.

The locking tool 3000 is then advanced into the opening 400 of the cap drive member 34 of the bone anchor assembly 20 and turned to move the cap drive member 34 toward the locked position. This expands the locking cap 36 of the bone anchor assembly 20 and tightly engages the locking cap 36 with the seating surface 103 of the support member 16. This shifts the portions 70, 72 of the support member 16 apart in directions 76, 78 against the throughbore walls 80, 82 (see FIG. 7) and thereby fixes the position of the support member 16 along the elongated throughbore 18. Further, because the cap drive member 34 is threadingly engaged with the bone screw head 30, shifting the cap drive member 34 to the locked position tightly engages the cap drive member 34 to the head 30 as well as the locking cap 36 therebetween. In this manner, the bone anchor assembly 20 is firmly engaged with the support member 16 which is in turn firmly engaged to the plate member 14 at the desired location along the throughbore 18.

Figure 54:
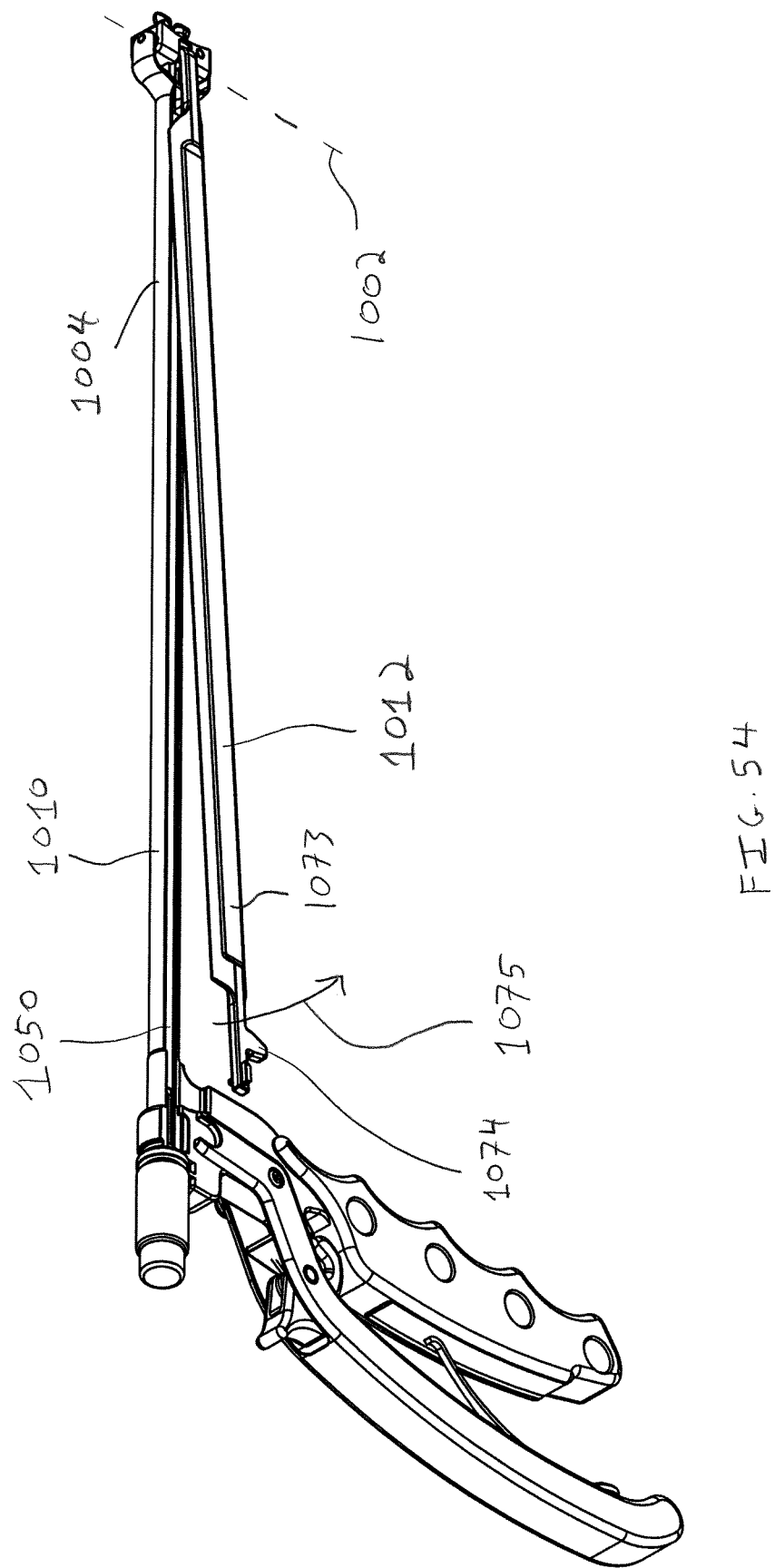
FIG. 54 is right side perspective view of the inserter tool of FIG. 53 showing the inserter tool partially disassembled including a pivot sleeve of the inserter tool disconnected from a lever of the tool and pivoted away from a shaft of the inserter tool.

With respect to FIGS. 53-61, an inserter tool 1000 is provided for positioning the bone plate 12 near one or more bones. The inserter tool 1000 is substantially similar to the inserter tool 500 described above such that the differences between the inserter tools 500, 1000 will be highlighted. One difference between the inserter tools 500, 1000 is that the inserter tool 1000 has components that can be partially disassembled and pivoted generally about an axis 1002 at a distal end 1004 of the inserter tool 1000, as shown in FIG. 54. The ability to partially disassemble and pivot the components of the inserter tool 1000 allows the inserter tool 1000 to be cleaned without complete disassembly of the tool 1000.

More specifically, the inserter tool 1000 has an outer body shaft 1010 and a partial pivot sleeve 1012 for controlling pivoting of a pivot body 1014. The distal end of the pivot sleeve 1012 is connected to the pivot body 1014 at a pin 1030 so that translational movement of the pivot sleeve 1012 produces pivoting of the pivot body 1014. The inserter tool 1000 has a lever 1016 connected to the pivot sleeve 1012 for controlling pivoting of a pivot body 1014 at the distal end 1004 of the inserter tool 1000. Moving the pivot lever 1016 toward a handle 1018 of the inserter tool 1000 shifts the pivot sleeve 1012 in direction 1020 toward a proximal end 1019 of the inserter tool 1000 and pivots the pivot body 1014 about a pin 1022. A spring 1019 may bias the handle 1018 toward an open position to limit unintentional pivoting of the pivot body 1014 and bone plate 12 connected thereto.

Figure 55:
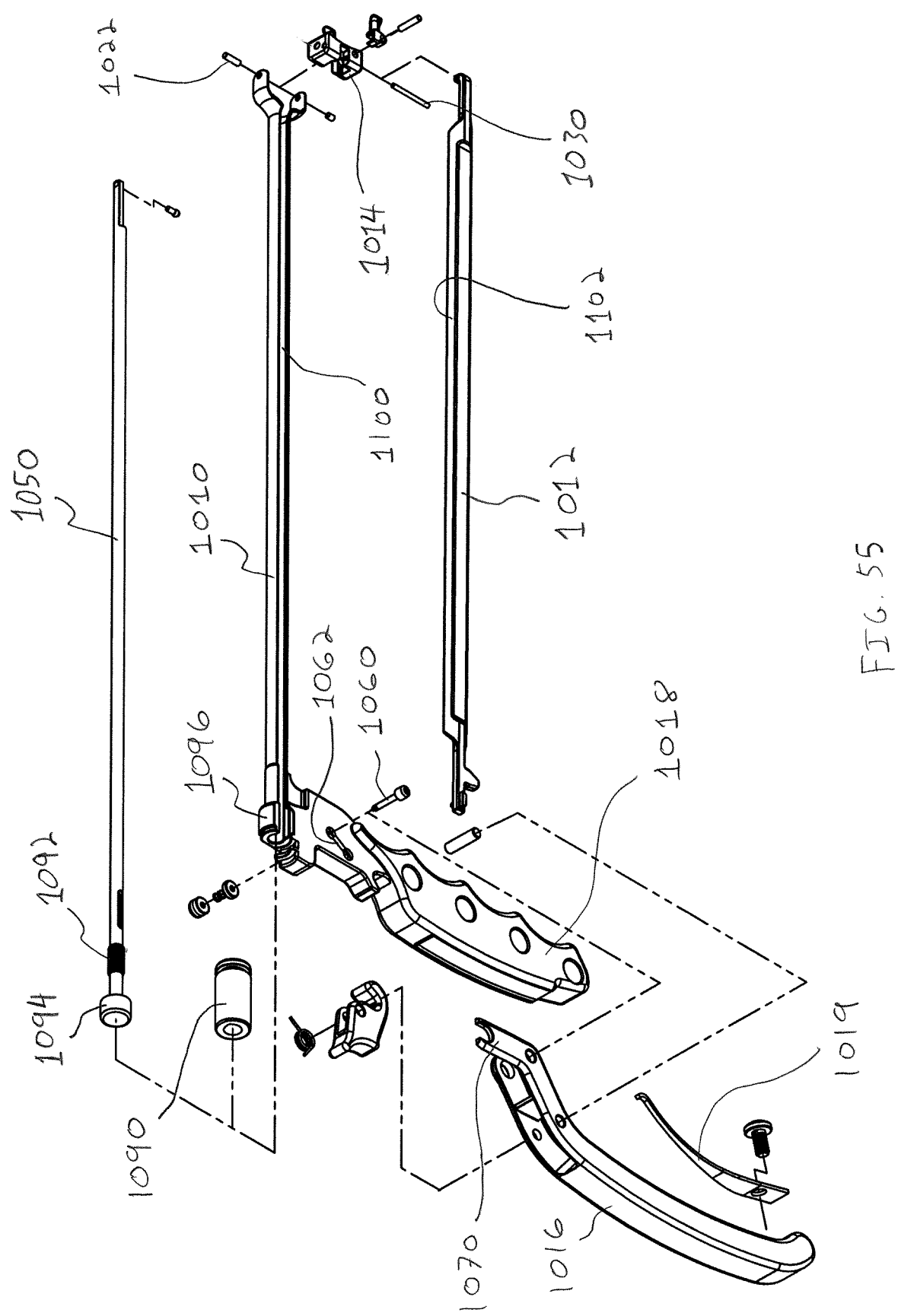
FIG. 55 is an exploded schematic view of the inserter tool of FIG. 53 showing a body shaft, the pivot sleeve, and a pivot control shaft of the inserter tool.
Figure 56:
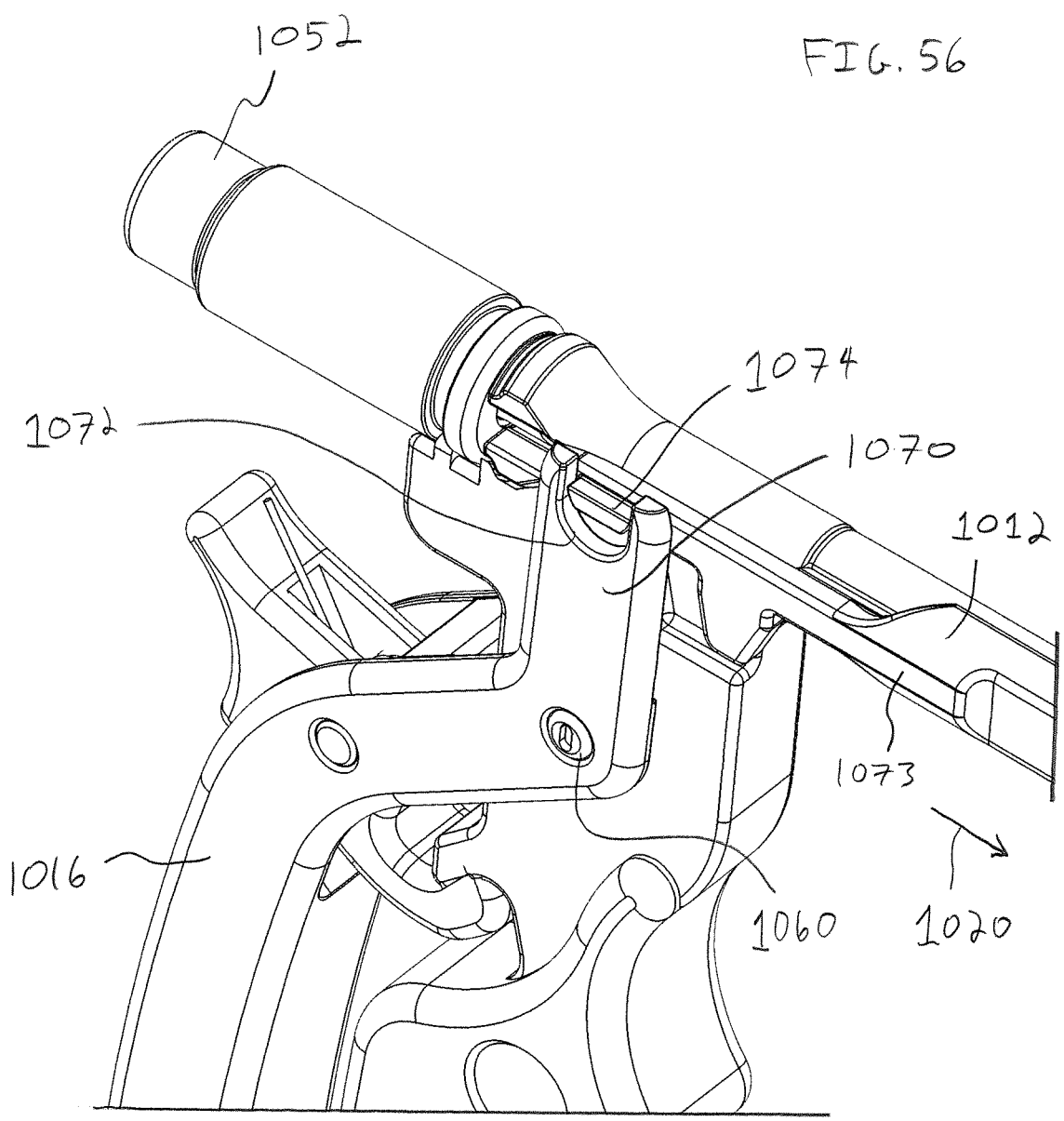
FIG. 56 is an enlarged right side perspective view of the inserter tool of FIG. 53 showing the pivot sleeve connected to the lever.
Figure 57:
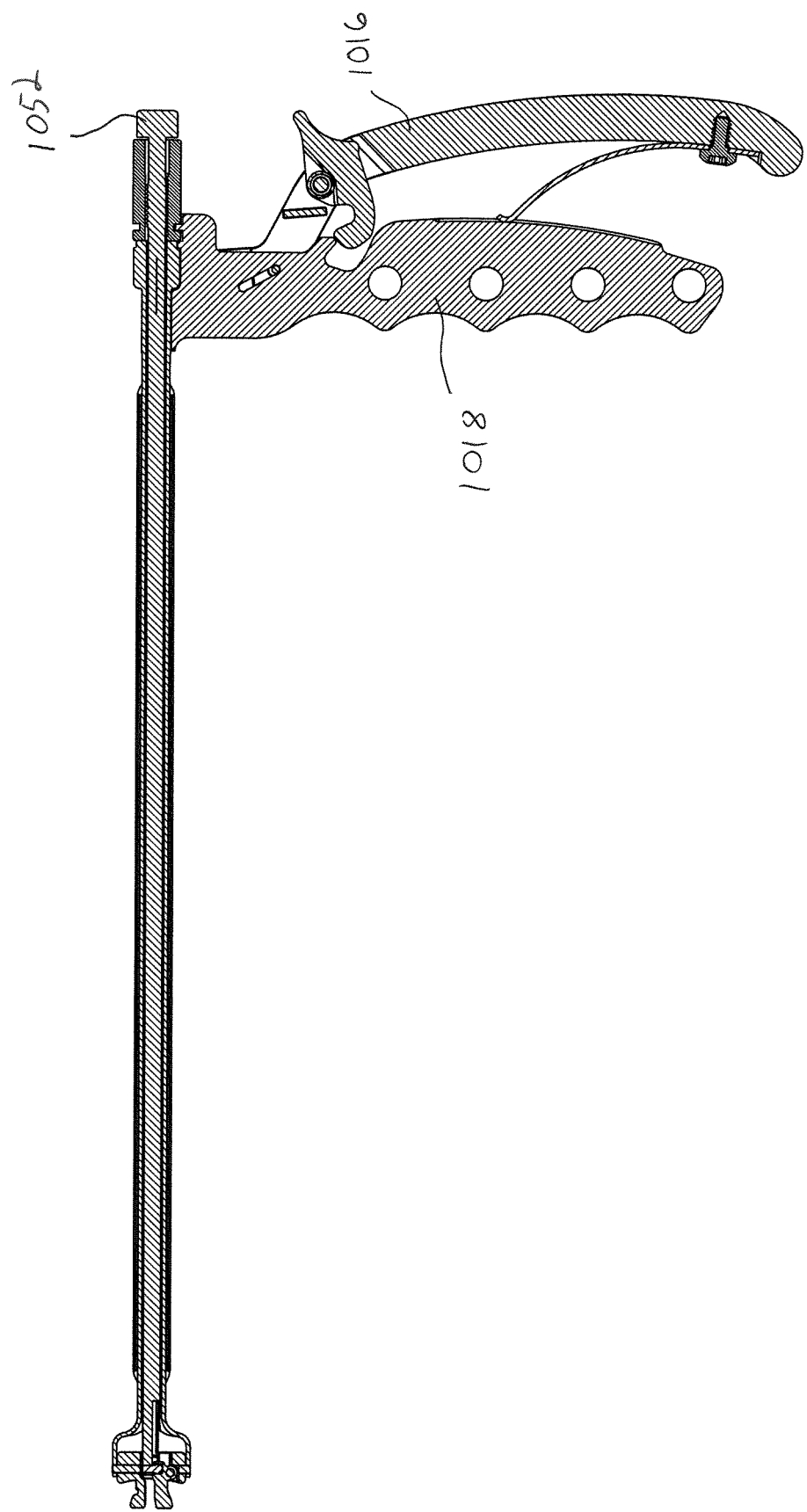
FIG. 57 is a cross-sectional view of the inserter tool of FIG. 53 showing a lever of the inserter tool in an open position.
Figure 58:
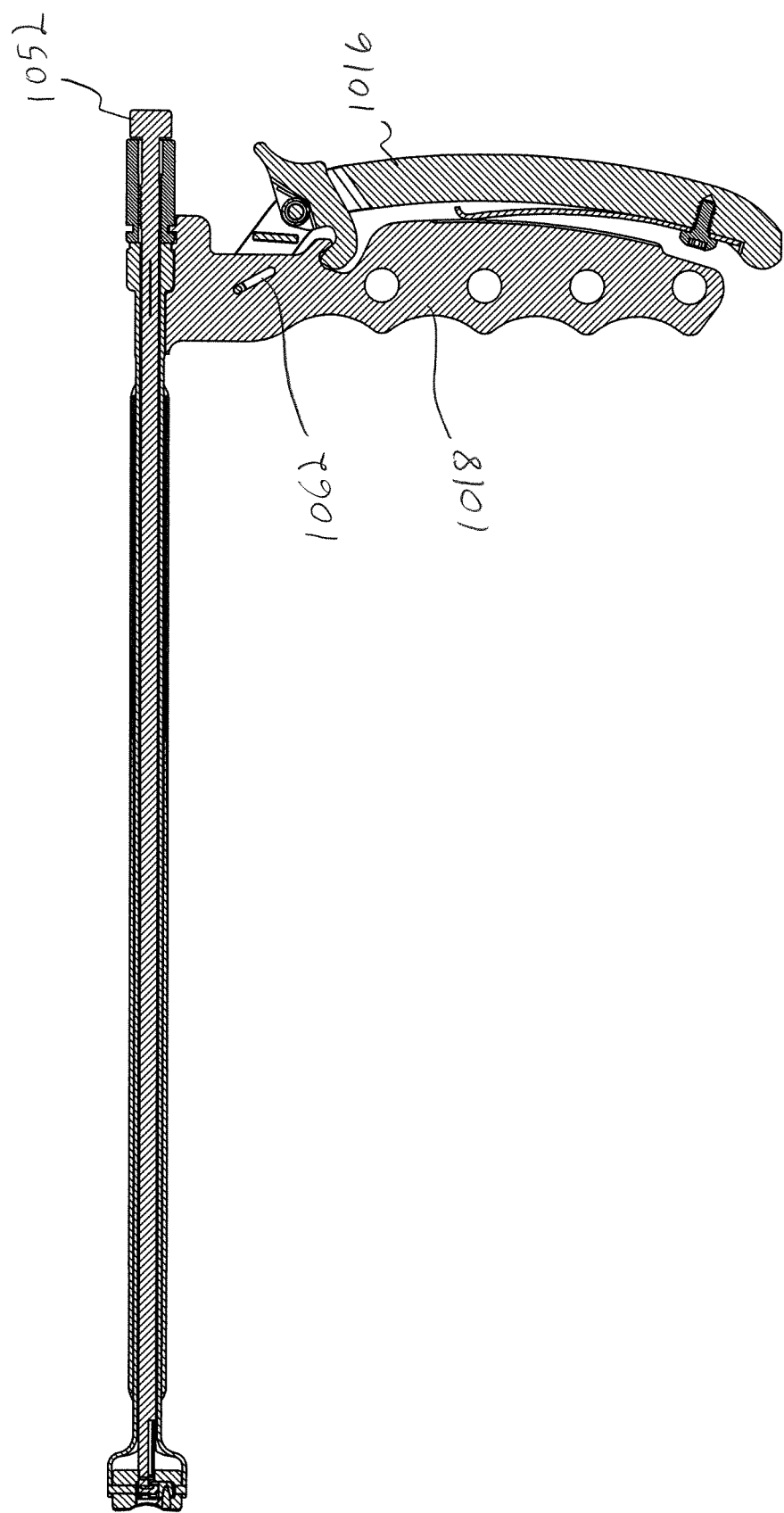
FIG. 58 is a cross-sectional view similar to FIG. 57 showing the lever in a closed position.
Figure 59:
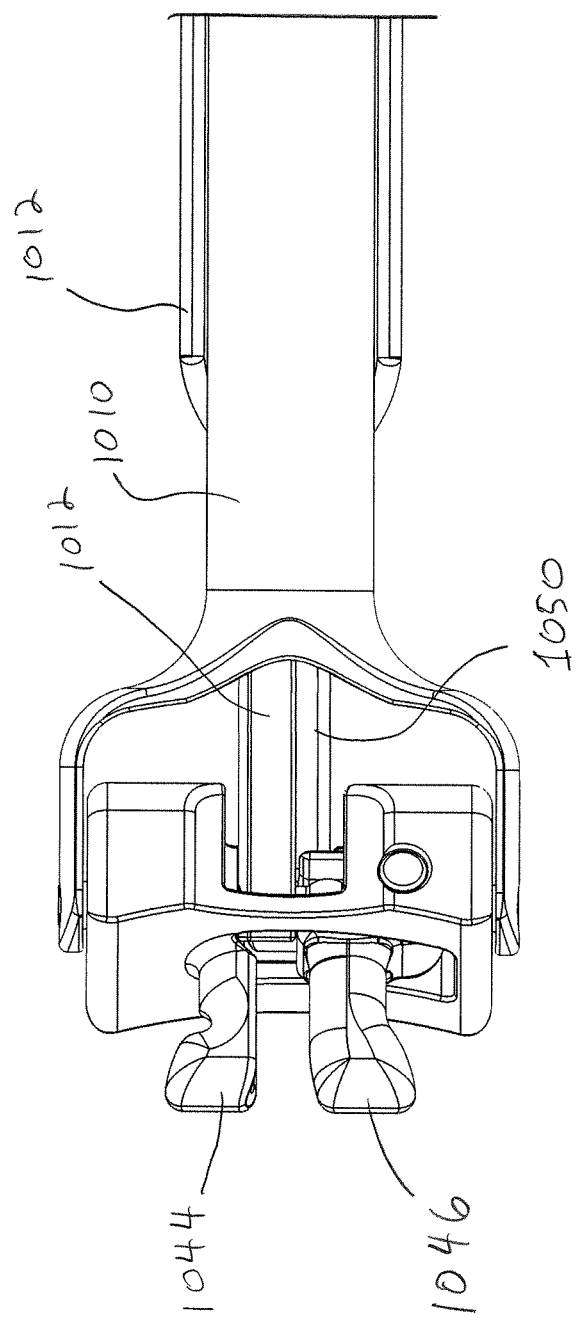
FIGS. 59 and 60 are enlarged, elevational views of different sides of the inserter tool of FIG. 53 showing arms of the body shaft which support a pivot body of the distal end of the inserter tool.
Figure 60:
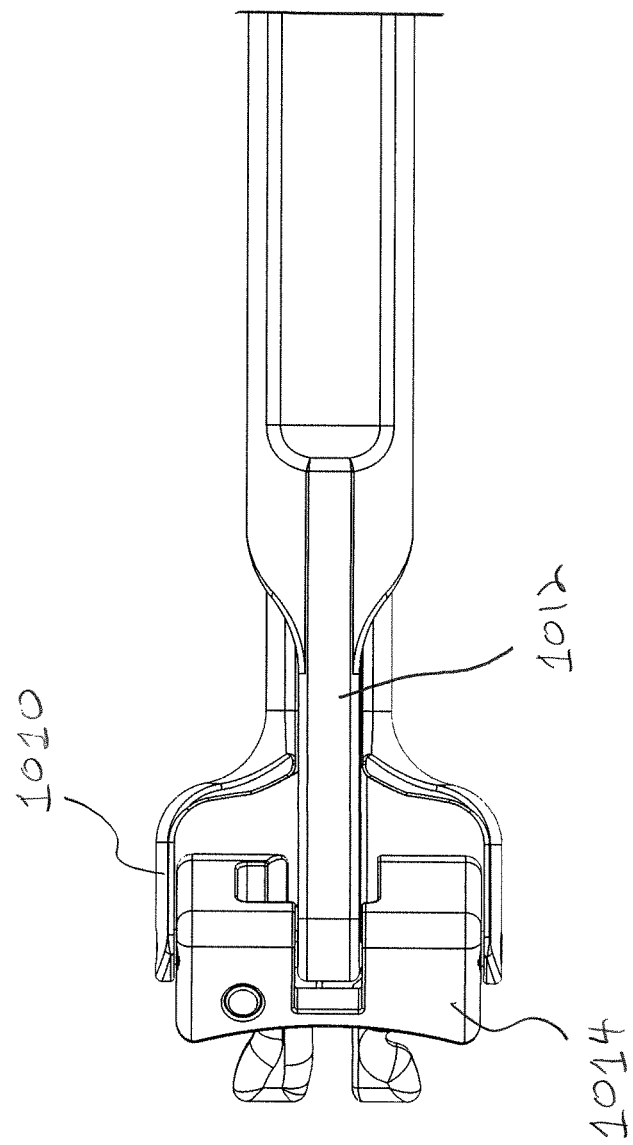
Figure 61:
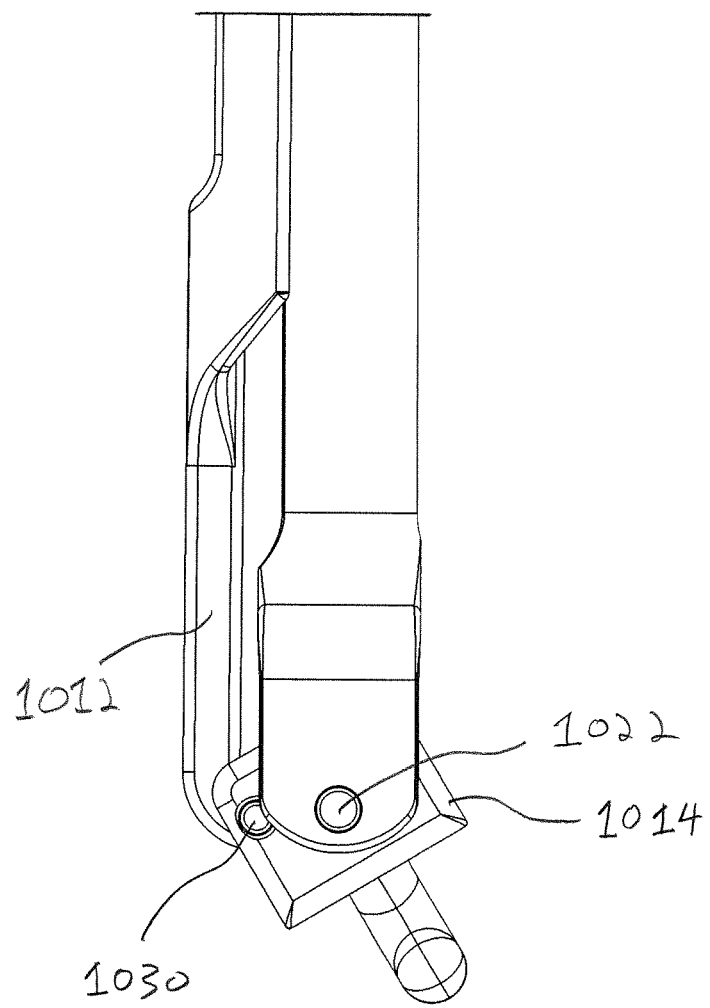
FIG. 61 is an enlarged plan view of the distal end of the inserter showing the pivot body pivoted relative to the body shaft.
Figure 62:
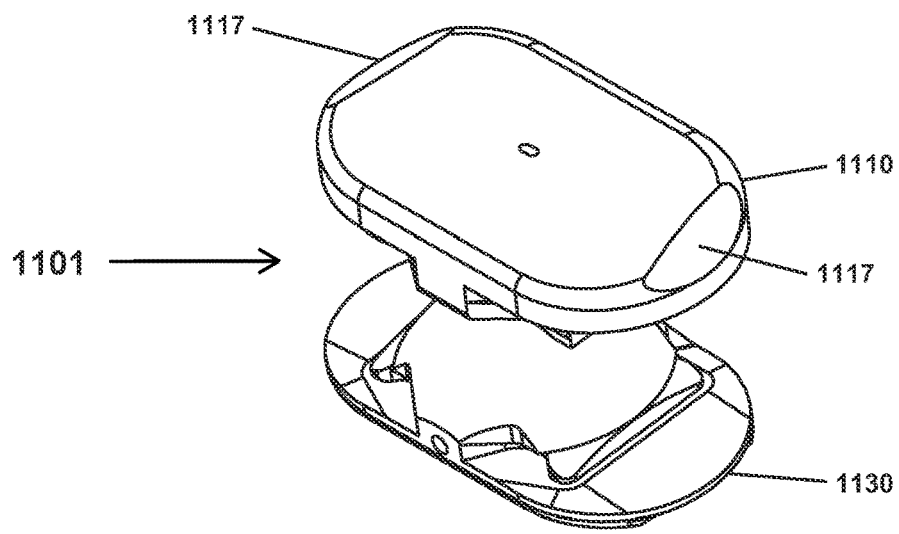
FIG. 62 is an exploded perspective view of a spinal nucleus replacement device having top and bottom shells in accordance with another aspect of the present invention.

The lever 1016 is connected to the handle 1018 by a pin 1060 received within a slot 1062 of the handle 1018 (see FIGS. 55, 57). The lever 1016 has a transmission end 1070 with a recess 1072 sized to receive a tab 1074 of the pivot sleeve 1012, as shown in FIG. 56. The tab 1074 of the pivot sleeve 1012 rides in the recess 1072 during back and forth movement of the pivot sleeve 1012. During disassembly of the inserter tool 1000, the lever 1016 can be shifted in direction 1064 (see FIG. 53) to disengage the transmission end 1070 of the lever 1016 from the tab 1074 of the pivot sleeve 1012. With the lever transmission end 1070 disengaged from the pivot sleeve 1012, a proximal end 1073 of the pivot sleeve 1012 can be pivoted in direction 1075 away from the pivot body 1014, as shown in FIG. 54. Pivoting the pivot sleeve 1012 in direction 1075 moves the pivot sleeve 1012 about the pin 1030 which connects the pivot sleeve 1012 to the pivot body 1014.

Another difference between the inserter tools 500, 1000 is that the inserter tool 1000 has a grip control shaft 1050 and a grip adjustment member 1090 engaged with threads 1092 of the grip control shaft 1050. The grip adjustment member 1090 is captured by the threads 1092 between an enlarged knob 1094 of the grip control shaft 1050 and a collar 1096 of the body shaft 1010. The grip adjustment member 1090 is turned clockwise or counterclockwise to produce proximal or distal longitudinal movement of the grip control shaft 1050 by way of the engagement between internal threads of the grip adjustment member 1090 and the threads 1092 on the grip control shaft 1050.

During disassembly, the knob 1094 is turned ninety degrees clockwise to rotate a foot 1095 of the grip control shaft 1050 into a recess 1097 of the pivot body 1014 (see FIGS. 55 and 57). The grip adjustment member 1090 is then turned to produce longitudinal movement of the grip control shaft 1050 toward the proximal end of the inserter tool 1000 until the threads 1092 of the grip control shaft 1050 disengage the internal threads of the grip adjustment member 1090. Next, the knob 1094 is grasped and pulled in direction 1099 (see FIG. 54) to withdraw the grip control shaft 1050 from within the outer body shaft 1010. At this point, the pivot sleeve 1012 is pivoted away from the outer body shaft 1010 and the grip control shaft 1050 has been withdrawn from the outer body shaft 101. Because both the pivot sleeve 1012 and grip control shaft 1050 are separated from the body shaft 1010, the surfaces of the body shaft 1010, pivot sleeve 1012, and grip control shaft 1050 may be easily accessed and cleaned. Further, as shown in FIG. 55, the body shaft 1010 has a generally C-shaped cross section with an opening 1100 along one side thereof and the pivot shaft 1012 has a generally U-shaped cross section with an opening 1102 along one side thereof. The cross sections of the body shaft 1010 and the pivot shaft 1012 provide ready access to the internal surfaces of the body shaft 1010 and the pivot shaft 1012 so that the internal surfaces may be easily cleaned.

One form of the invention includes a device for positioning an intervertebral spacer between adjacent vertebral members. FIG. 74B illustrates one embodiment of an implant insertion instrument 2100 movably attached to intervertebral spacer 1101. Spacer 1101 is positioned between adjacent vertebrae and is selectively adjustable between an orientation wherein the longitudinal axis 1L of spacer 1101 is generally aligned with longitudinal axis L of instrument 1200 to an orientation wherein axis 1L is generally transverse to instrument axis L, and graduations therebetween. Instrument 2100 allows the surgeon to manipulate, and release the implant at any of the desired orientations.

FIGS. 62-68 illustrate one embodiment of an intervertebral spacer, in particular a two-piece articulating spinal nucleus replacement device (NRD) according to the present invention. The NRD 1101 comprises a top shell 1110 and a bottom shell 1130. Top shell 1110 has at least one inner concave articulating surface 1111 with a radius of curvature, and bottom shell 1130 has at least one inner convex articulating surface 1131 with a radius of curvature. Inner articulating surfaces of shells 1110, 1130 once implanted, interact to mimic the natural motion of the spine. Both shells comprise bodies including outer vertebral engaging surfaces 1112, 1132 configured to slidingly engage the surface of an endplate of a vertebral body while allowing the implant to translate relative thereto. It should be noted the arrangement of top and bottom shells 1110, 1130 could be reversed such that the top or superior shell 1110 could be placed inferior to shell 1130. Opposing ends of implant bodies 1110, 1130 comprise entry surfaces 1117, 1137 configured to reduce insertion forces upon entry into the nuclear space. Entry surfaces 1117, 1137 may take the form of radiused or tapered ends. The tapered ends ease the introduction of the implant into the nuclear space. The implant insertion instruments 1200, 2200 may also be configured to hold the implant in a wedge configuration as will be described below to help further reduce the insertion force upon entry of the implant into the nuclear space.

Both top and bottom shells 1110, 1130 have one or more instrument engaging portions. The lower shell 1130 comprises instrument engaging portions 1133-1136, while upper shell 1110 comprises instrument engaging portions 1113-1116. The location, shape and configuration of engaging portions 1113-1116 of top shell 1110 are substantially equivalent. Engagement portions 1133-1136 of shell 1130 are also substantially equivalent, but differ from that of portions 1113-1116. While engagement portions of the individual shells may be equivalent, it should be understood that other arrangements may be contemplated. The engaging portions of both shells are generally located between the inner facing surfaces of the upper and lower shells 1110, 1130, and are formed recessed within bearing surfaces 1131, 1111 located on lateral sides generally opposite one another along the outer proximity of the bearing surfaces. The location and configuration of recesses 1133-1136, 1113-1116 do not interrupt the contour of the bearing surfaces and therefore do not interfere with the polyaxial articulation of the top and bottom shells 1110, 1130. Accordingly, the bearing surfaces 1111, 1131 provide consistent smooth surface contact between the top and bottom shells which helps reduce wear debris. The configuration of clamping fingers 1141-1144 of one embodiment of the insertion tool residing within the recesses of the bearing surfaces allows for the exterior surfaces of the clamping fingers to remain within side walls 1120, 1121 of implant 1101, providing a preferred arrangement for minimally invasive insertion. In other words, when the clamping fingers 1141-1144 are operably engaged within the tool engaging recessed portions 1113-1116, 1133-1136, the outer surfaces of the fingers 1141-1144 will not project beyond the side walls 1120 and 1121 of the implant 1101. Engaging portions 1113-1116, 1133-1136 generally are in the form of an undercut that creates a shelf with a pocket or recess comprising top portions 1110T, 1130T, and bottom portions 1110B, 1130B having heights 1110H, 130H therebetween. The top and bottom portions of the implant engaging recesses are designed to cooperate with the superior and inferior surfaces of implant clamping fingers 1141-1144 for capturing and retaining the substantially flat implant clamping fingers of insertion instrument 1200, 2200 therein.

Figure 69:
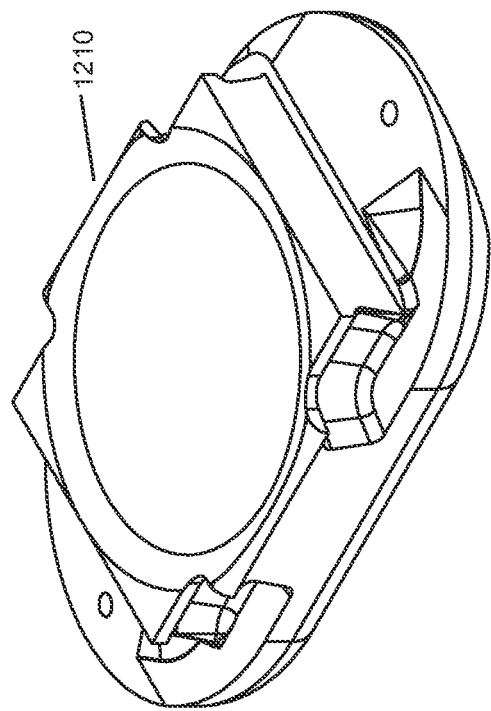
FIG. 69 is a perspective view of an alternative embodiment of the top shell of a spinal nucleus replacement device according to the present invention.
Figure 71:
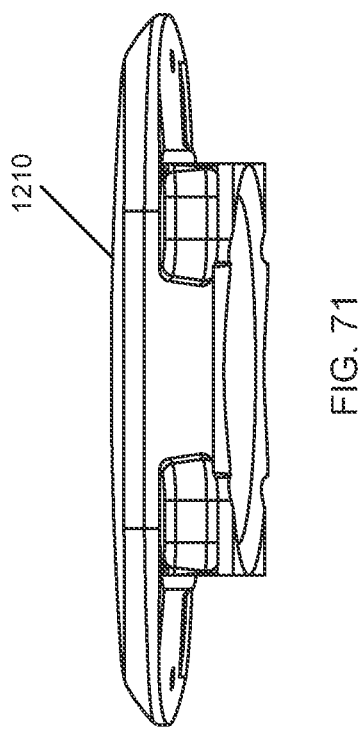
FIG. 71 is a side view of the top shell of the spinal nucleus replacement device of FIG. 69.

The instrument engagement portions of both shells 1110, 1130 of the present invention are similar with the exception of the relative height of the recesses. As best seen in FIG. 69, the recesses have an inner configuration to compliment that of implant clamping fingers 1141-1144; in the case of the present invention the inner recess surfaces have an arcuate configuration comprising a radius that is substantially equal to that of the radius of the inwardly facing surfaces of clamping fingers 1141-1144. Optionally, the geometries of the clamping fingers and engaging portions employed could be any of a variety of shapes.

Figure 63:
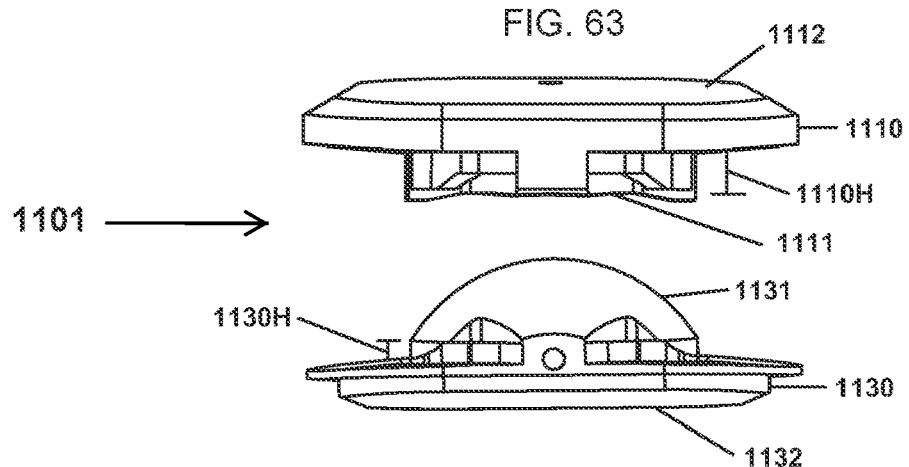
FIG. 63 is an exploded elevation view of the spinal nucleus replacement device of FIG. 62.

As shown in FIG. 63, the relative height 1130H of recesses 1133-1136 formed in lower shell 1130 are consistent throughout. Heights 1110H, 1130H are preferably slightly larger than the thickness of implant clamping fingers 1141-1144. Upper shell 1110 comprises recesses 1113-1116 which include height 1110H, 1110H2 and transition zone 1118. Height 1110H is substantially equivalent to height 1130H of lower shell 1130. Transition zone 1118, in the form of a radius or angle, makes the transition from height 1110H to substantially greater height 1110H2 disposed adjacent the outer perimeter of articulating surface 1111. The arrangement of varying heights with a transition zone allows the surgeon to manually urge the distal ends of the top and bottom shells closer together causing clamping fingers 1141, 1144 to travel inferiorly within their corresponding recesses of the upper shell. The proximal end of upper shell 10 may be shifted and held at different locations within recesses 13-16, including a position wherein the inferior portion of clamping fingers 1141, 1144 contact the inferior portion of height 1110H2 in recesses 1113-1116 near the outer proximity of bearing surface 1112. The urging of the distal end of shell 1110 inferiorly toward that of firmly held lower shell 1130 results in upper shell 1110 being held at an angle with respect to lower shell 1130 with their respective longitudinal axes at an oblique angle to each other such that the distal ends of the upper and lower shells are positioned more closely together thus giving the implant a wedge configuration for promoting ease of insertion of the implant.

Figure 64:
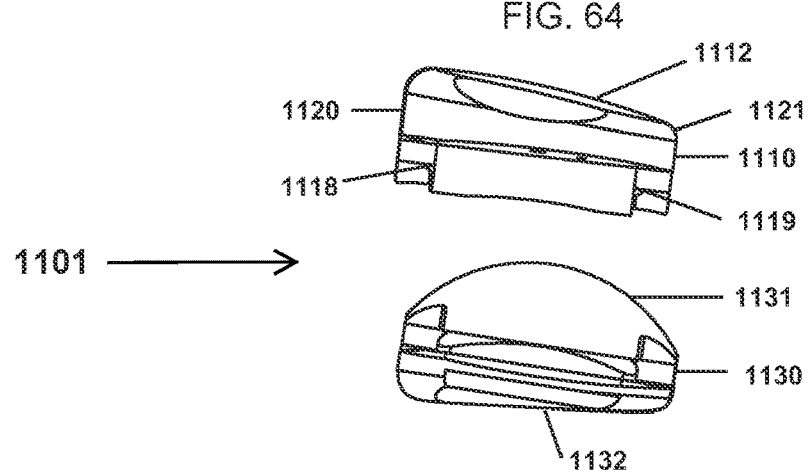
FIG. 64 is an exploded end view of the spinal nucleus replacement device of FIG. 62.
Figure 66:
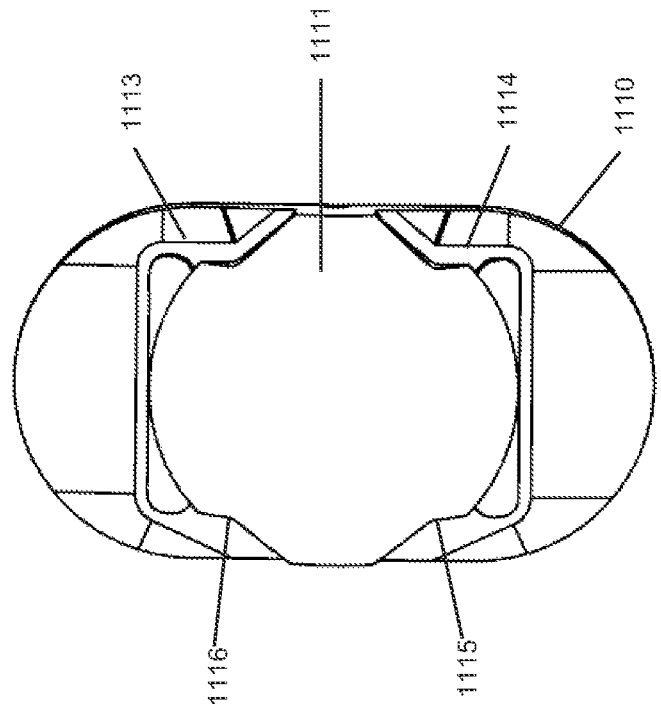
FIG. 66 is a plan view of the bottom shell of the spinal nucleus replacement device of FIG. 62.
Figure 65:
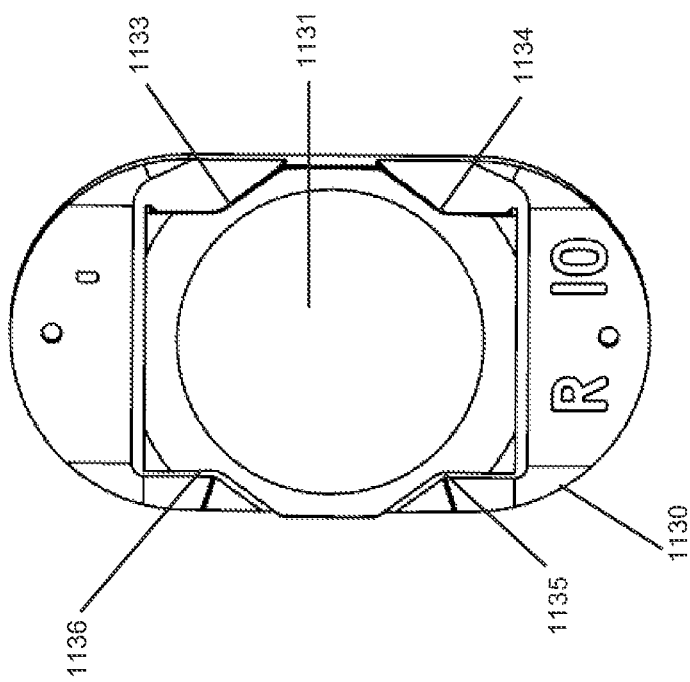
FIG. 65 is a plan view of the top shell of the spinal nucleus replacement device of FIG. 62.
Figure 67:
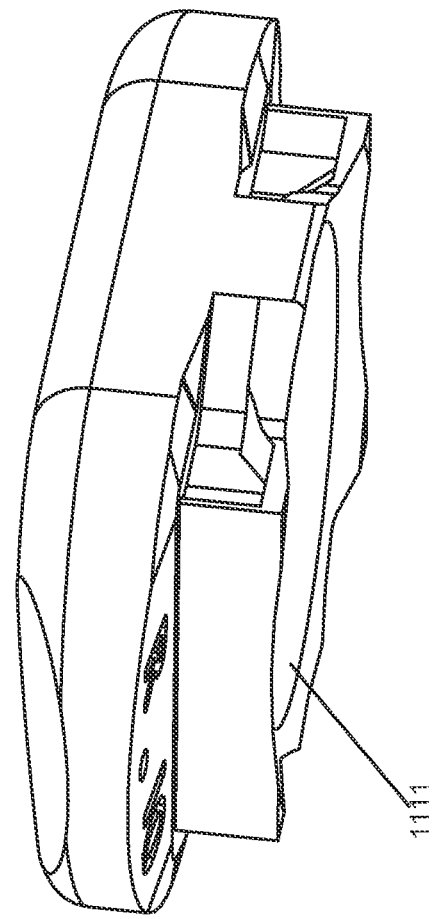
FIG. 67 is a perspective view of the top shell of the spinal nucleus replacement device of FIG. 62.
Figure 68:
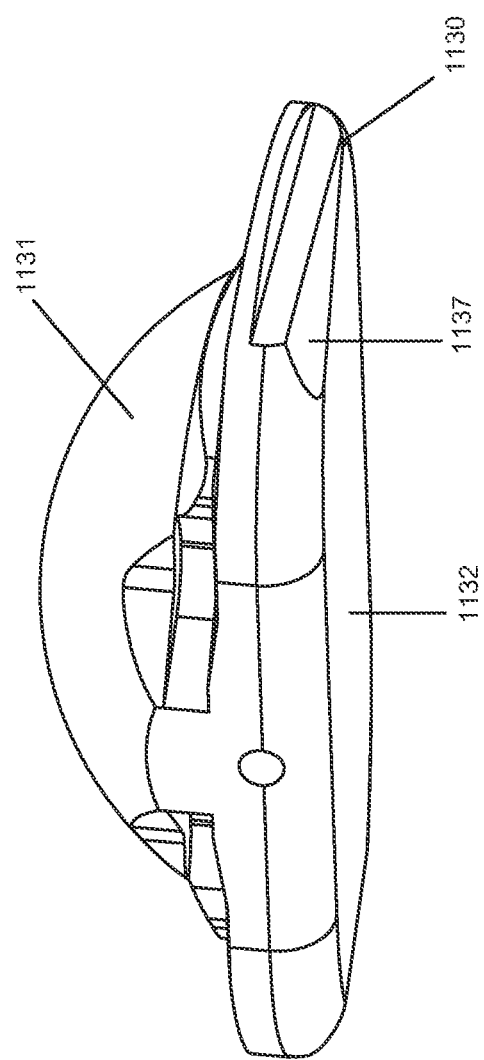
FIG. 68 is a perspective view of the bottom shell of the spinal nucleus replacement device of FIG. 62.
Figure 70:
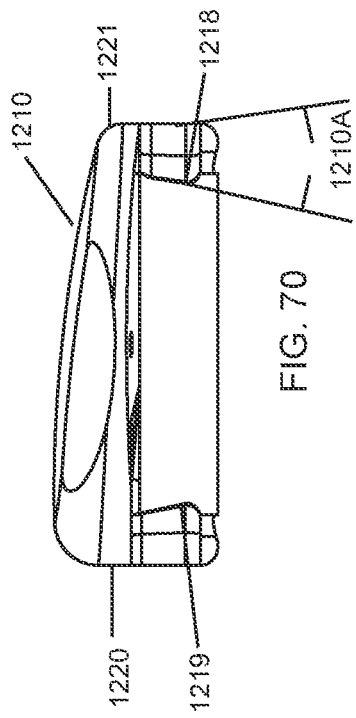
FIG. 70 is an end view of the top shell of the spinal nucleus replacement device of FIG. 69.
Figure 72:
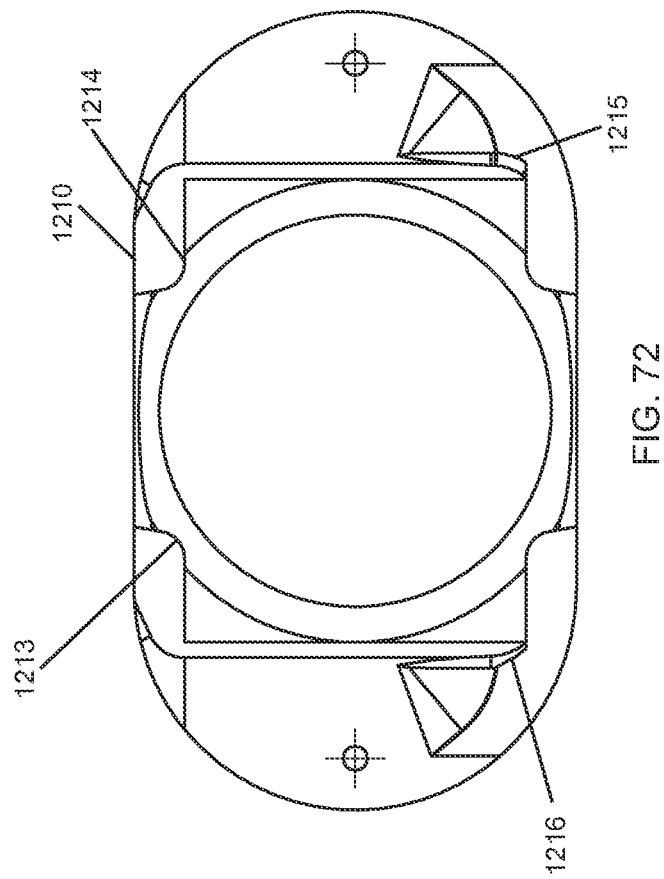
FIG. 72 is a plan view of the top shell of the spinal nucleus replacement device of FIG. 69.

An alternative embodiment of a top shell 1110A for NRD 1101 is illustrated in FIGS. 69-72, bottom shell 1130 remains unchanged. Shell 1110A is substantially identical to top shell 1110 with the exception of the angle of the walls within pockets 1213-1216, and the absence of varying heights. In FIG. 64, walls 11118, 1119 of top shell 1110 are shown as being substantially parallel to side walls 1120, 1121. In the alternative embodiment 1110A, the walls 1118A, 1119A of pockets 1113A, 1116A are at a slight angle 1110B with respect to implant side walls 1220 and 1221. The superior portions of recess sidewalls 1118A, 1119A are in proximity to implant sidewalls 1120A, 1121A and angle slightly inward toward the inferior portions nearer the longitudinal axis. This slight angle encourages the clamping fingers of the insertion instrument to move inferiorly, urging the proximal end of top shell 1110A superiorly relative to lower shell 1130. The encouraged movement of the upper shell causes the distal end of shell 1110A to move adjacent to lower shell 1130, thus achieving, automatically, the same wedge configuration achieved manually with shells 1110 and 1130. Transition zone 1118 and angled sidewalls 1120A, 1121A additionally allow shell 1110, 1110A while being firmly grasped during implant insertion, to assume any number of configurations as dictated by insertion angle and patient anatomy.

FIGS. 73-75 illustrate first and second embodiments 1100, 2200 of aspects of the present invention. Both embodiments are configured to minimally invasively insert an orthopedic implant, actively steer the implant from between at least 0 to 90 degrees percutaneously, and release the implant in any surgeon-desired orientation. Embodiments 1200, 2200 share some common elements.

FIGS. 74 and 75 depict two elongate implant insertion instruments 1200, 2200. Instrument 1200 and 2200 have a distal end D and a Proximal end P with a longitudinal axis L. For the purposes of describing similar elements, correlating numbers (i.e. 1200 and 2200) will be used. Elongate implant insertion instruments 1200 and 2200 have elongate external shaft members 1500, 2500 with implant engaging portions 1300, 2300 extending distally therefrom. Movably housed within the external shaft members are rotation shafts 1540, 2540 and inner elongate release shafts 460, 1460. Instruments 100, 1100 have handle portions 1400, 2400 housing a portion the elongate external shaft members 1500, 2500 and slap hammer knobs 1420, 2420 extending proximally therefrom. Implant rotating levers 1600, 2600 extend and are pivotally hinged to handle portions 1400, 2400. Implant release mechanisms 1800, 2800 respectively are present on both instrument embodiments, but appear in different forms and locations.

Figure 76:
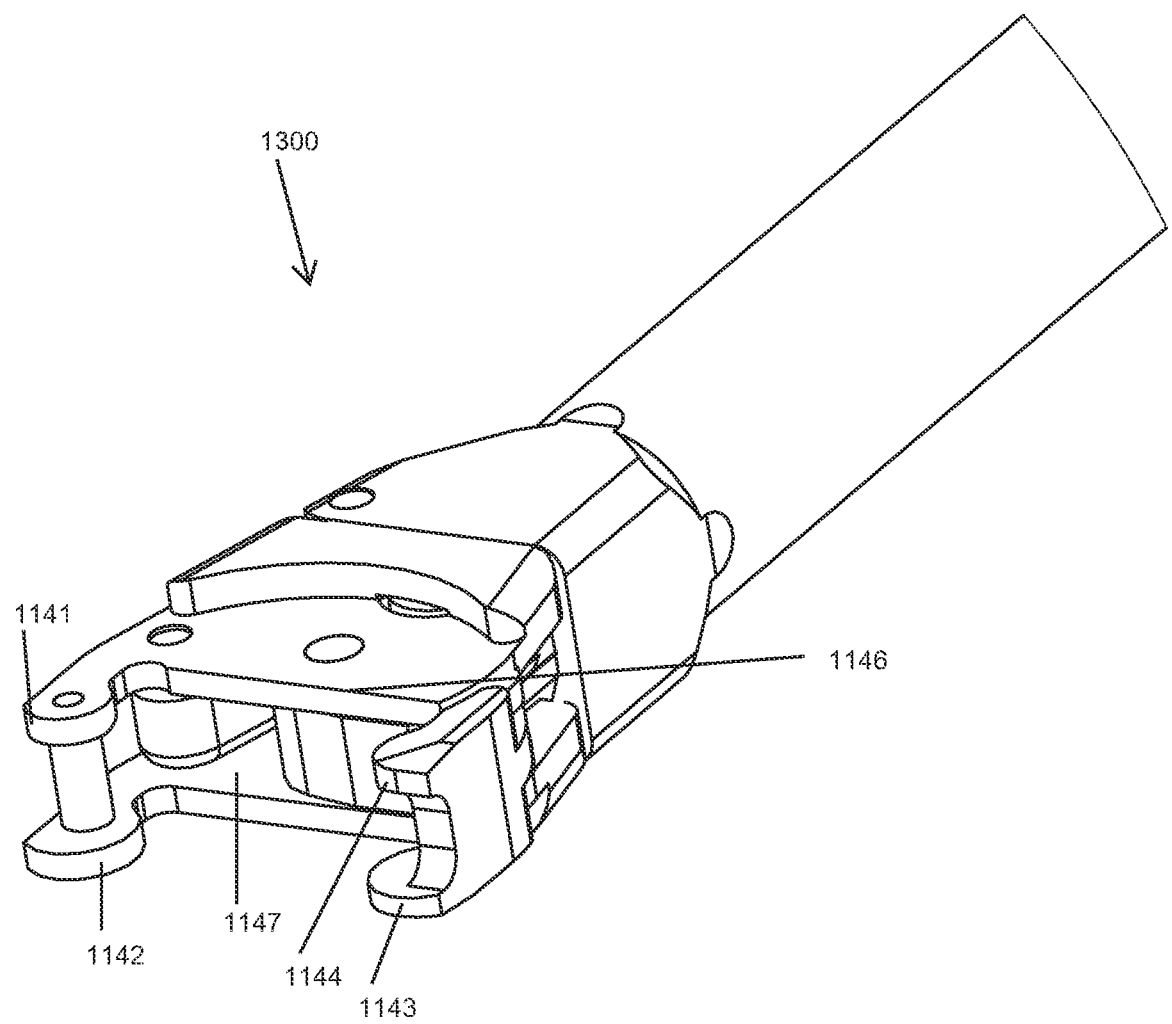
FIG. 76 is a perspective view of the implant engaging portion located at a distal end of an implant insertion instrument according to the present invention.
Figure 77:
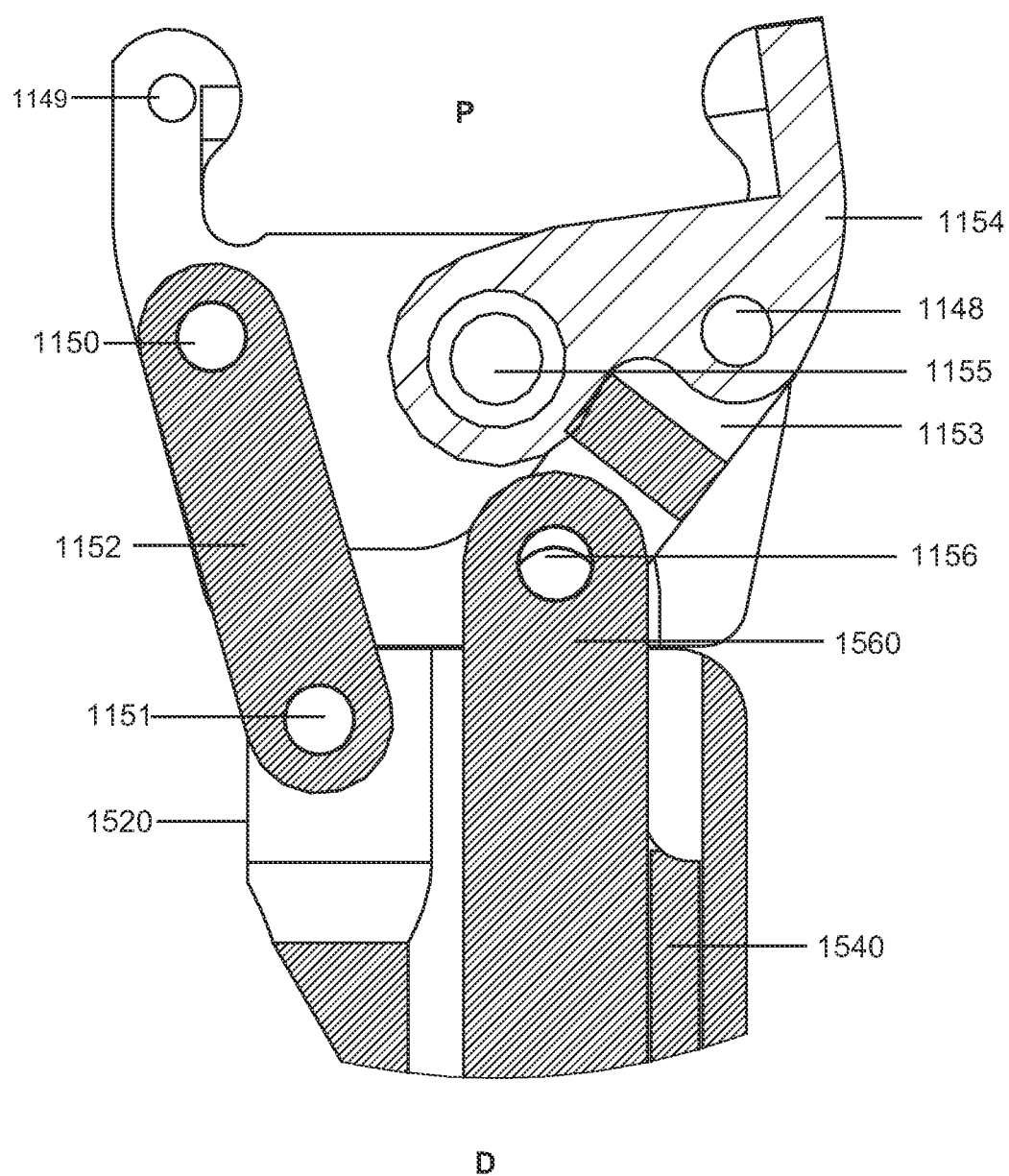
FIG. 77 is a cross-sectional view of the implant engaging portion shown in FIG. 76.
Figure 78:
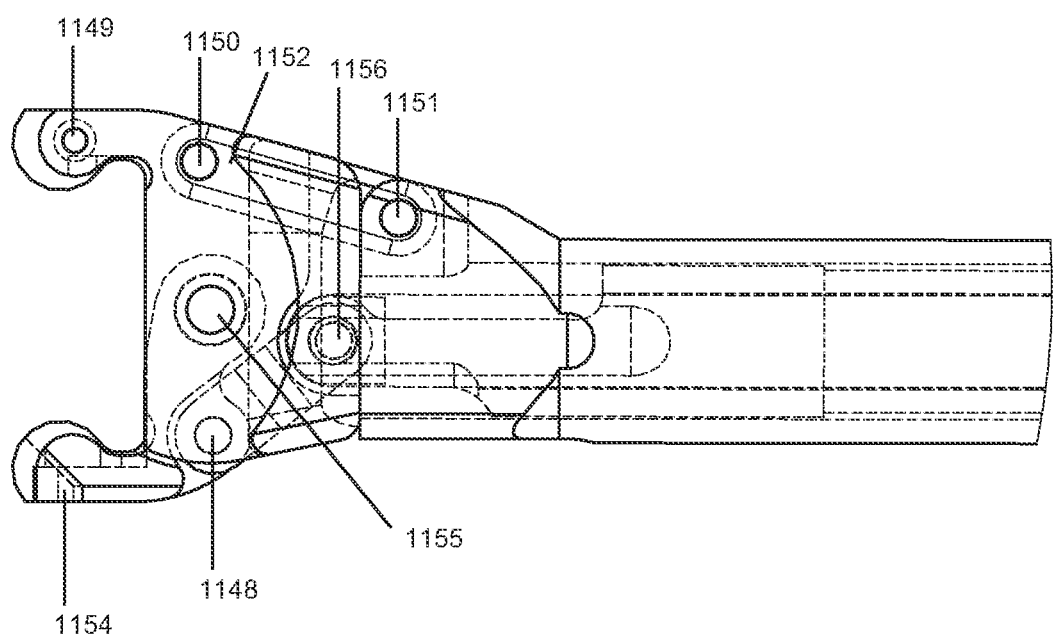
FIG. 78 is a plan view of the implant engaging portion shown in FIG. 76 with hidden components being shown in broken line.

Turning now to FIGS. 76-78 depicting implant engagement portions 1300, 2300. The implant engagement mechanisms are alike on both inserters 1200 and 2200 as are their respective operations of grasping, rotation and release of the NRD. Engagement mechanisms comprise implant clamping fingers, 1141-1144 which are configured to reside in the undercut or recesses of instrument engaging portions, 1113-1116, 1213-1216 and 1133-1136 of both upper 1110, 1110A and lower 1130 implant shells respectively.

Engagement mechanism 1300 includes two external plates 1146, 1147 which are pinned together at pivot points 1148-1151. This arrangement allows for the housing of linkage bars 1152-1154, with arcuate clamping fingers 1141-1144 disposed on the distal ends thereof for facilitating the ability to steer and release implant 1101. Linkage bar 1153 is movably pinned at its distal end to linkage 1154 at point 1155 and at its proximal end it is movably pinned to distal end of inner release shaft 1560, 2560 at point 1156. Detents (not shown) are machined on the inside of both external plates, 1146 and 1147 that mate with corresponding holes 1542, 2542 located on the distal end of the insertion instrument's rotating shaft 1540, 2540. Linkage bar 1152 is movably pinned at hole 1151 concentric to hole 1522, 2522 of elongate external shaft 1520, 2520 of instruments 1200, 2200

To ready instrument 1200, 2200 to receive implant 1101, the implant release shaft 1560, 2560 is advanced proximally independent of middle rotation shaft 1540, 2540 and fixed external shaft 1520, 2520. Because of the pinned relationship of release shaft 1560, 2560 to linkage bar 1153 and the relationship of linkage element 1153 with linkage element 1154, the urging of the release shaft in a proximal direction causes linkage elements 1153, 1154 to move proximally about hinge pin 1155 resulting in the distal end of linkage element 1154 moving away from longitudinal axis L. With the distal end of linkage element 1154 moved away from the longitudinal axis, the implant 1101 can easily be inserted onto the clamping fingers. With the implant 1101 placed in the insertion position, the operator allows inner release shaft 1560, 2560 to return distally to its original position, bringing the clamping fingers into engagement with the implant engaging recesses 1113-1116, 1133-1136, thus firmly grasping implant 1101.

Figure 79:
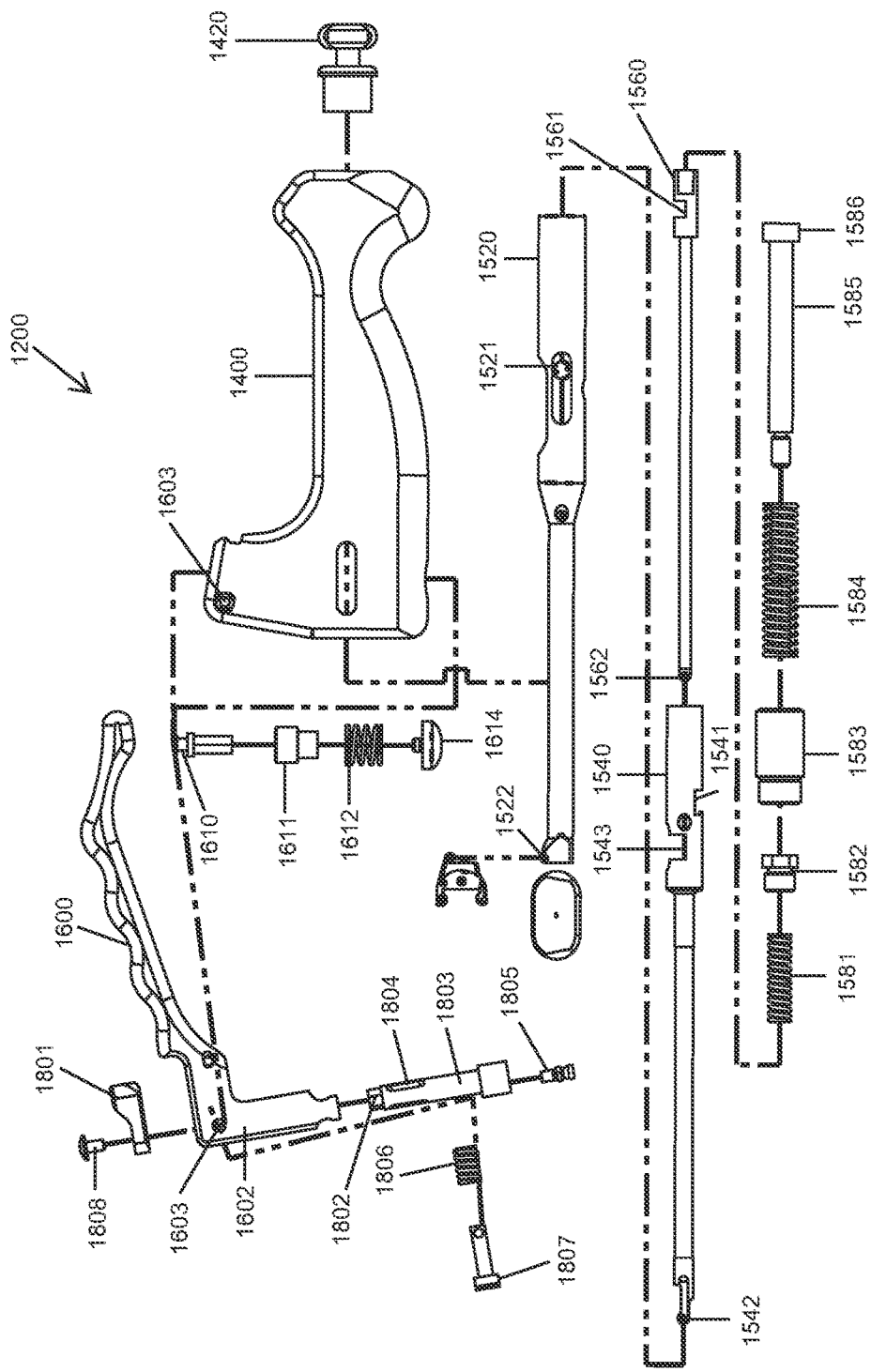
Figure 80A:
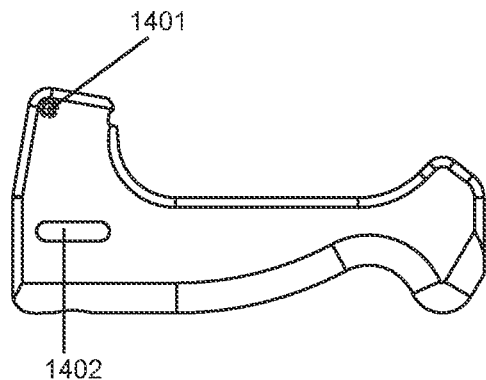
Figure 80B:
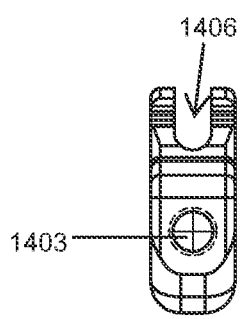
Figure 80C:
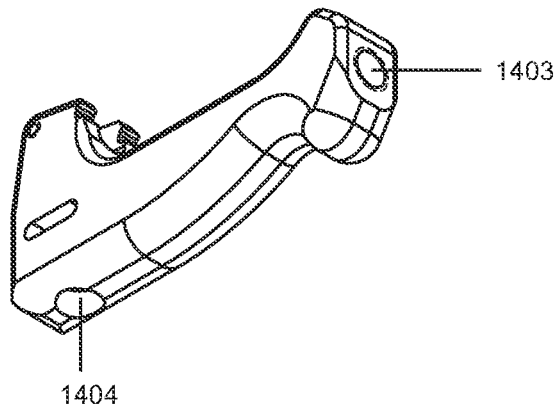
Figure 80D:
Figure 81A:
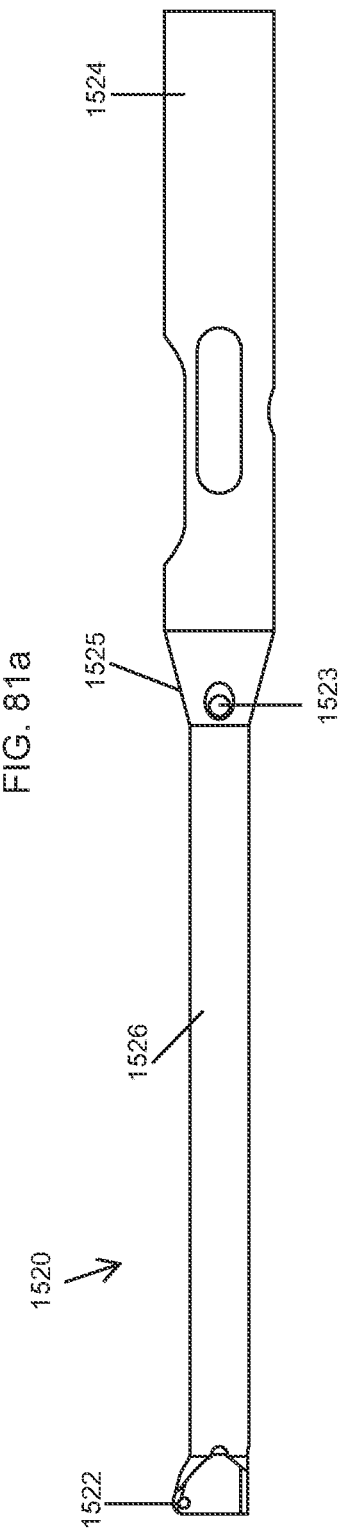
Figure 81B:
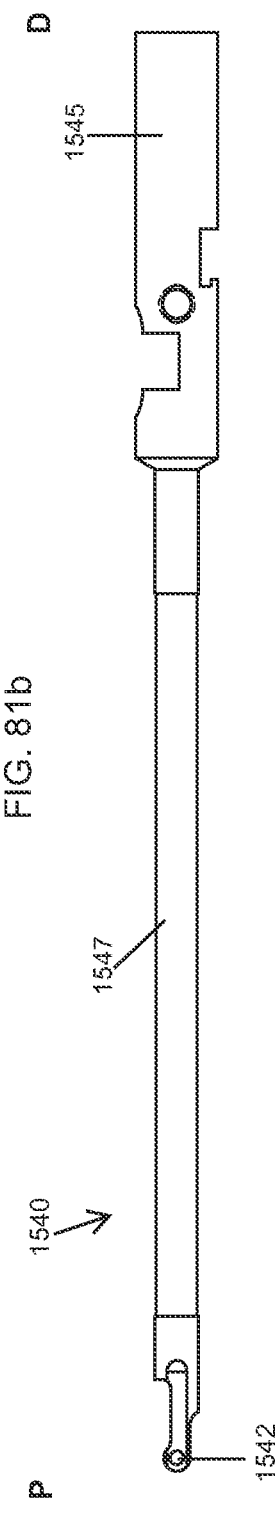
Figure 81C:
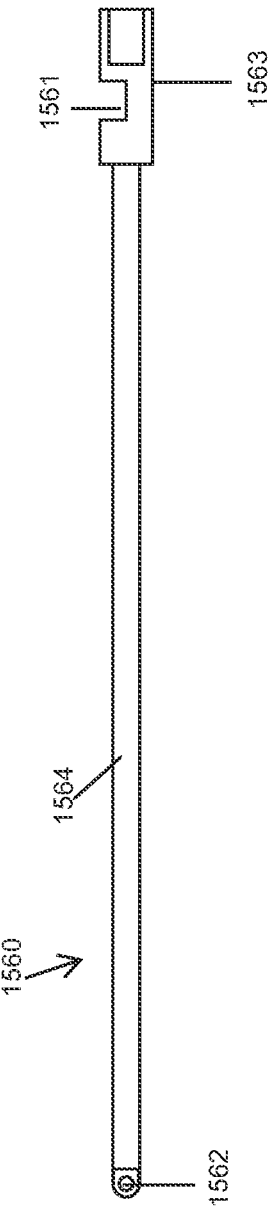

Implant insertion instrument 1200, 2200, 3200 has an elongate shape enabling the physician to position, manipulate, and release an implant through a narrow working corridor within the patient. FIG. 79 illustrates an exploded view of embodiment 1200 of an implant insertion device comprising a first elongate external shaft 1520, a second elongate intermediate rotation shaft 1540 and a third inner release shaft 1560. External shaft 1520 is fixedly attached to handle 1400. Rotation shaft 1540 movably resides in fixed external shaft 1520. Release shaft 1560 resides within the rotation shaft and translates, independently of or cooperatively with rotation shaft 1540.

Rotation spring housing 1583 comprises proximal end 1587 and distal end 1588 consisting of varying diameters with male threads disposed thereon. Threaded proximal end 1587 of housing 1583 engage female threads within handle 1400, distal end threads 1588 engage female threads in proximal end of the external shaft (not shown) fixing proximal end of external shaft 1520 to handle 1400. External shaft 1520 extends distally through bore 1403 in handle 1400 thus supporting and housing the shaft. Shoulder bolt 1585 extends longitudinally through rotation spring 1584 with the coils thereof extending thereabout and spring housing 1583 with the distal end of bolt 1585 threadedly residing in proximal end 1589 of release spring nut 1582. Distal end 1590 of release spring nut 1582 abuts release spring 1581 and threadedly engages proximal end of rotation shaft 1540. Elongate release shaft 1560 movably resides in rotation shaft 1540. The arrangement of shafts 1520, 1540, 1560, in cooperation with shoulder bolt 1585, rotation spring housing 1583, release spring nut 1582 and springs 1584, 1584 permits the translational movement of the release shaft independently or cooperatively with the rotation shaft. Both the rotation shaft and the release shaft are configured to translate independent of stationary external shaft 1520.

Proximal end of rotation spring 1584 abuts shoulder 1586 of shoulder bolt 1585 while distal end of spring 1584 resides within larger diameter of housing portion 1587 abutting the proximal smaller diameter 1588 of housing 1583. The outer diameter of spring 1584 is slightly less than the inner diameter of proximal end of housing portion 1587, but larger than the inner diameter of distal portion 1588 of housing 1583. Spring 1584 is captured between the housing and the shoulder of shoulder bolt 1586. As rotation shaft is advanced proximally, rotation spring 1584 is compressed thus urging rotation shaft in a proximal direction.

Figure 86:
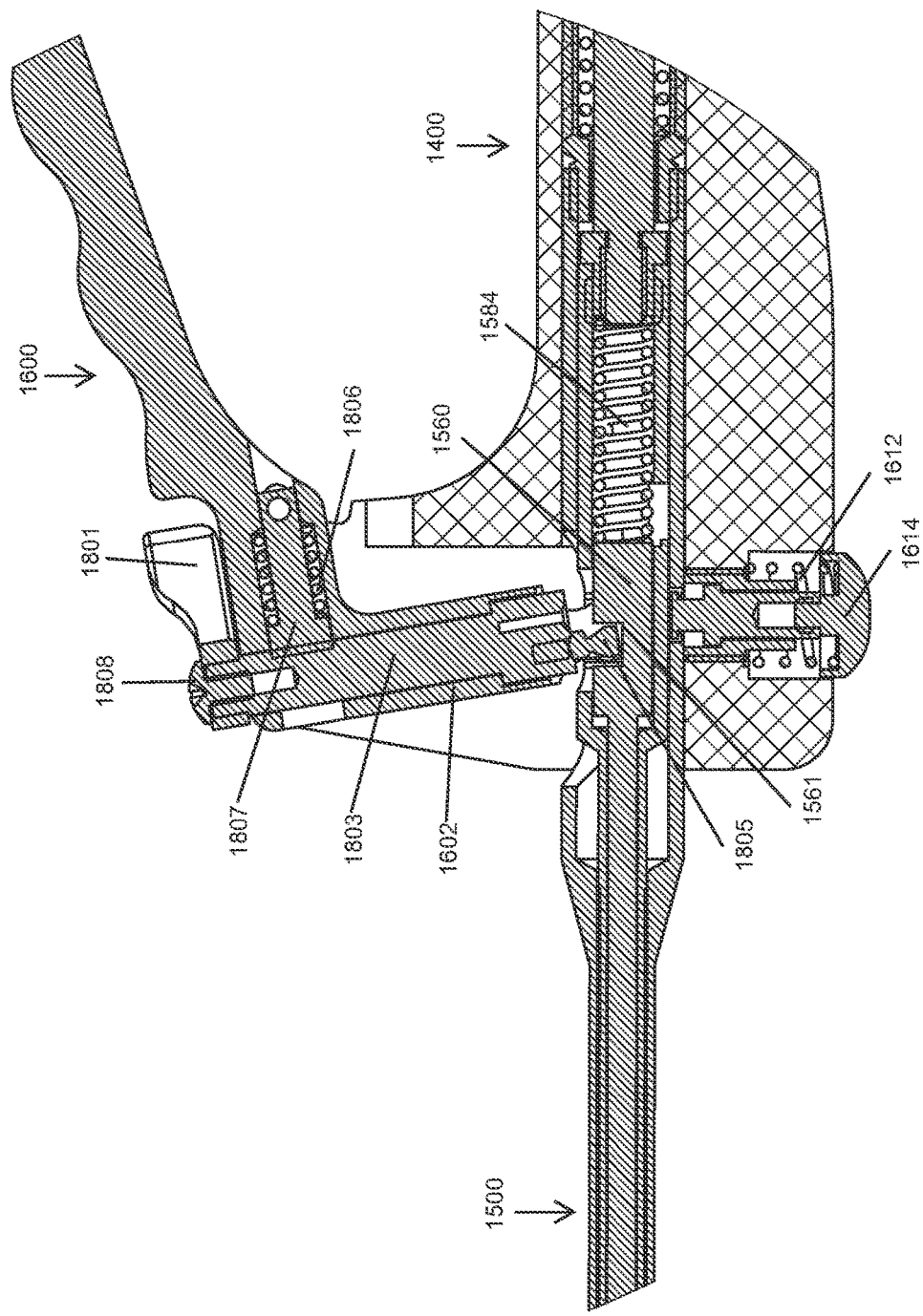

Referring now to FIG. 86 release spring 1581 is captured within the inner diameter of rotation shaft 1540 in a space defined by the proximal end of rotation shaft 1540 and the distal end of release collar 1582. During assembly release spring 1581 is installed in instrument 1200 in a compressed state. Since the release spring is in compressed and resides in the space previously described it constantly biases or urges release shaft 1560 in a distal direction. Due to the pinned relationship of release shaft 1560 with linkage bar 1153 and the pinned relationship of linkage bar 1153 with linkage bar 1154, the distal urging of the release shaft urges the linkage bars distally and thus the implant is firmly grasped as clamping fingers 1143, 1144 are persuaded toward the longitudinal axis of instrument 1200.

Figure 82:
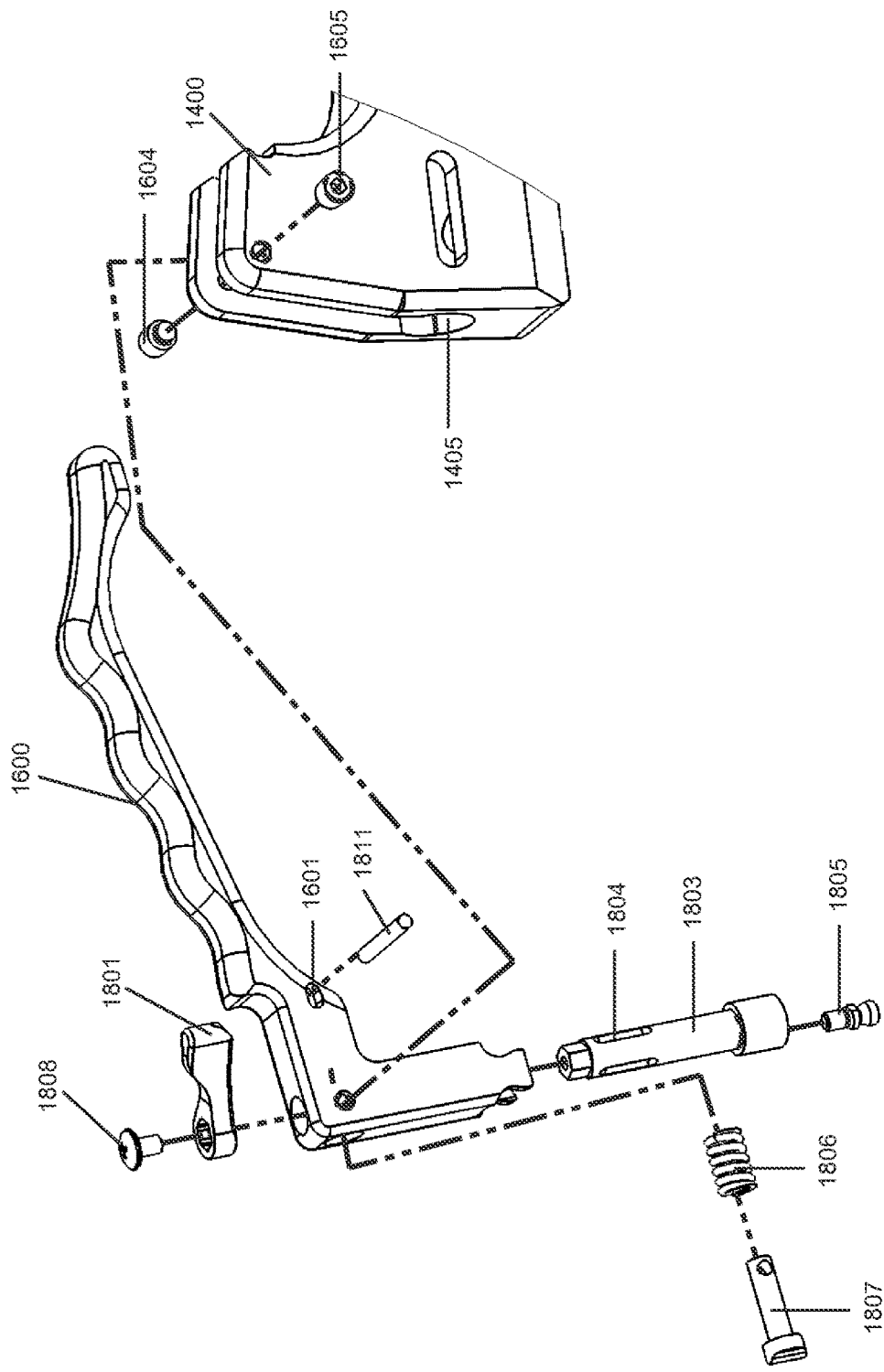

Turning now to FIGS. 82-92 relating to insertion instrument 1200. FIG. 82 is an exploded view of the rotation and release mechanisms. Both the rotation and release mechanisms are housed within distal portion of rotation lever 1600 and distal portion of handle 1400. Release mechanism comprises a release lever 1801, elongate release lever shaft 1803, offset release post 1805, locking post 1807, and release lever locking spring 1806.

Figure 88:
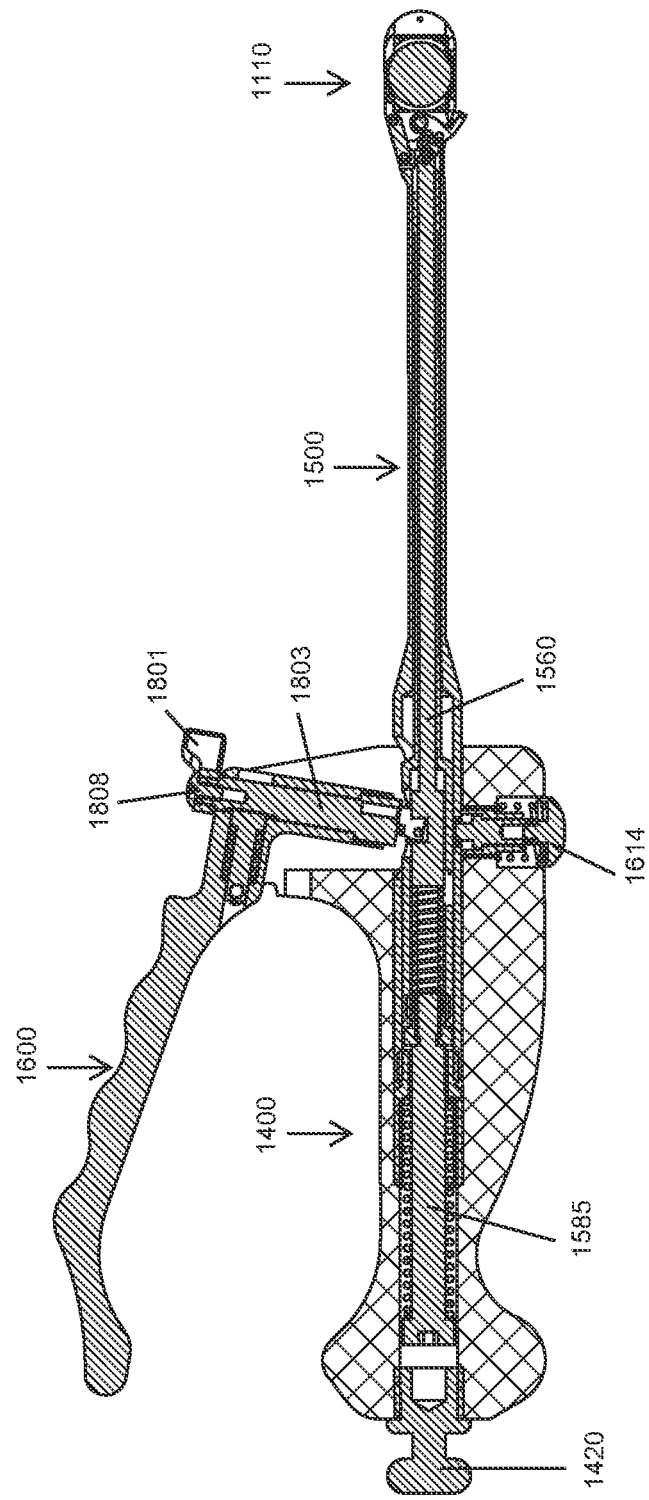
Figure 89:
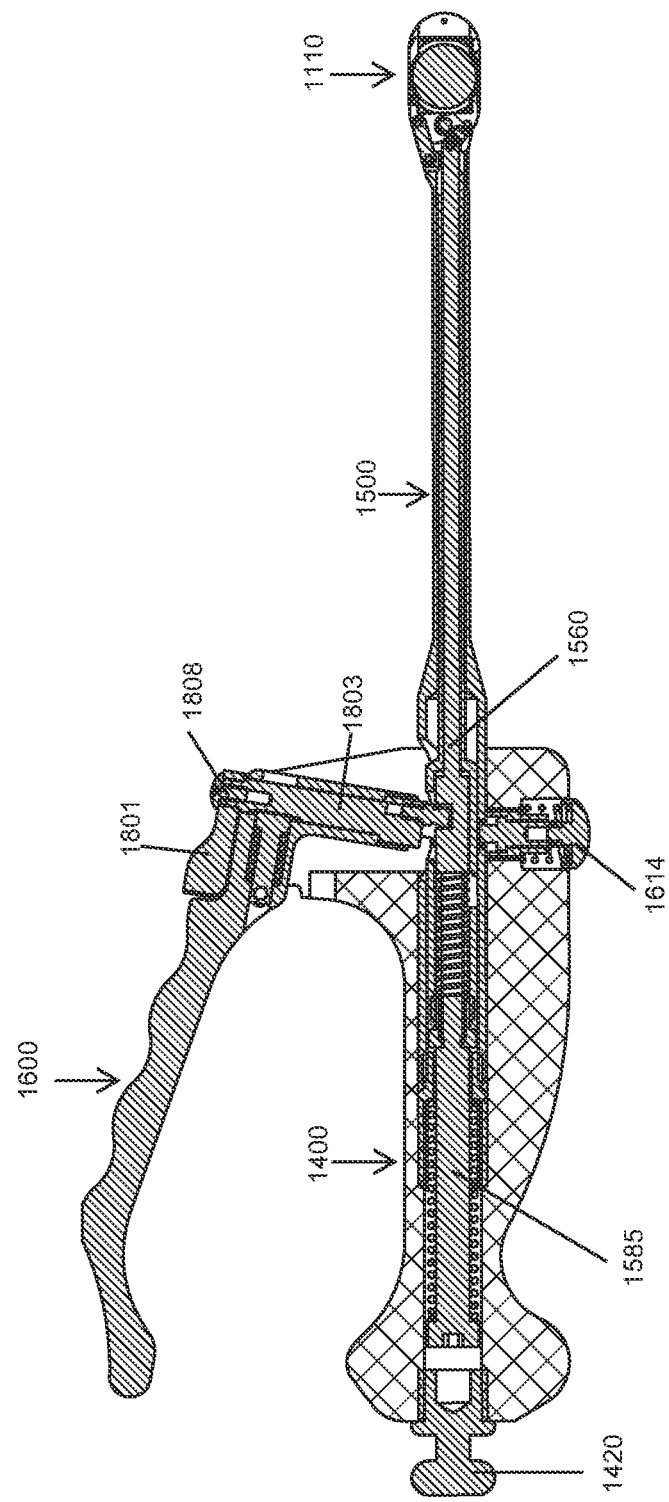
Figure 90:
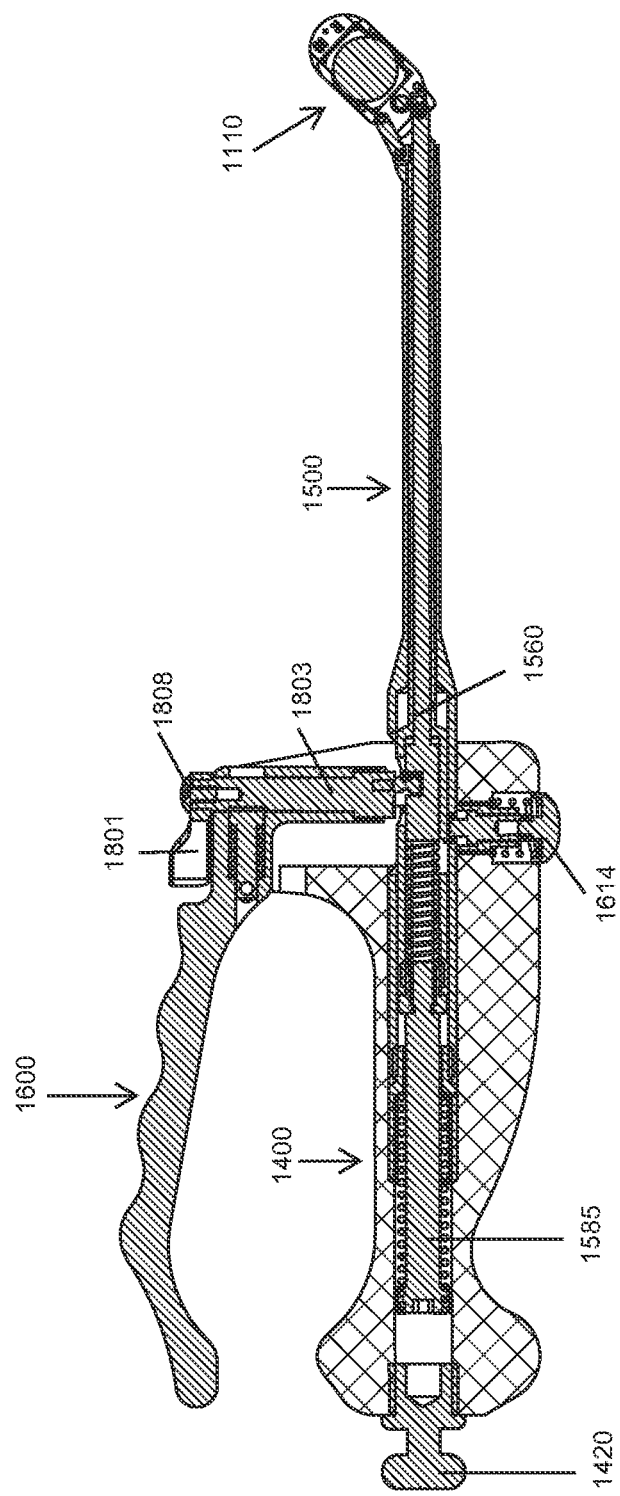

Elongate release lever shaft 1803 comprises a proximal and distal end. Disposed on the proximal end P of the release lever shaft has a multi-faceted male configuration 1802, in this case a hexagonal configuration that substantially matches the female configuration of aperture 1801A of release lever 1801. The diameter of distal end D of release shaft 1803 is slightly larger than that of the main shaft body portion. Disposed on the distal end of release shaft 1803 are three apertures 1809, 1810, 1812 which house offset release post 1805. The proximal end of post 1805 is disposed in any of the three apertures and thus is radially offset from the central axis of release shaft 1803. When release lever 1808 is rotated to the open position as seen in FIG. 88 the central axis of the offset post is proximal the central axis of the release shaft. When release lever 1808 is rotated to the closed position as seen in FIG. 89 the central axis of offset post 1805 is distal the central axis of release shaft 1803. Each of the three offset release post apertures are arranged at slightly differing distances from the central axis of the release shaft respectively. The variable distances allow for the post to be attached to the shaft in any of the three various positions thus allowing for minor adjustment when assembling instrument 1200 to obtain the desired proximal and distal travel of the offset release post relative to release post activation slot 1561 of release shaft 1560.

Figure 84:
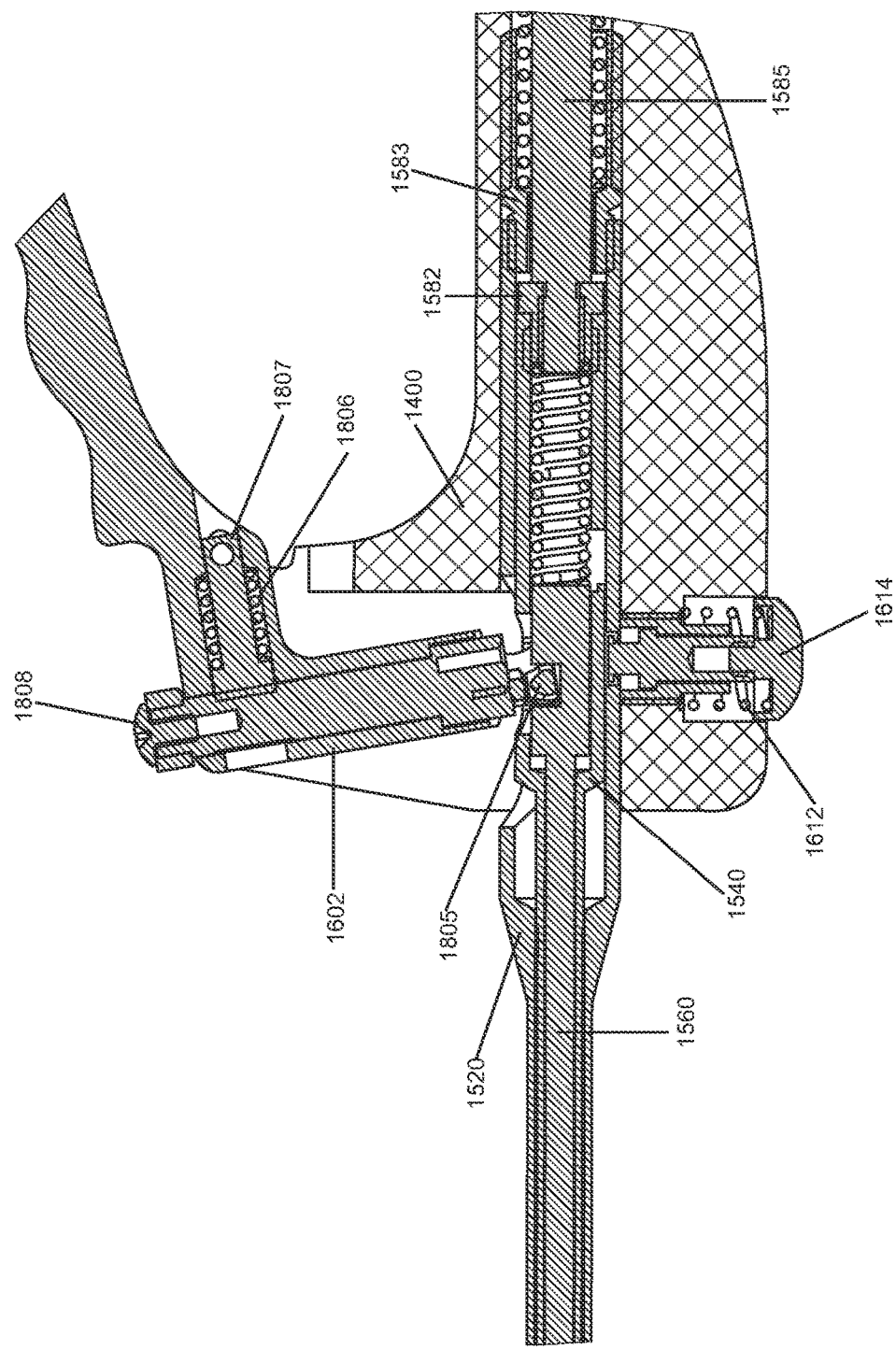

With the release shaft 1560 constantly being urged distally by release spring 1584, it is desirable to be able to lock the release shaft in the open position while the implant is readied for placement on the instrument. The locking of release shaft 1560 in the open position, as seen in FIG. 84, achieved by release lever locking post 1807 in concert with release shaft locking slots 1804, lever locking spring 1806, lever locking pivot pin 1811 and slot 1601 and locking pin ramp 1600R of handle 1600. In addition to holding the lever in the open position for the mounting of implant 1200, this arrangement also prevents the rotation of the implant while in the lever is in the open position.

As can best be seen in FIG. 84, lever locking post 1807, and spring 1806 are disposed in bore 1616 in rotation lever 1600. Bore 1616 has a proximal diameter 1616P and a distal diameter 1616D. Diameter 1616P is slightly larger than the diameter of the shaft portion of locking post 1807. Diameter 1616D is slightly larger than that of spring 1806 and the release slot engaging portion of locking post 1807. Locking post pin 1811 is disposed in slot 1601 of handle 1600 and press fit in the bore of the shaft portion of the locking post. Pin 1811 translates freely within slot 1601 and along ramp 1600R, as rotation lever 1600 is employed, while retaining the locking post within bore 1616. Spring 1806 urges locking post 1807 in a proximal direction toward release lever shaft 1803.

Turning now to FIG. 85, distal end of rotation lever 1600 is disposed within handle 1400. Rotation lever locking screws 1604, 1605 have a larger diameter threaded end with interior geometry to accept a tool for rotation during assembly. Inside portions 1604S, 1605S of the locking screws have a smooth surface with a smaller diameter which engage rotation lever 1600 in lever pivot pin bore 1603. The locking screws 1604, 1605 capture rotation lever 1600 in handle 1400 allowing the lever to pivot about the locking screws. The arrangement of two locking screws allows the interior of lever 1600 to receive release lever shaft 1803 therein.

When rotation lever 1600 is moved toward handle 1400 the rotation lever pivots about locking screws 1604, 1605 thus urging release lever shaft 1803 and offset post 1805 in a distal direction. The disposition of offset release post 1805 in release lever engagement slot 1561 of release shaft 1560 forces the release shaft and rotation shaft 1540 to move distally relative to elongate external shaft 1520 in response to the movement of the rotation lever on rotation shaft. Rotation shaft 1540 comprises a bore 1542 at its distal end. The distal end of the rotation shaft is sandwiched by plates 1146, 1147 of the implant clamping mechanism and two bosses (not shown) secure the rotation shaft 1540 to plates 1146, 1147. The bosses lie inferiorly on plate 1146 and superiorly on plate 1147. The location of the bosses is concentric with pivot point 1156 which is attached to release shaft 1560. The bosses do not protrude completely through distal bore 1542 thus the release shaft is able move proximally independent of the rotation shaft.

With rotation shaft 1540 moved distally relative to fixed elongate outer shaft 1520, the longitudinal axis of implant has been shifted from being substantially parallel to longitudinal axis L of instrument 1200 to being substantially transverse to the longitudinal axis of the instrument. It is preferable, but not required, to be able to temporarily lock rotation shaft 1540 in this position so that the surgeon can remove himself from the fluoroscopic field.

The locking of rotation shaft 1540 in the 90 degree configuration is accomplished by a rotation locking mechanism as seen in FIG. 84. The locking mechanism comprising rotation locking button 1613, locking collar spring 1612, locking collar 1611, and rotation shaft locking post 1610. Rotation locking collar 1611 comprises a superior diameter and an inferior diameter 1617. The inferior diameter of locking collar 1611 is fixedly disposed, by threads, press fit or any other means known in the art, in aperture 1404 of handle 1400. Rotation shaft locking post 1610 is disposed in locking collar 1611. Collar spring 1612 is disposed about inferior diameter 1617 abutting superior diameter of collar 1611. Shoulder of rotation locking button 1614 abuts inferior portion of spring 1612 and is fixedly attached to inferior end of post 1610. Spring 1612 urges button 1614 and fixedly attached post 1610 in a direction inferior to that of rotation shaft 1540.

Figure 91A:
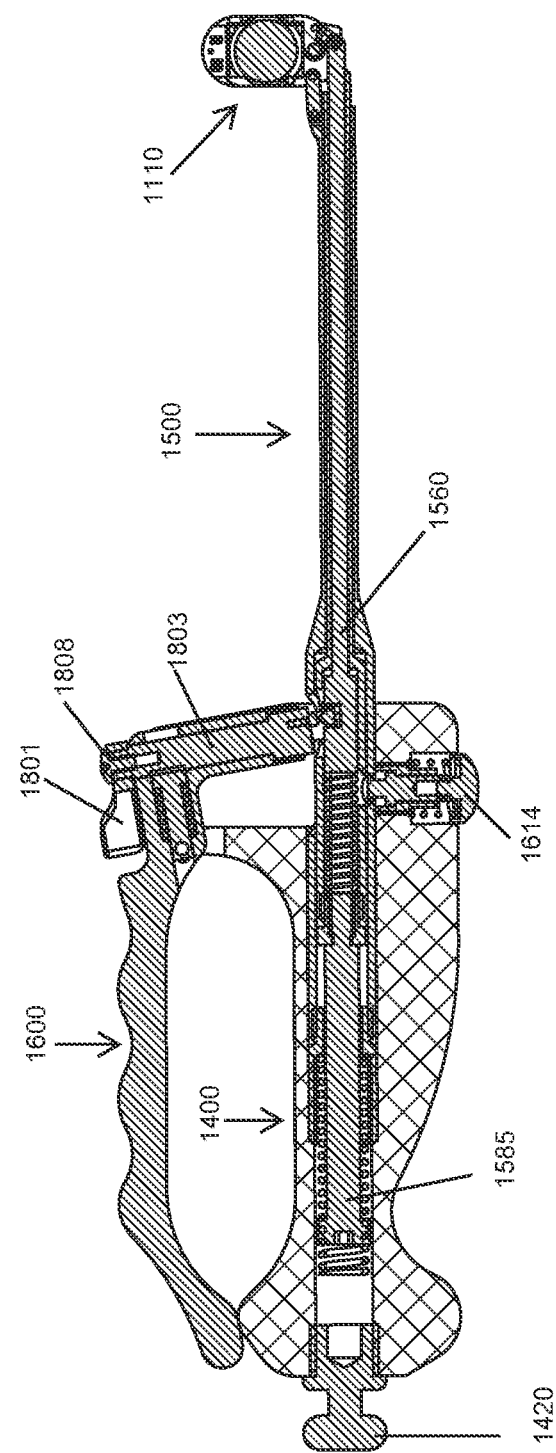
Figure 91B:
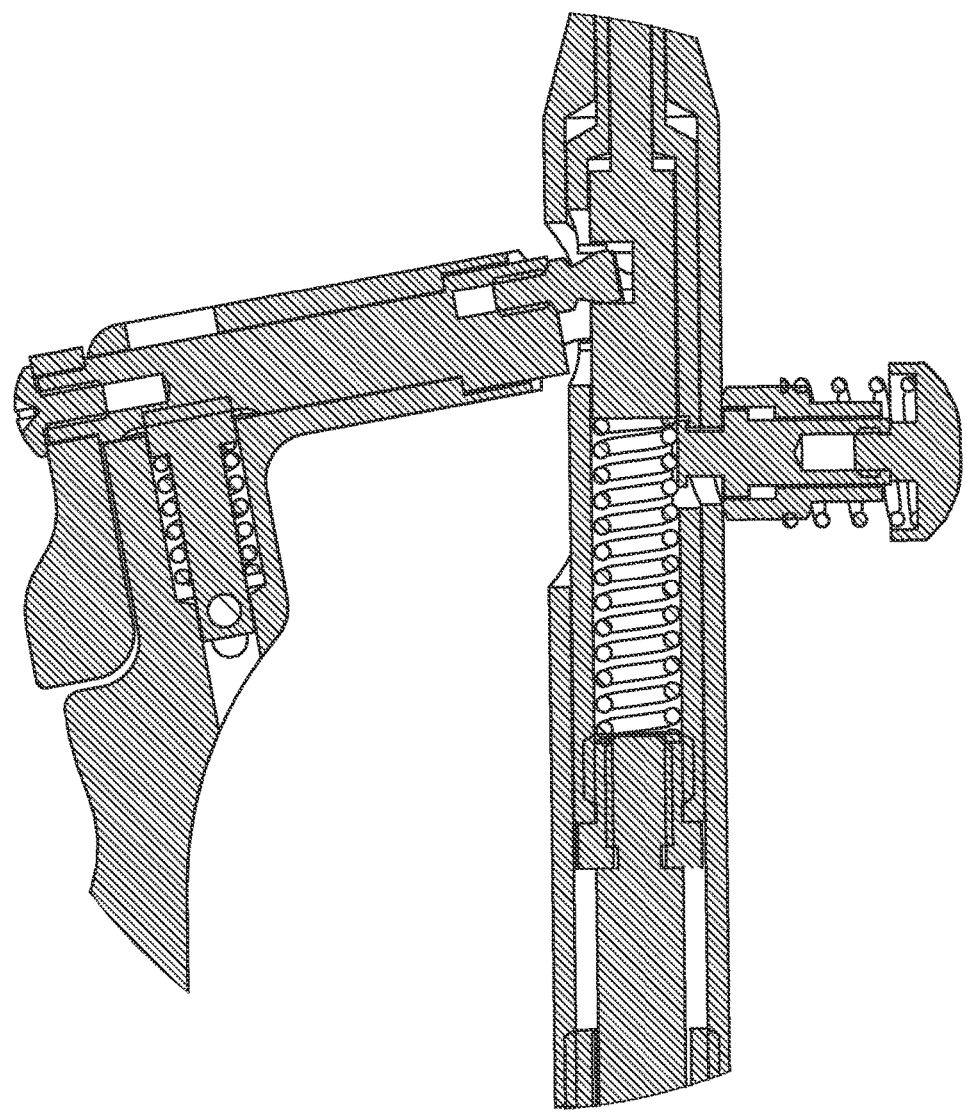

As seen in FIG. 91A, upon the distal advancement of rotation shaft 1540 due to the employment of rotation lever 1600 rotation locking engagement portion 1541 of shaft 1540 resides superior to that of rotation locking post 1610. In this position, the surgeon depresses button 1613 urging locking post 1610 into the locking engagement portion 1541 of rotation shaft 1540. As lever 1600 is released, spring 1584 urges rotation shaft proximally resulting in the locking post 1610 residing in the distal end of engagement portion 1541 of rotation shaft 1540, as can be seen in FIG. 91B. The locking post secures the rotation shaft in a distal position until such a time that rotation lever 1600 is moved inferiorly toward handle 1400. The inferior movement of lever 1600 urges rotation shaft distally allowing rotation lock spring 1612 to urge locking post 1610 out of engagement with locking portion 1541 of rotation shaft 1540. Spring 1584 urges the rotation shaft proximally returning the instrument back to a zero degree configuration.

Turning now to a method of employing embodiment 1200 in the implantation of artificial nucleus 1101. After the method and approach of insertion are determined and the target disc space identified, access is made to the surgical site via any number of surgically accepted methods. Access to the damaged disc is obtained by creating a small window in the annulus. Once the disc has been excised or otherwise prepared, instruments are deployed to determine the size of the implant to best suit the anatomy of the patient. Upon determining the appropriate size, the corresponding implant 1101 is selected and placed in a jig (not shown) to hold implant 1101 firmly while implant insertion instrument is prepared for clamping implant 1101.

Figure 87:
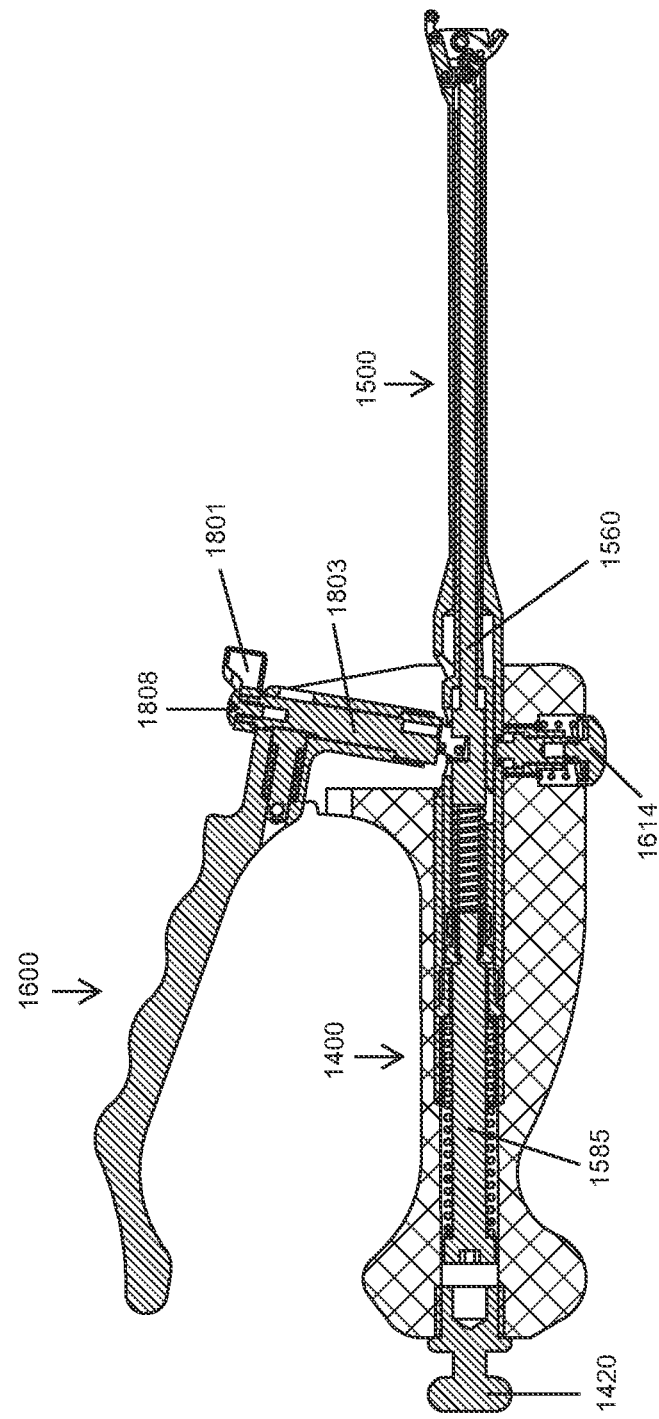

Turning now to FIGS. 87-92, instrument is grasped at handle 1400 and implant release ever 1801 is moved to the open position shown in FIG. 87. The clamping fingers 1141-1144 are placed near their respective instrument engagement recesses 1113-1116, 1133-1136 of the implant as shown in FIG. 88. Implant release lever 1801 is manually returned to the closed position as seen in FIG. 89 resulting in the implant being firmly grasped, with the longitudinal axis of implant 1101 substantially parallel to longitudinal axis L of instrument 1200, and ready for insertion. The implant is placed through the annular window and eased into the disc space in the zero degree configuration so that the footprint of implant 1101 and delivery device 1200 is reduced.

Once positioned between the vertebral members, rotation lever 1600 is squeezed toward handle 1400. As handle moves inferiorly, rotation lever pivot pin 1811 travels along ramp 1600R. The curved ramp as seen in FIG. 85 forces pivot pin in a proximal direction thus pulling release lever locking post 1807 out of engagement with release shaft locking slot 1804 of release shaft 1803. The force of spring 1581 urges release shaft 1560 distally. Although the surgeon should preferably have already returned the release lever to the zero degree configuration, the action of pivot pin 1811, in relation to the ramp 1600R moves the locking pin 1807 out of engagement with locking slot 1804 automatically returning the lever to the zero degree configuration. This arrangement is to assure that the implant is not rotated without the clamping fingers in firm grasp of implant 1101.

The implant 1101 is then rotated within the disc space to the substantially 90 degree configuration. The rotation shaft locking button 1614 is depressed moving locking post 1610 to engage slot 1541 in rotation shaft 1540 thus locking the instrument in the 90 degree configuration. The surgeon may then remove himself from the fluoroscopic field while the exact position of the implant is determined. Adjustments are made and location determination is repeated until the desired position of the implant within the intervertebral space is achieved.

Figure 92:
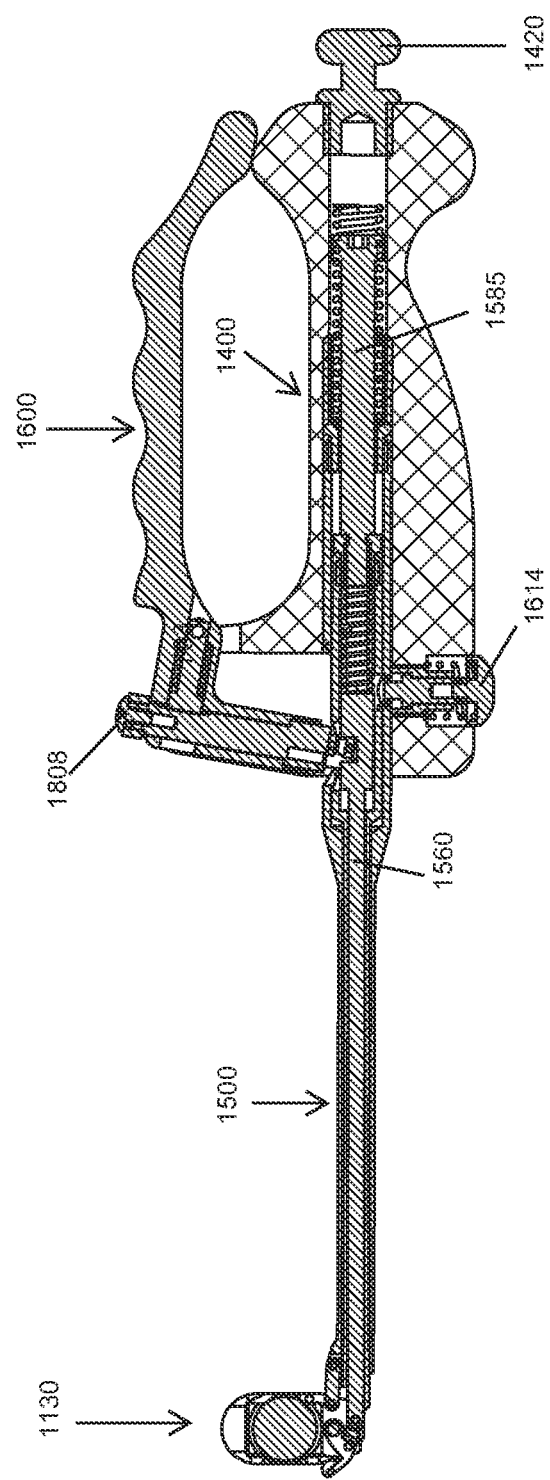
Figure 94A:
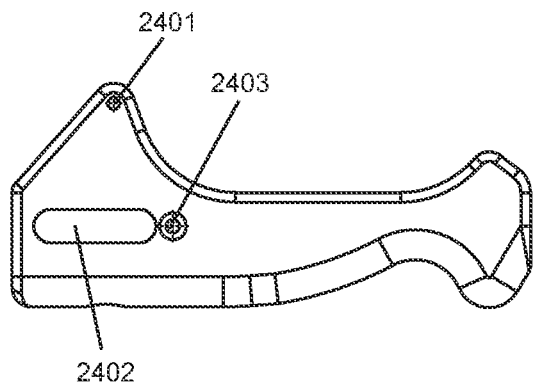
FIGS. 94a-d are various views of a handle portion of the insertion instrument of FIG. 93.
Figure 94B:
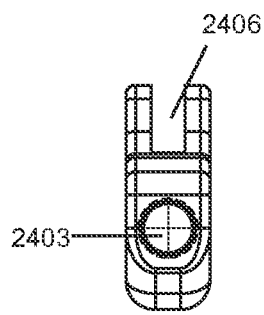
Figure 94C:
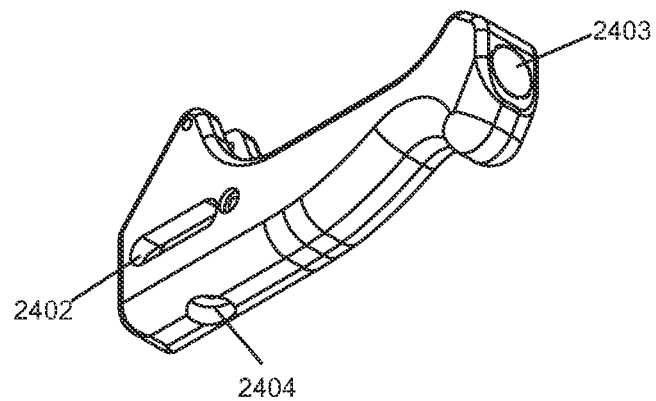
Figure 94D:

The surgeon then releases implant 1101 from instrument 1200 and removes distal end of the instrument through the annular window. Once removed from the implant, the instrument is preferably returned to the zero degree configuration and the clamping fingers returned to the grasping position so as to provide a smaller footprint. The smaller footprint limits damage that can be done to the interior of the annular window. To achieve this the surgeon turns release lever 1801 to the release position as seen in FIG. 92 and slowly moves instrument 1200 from contact with implant 1101. A slight depression of rotation lever 1600 toward handle 1400 urges release shaft distally allowing spring 1612 to force locking post 1610 out of engagement with slot 1541 of rotation shaft 1540. Lever 1600 is allowed to return to the neutral position causing pivot pin 1811 to move proximally on ramp 1600R. The proximal movement of pivot pin 1811 in slot 1601 disengages post 1807 from slot 1804. Spring 1581 forces release shaft 1560 distally thus returning clamping members 1141-1144 to the clamping position, as seen in FIG. 85A, providing a small footprint for removal via the annular window.

An alternative embodiment 2200 of an artificial disc insertion device can be seen in FIGS. 93-107. FIG. 93 is an exploded view of instrument 2200 comprising similar elements to that of instrument 1200 including, but not limited to; fixed external shaft 2520, rotation shaft 2540, release shaft 2560, release lever 2801, handle 2400, implant engagement mechanism 2300, and rotation lever 2600. Instrument 2200 performs a similar function as instrument 1200, with some design changes resulting in a slightly different method of operation.

In assembly, external shaft 2520 is fixedly attached to handle 2400 by fixation pins 2816, 2817 through aperture 2403 in handle 2400 and aperture 2527 in external shaft 2520. The pins 2816, 2817 breach the interior wall of external shaft 2520. Fixation pins may be attached to the external shaft by threads, press fit, welding or any fixation method commonly recognized in the art. Shaft 2520 comprises clamping mechanism engagement portion 2522 at its distal end, an aperture 2523 to receive a cleaning device (not shown) for sterilizing the inside, and disposed about the anterior and posterior of shaft 2520 are rotation lever slots 2529, 2530.

Movably disposed in external shaft 2520 is rotation shaft 2540 having an elongate configuration with proximal end P and distal end D. Proximal end has an internal female thread (not seen) that mates with male thread of shoulder bolt 2585. Rotation shaft spring 2584 is disposed between shoulder 2586 of shoulder bolt 2585 and proximal end of elongate external shaft 2520. Distal end D includes aperture 2542 for engaging the implant clamping mechanism. Rotation shaft 2540 further comprises a slot 2548 which houses the portion of fixation pins 2816, 2817 that have breached the internal wall of external shaft 2520 and allows rotation shaft 2540 to move freely in a proximal and distal direction relative to external shaft 2520. Aperture 2544 receives rotation lever attachment bolt 2814 therethrough. Release shaft camming slot 2551 receives distal portion of offset release lever shaft 2803 therethrough. Distal to slot 2551 is slot 2550 which receives release lever locking ball 2819 in the closed position. Proximal to slot 2551 is slot 2549 which receives release lever locking ball in the open position. Disposed about the anterior and posterior of shaft 2540 is rotation lever slot 2552.

Movably disposed in rotation shaft 2540 is elongate release shaft 2560. Release shaft 2560 comprises proximal end P and distal end D. The release shaft further comprises an aperture 2562 disposed about the distal end of shaft 2560 for movable engagement with the implant clamping mechanism. Enlarged proximal shaft portion 2563 houses release lever engagement aperture 2561. In assembly, camming portion 2805 of offset release shaft 2803 is disposed within aperture 2560.

Figure 96A:
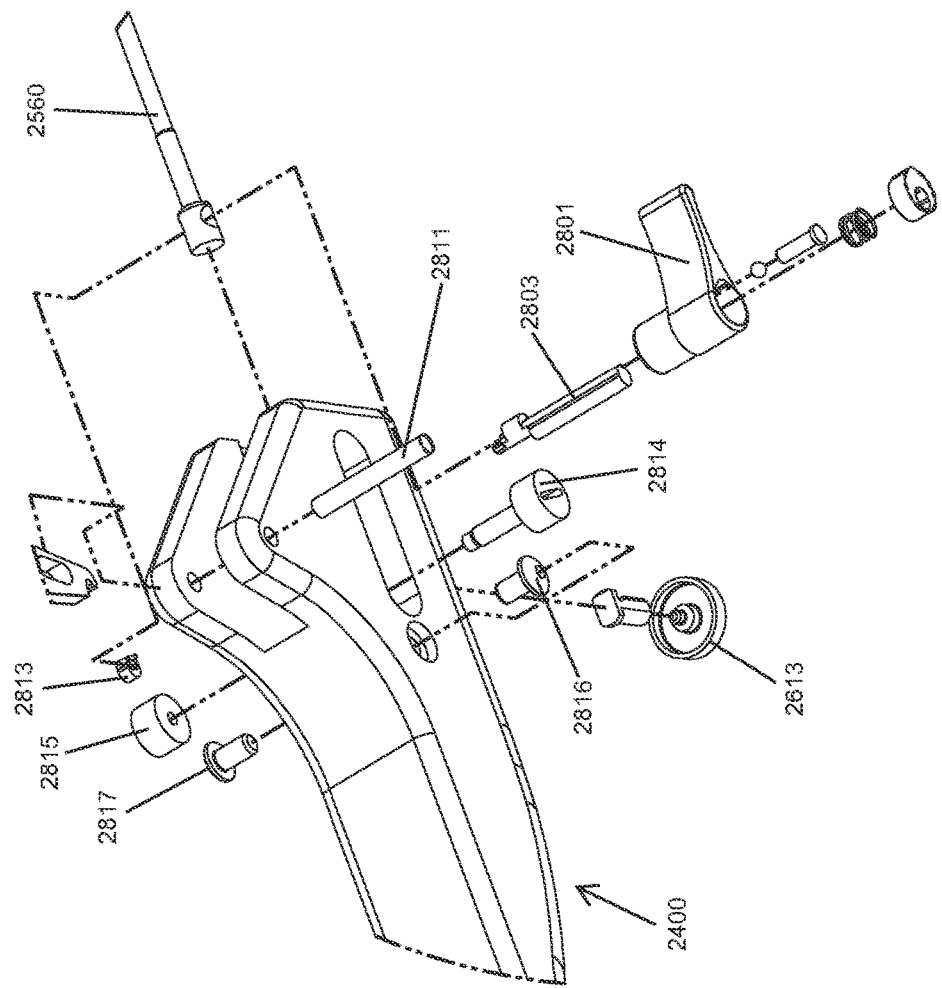
FIG. 96a is an exploded view of an actuator assembly of the insertion instrument of FIG. 93.
Figure 96B:
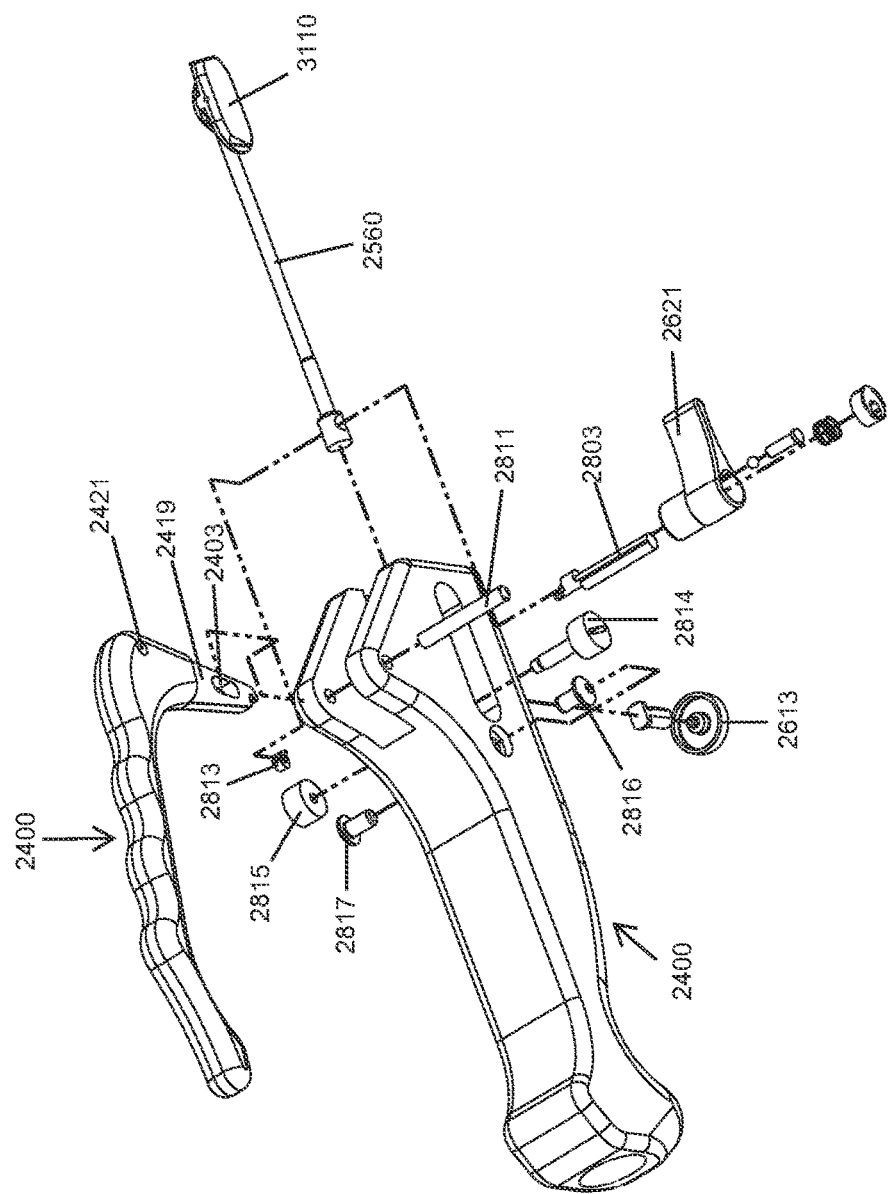
FIG. 96b is a partial exploded view of an actuator assembly of the insertion instrument of FIG. 93.
Figure 98:
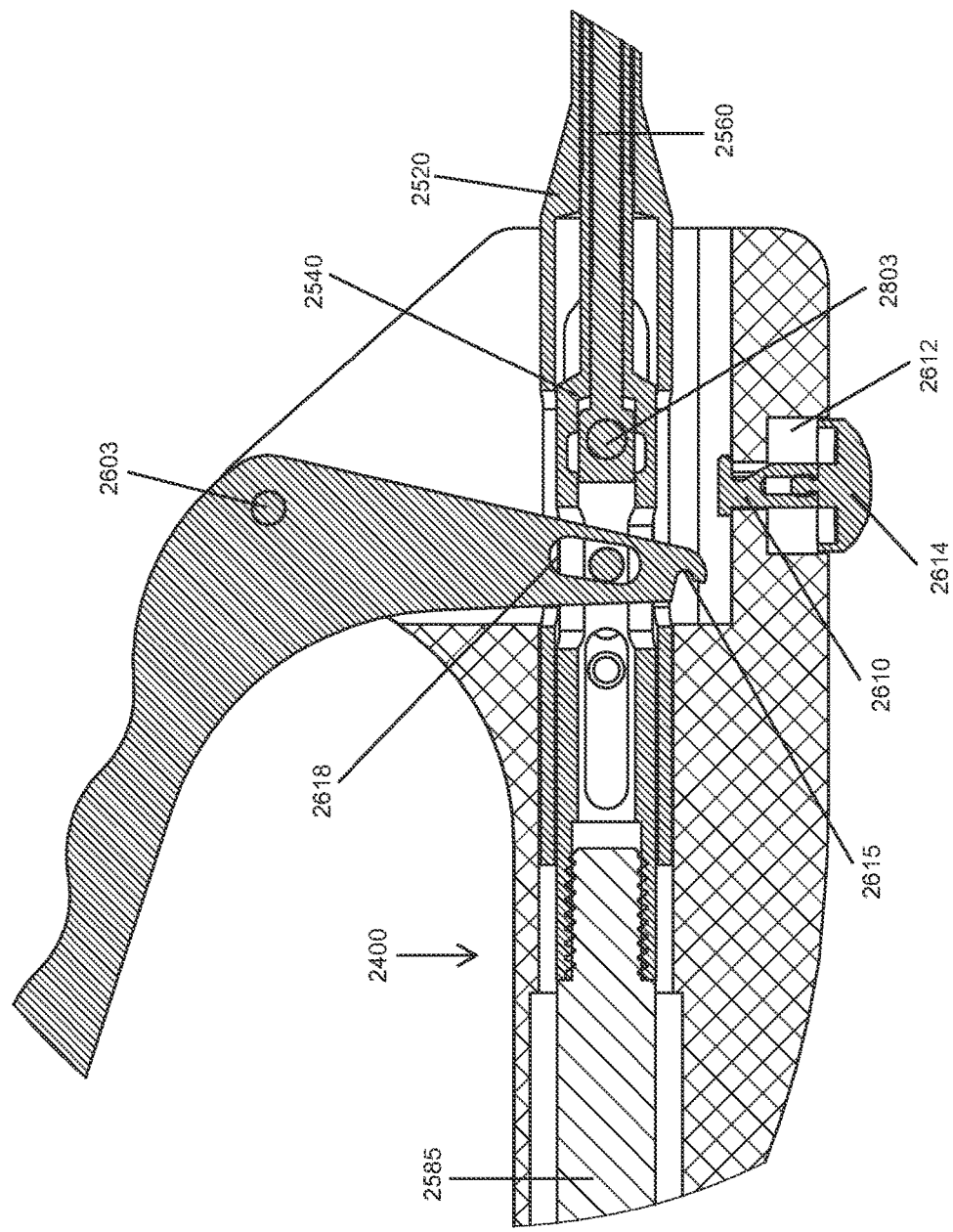

As best seen in FIG. 96B, rotation lever 2600 comprises a narrow shaft engaging portion 2619 having a width slightly less than the width of slots 2529, 2552 of external and rotation shafts respectively. Shaft engaging portion 2619 includes a slot 2620 therein for engaging the rotation lever attachment pin 2811. Inferior end of narrow engaging portion 2619 comprises a notch 2615 for engaging the superior portion of rotation shaft locking post 2610 for locking of the rotation shaft relative to the external shaft while the instrument is in the substantially 90 degree orientation. In assembly, inferior portion of rotation lever 2600 is deposited in slot 2406 of handle 2400. Narrow shaft engaging portion is disposed through slot 2529 of external shaft 2520, and slot 2552 of rotation shaft 2540 as seen in FIG. 98. Rotation lever pivot pin aperture 2621 is aligned with rotation lever pivot bore 2401 of handle 2400. Pivot pin 2811 is disposed in both bores and fixedly attached via press fit or laser weld. The arrangement allows rotation lever 2600 to move freely in handle slot 2406 and engage rotation shaft 2540. The bias force, in a distal direction, of rotation spring 2584 on shaft 2540 always urges distal portion of lever 2600 away from handle 2400.

Figure 106:
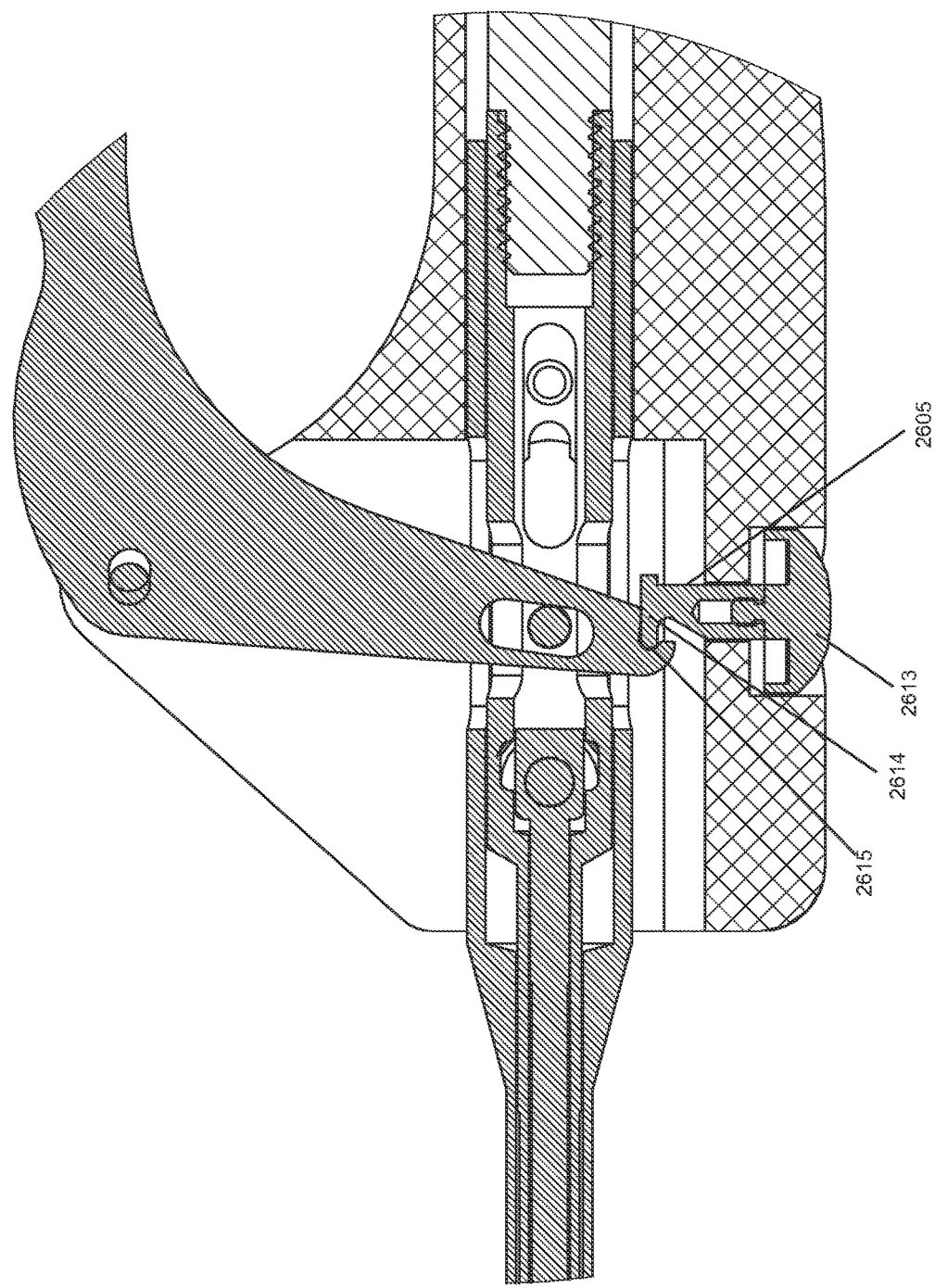
Figure 107:
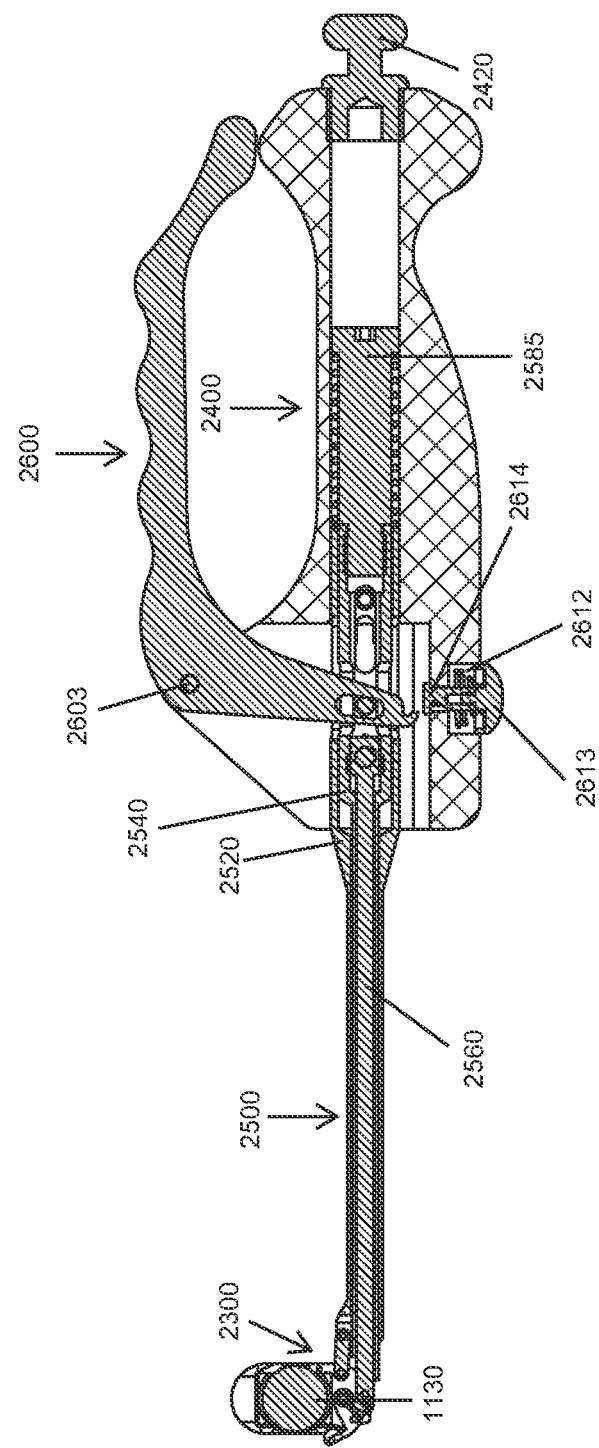

The locking of the rotation shaft in the 90 degree configuration is accomplished with a similar button, post, collar and spring configuration as that of instrument 1200. As distal end of rotation lever 2600 is deployed about pivot pin 2811, locking notch 2615 nears locking post 2610 eventually residing distal post 2610. Locking button 2613 is depressed thus engaging locking post 2610 with locking notch 2615, as seen in FIG. 106, preventing rotation shaft 2540 from traveling in the proximal direction.

FIGS. 97A-C, 99 illustrate components of release mechanism 2800. Release mechanism 2800 comprises release lever 2801, release lever shaft 2803, fixed cap 2818, locking spring 2806, locking post 2807, locking ball 2819, and distal attachment cap 2813. The release mechanism 2800 performs the same function as that of previously disclosed mechanism 1800 in that it engages release shaft urging release shaft 2560 proximally or distally thus engaging or disengaging implant 1101 from clamping mechanism 2300.

Figure 99:
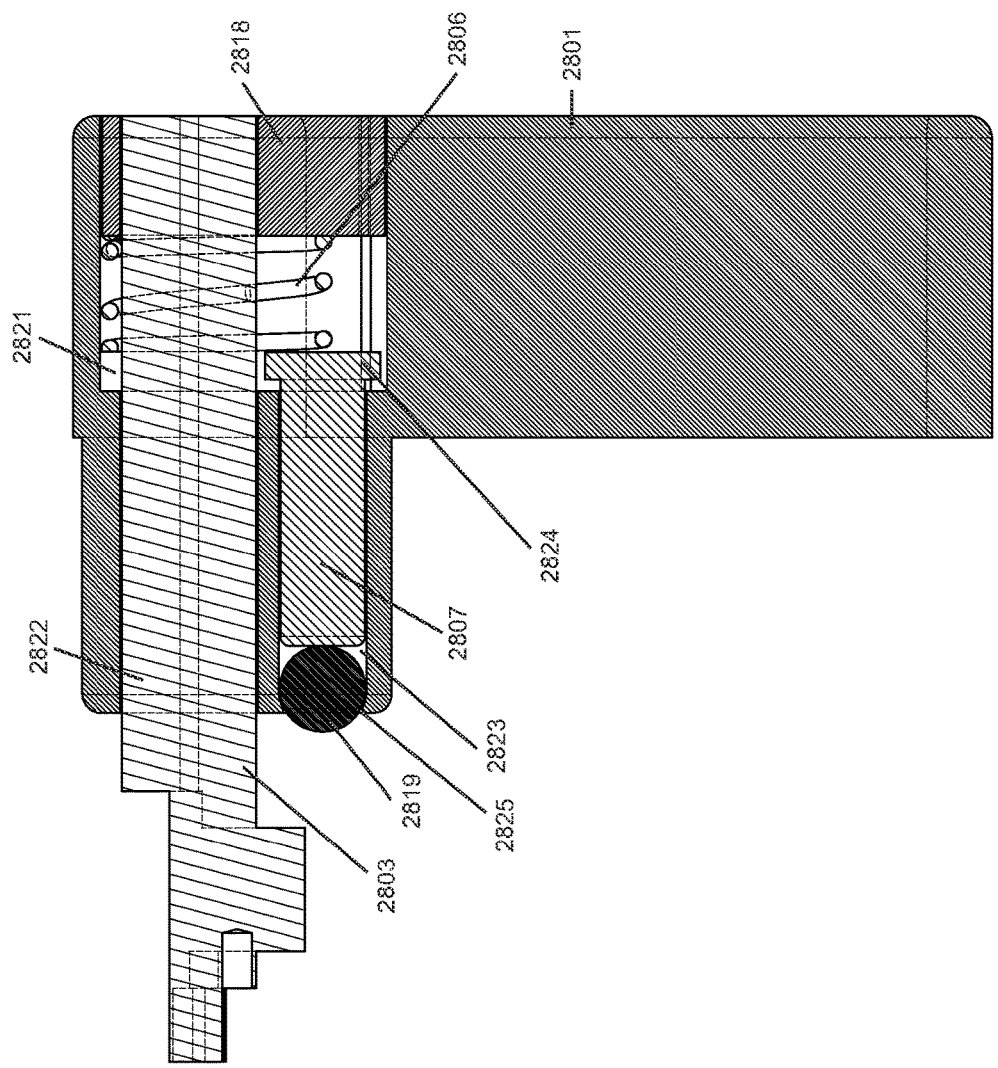
Figure 101:
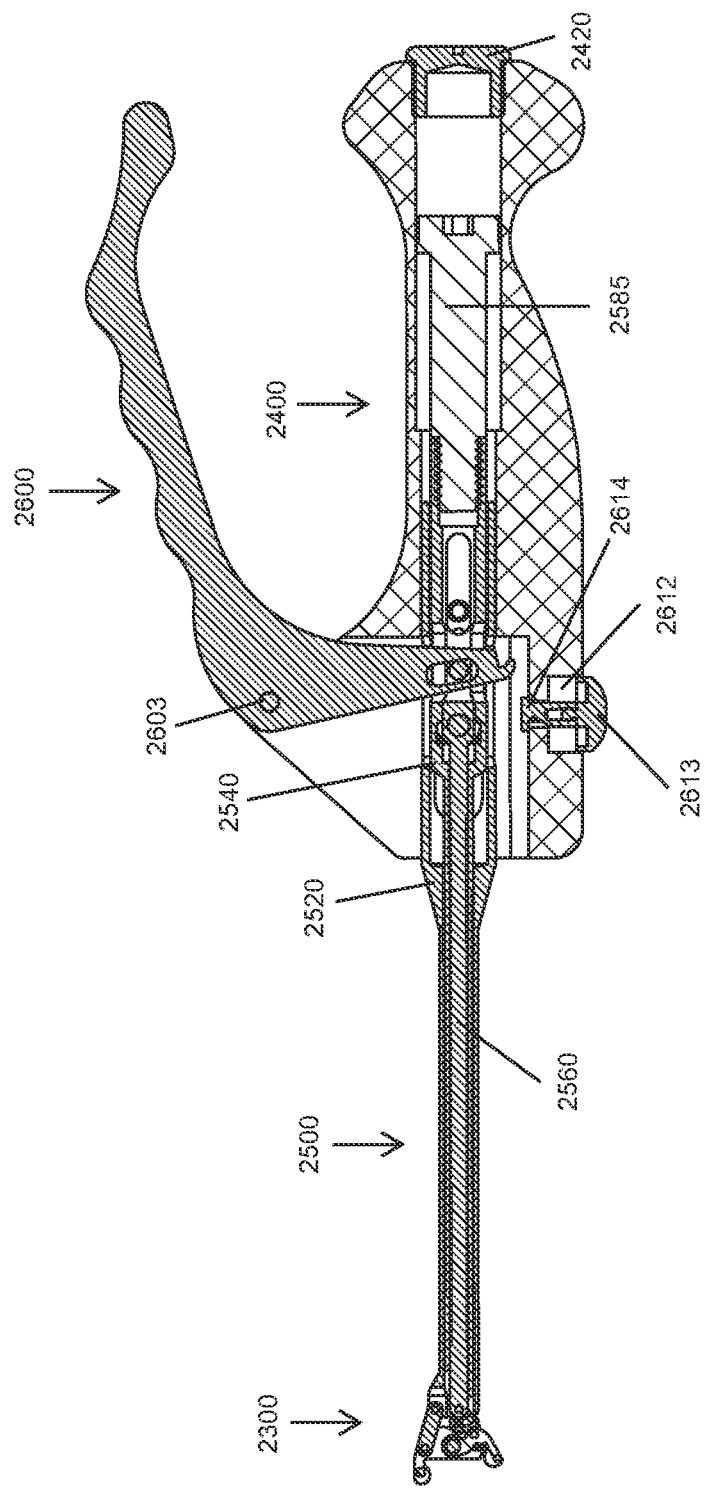
Figure 102:
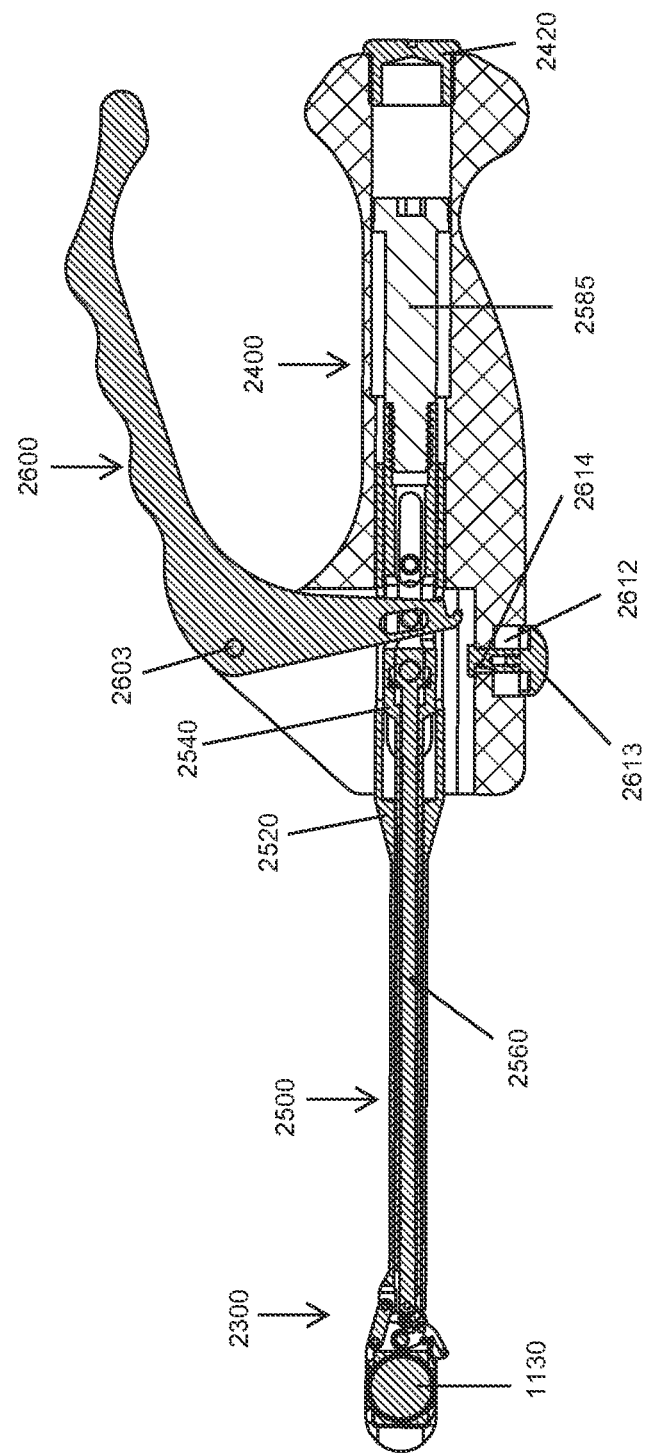
Figure 103:
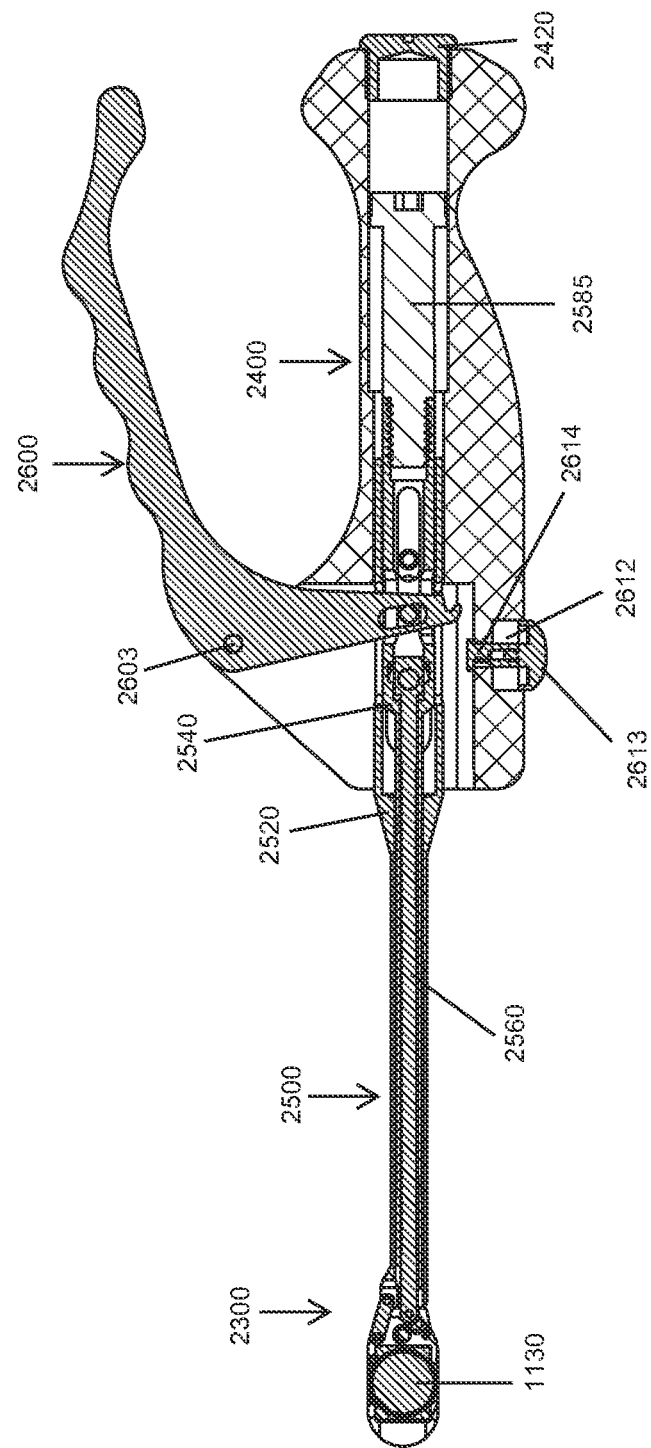
Figure 104:
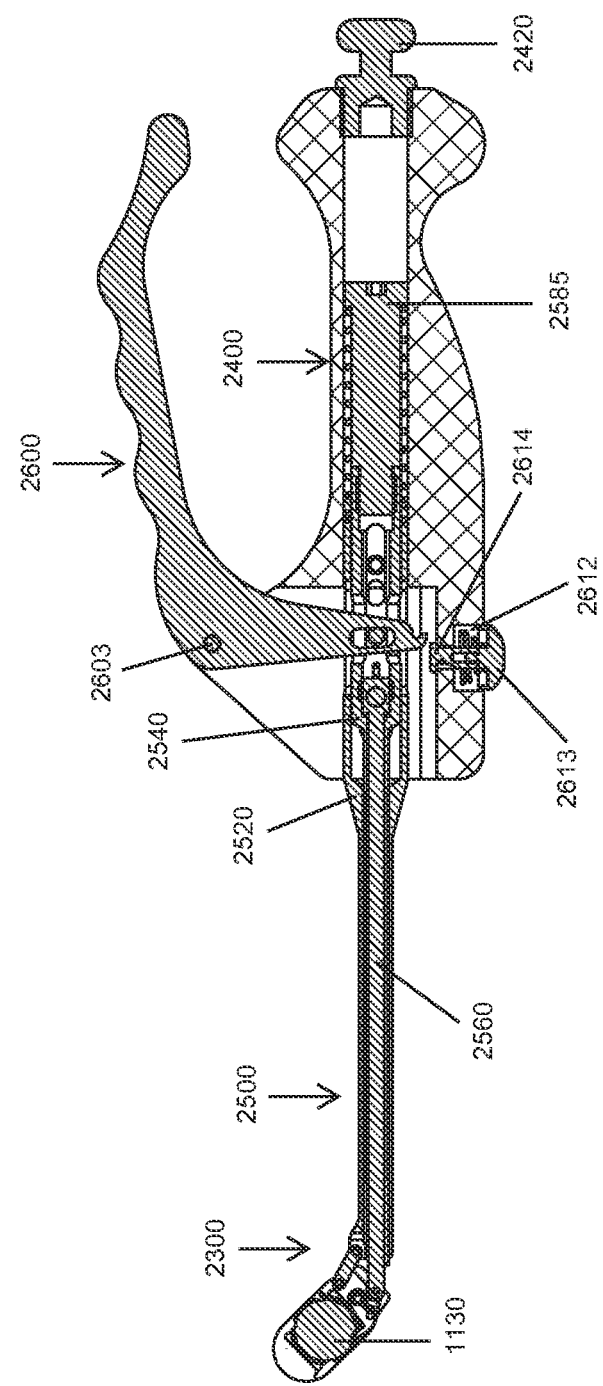
Figure 105:
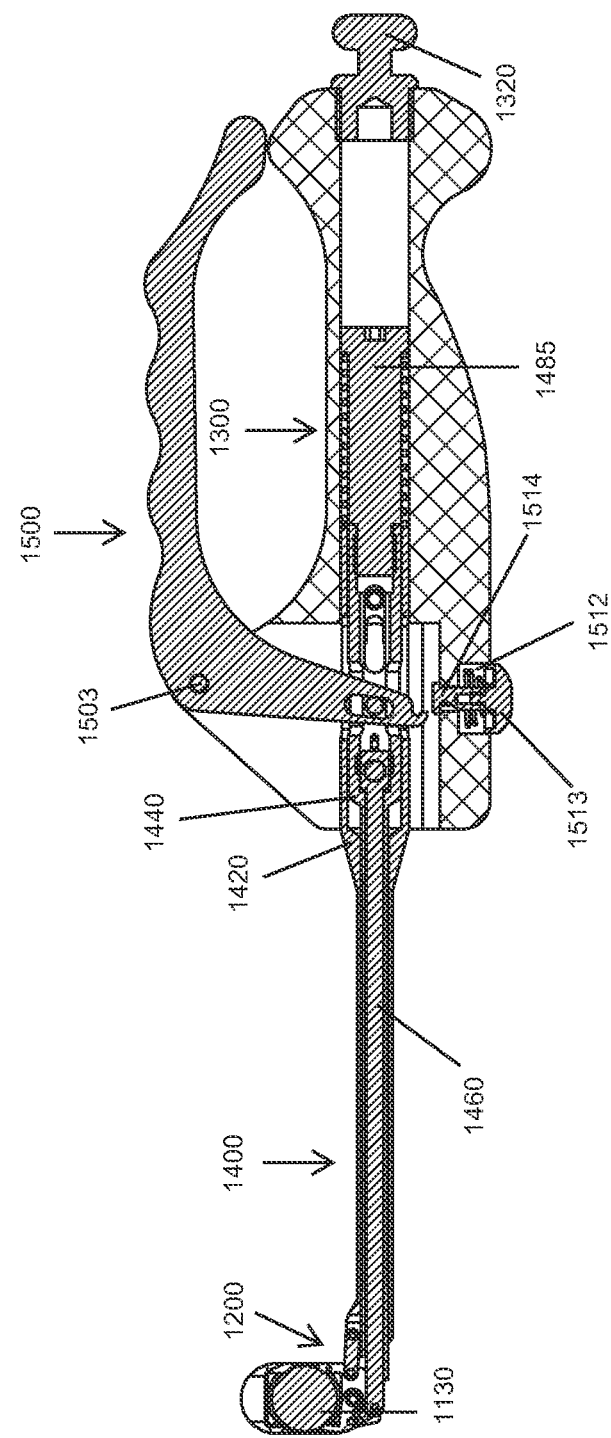

Elongate offset release shaft 2803 comprises a proximal end P, distal end D, camming portion 2805, release shaft abutment shoulder 2812, cap abutment shoulder 2820, lever cap bore, and elongate shaft portion bore 2822. As seen in FIG. 99 proximal end of offset shaft 2803 is fixedly attached to cap 2818 which resides in lever cap bore 2821. Elongate portion of offset shaft adjacent proximal end P is disposed in shaft portion bore 2822 of lever 2801. Parallel to shaft portion bore 2822 resides lever locking post bore 2823. Bore 2823 has tapered end 2825 with a diameter slightly less than that of the remainder of the bore 2823, post 2807 and locking ball 2819. Tapered end 2825 prevents locking ball 2819 and locking post 2807 from escaping locking post bore 2823. Coil Spring 2806 is disposed in bore 2821 extending about offset shaft 2803 and abutting cap 2818 and head 2824 of locking post 2807. Though offset shaft 2803 is fixed in lever 2801, locking ball 2819 and post 2807 may travel within bore 2823. Spring 2806 biases ball 2819 and post 2807 toward tapered end 2825 but allows movement in the opposite direction in reaction to forces placed on ball 2819.

In assembly, offset shaft 2803 is disposed in elongate slot 2402 of handle 2400 and elongate slot 2528 of external shaft 2520. Camming portion 2805 of shaft 2803 resides in bore 2561 of release shaft 2560. Shoulder 2812 of the offset shaft abuts external diameter of release shaft 2560. Distal end of shaft 2803 receives cap 2813 fixedly attached thereon and resides in slot 2551 of rotation shaft 2540. When release lever 2801 is rotated, distal end of offset shaft 2803 cams against the sides of slot 2551 of rotation shaft 2540 moving release shaft 2560 in a proximal or distal direction relative to rotation shaft 2540 thus opening or closing clamping fingers 1143, 1144.

In the release position, locking ball 2819 is engaged with slot 2549 thus locking instrument 2200 in the open or release configuration. As the release lever 2801 is turned, locking ball 2819 and locking post rotated about the central axis of lever 2801. Locking ball 2819 and locking post 2807 are urged into lever 2801 overcoming the force of spring 2806. When the release lever has reached the locking position, the locking ball is engaged with slot 2550 as spring 2806 biases locking post 2807 and ball 2819 toward instrument 2200. The instrument is now locked in the grasping configuration.

The preferred method of inserting a spinal implant with instrument 3200 is similar to the method of insertion with instrument 1200. The release lever 1801 of instrument 1200 returns to the grasping or locked configuration automatically. Release lever 2801 of instrument 2200 must be returned manually. Although release lever 2801 need be rotated manually, instrument 2200 has fewer moving parts and is relatively less costly to manufacture than instrument 1200.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A tool for inserting an implant, comprising:
a handle;
a shaft assembly having a longitudinal axis and being operably connected to the handle;
a pivotable head portion for gripping the implant and being pivotally connected to a distal end portion of the shaft assembly;
a movable jaw member movably connected to the pivotable head portion for selectively gripping and releasing the implant;
a stationary jaw member fixedly connected to the pivotable head portion opposite from the movable jaw member for gripping the implant therebetween;
a first actuator operably connected to a proximal end portion of the shaft assembly operable to selectively pivot the head portion and the movable and stationary jaw members thereof to a plurality of different positions with respect to the shaft assembly; and
a second actuator operably connected to the proximal end portion of the shaft assembly operable to selectively shift the movable jaw member relative to the pivotable head portion towards and away from the stationary jaw member for selectively gripping and releasing the implant;
the shaft assembly and head portion being configured to allow the movable jaw member to be shifted independently of the pivotable head portion and the implant to be selectively released by the movable jaw member in each of the plurality of different positions of the pivotable head portion;
wherein the plurality of different positions of the pivotable head portion include an insertion configuration, wherein the head portion holds the implant in a first orientation relative to the shaft assembly, and a rotated configuration, wherein the head portion holds the implant in a second orientation relative to the shaft assembly different from the first orientation; and
wherein the pivotable head portion is biased to return to the insertion configuration when the pivotable head portion is shifted by the first actuator to the rotated configuration.

2. The tool of claim 1, further comprising a biasing member associated with the shaft assembly operable to bias the movable jaw member toward a gripping orientation for gripping the implant in each of the plurality of different positions of the pivotable head portion.

3. The tool of claim 1, wherein the shaft assembly is releasably connected to the handle portion to allow the shaft assembly to be removed from the handle for cleaning.

4. The tool of claim 1, further comprising a latch member for releasably connecting the shaft assembly to the handle, wherein the latch member is shiftable between a closed orientation for keeping the shaft assembly locked to the handle, and a released orientation, for removing the shaft assembly from the handle.

5. The tool of claim 1, wherein the shaft assembly comprises a first shaft operably connected to the first actuator and the head portion for shifting the head portion via the first actuator, and a second shaft operably connected to the second actuator and the movable jaw member for shifting the movable jaw member via the second actuator.

6. The tool of claim 1, further comprising a biasing member associated with the shaft assembly operable to generate a biasing force to urge the pivotable head portion from the rotated configuration to the insertion configuration.

7. The tool of claim 6, wherein the biasing member is a spring operably connected to the shaft assembly.

8. The tool of claim 1, wherein the first actuator comprises a lever configured to shift between a plurality of different positions corresponding with the plurality of different positions of the pivotable head portion.

9. A tool for inserting an implant, comprising:
a handle;
a shaft assembly having a longitudinal axis and being operably connected to the handle;
a pivotable head portion for gripping the implant and being pivotally connected to a distal end portion of the shaft assembly;
a movable jaw member movably connected to the pivotable head portion for selectively gripping and releasing the implant;
a stationary jaw member fixedly connected to the pivotable head portion opposite from the movable jaw member for gripping the implant therebetween;
a first actuator operably connected to a proximal end portion of the shaft assembly operable to selectively pivot the head portion and the movable and stationary jaw members thereof to a plurality of different positions with respect to the shaft assembly; and
a second actuator operably connected to the proximal end portion of the shaft assembly operable to selectively shift the movable jaw member relative to the pivotable head portion towards and away from the stationary jaw member for selectively gripping and releasing the implant;
the shaft assembly and head portion being configured to allow the movable jaw member to be shifted independently of the pivotable head portion and the implant to be selectively released by the movable jaw member in each of the plurality of different positions of the pivotable head portion;
wherein the plurality of different positions of the pivotable head portion include an insertion configuration, wherein the head portion holds the implant in a first orientation relative to the shaft assembly, and a rotated configuration, wherein the head portion holds the implant in a second orientation relative to the shaft assembly different from the first orientation; and
wherein the movable jaw member is shiftable between a gripping orientation for gripping the implant and a releasing orientation for releasing the implant, and the movable jaw member is biased to return to the gripping orientation from the releasing orientation.

10. The tool of claim 1, wherein the first actuator comprises a lever configured to shift between a plurality of different positions corresponding with the plurality of different positions of the pivotable head portion, and the tool further comprises a latch member for holding the lever in at least one of the plurality of different positions corresponding to the rotated configuration of the pivotable head portion.

11. The tool of claim 9, further comprising a latch member configured to keep the pivotable head portion from returning to the insertion configuration when in the rotated configuration.

12. The tool of claim 11, further comprising a biasing member associated with the shaft assembly operable to generate a biasing force to urge the pivotable head portion from the rotated configuration to the insertion configuration.

13. The tool of claim 11, wherein the shaft assembly comprises a plurality of shafts including an outer shaft that extends about the other of the plurality of shafts.

14. The tool of claim 11, wherein the pivotable head portion is biased to return to the insertion configuration when the pivotable head portion is shifted by the first actuator to the rotated configuration.

15. The tool of claim 11, further comprising a latch member configured to keep the pivotable head portion from returning to the insertion configuration when in the rotated configuration.

* * * * *